United States Patent
Bittinger et al.

(10) Patent No.: US 10,947,596 B2
(45) Date of Patent: Mar. 16, 2021

(54) COMPOSITIONS AND METHODS FOR IDENTIFICATION, ASSESSMENT, PREVENTION, AND TREATMENT OF CANCER USING NFS1 BIOMARKERS AND MODULATORS

(71) Applicant: Dana-Farber Cancer Institute, Inc., Boston, MA (US)

(72) Inventors: Mark Bittinger, Dover, MA (US); Jessie M. English, Cambridge, MA (US); Kwok-Kin Wong, Arlington, MA (US); Sima Zacharek, Jamaica Plain, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 86 days.

(21) Appl. No.: 15/308,268

(22) PCT Filed: May 6, 2015

(86) PCT No.: PCT/US2015/029439
§ 371 (c)(1),
(2) Date: Nov. 1, 2016

(87) PCT Pub. No.: WO2015/171741
PCT Pub. Date: Nov. 12, 2015

(65) Prior Publication Data
US 2017/0051358 A1 Feb. 23, 2017

Related U.S. Application Data

(60) Provisional application No. 61/989,037, filed on May 6, 2014.

(51) Int. Cl.
*C12Q 1/6886* (2018.01)
*G01N 33/68* (2006.01)

(52) U.S. Cl.
CPC ....... *C12Q 1/6886* (2013.01); *G01N 33/6848* (2013.01); *C12Q 2600/106* (2013.01); *C12Q 2600/118* (2013.01); *C12Q 2600/136* (2013.01); *C12Q 2600/156* (2013.01); *C12Q 2600/158* (2013.01); *G01N 2333/91194* (2013.01)

(58) Field of Classification Search
CPC ... A61P 35/00; C12Q 1/6883; C12Q 2600/58; G01N 33/57484
USPC ............ 514/44 A; 435/6.1, 91.1, 91.31, 455, 435/458; 536/23.1, 24.5
See application file for complete search history.

(56) References Cited
U.S. PATENT DOCUMENTS

2010/0028334 A1* 2/2010 Cottarel ................. A61K 31/16
514/1.1
2010/0190656 A1 7/2010 Li et al.

OTHER PUBLICATIONS

Pai et al, Gene Therapy 2005; 1-14.*
Ryther et al, Gene Therapy 2005; 12: 5-11.*
Schiffelers et al., Nucleic Acids Research 2004; 32: e49.*
Abruzzo et al.,"Frataxin mRNA Isoforms in FRDA Patients and Normal Subjects: Effect of Tocotrienol Supplementation," BioMed Res. Intl., 2013: 276808 (2013).
Anthony et al., "New Classes of Alanine Racemase Inhibitors Identified by High-Throughput Screening Show Antimicrobial Activity against *Mycobacterium tuberculosis*," PLoS One, 6: e20374 (2011).
Biderbick et al., "Role of Human Mitochondrial Nfs1 in Cytosolic Iron-Sulfur Protein Biogenesis and Iron Regulation," Mol Cell Biol, 26: 5675-5687 (2006).
Colin et al., "Mammalian Frataxin Controls Sulfur Production and Iron Entry during de Novo Fe4S4 Cluster Assembly," J Am Chem Soc, 135: 733-740 (2013).
Cupp-Vickery et al., "Crystal Structure of IscS, a Cysteine Desulfurase from *Escherichia coli*," J Mol Biol, 330:1049-1059 (2003).
Dixon et al., "Ferroptosis: An Iron-Dependent Form of Nonapoptotic Cell Death," Cell 149:1060-1072 (2012).
Farhan et al., "Exome Sequencing Identifies NFS1 Deficiency in a Novel Fe—S Cluster Disease, Infantile Mitochondrial Complex II/III Deficiency," Mol Genet Genom Med, 2:73-80 (2014).
Kurihara et al., "Assembly of Iron-Sulfur Mediated by Cysteine Desulfurases, IscS, CsdB and CSD, from *Escherichia coli*," Biochim Biophys Acta, 1647:303-309 (2003).
Li et al., "Yeast Mitochondrial Protein, Nfs1p, Coordinately Regulates Iron-Sulfur Cluster Proteins, Cellular IronUptake, and Iron Distribution," J Biol Chem, 274: 33025-33034 (1999).
Li et al., "Detection of Intracellular Iron by Its Regulatory Effect," Am J Physiol Cell Physiol, 287: C1547-C1559 (2004).
Li et al., "Thermodynamic and Structural Analysis of Human NFU Conformational Chemistry," Biochem, 52: 4904-4913 (2013).
Lill et al., "Iron-Sulfur-Protein Biogenesis in Eukaryotes," Trends Biochem Sci, 30: 133-141 (2005).
Lim et al., "Mutations in LYRM4, Encoding Iron-Sulfur Cluster Biogenesis Factor ISD11, Cause Deficiency of Multiple Respiratory Chain Complexes," Hum Mol Genet, 22: 4460-4473 (2013).
Majewska et al.,"Binding of the Chaperone Jac1 Protein and Cysteine Desulfurase Nfs1 to the Iron-Sulfur Cluster Scaffold Isu Protein Is Mutually Exclusive," J Biol Chem, 288: 29134-29142 (2013).
Marelja et al., "A Novel Role for Human Nfs1 in the Cytoplasm: Nfs1 Acts as a Sultur Donor for MOCS3, a Protein Involved in Molybdenum Cofactor Biosynthesis," J Biol Chem, 283: 25178-25185 (2008).
Olson et al., "Characterization of the NifU and NifS Fe—S Cluster Formation Proteins Essential for Viability in Helicobacter pylori," Biochem, 39: 16213-16219 (2000).
Pandey et al., "Isd11p Protein Activates the Mitochondrial Cysteine Desulfurase Nfs1p Protein," J Biol Chem, 286: 38242-38252 (2011).

(Continued)

*Primary Examiner* — Jane J Zara
(74) *Attorney, Agent, or Firm* — Foley Hoag LLP

(57) ABSTRACT

The present invention is based, in part, on the identification, of novel mitochondrial iron-sulfur (Fe—S) cluster biosynthesis pathway biomarkers and modulators, and methods of use thereof, for identifying, assessing, preventing, and treating cancer.

1 Claim, 24 Drawing Sheets
Specification includes a Sequence Listing.

(56) References Cited

OTHER PUBLICATIONS

Pandey et al., "Fraxatin Directly Stimulates Mitochondrial Cysteine Desulfurase by Exposing Substrate-binding Sites, and a Mutant Fe—S Cluster Scaffold Protein with Frataxin-bypassing Ability Acts Similarly," J Biol Chem, 288: 36773-36786 (2013).

Prischi et al., "Structural Bases for the Interaction of Frataxin with the Central Components of Iron-Sulphur Cluster Assembly," Nat Commun, 1: 95 (2010).

Rouault et al., "Iron-Sulphur Cluster Biogenesis and Mitochondrial Iron Homeostasis," Nat Rev Mol Cell Biol, 6: 345-351 (2005).

Rybniker et al., "The Cysteine Desulfurase IscS of Mycobacterium Tuberculosis is Involved in Iron-Sulfur Cluster Biogenesis and Oxidative Stress Defence," Biochem J, 459: 467-478 (2014).

Schmucker et al., "Mammalian Frataxin: An Essential Function for Cellular Viability through an Interaction with a Preformed ISCU/NFS1/IDS11 Iron-Sulfur Assembly Complex," PLoS One, 6: e16199 (2011).

Stemmler et al., "Frataxin and Mitochondrial FeS Cluster Biogenesis," J Biol Chem, 285: 26737-26743 (2010).

Thompson et al., "Hypoxia-inducible Factor 2beta Regulates Key Neutrophil Functions in Humans, Mice, and Zebrafish," Blood, 123: 366-376 (2014).

Thorson et al., "Identification of Cystathionine Beta-Synthase Inhibitors Using a Hydrogen Sulfide Selective Probe," Angew Chem. Int. Ed. Engl., 52: 4641-4644 (2013).

Tsai et al., "Human Frataxin Is an Allosteric Switch that Activates the Fe—S Cluster Biosynthetic Complex," Biochem., 49: 9132-9139 (2010).

Weerapana et al., "Quantitative Reactivity Profiling Predicts Functional Cysteines in Proteomes," Nature, 468: 790-795 (2010).

Yang et al., "Regulation of Ferroptotic Cancer Cell Death by GPX4," Cell, 156: 317-331 (2014).

Ye et al., "Human Iron-Sulfur Cluster Assembly, Cellular Iron Homeostasis, and Disease," Biochem., 49: 4945-4956 (2010).

Zimmer et al., "Small-Molecule Inhibitors of HIF-2a Translation Link Its 5'UTR Iron-Responsive Element of Oxygen Sensing," Mol. Cell, 32: 838-848 (2008).

International Search Report for International Application No. PCT/US2015/029439 dated Sep. 29, 2015.

\* cited by examiner

Figure 22
A
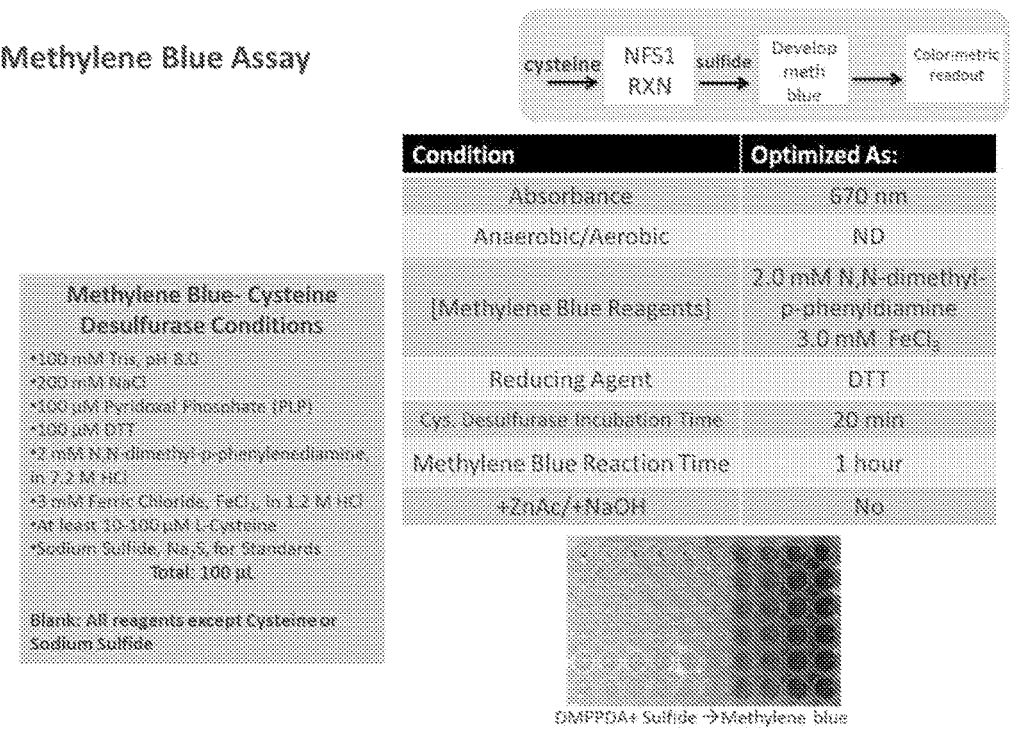
B
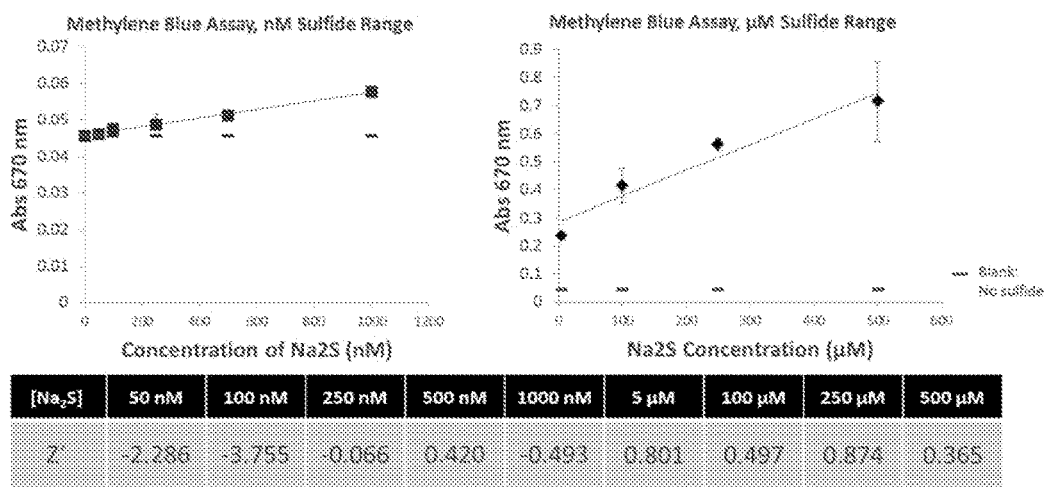

AzMC Assay

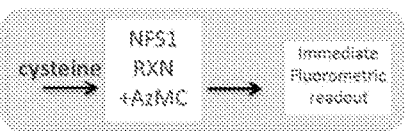

**AzMC Fluorescence Sulfide Assay-
NFS1 Assay Conditions**
- 100 mM Tris-HCl, pH 8.0
- 200 mM NaCl
- 5 mM Glutathione
    - *DTT reacts with AzMC probe
- 100 μM Pyridoxal Phosphate
- 0.5 mg/mL BSA, pH 8.0
- 10 μM 7-azido-4-methylcoumarin (AzMC)
- At least 10-100 μM L-Cysteine
- Sodium Sulfide, $Na_2S$, for standards
    Total: 100 μL Blank: All reagents except Cysteine or NaSulfide

| Condition | Optimized As: |
|---|---|
| Excitation/Emission | 365/450 |
| Source of Sulfide for Standards | $Na_2S$ |
| Storage of Sulfide Solution | Water |
| Anaerobic/Aerobic | Anaerobic(?) |
| [NFS1]/[Iscs] | 250 nM |
| [Cysteine] | 10 – 100 μM |
| Reducing Agent | Glutathione |
| Cys. Desulfurase Incubation Time | 2 Hours |
| Cys. Desulfurase Incubation Temperature | 37°C |
| +ZnAc/+NaOH | No |
| Addition of $FeCl_3$ | Unclear |

B

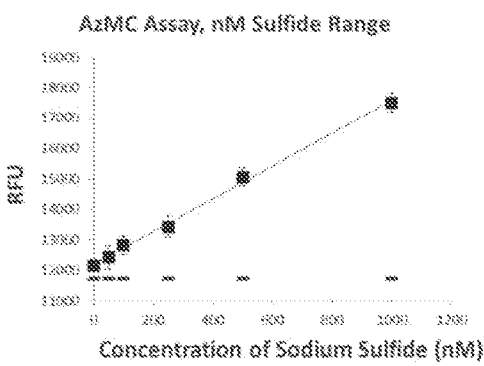
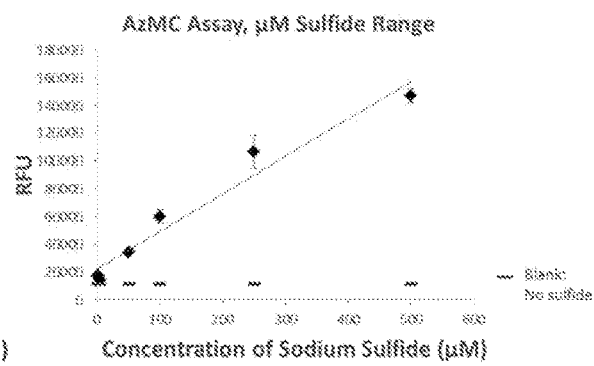

| [$Na_2S$] | 50 nM | 100 nM | 250 nM | 500 nM | 1 μM | 5 μM | 50 μM | 100 μM | 250 μM | 500 μM |
|---|---|---|---|---|---|---|---|---|---|---|
| Z' | -1.344 | -0.258 | 0.132 | 0.594 | 0.754 | 0.349 | 0.604 | 0.665 | 0.628 | 0.884 |

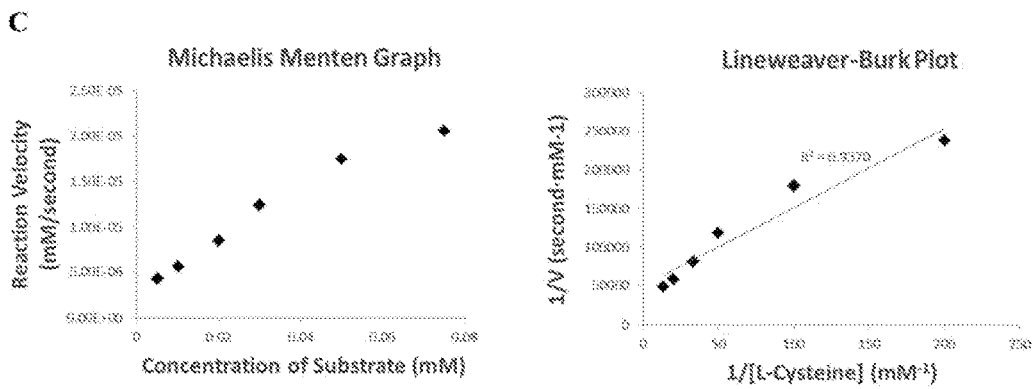

Enzyme velocities determined for different L-Cysteine concentrations under aerobic conditions $V_{max}$ = 2.004 x $10^{-5}$ mM/second $K_m$ = 20.37 uM Published $K_m^{cys}$ for IscS: 17 uM (based on Meth Blue assay)

Ave Km from 3 separate experiments: 61.03 uM +/- 42.49 uM

Alanine Assay, Optimization

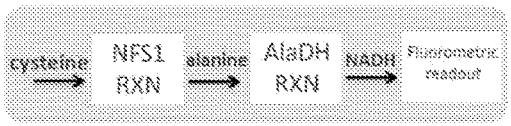

| Condition | Optimized As: |
|---|---|
| Excitation/Emission | 340/460 |
| Anaerobic/Aerobic | Anaerobic(?) |
| [AlaDH] | 0.03 units/mL |
| [NFS1]/[IscS] | 250 nM |
| [Cysteine] | 10-100 uM |
| [NAD⁺] | 1 mM |
| Reducing Agent | DTT |
| pH | NFS1 Rxn = 8-8.5  AlaDH Rxn = 10-10.5 |
| Cys. Desulfurase Incubation Time | 1-2 Hours |
| Cys. Desulfurase Incubation Temperature | 37 C |
| AlaDH Incubation Time | 30 minutes |
| AlaDH Incubation Temperature | 25 C |

Combined with Cysteine Desulfurase Reaction Conditions

- 100 mM Tris-HCl, pH 8.0
- 200 mM NaCl
- 100 µM DTT
- 100 µM Pyridoxal Phosphate
- At least 10-100 µM L-Cysteine
- 100 mM $Na_2CO_3$, $NaHCO_3$ buffer, pH 10
- 1 mM $NAD^+$
- L-Alanine for standards
- 0.03 units/mL Alanine Dehydrogenase Blank: All reagents except Cysteine or alanine (for st curve)

Figure 25 (cont).
B
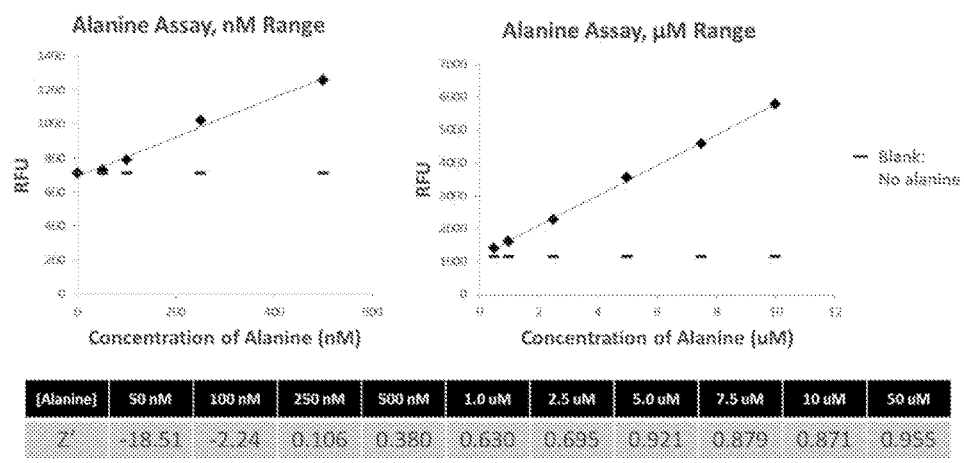
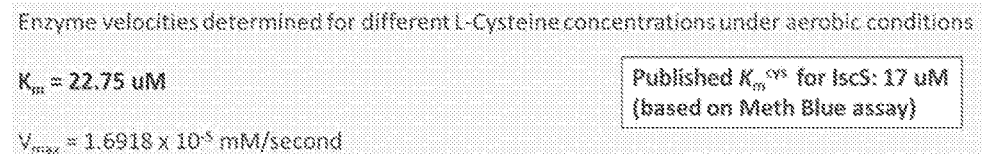
C
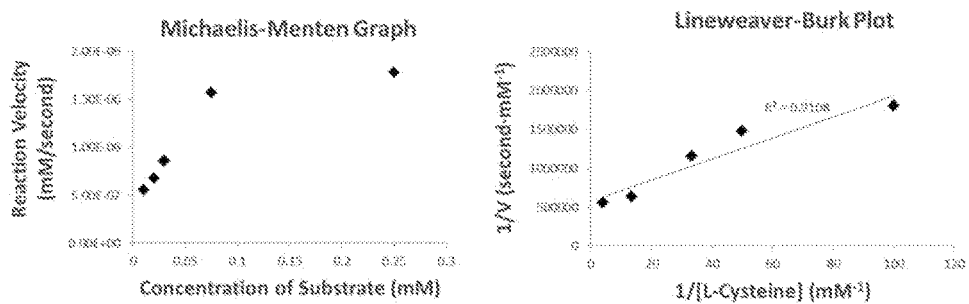

COMPOSITIONS AND METHODS FOR IDENTIFICATION, ASSESSMENT, PREVENTION, AND TREATMENT OF CANCER USING NFS1 BIOMARKERS AND MODULATORS

CROSS-REFERENCE TO RELATED APPLICATION

This application claims the benefit of U.S. Provisional Application No. 60/989,037, filed on 6 May 2014; the entire contents of said application are incorporated herein in their entirety by this reference.

BACKGROUND OF THE INVENTION

Despite advances in understanding the etiology of cancer and effective methods for treating cancer, malignant neoplasms represent the second most frequent cause of death worldwide surpassed only by heart diseases. Although effective anti-cancer treatments exist for many malignancies, such treatments are directed against well-known targets that do not fully control such malignancies. Accordingly, there is a great need to identify new cancer-related targets and biomarkers useful for the identification, assessment, prevention, and treatment of cancer.

SUMMARY OF THE INVENTION

The present invention is based, at least in part, on the discovery that the iron-sulfur cluster biosynthesis pathway plays a significant role in driving hyperproliferative cell growth and that modulating the pathway (e.g., inhibiting the function of one or more iron-sulfur cluster biosynthesis pathway members) can inhibit such hyperproliferative cell growth. In addition, biomarkers related to the iron-sulfur cluster biosynthesis pathway have been identified that are useful for identifying and assessing modulation of such hyperproliferative cell growth.

In one aspect, a method of treating a subject afflicted with a cancer comprising administering to the subject an agent that inhibits the copy number, amount, and/or activity of at least one biomarker listed in Table 1, thereby treating the subject afflicted with the cancer, is provided. In one embodiment, the agent is administered in a pharmaceutically acceptable formulation. In another embodiment, the agent directly binds the at least one biomarker listed in Table 1. In still another embodiment, the at least one biomarker listed in Table 1 is human NFS1 or an ortholog thereof. In yet another embodiment, the method further comprises administering one or more additional anti-cancer agents, optionally comprising mitochondrial cofactor therapy.

In another aspect, a method of inhibiting hyperproliferative growth of a cancer cell or cells, the method comprising contacting the cancer cell or cells with an agent that inhibits the copy number, amount, and/or activity of at least one biomarker listed in Table 1, thereby inhibiting hyperproliferative growth of the cancer cell or cells, is provided. In one embodiment, the step of contacting occurs in vivo, ex vivo, or in vitro. In another embodiment, the agent is administered in a pharmaceutically acceptable formulation. In still another embodiment, the agent directly binds the at least one biomarker listed in Table 1. In yet another embodiment, the at least one biomarker listed in Table 1 is human NFS1 or an ortholog thereof. In another embodiment, the method further comprises administering one or more additional anti-cancer agents, optionally comprising mitochondrial cofactor therapy.

In still another aspect, a method of determining whether a subject afflicted with a cancer or at risk for developing a cancer would benefit from iron-sulfur cluster (ISC) biosynthesis pathway inhibitor therapy, the method comprising: a) obtaining a biological sample from the subject; b) determining the copy number, amount, and/or activity of at least one biomarker listed in Table 1 in a subject sample; c) determining the copy number, amount, and/or activity of the at least one biomarker in a control; and d) comparing the copy number, amount, and/or activity of the at least one biomarker detected in steps b) and c); wherein a significant increase in the copy number, amount, and/or activity of the at least one biomarker in the subject sample relative to the control copy number, amount, and/or activity of the at least one biomarker indicates that the subject afflicted with the cancer or at risk for developing the cancer would benefit from ISC biosynthesis pathway inhibitor therapy, is provided. In one embodiment, the method further comprises recommending, prescribing, or administering ISC biosynthesis pathway inhibitor therapy if the cancer is determined to benefit from ISC biosynthesis pathway inhibitor therapy. In another embodiment, the method further composes recommending, prescribing, or administering anti-cancer therapy other than ISC biosynthesis pathway inhibitor therapy if the cancer is determined to not benefit from ISC biosynthesis pathway inhibitor therapy. In still another embodiment, the anti-cancer therapy is selected from the group consisting of targeted therapy, chemotherapy, radiation therapy, and/or hormonal therapy. In yet another embodiment, the control sample is determined from a cancerous or non-cancerous sample from either the patient or a member of the same species to which the patient belongs. In another embodiment, the control sample comprises cells. In still another embodiment, the method further comprises determining responsiveness to ISC biosynthesis pathway inhibitor therapy measured by at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

In yet another aspect, a method of assessing the efficacy of an agent for treating a cancer in a subject, comprising: a) detecting, in a first subject sample and maintained in the presence of the agent the copy number, amount or activity of at least one biomarker listed in Table 1; b) detecting the copy number, amount, and/or activity of the at least one biomarker listed in Table 1 in a second subject sample and maintained in the absence of the test compound; and c) comparing the copy number, amount, and/or activity of the at least one biomarker listed in Table 1 from steps a) and b), wherein a significantly increased copy number, amount, and/or activity of the at least one biomarker listed in Table 1 in the first subject sample relative to the second subject sample, indicates that the agent treats the cancer in the subject, is provided.

In another aspect, a method of monitoring the progression of a cancer in a subject, comprising: a) detecting in a subject sample at a first point in time the copy number, amount, and/or activity of at least one biomarker listed in Table 1; b) repeating step a) during at least one subsequent point in time after administration of a therapeutic agent; and c) comparing the copy number, amount, and/or activity detected in steps a) and b), wherein a significantly increased copy number, amount, and/or activity of the at least one biomarker listed in Table 1 in the first subject sample relative to at least one subsequent subject sample, indicates that the agent treats the cancer in the subject, is provided. In one embodiment, the subject has undergone treatment, completed treatment, and/or is in remission for the cancer in between the first point in time and the subsequent point in time.

In another embodiment, the subject has undergone ISC biosynthesis pathway inhibitor therapy in between the first point in time and the subsequent point in time. In still another embodiment, the first and/or at least one subsequent sample is selected from the group consisting of ex vivo and in vivo samples. In yet another embodiment, the first and/or at least one subsequent sample is obtained from an animal model of the cancer. In another embodiment, the first and/or at least one subsequent sample is a portion of a single sample or pooled samples obtained from the subject.

In still another aspect, a cell-based method for identifying an agent which inhibits a cancer, the method comprising: a) contacting a cell expressing at least one biomarker listed in Table 1 with a test agent; and b) determining the effect of the test agent on the copy number, level of expression, or level of activity of the at least one biomarker listed in Table 1 to thereby identify an agent that inhibits the cancer, is provided. In one embodiment, the cells are isolated from an animal model of a cancer. In another embodiment, the cells are from a subject afflicted with a cancer. In still another embodiment, the cells are unresponsive to ISC biosynthesis pathway inhibitor therapy. In yet another embodiment, the step of contacting occurs in vivo, ex vivo, or in vitro. In another embodiment, the method further comprises determining the ability of the test agent to bind to the at least one biomarker listed in Table 1 before or after determining the effect of the test agent on the copy number, level of expression, or level of activity of the at least one biomarker listed in Table 1. In another aspect, the sample comprises cells, cell lines, histological slides, paraffin embedded tissue, fresh frozen tissue, fresh tissue, biopsies, blood, plasma, serum, buccal scrape, saliva, cerebrospinal fluid, urine, stool, mucus, or bone marrow, obtained from the subject.

In yet another aspect, a cell-free method for identifying a compound which inhibits a cancer, the method comprising: a) determining the effect of a test compound on the amount or activity of at least one biomarker listed in Table 1 contacted with a test compound; b) determining the amount or activity of the at least one biomarker listed in Table 1 maintained in the absence of the test compound; and c) comparing the amount and/or activity of the at least one biomarker listed in Table 1 from steps a) and b), wherein a significantly increased amount, and/or activity of the at least one biomarker listed in Table 1 in step a) relative to step b), identifies a compound which inhibits the cancer, is provided. In one embodiment, the method further comprises determining the ability of the test compound to bind to the at least one biomarker listed in Table 1 before or after determining the effect of the test compound on the amount or activity of the at least one biomarker. In another embodiment, the steps a) and b) are selected from the group consisting of a methylene blue assay, a 7-azido-4-methylcoumarin (AzMC) assay, an alanine assay, and a mass spectrometry assay. In still another embodiment, the methylene blue assay comprises i) reacting the at least one biomarker listed in Table 1 in a buffer comprising a) cysteine, b) a pyridoxal phosphate cofactor, and c) optionally the test compound; ii) stopping the reaction by adding N,N-dimethyl-p-phenylenediamine and iron chloride (FeCl3)(in hydrogen chloride (HCl) solution, and iii) determining the production of methylene blue via absorbance of light having a wavelength of 670 nm. In yet another embodiment, the AzMC assay comprises i) reacting the at least one biomarker listed in Table 1 in a buffer comprising a) cysteine, b) a pyridoxal phosphate cofactor, glutathione as reducing agent, d) bovine serum albumin, e) 7-azido-4-methylcoumarin, and f) optionally, the test compound; and ii) fluorometrically monitoring the reaction product, 7-amino-4-methylcoumarin. In another embodiment, the alanine assay comprises i) reacting the at least one biomarker listed in Table 1 in a buffer comprising a) cysteine, b) a pyridoxal phosphate cofactor, c) DTT as reducing agent, and d) optionally, the test compound; ii) performing a secondary reaction to measure alanine production in a buffer containing a) NAD (nicotinamide adenine dinucleotide) and b) alanine dehydrogenase enzyme; and iii) fluorometrically measuring the reaction product, NADH. In still another embodiment, the mass spectrometry assay comprises i) reacting the at least one biomarker listed in Table 1 in a buffer comprising a) cysteine, b) a pyridoxal phosphate cofactor, and c) optionally the test compound; and ii) determining, the production of alanine using mass spectrometry.

Other embodiments of the present invention are applicable to any of the methods, compositions, assays, and the like presented herein. For example, in one embodiment, the copy number is assessed by microarray, quantitative PCR (qPCR), high-throughput sequencing, comparative genomic hybridization (CGH), or fluorescent in situ hybridization (FISH). In another embodiment, the amount of the at least one biomarker is assessed by detecting the presence in the samples of a polynucleotide molecule encoding the biomarker or a portion of said polynucleotide molecule. In still another embodiment, the polynucleotide molecule is a mRNA, cDNA, or functional variants or fragments thereof. In yet another embodiment, the step of detecting further comprises amplifying the polynucleotide molecule. In another embodiment, the amount of the at least one biomarker is assessed by annealing a nucleic acid probe with the sample of the polynucleotide encoding the one or more biomarkers or a portion of said polynucleotide molecule under stringent hybridization conditions. In still another embodiment, the amount of the at least one biomarker is assessed by detecting the presence a polypeptide of the at least one biomarker. In yet another embodiment, the presence of a polypeptide is detected using a reagent which specifically binds with the polypeptide (e.g., a reagent selected from the group consisting of an antibody, an antibody derivative, and an antibody fragment). In another embodiment, the activity of the at least one biomarker is assessed by determining the magnitude of modulation of at least one NFS1 pharmacodynamic biomarker listed in Table 1. In still another embodiment, the activity of the at least one biomarker is assessed by determining the magnitude of modulation of the activity or expression level of at least one downstream target of the at least one biomarker. In yet another embodiment, the ISC biosynthesis pathway inhibitor agent or test compound modulates a biomarker selected from the group consisting of human NFS1, human LYRM4, human ISCU, human FXN, human NFU1, human GLRX5, human BOLA3, human HSCB, human HSPA9, human ISCA1, human ISCA2, human IBA57, human NUBPL, human SLC25A28, human FDXR, human FDX2, and orthologs of said biomarkers thereof. In another embodiment, the ISC biosynthesis pathway inhibitor agent or test compound is an inhibitor selected from the group consisting of a small molecule, antisense nucleic acid, interfering RNA, shRNA, siRNA, aptamer, ribozyme, dominant-negative protein binding partner, and combinations thereof. In another embodiment, the at least one biomarker is selected from the group consisting of 2, 3, 4, 5, 6, 7, 8, 9, 10, or more biomarkers. In still another embodiment, the at least one biomarker is selected from the group of ISC biosynthesis pathway biomarkers listed in Table 1. In yet another embodiment, the ISC biosynthesis pathway biomarkers listed in Table 1 are selected from the group consisting of human NFS1, human LYRM4, human ISCU, human FXN, human NFU1, human GLRX5, human BOLA3, human HSCB, human HSPA9, human ISCA1, human ISCA2, human IBA57, human NUBPL, human SLC25A28, human FDXR, human FDX2, and orthologs of said biomarkers thereof. In another embodiment, the at least one biomarker is selected from the group of NFS1 pharmacodynamic biomarkers listed in Table 1. In still another embodiment, the NFS1 pharmacodynamic biomarkers listed in Table 1 are selected from the group consisting of human aconitase, human succinate dehydrogenase, human ferritin, human transferrin-receptor, human Hif2alpha, human PTGS2, and lipid reactive oxygen species (ROS). In yet another embodiment, the cancer is selected from the group consisting of paragangliomas, colorectal cancer, cervical cancer, lung adenocarcinoma, ovarian cancer, and myeloid cancer within a hypoxic tumor microenvironment. In another embodiment, the subject is a mammal, such as an animal model of cancer or a human.

BRIEF DESCRIPTION OF THE DRAWINGS

FIG. 22 includes 2 panels, identified as panels A and B, which provide a representative methylene blue assay suitable for high-through put formats (panel A) and representative sulfide detection range analyses (panel B). A Z' value of >0.5 is preferred for enzymatic assays and Z' was calculated as equaling 1-[3 (SD of signal+SD of background)/(Mean of signal−Mean of background)].

FIG. 24 includes 3 panels, identified as panels A, B, and C, which provide a representative AzMC assay suitable for high-through put formats (panel A) and representative sulfide detection range analyses (panel B). Z' values were calculated as equaling 1-[3 (SD of signal+SD of background)/(Mean of signal−Mean of background)]. Panel C shows the enzyme kinetics of IscC using an AzMC assay optimized for high-throughput analyses.

FIG. 25 includes 3 panels, identified as panels A, B, and C, which provide a representative alanine assay suitable for high-through put formats (panel A) and representative sulfide detection range analyses (panel B), Z values were calculated as equaling 1-[3 (SD of signal+SD of background)/(Mean of signal−Mean of background)]. Panel C shows the enzyme kinetics of IscC using an alanine assay optimized for high-throughput analyses.

Figure 1:
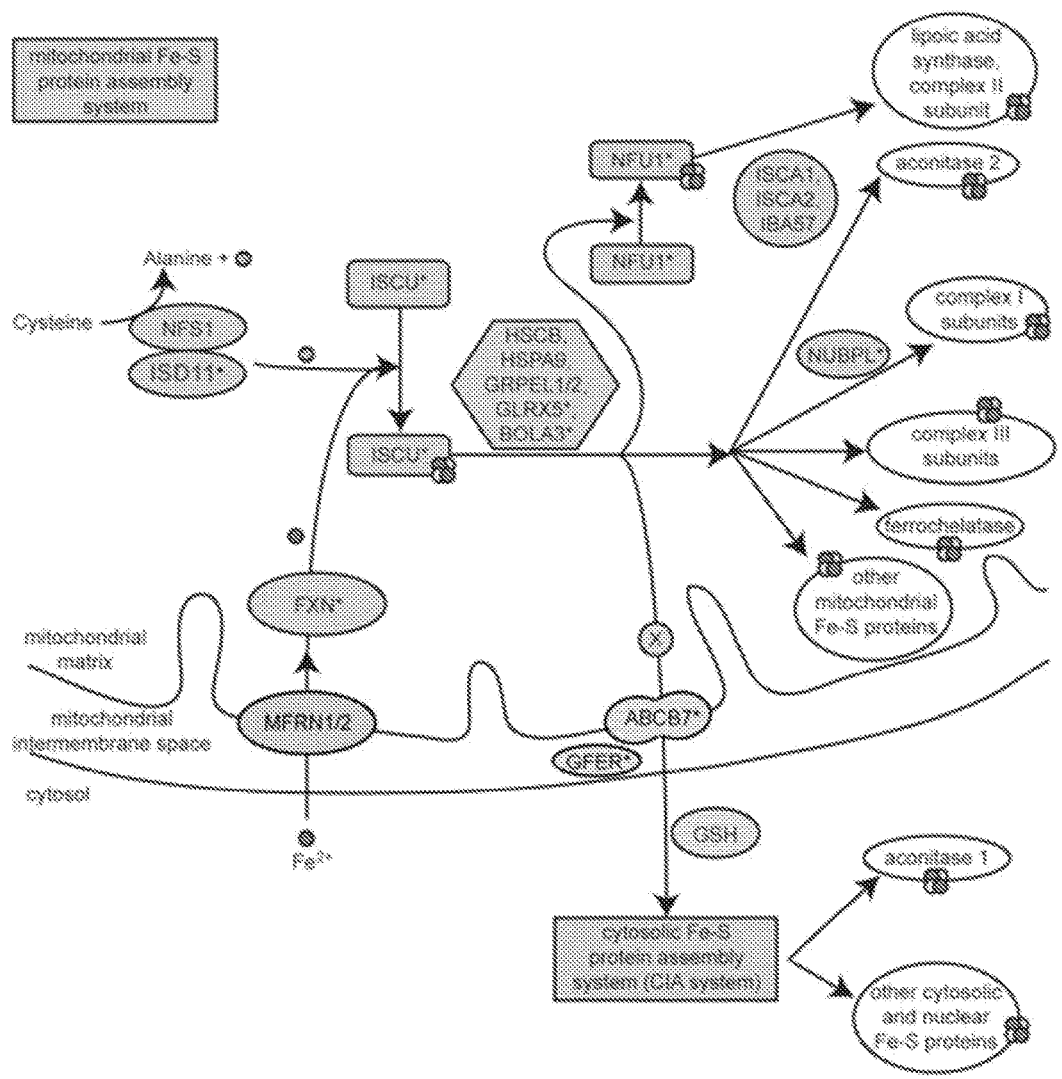
FIG. 1 shows a schematic diagram of the iron-sulfur cluster biogenesis pathway as adapted from Lim et al. (2013) *Hum. Mol. Genet.* 22:4460-4473.

Note that for every figure containing a histogram, the bars from left to right for each discreet measurement correspond to the figure boxes from top to bottom in the figure legend as indicated.

DETAILED DESCRIPTION OF THE INVENTION

Iron-sulfur cluster biogenesis is necessary for the generation of iron-sulfur containing proteins. It has been determined herein that the presence, absence, amount (e.g., copy number or level of expression), and/or activity of iron-sulfur duster biogenesis pathway members are biomarkers for the diagnosis, prognosis, and treatment of cancers. A variety of cancers can be so analyzed and treated, such as those having overexpression of NFS1 and/or those having activating mutations in the HIF2a pathway.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal amount if the amount is at least about two, and preferably at least about three, four, or five times, higher or lower, respectively, than the normal amount of the biomarker.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarily determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see Bird et al. (1988) *Science* 242:423-426; and Huston et. al. (1988) *Proc. Natl. Acad Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodics are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. U.S.A.* 90:6444-6448; Pollak et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov et al. (1994) *Mol. Immunol.* 31:104?-1058). Antibody portions, such as Fab and (Fab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized," which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis h vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the predictive score."

The term "biomarker" refers to a measurable entity of the present invention that has been determined to be predictive of anti-cancer therapy (e.g., iron-sulfur cluster biosynthesis pathway inhibitory therapy) effects on a cancer. Biomarkers can include, without limitation, nucleic acids (e.g., genomic nucleic acids and/or transcribed nucleic acids) and proteins, particularly those involved shown in Table 1. Many biomarkers listed in Table 1 are also useful as therapeutic targets. In one embodiment, such targets are the iron-sulfur cluster biosynthesis pathway members shown in section A of Table 1.

A "blocking" antibody or an antibody "antagonist" is one which inhibits or reduces at least one biological activity of the antigen(s) it binds. In certain embodiments, the blocking antibodies or antagonist antibodies Or fragments thereof described herein substantially or completely inhibit a given biological activity of the antigen(s).

The term "body fluid" refers to fluids that are excreted or secreted from the body as well as fluid that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, and vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of oncogenes, such as c-MYC. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, hut are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera lymphoma (Hodgkin's disease and non-Hodgkin's disease), multiple myeloma, Waldenstrom's macroglobulineinia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung, cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

The term "coding region" refers to regions or a nucleotide sequence comprising codons which are translated into amino acid residues, whereas the term "non-coding region" refers to regions of a nucleotide sequence that are not translated into amino acids (e.g., 5' and 3' untranslated regions).

The term "complementary" refers to the broad concept of sequence complementarily between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample From a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample) a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former ease, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid, or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide anti-cancer therapy (e.g., iron-sulfur cluster biosynthesis pathway inhibitory therapy). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "expression signature" or "signature" refers to a group of two or more coordinately expressed biomarkers. For example, the genes, proteins, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "highly structured 5' untranslated region (5' UTR)" refers to the region of an mRNA directly upstream from the initiation codon, which) begins at the transcription start site and ends one nucleotide (nt) before the initiation codon (usually AUG) of the coding region and 2) contains a hairpin loop or other secondary structures. Such secondary structures are usually predicted by modeling but there are experimental means to define them more quantitatively, such as by measuring the resistance of the structure to nucleases which do not attack double stranded regions or performing physical techniques, such as measuring the optical density at 260 nm as a function of temperature. In one embodiment, the highly structured 5' UTR renders the mRNA a relatively poor substrate for translation, mRNAs encoding proteins necessary for cell growth and survival typically contain a complex, highly structured 5' UTR in order to limit the availability of the protein. Structured 5' UTRs prevent CAP-dependent initiation of translation. Regulation of translation by structured 5' UTRs typically occurs due to long 5' UTRs and stable secondary structures and sequence segments which comprise a high proportion of guanine and cytosine bases since, when present in the 5' UTR of an mRNA, very efficiently inhibit the CAP-dependent initiation of protein biosynthesis according to the ribosome scanning model. In vitro investigations have shown that a hairpin structure in the 5' UTR of an mRNA having a free energy of 30-70 kcal/mol or less is able to inhibit translation effectively. Thus, it has been possible to show that mRNAs coding for a particular protein and having a 5' UTR exhibiting such a structure are translated only very weakly, whereas mRNAs coding for the same protein and having a shorter 5' UTR with a weaker structure are translated considerably more efficiently. Non-limiting, representative examples of RNAs with a highly structured 5' UTR include transferrin, transferrin receptor, c-MYC, X-linked inhibitor of apoptosis protein (XIAP), and ornithine decarboxylase (ODC1).

The term "homologous" refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3 and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

The "iron-sulfur cluster biogenesis pathway" refers to the full set, or relevant subsets thereof, of proteins required for generating iron-sulfur (Fe—S) clusters composed of iron and inorganic sulfur for use as cofactors in generating Fe—S proteins (sec, for example, Lill et al. (2012) Biochim. Biophys. Acta 1823:1491-1508; Lill and Mulenhoff (2005) Trends Biochem. Sci. 30:133-141; Rouault (2012) Dis. Model Mech. 5:155-164, Ye and Touault (2010) Biochem. 49:4945-4956, and Rouault and Tong (2005) Nat. Rev. Mol. Cell Biol. 6:345-351). Iron-sulfur clusters are critical for the production of a subset of enzymes involved in critical cellular processes, such as oxidative phosphorylation, the citric acid cycle, heme biosynthesis, iron homeostasis, and DNA repair. FIG. 1 shows an exemplary schematic diagram of the pathway. Members of the pathway, including terminology, sequences, and function, are well known in the art.

For example, "NFS1" refers to the nitrogen fixation 1 homolog cysteine desulfurase member of the class-V family of pyridoxal phosphate-dependent aminotransferase family and is alternatively known as "IscS," "NIFS," and "HUSSY-08," NFS1, whose structure-function relationship is known, supplies inorganic sulfur to iron-sulfur clusters by removing the sulfur from cysteine thereby creating alanine in the process (Farhan et al. (2014) Mol. Genet. Genom. Med. 2:73-80; Kurihara et al. (2003) Biochim. Biophys. Acta 1647:303-309; Cupp-Vickery et al. (2003) J. Mol. Biol. 330:1049-1059). The NFS1 gene uses alternate in-frame translation initiation sites to generate mitochondrial forms and cytoplasmic/nuclear forms. Selection of the alternative initiation sites is determined by the cytosolic pH. In one embodiment, mitochondrial forms are used according to the present invention. In another embodiment, cytoplasmic/nuclear forms are used according to the present invention. At least two splice variants encoding two distinct human mitochondrial NSF1 isoforms exist and sequences are publicly available on the GenBank database maintained by the U.S. National Center for Biotechnology information. For example, human NSF1 transcript variant 1 (NM_021100.4) encodes the long human NSF1 isoform 1 (NP_066923.3). Human NSF1 transcript variant 2 (NM_001198989.1) lacks an in-frame exon in the 5' coding region compared to variant 1, resulting in an isoform (NP_001185918.1) that is shorter compared to isoform 1. Nucleic acid and polypeptide sequences of NFS orthologs in species other than humans are also well known and include, for example, monkey NFS1 (XM_0010976989.2. XP_001097699.1. XM_001097983.2, and XP_001097983.1), dog NFS1 (XM_534405.4, XP_534405.2, XM_003433251.2, and XP_903433299.1), cow NFS1 (NM_001099001.1 and NP_901092471.1), mouse NFS1 (NM_010911.2 and NP_935041.2), and rat NFS1 (NM_53462.2 and NP_445914.2). Representative sequences of NFS1 orthologs are presented below in Table 1. Anti-NFS1 agents, including antibodies, nucleic acids, and the like are well-known in the art and include, for example, iron, L-alanine, L-cysteine, pyridoxal 5"-phosphate and derivatives. It is to be noted that the term can further be used to refer to any combination of features described herein regarding NFS1 molecules. For example, any combination of sequence composition, percentage identify, sequence length, domain structure, functional activity, etc. can be used to describe an NFS1 molecule of the present invention.

As used herein, "LYRM4" refers to the LYR motif containing 4 and is alternatively known as "homolog of yeast Isd11" and "mitochondrial matrix Nfs1 interacting protein." The LYRM4 gene encodes the ISD11 protein that forms a stable complex in vivo with the human cysteine desulfurase ISCS to generate the inorganic sulfur needed for iron-sulfur protein biogenesis (Shi et al. (2009) *Hum. Mol. Genet.* 18:3014-3025). At least three splice variants encoding three distinct human LYRM4 isoforms exist and sequences are publicly available on the GenBank database maintained by the U.S. National Center for Biotechnology Information. For example, human LYRM4 transcript variant 1 (NM_020408.5) encodes the short human LYRM4 isoform 1 (NP_065141.3). Human LYRM4 transcript variant 2 (NM_001164840.2) contains an alternate 3' terminal exon to create a different 3' coding region and 3' UTR compared to variant 1 and to thereby encode an isoform (NP_001158312.1) having a distinct C-terminus and a longer sequence than that of isoform 1. Human LYRM4 transcript variant 3 (NM_001164841.2) includes an additional exon that results in an alternate 3' coding region and 3' UTR compared to variant 1 to thereby encoded an isoform (NP_3101158313.1) having a distinct C-terminus and a longer sequence than that of isoform 1. Each of the isoforms is functional. Nucleic acid and polypeptide sequences of LYRM4 orthologs in species other than humans are also well known and include, for example, monkey LYRM4 (XM_001095995.2 and XP_001095995.2), dog LYRM4 (XM_005640157.1 and XP_005640214.1), cow LYRM4 (NM_001076306.1 and NP_001069774.1), mouse LYRM4 (NM_201358.2 and NP_958746.1), and chicken LYRM4 (NM_001198888.1 and NP_001185817.1). Representative sequences of LYRM4 orthologs are presented below in Table 1. Anti-LYRM4 agents, including antibodies, nucleic acids, and the like are well-known in the art and include, for example, dominant-negative binding proteins such as versions of NFS1 without a catalytic domain. It is to be noted that the term can further be used to refer to any combination of features described herein regarding LYRM4 molecules. For example, any combination of sequence composition, percentage identify, sequence length, domain structure, functional activity, etc. can be used to describe an LYRM4 molecule of the present invention.

As used herein, "ISCU" refers to the iron-sulfur cluster assembly enzyme and is alternatively known as "ISU2," "NIFU," and "NIFUN." The ISCU gene encodes two isomeric forms, ISCU1 and ISCU2, of the iron-sulfur cluster scaffold protein and the structures of the proteins in complex with other iron-sulfur cluster assembly proteins is known (see, for example, Majewska et al. (2013) *J. Biol. Chem.* 288:29134-29142). In one embodiment, ISCU1 is used according to the present invention. In another embodiment, ISCU2 is used according to the present invention. In still another embodiment, both ISCU1 and ISCU2 are used in combination according to the present invention. At least two splice variants encoding the two distinct human ISCU isoforms exist and sequences are publicly available on the GenBank database maintained by the U.S. National Center for Biotechnology Information. For example, human ISCU transcript variant 1 (NM_014301.3) contains an alternate segment in the 5' coding region and uses a downstream start codon compared to variant 2 such that the ISCU1 isoform (NP_955116.1) has a shorter and distinct N-terminus compared to the ISCU2 isoform. The ISCU1 isoform is found in the cytosol and nucleus. Human ISCU transcript variant 2 (NM_213595.2) encodes the longer ISCU2 isoform (NP_998760.1), which is found in mitochondria. Nucleic acid and polypeptide sequences of NFS orthologs in species other than humans are also well known and include, for example, monkey ISCU (NM_901261474.1 and NP_01248403.1), cow ISCU (NM_001075683.2 and NP_01069151.1), mouse ISCU (NM_025526.4 and NP_079802.1), rat ISCU (NM_001105936.1 and NP_001099406.1), and chicken ISCU (XM_903642182.2 and XP_003642230.2). Representative sequences of ISCU orthologs are presented below in Table 1. Anti-ISCU agents, including antibodies, nucleic acids, and the like are well-known in the art and include, for example, iron and derivatives thereof. It is to be noted that the term can further be used to refer to any combination of features described herein regarding ISCU molecules. For example, any combination of sequence composition, percentage identify, sequence length, domain structure, functional activity, etc. can be used to describe an ISCU molecule of the present invention.

As used herein, "FXN" refers to frataxin and is alternatively known as "CyaY" and "FARR." The FXN gene encodes the mitochondrial frataxin protein that functions in regulating mitochondrial iron transport and respiration (Stemmler et al. (2010) *J. Biol. Chem.* 285:26737-26743; Gentry et al. (2013) *Biochem.* 52:6085-6096; Abruzzo et al. (2013) BioMed Res. Intl. 2013, article ID 276808; and Pastore and Puccio (2013) *J. Neurochem.* 126:43-52). At least three splice variants encoding three distinct human FXN isoforms exist and sequences are publicly available on the GenBank database maintained by the U.S. National Center for Biotechnology Information. For example, human FXN transcript variant 1 (NM_00144.4) encodes the long human FXN isoform 1 (NP_000135.2). The mature peptide is represented by residues 56-210 and the proprotein is represented by residues 42-210. Human FXN transcript variant 2 (NM_181425.2) uses an alternate splice site in the 3' coding region compared to variant 1 resulting in a frameshift and encodes isoform 2 (NP_852090.1) that is shorter and has a distinct C-terminus compared to that of isoform 1. The mature peptide is represented by residues 56-196 and the proprotein is represented by residues 42-196. Human FXN transcript variant 3 (NM_001161706.1) uses an alternate exon in the 3' coding region compared to variant 1 that results in a frameshift and encodes isoform 3 (NP_001155178.1) that is shorter and has a distinct C-terminus compared to that of isoform 1. The mature peptide is represented by residues 56-171 and the proprotein is represented by residues 42-171. Each of the isoforms is functional. Nucleic acid and polypeptide sequences of FXN orthologs in species other than humans are also well known and include, for example, chimpanzee FXN (XM_001137864.2 and XP_001137864.2), monkey FXN (NM_001260741.1 and NP_001247670.1), dog FXN (NM_001109958.1 and NP_01103428.1), cow FXN (NM_001080727.1 and NP_001074196.1), mouse FXN (NM_008044.2 and NP_032070.1), rat FAN (NM_001191952.1 and NP_001178881.1), and chicken FXN (XM_424827.4 and XP_424827.3). Representative sequences of FXN orthologs are presented below in Table 1. Anti-FXN agents, including antibodies, nucleic acids, and the like are well-known in the art and include, for example, iron and heme. It is to be noted that the term can further be used to refer to any combination of features described herein regarding FXN molecules. For example, any combination of sequence composition, percentage identify, sequence length, domain structure, functional activity, etc. can be used to describe an FXN molecule of the present invention.

Other members of the iron-sulfur cluster biosynthetic pathway are well-known. For example, NFU1 encodes a protein that is localized to mitochondria and plays a critical role in iron-sulfur cluster biogenesis (Li et al. (2013) *Biochem.* 52:4904-4913). The encoded protein assembles and transfers 4Fe-4S clusters to target apoproteins including succinate dehydrogenase and lipoic acid synthase. Nucleic acid and polypeptide sequences of NFU1 orthologs in species including, humans are also well known and include, for example, human NFU1 (NM_015700.3, NP_056515.2, NM_001002755.2, NP_001002755.1 (mature peptide represented by residues 10-254), NM_001002756.2, and NP_001002756.1, all of which isoforms are functional), cow NFU1 (NM_001046566.2 and NP_001040031.1) mouse NFU1 (NM_001170591.1. NP_001164062.1, NM_020045.3, and NP_064429.2), rat NFU1 (NM_001106606.2 and NP_001100076.2), and chicken NFU1 (NM_001006305.2 and NP_001006305.2).

GLRX5 encodes a mitochondrial protein, whose crystal structure-function relationship is known, that is involved in the biogenesis of iron-sulfur clusters and is required for normal homeostasis (Ye et al, (2010) *J. Clin. Invest.* 120: 1749-1761 and Johansson et al. (2011) *Biochem J.* 433:303-311). Nucleic acid and polypeptide sequences of GLRX5 ortholoas in species including humans are also well known and include, for example, human GLRX5 (NM_016417.2 and NP_057501.2 (mature peptide represented by residues 32-157)), chimpanzee GLRX5 (XM_001154482.1 and XP_001154482.1), monkey GLRX5 (NM_001265635.2 and NP_001252564.1), cow GLRX5 (NM_001100303.1 and NP_901093773.1), mouse GLRX5 (NM_028419.2 and NP_082695.1), rat GLRX5 (NM_001108722.1 and NP_001102192.1), and chicken GLRX5 (NM_101008472.1 and NP_001008472.1).

BOLA3 encodes a protein, for which the structure-function relationship is known that plays an essential role in the production of iron-sulfur (Fe—S) clusters for the normal maturation of lipoate-containing 2-oxoacid dehydrogenases, and for the assembly of the mitochondrial respiratory chain complexes (Cameron et al. (2011) *Am. J. Hum. Genet.* 89:486-495; Zhou et al. (2008) *Mol. Cell. Biochem.* 317: 61-68; and Kasai et al. (2004) *Protein Sci.* 13:545-548). Two alternatively spliced transcript variants encoding different isoforms with distinct subcellular localization are known. Isoform 1 (NM_212552.2 and NP_997717.2) are mitochondrial, whereas isoform 2 (NM_001035505.1 and NP_001030582.1) are cytoplasmic. Nucleic acid and polypeptide sequences of BOLA3 ortholoas in species other than humans are also well known and include, for example, chimpanzee BOLA3 (XM_001153666.2, XP_001153666.1, XM_515554.2, and XP_515554.1), monkey BOLA3 (NM_0012.65651.1 and NP_001252580.1), cow BOLA3 (NM_001035452.2 and NP_001030529.1), mouse BOLA3 (NM_175277.4 and NP_780486.1), and rat BOLA3 (NM_001106601.1 and NP_001100071.1).

HSCB, also known as the HscB iron-sulfur cluster co-chaperone homolog, encodes a protein, for which the structure-function relationship is known, that is an integral component of the human iron-sulfur cluster biosynthetic machinery (Uhrigshardt et al. (2010) *Hum. Mol. Genet.* 19:3816-3834 and Bitto et al. (2008) *J. Biol. Chem.* 283: 30184-30192). Nucleic acid and polypeptide sequences of HSCB orthologs in species including humans are also well known and include, for example, human HSCB (NM_172002.3 and NP_741999.3 (mature peptide represented by residues 30-235)), chimpanzee HSCB (XM_515052.3, XP_515052.2, XM_003953858.1, and XP_003953907.1), monkey HSCB (NM_001194228.1 and NP_001181157.1), dog HSCB (XM_534725.4 and XP_534725.2), cow HSCB (NM_001102340.1 and NP_001095810.1), mouse HSCB (NM_153571.2 and NP_705799.2), rat HSCB (NM_001108340.1 and NP_001101810.1), and chicken BSCB (XM_0036422.07.2 and XP_003642255.1).

HSPA9, also known as mortalin, encodes a member of the heat shock protein 70 gene family. The encoded protein, for which the structure-function relationship is known, is primarily localized to the mitochondria but is also found in the endoplasmic reticulum, plasma membrane and cytoplasmic vesicles (Luo (2010) *Protein. Expr. Purif.* 72:75-81 and Craig and Marszalek (2002) *Cell Mol. Life Sci.* 59:1658-1665). Nucleic acid and polypeptide sequences of HSPA9 orthologs in species including humans are also well known and include, for example, human HSPA9 (NM_004134.6 and NP_004125.3 (mature peptide represented by residues 47-679)), chimpanzee HSPA9 (XM_001171426.3 and XP_001171426.2), dog HSPA9 (XM_531923.4 and XP_531923.2), cow HSPA9 (NM_001034524.2 and NP_001029696.1), mouse HSPA9 (NM_010481.2 and NP_034611.2), rat HSPA9 (NM_001100658.2 and NP_001094128.2), and chicken HSPA9 (NM_01006147.1 and NP_001006147.1).

ISCA1, also known as iron-sulfur cluster assembly 1, encodes a mitochondrial protein involved in the biogenesis and assembly of iron-sulfur clusters, which play a role in electron-transfer reactions. The encoded protein, for which the structure-function relationship is known, is primarily localized to the mitochondria but is also found in the endoplasmic reticulum, plasma membrane and cytoplasmic vesicles (Cozar-Castellano et al. (2004) *Biochim. Biophys. Acta.* 1700:179-188; Lu et al. (2010) *Biochem. J.* 428:125-131; and Song et al. (2009) *J. Biol. Chem.* 284:35297-35307). Nucleic acid and polypeptide sequences of ISCA1 orthologs in species including humans are also well known and include, for example, human ISCA1 (NM_030940.3 and NP_112202.2 (mature peptide represented by residues 13-129)), chimpanzee ISCA1 (NM_001242612.1 and NP_001229541.1), dog ISCA1 (XM_844342.3 and XP_849435.2), cow ISCA1 (NM_001034470.2 and NP_001029642.1), mouse ISCA1 (NM_926921.4 and NP_081197.1), rat ISCA1 (NM_181626.3 and NP_853657.1), and chicken ISCA1 (NM_001271936.1 and NP_001258865.1).

ISCA2, also known as iron-sulfur cluster assembly 2, encodes an A-type iron-sulfur cluster mitochondrial protein involved in the maturation of mitochondrial iron-sulfur proteins (Sheftel et al. (2012) *Mol. Biol. Cell.* 23:1157-1166 and Hendrickson et al. (2010) *PLoS* 5:e12862). Two alternatively spliced human transcript variants encoding different isoforms are known. Isoform 1 (NM_194279.3 and NP_919255.2 (mature peptide represented by residues 9-154)) represents the longer isoform and isoform 2 (NM_001272007.1 and NP_001258936.1 (mature peptide represented by residues 9-60)) is encoded by a nucleic acid that lacks an alternate coding exon compared to transcript variant 1 resulting in a frameshift and a shorter isoform having a distinct C-terminus relative to isoform 1. Each isoform is functional. Nucleic acid and polypeptide sequences of ISCA2 orthologs in species other than humans are also well known and include, for example, chimpanzee ISCA2 (XM_143075.3 and XP_001143075.2), monkey ISCA2 (NM_001261007.1 and NP_0012547936.1), dog ISCA2 (XM_547905.4 and XP_547905.3), cow ISCA2 (NM_001038683.2 and NP_001033772.1), mouse ISCA2 (NM_028863.1 and NP_083139.1), and rat ISCA2 (NM_001109278.2 and NP_001102748.1).

IBA57, also known as MMDS3, encodes a protein involved in iron-sulfur protein biosynthesis and normal home biosynthesis (Bolar et al. (2013) *Hum. Mol. Genet* 22:2590-2602; Sheftel et al. (2012) *Mol. Biol. Cell.* 23:1157-1166; and Nilsson et al. (2009) *Cell Metabol.* 10:119-130).

Nucleic acid and polypeptide sequences of ISCA1 orthologs in species including humans are also well known and include, for example, human ISCA1 (NM_001010867.2 and NP_001010867.1; the mature peptide is represented by residues 40-356 since residues 1-39 represent a transit peptide), chimpanzee IBA57 (XM_514253.3 and XP_514253.2), monkey IBA57 (XM_00108340.2 and XP_001083460.1), cow IBA57 (NM_001205580.1 and NP_001192509.1), mouse IBA57 (NM_73785.6. NP_776146.1, NM_901270791.1, and NP_001257720.1), rat IBA57 (NM_001008827.1 and NP_001102297.1), and chicken IBA57 (NM_001030958.2 and NP_001026129.2).

NUBPL, also known as IND1 and HULND1, encodes a member of the Mrp/NBP35 ATP-binding proteins family. The encoded protein is required for the assembly of the respiratory chain NADH dehydrogenase (complex I), an oligomeric enzymatic complex located in the inner mitochondrial membrane. The respiratory complex I consists of 45 subunits and 8 iron-sulfur (Fe/S) clusters. This protein is an Fe/S protein that plays a critical role in the assembly of respiratory complex I, likely by transferring Fe/S into the Fe/S-containing complex I subunits (Sheftel et al. (2009) *Mol. Biol. Cell.* 29:6059-6073; Calvo et al. (2010) *Nat. Genet.* 42:851-858; and Kevelam at al. (2013) *Neural.* 80:1577-1583). Three alternatively spliced human transcript variants encoding different isoforms are known. Isoform 1 (NM_025152.2 and NP_079428.2 (mature peptide represented by residues 39-319)) represents the longest isoform, whereas isoform 2 (NM_001201573.1 and NP_001188502.1) is encoded by a nucleic acid that lacks two exons from the 5' end and has an alternate 5' exon resulting in an isoform having a shorter N-terminus as compared to isoform 1 and isoform 3 (NM_001201574.1 and NP_001188503.1) is encoded by a nucleic acid that lacks several exons from the 5' end and has an alternate 5' exon resulting in an isoform having a much shorter N-terminus as compared to isoform 1. Nucleic acid and polypeptide sequences of NUBPL orthologs in species other than humans are also well known and include, for example, monkey NUBPL (XM_001108145.2 and XP_001108145.2), cow NUBPL (NM_001193042.1 and NP_001179971.1), mouse NUBPL (NM_029760.2 and NP_084036.2) and rat NUBPL (NM_001185025.1 and NP_001171954.1).

SLC25A28, also known as solute carrier family 25 (mitochondrial iron transporter) member 28 and mitoferrin2 and MRS3/4, encodes a mitochondrial iron transporter that mediates iron uptake and is required for heme synthesis of hemoproteins and Fe—S cluster assembly in non-erythroid cells. The iron delivered into the mitochondria, presumably as Fe(2+), is then delivered to ferrochelatase to catalyze Fe(2+) incorporation into protoprophyrin IX to make heme (Li et al. (2001) *FEBS Lett.* 494-79-84; Palmieri (2013) *Mol. Aspects Med.* 34:465-484; and Hung et al. (2013) *J. Biol. Chem.* 288:677-686). Nucleic acid and polypeptide sequences of SLC25A28 orthologs in species including humans are also well known and include, for example, human SLC25A28 (NM_031212.3 and NP_12489.3), monkey SLC25A28 (NM_001265757.1 and NP_001252686.1), dog SLC25A28 (XM_846248.3 and XP_851341.2), cow SLC25A28 (NM_001205552.1 and NP_001192481.1), mouse SLC25A28 (NM_145156.1 and NP_650138.1), rat SLC25A28 (NM_001109515.1 and NP_001102985.1), and chicken SLC25A28 (XM_421702.3 and XM_421702.3).

FDXR, also known as ferrodoxin reductase, encodes a mitochondrial flavoprotein that initiates electron transport for cytochromes P450 receiving electrons from NADPH (Shi et al. (2012) *Biochem. Biophys. Acta* 1823:484-492; Lin et al. (1990) *Proc. Natl. Acad. Sci. USA.* 87:8516-8520; and Liu and Chen (2002) *Oncogene* 21:7195-7204). Seven alternatively spliced human transcript variants encoding seven different isoforms are known (NM_024417.3, NP_077728.2 (mature peptide represented by residues 33-491), NM_004110.4, NP_004101.2 (mature peptide represented by residues 30-493), NM_001258012.2, NP_001244941.1 (mature peptide represented by residues 33-534), NM_001258013.2, NP_001244942.1. NM_001258014.2, NP_001244943.1 (mature peptide represented by residues 33-483), NM_001258015.2, NP_001244944.1 (mature peptide represented by residues 33-451), NM_001258016.2, and NP_001244945.1), each of which is functional. Nucleic acid and polypeptide sequences of FDXR orthologs in species other than humans are also well known and include, for example, chimpanzee FDXR (XM_511666.4 and XP_511666.3), monkey FDXR (XM_11091261.2 and XP_001091261.2), cow FDXR (NM_174691.1 and NP_777116.1), mouse FDXR (NM_07997.1 and NP_032023.1), and rat FDXR (NM_024153.1 and NP_077067.1).

FDX2, also known as ferrodoxin 1 like, encodes a mitochondrial-ferrodoxin required for iron-sulfur protein biogenesis and cellular iron homeostasis as FDX2 deficiency leads to increased cellular iron uptake, iron accumulation in mitochondria, and impaired Fe/S protein biogenesis (Sheftel et al. (2010) *Proc. Natl. Acad. Sci. U.S.A.* 107:11775-11780 and Qi et al. (2013) *Dalton Trans.* 42:3088-3091). Nucleic acid and polypeptide sequences of FDX2 orthologs in species including humans are well known and include, for example, human FDX2 (NM_001031734.2 and NP_001026904.1 (mature peptide represented by residues 53-183)), chimpanzee FDX2 (XM_512366.4 and XP_512366.3), monkey FDX2 (XM_001105309.2 and XP_001105309.2), dog FDX2 XM_542073.4 and XP_542073.1), cow FDX2 (NM_001080226.2 and NP_001073695.1), mouse FDX2 (NM_001039824.2 and NP_001034913.1), and rat FDX2 (NM_001108002.1 and NP_001101472.1).

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g., a probe or small molecule, for specifically detecting and/or affecting the expression of a marker of the invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The term "NFS1 pharmacodynamic biomarkers" refers to biomarkers and related assays whose modulation is correlated with that of NFS1 such that they can be used as surrogates, combinations, or other readouts associated with NFS1 modulation. Representative examples include, without limitation 1) decreased conversion of cysteine to alanine or methylene blue; 2) Induction and/or promotion of mitochondrial dysfunction, such as a) a decrease in aconitase copy number, amount, and/or activity and/or b) a decrease in succinate dehydrogenase copy number, amount, and/or activity; 3) induction and/or promotion of iron regulatory protein dysfunction, such as a) a decrease in ferritin copy number, amount and/or activity and/or b) an increase in transferrin-receptor copy number, amount, and/or activity and/or c) a decrease in Hif2alpha copy number, amount, and/or activity; and 4) induction and/or promotion of ferroptosis, such as a) an increase and/or accumulation of lipid reactive oxygen species (ROS) and/or b) an increase in PTGS2 (COX2) copy number, amount, and/or activity.

Molecules and reagents useful as NFS1 pharmacodynamic biomarkers are well known in the art.

For example, "aconitases" are iron-sulfur proteins that function to catalyze the conversion of citrate to isocitrate. When cellular iron levels are low, the protein binds to iron-responsive elements (IREs), which are stem-loop structures found in the 5' UTR of ferritin mRNA, and in the 3' UTR of transferrin receptor mRNA. When the protein binds to IRE, it results in repression of translation of ferritin mRNA, and inhibition of degradation of the otherwise rapidly degraded transferrin receptor mRNA. There are two forms of aconitases in mammalian cells, including a cytoplasmic aconitase encoded by Aco1 and a mitochondrial aconitase encoded by Aco2, certain embodiments, the term "aconitase" encompasses the combination of nucleic acids and/or proteins of Aco1 and Aco2. In other embodiments, the term "aconitase" encompasses the nucleic acids and/or proteins of Aco1 alone or of Aco2 alone.

Aco1 encodes a bifunctional, cytosolic protein that functions as an essential enzyme in the TCA cycle and interacts with mRNA to control the levels of iron inside cells. When cellular iron levels are blab, this protein binds to a 4Fe-4S cluster and functions as an aconitase Philpott et ed. (1994) *Proc. Natl. Acad. Sci. U.S.A.* 91:7321-7325, Brazzolotto et al. (1999) *J. Biol. Chem.* 274:21625-21630; Kaptain et al. (1991) *Proc. Natl. Acad. Sci. U.S.A.* 88:10109-10113; and Li et al. (2006) *J. Biol. Chem.* 281:12344-12351). Two alternatively spliced human transcript variants encoding the same isoforms are known. Transcript variant 1 (NM_001278352.1) represents the longer transcript and transcript variant 2 (NM_002197.2) differs from transcript variant 1 by having a different 5' UTR despite the fact that both transcript variants encode the same protein (NP_002188.1 and NP_001265281.1). Nucleic acid and polypeptide sequences of Aco1 orthologs in species other than humans are also well known and include, for example, chimpanzee Aco1 (XM_001156102.3 and XP_001156102.1), monkey Aco1 (NM_001257865.1 and NP_001244794.1), dog Aco1 (XM_538698.4 and XP_538698.2), cow Aco1 (NM_001075591.1 and NP_001069059.1), mouse Aco1 (NM_007386.2 and NP_031412.2), rat Aco1 (NM_017321.1 and NP_059017.1), and chicken Aco1 (NM_001030536.1 and NP_001025707.1).

Aco2 encodes a bifunctional, mitochondrial protein that catalyzes the interconversion of citrate to isocitrate via cis-aconitate in the second step of the TCA cycle. This protein is encoded in the nucleus and functions in the mitochondrion (Mirel et al. (1998) *Gene* 213:205-218: Klausner and Rouault (1993) *Mol. Biol. Cell* 4:1-5; and (Gruer et al. (1997) *Trend. Biochem. Sci.* 22:3-6). Nucleic acid and polypeptide sequences of Aco2 orthologs in species including humans are well known and include, for example, human Aco2 (NM_001098.2 and NP_001089.1 (mature peptide represented by residues 28-780)), monkey Aco2 (NM_001261164.2 and NP_001248093.1), dog Aco2 (XM_844073.3 and XP_849166.1), cow Aco2 (NM_173977.3 and NP_776402.1), mouse Aco2 (NM_080633.2 and NP_542364.1), rat Aco2 (NM_024398.2 and NP_077374.2), chicken Aco2 (NM_204188.2 and NP_989519.1), and zebrafish Aco2 (NM_198908.1 and NP_944590.1).

"Succinate dehydrogenase" also known as SDH, succinate-coenzyme Q reductase (SQR), and respiratory Complex II, is a well-known enzyme complex that exists in bound form on the inner mitochondrial membrane of mammalian mitochondria (Yankovskaya et al. (2003) *Science* 299:700-704; Cheng et al. (2008) *Biochemistry* 47: 6107). In the citric acid cycle, SDH catalyzes the oxidation of succinate to fumarate with the reduction of ubiquinone to ubiquinol. Mammalian and mitochondrial SDH are composed of four subunits: two hydrophilic and two hydrophobic. The first two subunits, a flavoprotein (SdhA) and an iron-sulfur protein (SdhB), are hydrophilic. SdhA contains a covalently attached flavin adenine dinucleotide (FAD) cofactor and the succinate binding site and SdhB contains three iron-stain dusters: [2Fe-2S]. [4Fe-4S], and [3Fe-4S]. The second two subunits are hydrophobic membrane anchor subunits, SdhC and SdhD. Human mitochondria contain two distinct isoforms of SdhA (Fp subunits type I and type II). The subunits form a membrane-bound cytochrome b complex with six transmembrane helices containing one home b group and a ubiquinone-binding site. Two phospholipid molecules, one cardiolipin and one phosphatidylethanolamine, are also found in the SdhC and SdhD subunits and serve to occupy the hydrophobic space below the twine. There are two distinct classes of inhibitors of complex II: those that bind in the succinate pocket and those that bind in the ubiquinone pocket. UBQ inhibitors include carboxin and the noyltrifluoroacetone. Succinate-analogue inhibitors include the synthetic compound malonate as well as the TCA cycle intermediates, malate and oxaloacetate. Indeed, oxaloacetate is one of the most potent inhibitors of Complex II. In addition, assays for analyzing SDH activity are well known in the art and include, for example, spectrophotometric analysis of enzyme reactions, analysis of reduction of artificial electron acceptors such as 2,6 dichlorophenolindophenol (DCIP) (see, for example, Jones et al. (2013) *Anal. Biochem.* 442: 19-23).

"Ferritin" refers to a well-known intracellular protein that stores and releases iron and exists as a globular protein complex consisting of 12 or 24 protein subunits wherein the submits associate to form a spherical nanocage. Ferritin that is not combined with iron is referred to "apoferritin." A "ferritin protein subunit" is defined as one of the 12 or 24 polypeptide subunits that make up a ferritin protein. The numbering system used herein for the identification of amino acids within ferritin subunits is based on the original sequence of horse spleen L ferritin (Swiss Protein Database Accession Number P02791). The horse spleen numbering system can be easily converted to a numbering system based on the human H sequence (Swiss Protein Database accession number P02794; the human L sequence accession number is P02792), which has four additional amino acids at the N-terminus. The human H sequence numbering therefore adds 4 to the corresponding amino acid number in horse spleen ferritin. For example, L134 by horse spleen numbering corresponds to L138 by human H sequence numbering. Alignments of ferritin subunit sequences can be found, e.g., in Theil, E. C., in Handbook of Metalloproteins, (Messersehmidt, A. et al., eds.), John Wiley & Sons. Chichester, UK, pp. 771-81, 2001; Waldo, G. S. and Theil, E. C., in Comprehensive Supramolecular Chemistry, Vol. 5, (K. S. Suslick, ed.), Pergamon Press, Oxford, UK, pp. 65-89, 1996; Orino Koichi et al., Veterinary Biochem. 42:7-11 (2005); Accession number: 06A006486; and U.S. Pat. Pubis. 2013-0267041 and 2011-0287033. In vertebrates, the subunits are both the light (L) and the heavy (H) type with an apparent molecular weight of 19 kDa or 21 kDa respectively. Some ferritin complexes in vertebrates are hetero-oligomers of two highly related gene products with slightly different physiological properties. The ratio of the two homologous proteins in the complex depends on the relative expression levels of the two genes. Assays for analyzing ferritin present, amount, and activity are well known in the art as described above.

"Transferrin receptors" are carrier proteins for transferrin. When cellular iron levels are low, cells increase the level of transferrin receptor produced in order to increase iron intake and this process is regulated by iron via iron response/regulatory element binding protein (IRE-BP or IRP) that binds to the hairpin structure of the iron response element located in the 3' UTR of the transferrin receptor-encoding gene. When the protein binds to IRE, it results in repression of translation of ferritin mRNA, and inhibition of degradation of the otherwise rapidly degraded transferrin receptor mRNA. There are two forms of transferrin receptor in mammalian cells, TER1 and TER2. In certain embodiments, the term "transferrin receptor" encompasses the combination of nucleic acids and/or proteins of TFR1 and TER2. In other embodiments, the term "transferrin receptor" encompasses the nucleic acids and/or proteins of TFR1 alone or of TFR2 alone.

"TFR1," also known as CD71, encodes a type-II receptor that resides on the outer cell membrane and cycles into acidic endosomes into the cell in a clathrin/dynamin-dependent manner (Worthen and Enns (2014) *Front. Pharmacol.* 5:34; Frazer and Anderson (2014) *Biofactors* 40:206-214; Daniels et al. (2012) *Biochem. Biophys. Acta* 1820:291-317). Two alternatively spliced human transcript variants encoding the same isoforms are known. Transcript variant 1 (NM_003234.2) represents the longer transcript and transcript variant 2 (NM_001128148.1) differs from transcript variant 1 by having a different 5' UTR despite the fact that bath transcript variants encode the same protein (NP_003225.2 and NP_001121620.1; mature peptide represented by residues 101-760)). Nucleic acid and polypeptide sequences of TFR1 orthologs in species other than humans are also well known and include, for example, monkey TFR1 (NM_001257303.1 and NP_001.244232.1), dog TFR1 (NM_001003111.1 and NP_001003111.1), cow TFR1 (NM_001206577.1 and NP_001193506.1), mouse TFR1 (NM_011638.4 and NP_035768.1), and chicken TFR1 (NM_205256.1 and NP_990587.1).

"TFR2" encodes a transferrin receptor that is highly homologous to TFR1 that mediates cellular uptake of transferrin-bound iron but whose expression is largely restricted to hepatocytes (Daniels et al. (2006) *Clin. Immunol.* 121: 144-158 and Zhao et al. (2013) *Biochem.* 52:3310-3319). Two alternatively spliced human transcript variants encoding different isoforms are known. Isoform 1 (NM_003227.3 and NP_003218.2) represents the longer isoform and isofarfil 2 (NM_001206855.1 and NP_001193784.1) is encoded by a nucleic acid that differs at the 5' end compared to variant 1 and initiates translation from an in-frame downstream AUG resulting in an isoform with a shorter N-terminus and lacking the transmembrane domain relative to isoform 1. Each isoform is functional, Nucleic acid and polypeptide sequences of TFR2 orthologs in species other than humans are also well known and include, for example, chimpanzee TFR2 (XM_003318650.1 and XP_003318698.1), monkey TFR2 (XM_001113151.2 and XP_001113151.1), cow TFR2 (NM_001177741.1 and NP_001171212.1), mouse TFR2 (NM_001289507.1, NP_001276436.1, NM_001289509.1, NM_001289511.1, NM_015799.4, and NP_56614.3), rat TFR2 (NM_001105916.1 and NP_001099386.1), and zebrafish TFR2 (NM_001009916.1 and NP_001009916.1).

"Hif2a," also known as endothelial PAS domain protein 1, encodes a transcription factor involved in the induction of genes regulated by oxygen, which is induced as oxygen levels fall (Mastrogiannaki et al. (2013) *Blood* 122:885-892 and Haase (2010) *Am. J. Physiol. Renal. Physiol.* 299:F1-F13). The encoded protein contains a basic-helix-loop-helix domain protein dimerization domain as well as a domain found in proteins in signal transduction pathways which respond to oxygen levels. Nucleic acid and polypeptide sequences of Hif2a orthologs in species including humans are well known and include, for example, human Hif2a (NM_001430.4 and NP_001421.2), chimpanzee Hif2a (XM_001147219.3 and XP_001147219.1), monkey Hif2a (XM_001112947.2 and XP_001112947.2), dog Hif2a (XM_005626080.1 and XP_005626137.1), cow Hif2a (NM_174725.2 and NP_777150.1), mouse Hif2a (NM_010137.3 and NP_034267.3), rat Hif2a (NM_023090.1 and NP_075578.1), and chicken Hif2a (NM_204807.1 and NP_990138.1).

"PTGS2" refers to a specific isozyme of the prostaglandin-endoperoxide synthase (PTGS), also known as cyclooxygenase-2, which is the key enzyme in prostaglandin biosynthesis and acts as both a dioxygenase and as a peroxidase. There are two isozymes of PTGS: a constitutive PTGS1 and an inducible PTGS2, which differ in their regulation of expression and tissue distribution. PTGS2 encodes the inducible isozymes and is regulated by specific stimulatory events, indicating that it is responsible for the prostanoid biosynthesis involved in inflammation and mitogenesis (Percy et al. (1998) *Analyst* 123:41-50). Nucleic acid and polypeptide sequences of PTGS2 orthologs in species including humans are well known and include, for example, human PTGS2 (NM_000963.3 and NP_000954.1 (signal peptide sequence represents residues 1-23), chimpanzee PTGS2 (XM_524999.4 and XP_524999.3), monkey PTGS2 (XM_001107538.2 and XP_001107538.2), dog PTGS2 (NM_001003354.1 and NP_001003354.1), cow PTGS2 (NM_174445.2 and NP_776870.1), mouse PTGS2 (NM_011198.3 and NP_035328.2), and rat PTGS2 (NM_017232.3 and NP_058928.3).

"Lipid reactive oxygen species (ROS)" refer to lipids that can participate in reactions that give rise to free radicals to thereby cause oxidative damage. Lipids are prone to oxidative damage since ROS species can act on unsaturated lipids to yield reactive unsaturated aldehydes. These unsaturated aldehydes can react with other cellular components, such as membrane-bound or associated proteins and nucleic acids, thereby crosslinking them to the lipid. Oxidized lipids may be identified by presence of lipid peroxides. Exemplary ROS include hydroxyl radicals (OH.), superoxide radical (O2.-), nitric oxide (NO.), thyl (RS.), peroxyl (RO2.), and lipid peroxyl (LOO). Lipids can form lipid ROS when present in conditions of oxidative challenge or stress, wherein lipids are vulnerable to oxidative damage. An oxidative challenge can involve the introduction of free radicals, ROS, or reactive nitrogen species, such as to RBC or lysed RBC, for example in an assay of antioxidant activity. The oxidative challenge may be created by adding a free radical generator, such as hydrogen peroxide or AAPH. Assays for detection of lipid ROS are well known in the art (see, for example, U.S. Pat. Publs. 2014-0017341 and 2013-0260418 and Dixon et al. (2012) *Cell* 149:1060-1072).

The "normal" level of expression of a biomarker is the level of expression of the biomarker in cells of a subject, a human patient, not afflicted with a cancer. An "overexpression" or "significantly higher level of expression" of a biomarker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7.7.5, 8, 8.5.9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample front a healthy subject not having the biomarker associated disease) and preferably, the average expression level of the biomarker in several control samples. Such "significance" levels can also be applied to any other measured parameter described herein, such as for expression, inhibition, cytotoxicity, cell growth, and the like.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to anti-cancer therapy, such as iron-sulfur cluster biosynthesis pathway inhibitor treatment (e.g., NFS1 inhibitors). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker target, or increased or decreased activity. e.g., in more than about 5%. 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular anti-cancer therapy (e.g., iron-sulfur cluster biosynthesis pathway inhibitory therapy) or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA. DNA, proteins, antibodies, and organic molecules.

The term "prognosis" includes a prediction of the probable course and outcome of cancer Or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to anti-cancer therapy (e.g., iron-sulfur cluster biosynthesis pathway inhibitory therapy)" relates to any response of the hyperproliferative disorder (e.g., cancer) to an anti-cancer therapy (e.g., iron-sulfur cluster biosynthesis pathway inhibitory therapy), such as anti-NFS1 inhibitor therapy), preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for t least 2, 4, 6, 8, 10, 12, 14, 16, 18, 20, 25, 10, 35, 40, 45, 50, 55, or 60 months. Biomarker measurement threshold values that correlate to outcome of a cancer therapy can be determined using well-known methods in the art, such as those described in the Examples section.

The tarn "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold. 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (See Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs, shRNAs, or other RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., iron-sulfur cluster biosynthesis pathway inhibitor, chemotherapeutic, and/or radiation therapy). In some embodiments, normal cells are not affected to an extent that causes the normal cells to be unduly injured by the anti-cancer therapy (e.g., iron-sulfur cluster biosynthesis pathway inhibitory therapy). An increased sensitivity or a reduced sensitivity to a therapeutic treatment is measured according to a known method in the art for the particular treatment and methods described herein below, including, but not limited to, cell proliferative assays (Tanigawa N. Kern D H, Kikasa Y, Morton D L, Cancer Res 1982; 42: 2159-2164), cell death assays (Weisenthal L M. Shoemaker R H, Marsden J A, Dill P L, Baker J A, Moran E M, Cancer Res 1984; 94; 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma, Langhorne, P A: Harwood Academic Publishers, 1993: 415-432; Weisenthal L M, Contrib Gynecol Obstet 1994 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more iron-sulfur cluster biosynthesis pathway inhibitor agents can be greater than the sum of the separate effects of the anticancer agents alone.

"Short interfering RNA" (siRNA), also referred to herein as "small interfering RNA" is defined as an agent which functions to inhibit expression of a target biomarker nucleic, acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e. the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see. e.g., Stewart, et al. (2003) *RNA April;* 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis), in addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 50%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |

| GENETIC CODE | |
|---|---|
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention and related biomarkers listed in Table 1) are well known in the art and readily available on publicly available databases, such as the National Center for Biotechnology Information (NCBI). For example, exemplary nucleic acid and amino acid sequences derived from publicly available sequence databases are provided below.

Representative sequences of the biomarkers described above are presented below in Table 1. It is to be noted that the terms described above can further be used to refer to any combination of features described herein regarding the biomarkers. For example, any combination of sequence composition, percentage identify, sequence length, domain structure, functional activity, etc, can be used to describe a biomarker of the present invention.

TABLE 1

---
a) ISC Biosynthesis Pathway Biomarkers
---

SEQ ID NO: 1 Human NFS1 cDNA sequene (transcript variant 1)
```
   1    atgctgctcc gagccgcttg gaggcgggcg gcagtggcgg tgacagcggc tccagggccg
  61    aagcccgcgg cgcccactcg ggggctgcgc ctgcgcgttg gagaccgtgc tcctcagtct
 121    gcggttcccg cagatacagc cgctgccccg gaggtggggc cagtgctgcg acctctctat
 181    atggatgtgc aagctacaac tcctctggac ccccgggtgc ttgatgccat gctcccttac
 241    ctaatcaact actatgggaa cccacactcc cggacacatg cttatggctg ggagagtgag
 301    gcagccatgg aacgtgctcg tcagcaagta gcatstctga ttggagctga tcctcgtgag
 361    atcatttta ctagtggtgc tactgaatcc aacaacatag caattaaggg ggtggcccga
 421    ttctacaggt cacggaaaaa gcacttgatc accacccaga cagaacacaa atgtgtcttg
 481    gactcctgcc gttcactgga agctgagggc tttcaggtca cctacctccc agtgcagaag
 541    agtgggatca ttgacctaaa ggaactagag gctgctatcc agccagatac tagcctggtg
 601    tcagtcatga ctgtgaacaa tgagattgga gtgaagcagc ctattcaga aatagggcgg
 661    atttgcagtt ccagaaaggt atatttccat actgatgcag cccaggctgt tggaaaaatc
 721    ccacttgatg tcaatgacat gaaaattgat ctcatgagca ttagtggtca caaaatctac
 781    ggtcccaaag gggttggtgc catctcatc cgtcgccggc cccgtgtgcg tgtggaggcc
 841    ctgcagagtg gaggggggca ggagcggggt atgcggtctg gacagtgcc cacacccta
 901    gtggtggggc tgggggctgc gtgtgaggtg gcacagcaag agatggagta tgaccacaag
 961    cgaatctcaa agttgtcaga gcggctgata cagaatataa tgaagagcct tccagatgtg
1021    gtgatgaatg gggaccctaa gcaccattat cccggctgta tcaacctctc ctttgcatat
1081    gtggaagggg aaagtctgct gatggcactg aaggacgttg ccttatcctc agggagtgcc
1141    tgcacctctg catccctgga gccctctat gtgcttagag caattggcac tgatgaggat
1201    ttagcgcact cttctatcag gtttggaatt ggccgcttca ctacagagga ggaagtggac
1261    tacacagtgg agaaatgcat tcagcatgtg aagcgtcttc gagaaatgag ccctctctgg
1321    gagatggttc aggatggcat tgacctcaag agcatcaagt ggacccaaca ctag
```

SEQ ID NO: 2 Human NFS1 amino acid sequence (isoform 1)
```
   1    mllraawrra avavtaapgp kpaaptrglr lrvgdrapqs avpadtaaap evgpvlyply
  61    mdvqattpld prvldamlpy linyygnphs rthaygwese amerarqqv asligadpre
 121    iiftsgates nniaikgvar fyrsrkkhli ttqtehkcvl dscrsleaeg fqvtylpvqk
 181    sgiidlkele aaiqpdtslv svmtvnneig vkqpiaeigr icssvkvyfh tdaaqavgki
 241    pldvndmkid lmsisghkiy gpkgvgaiyi rrrprvrvea lqsgggqerg mrsgtvptpl
 301    vvglgaacev aqqemeydhk risklserli qnimkslpdv vmngdphkky pgcinlsfay
 361    vegesllmal kdvalssgsa ctsaslepsy vlraigtded lahssirgfi grftteeevd
 421    ytvekciqhv krlremsplw emvqdgidlk sikwtqh
```

SEQ ID NO: 3 Human FFS1 sequence (transcript variant 2)
```
   1    atgctgctcc gagccgcttg gaggcgggcg gcagtggcgg tgacagcggc tccagggccg
  61    aagcccgcgg cgcccactcg ggggctgcgc ctgcgcgttg gagaccgtgc tcctcagtct
 121    gcggttcccg cagatacagc cgctgccccg gaggtggggc cagtgctgcg acctctctat
 181    atggatgtgc aagctacaac tcctctggac ccccgggtgc ttgatgccat gctcccttac
 241    ctaatcaact actatgggaa cccacactcc cggacacatg cttatggctg ggagagtgag
 301    gcagccatgg aacgtgctcg tcagcaagta gcatctctga ttggagctga tcctcgtgag
 361    atcatttta ctagtggtgc tactgaatcc aacaacatag caattaagga actagaggct
 421    gctatccagc cagatactag cctggtgtca gtcatgactg tgaacaatga gattggagtg
 481    aagcagccta ttgcagaaat agggcggatt tgcagttcca gaaaggtata tttccatact
 541    gatgcagccc aggctgttgg aaaaatccca cttgatgtca atgacatgaa aactgatctc
 601    atgagcatta gtggtcacaa aatctacggt cccaaggggt tggtgccat ctacatccgt
 661    cgccggcccc gtgtgcgtgt ggaggccctg cagagtggag ggggcagga gcggggtatg
 721    cggtctggga cagtgcccac acccttagtg gtgggctgg ggctgcgtg tgaggtggca
 781    cagcaagaga tggagtatga ccacaagcga atctcaaagt tgtcagagcg gctgatacag
 841    aatataatga gagccttcc agatgtggtg atgaatgggg accctaagca ccattatccc
 901    ggctgtatca acctctcctt tgcatatgtg gaggggaaa gtctgctgat ggcactggag
 961    gacgttgcct tatcctcagg gagtgcctgc acctctgcat ccctggagcc ctctatgtg
1021    cttagagcaa ttggcactga tgaggatcta gcgcactctt ctatcaggtt tggaattggc
1081    cgcttcacta cagaggagga agtggactac acagtggaga atgcattca gcatgtgaag
1141    cgtcttcgag aaatgagccc tctctgggag atggttcagg atggcattga cctcaagagc
1201    atcaagtgga cccaacacta g
```

SEQ ID NO: 4 Human NFS1 amino acid sequence (isoform 2)
```
   1    mllraawrra avavtaapgp kpaaptrglr lrvgdrapqs avpadtaaap evgpvlrply
  61    mdvqattpld prvldamlpy linyygnphs rthaygwese aamerarqqv asligadpre
 121    iiftsgates nniaikelea aiqpdtslvs vmtvnneigv kqpiaeigri cssrkvyfht
 181    daaqavgkip ldvndmkidl msisghkiyg pkgvgaiyir rrprvrveal qsgggqergm
 241    rsgtvptplv vglgaaceva qqemeydhkr isklserliq nimkslpdvv mngdpkhhyp
 301    gcinlsfayv egesllmalk dvalssgsac tsaslepsyv lraigtdedl ahssirfgig
 361    rftteeevdy tvekciqhvk rlremaplwe mvqdgidlks ikwtqh
```

SEQ ID NO: 5 Human LYRM4 cDNA sequence (transcript variant 1)
```
   1    atggcagcct ccagtcgcgc acaagtgtta tctctgtacc gggcgatgct gagagagagc
  61    aagcgtttca gcgcctacaa ttacagaaca tatgctgtca ggaggataag agatgccttc
 121    agagaaaata aaatgtaaa ggatcctgta gaaattcaaa ccctagtgaa taaagccaag
 181    agagaccttg gagtaattcg tcgacaggtc acattggcc aactgtattc aactgacaag
 241    ctgatcattg agaatcgaga catgcccagg acctag
```

SEQ ID NO: 6 Human LYRM4 amino acid sequence (isoform 1)
```
   1    maassraqvl slyramlres krfsaynyrt yavrrirdaf renknvkdpv eiqtlvnkak
  61    rdlgvirrqv higqlystdk liienrdmpr t
```

TABLE 1-continued

```
SEQ ID NO: 7 Human LYRM4 cDNA sequence (transcript variant 2)
    1  atggcagcct ccagtcgcgc acaagtgtta tctctgtacc gggcgatgct gagagagagc
   61  aagcgtttca gcgcctacaa ttacagaaca tatgctgtca ggaggataag agatgccttc
  121  agagaaaata aaaatgtaaa ggatcctgta gaaattcaaa ccctagtgaa taaagccaag
  181  agagaccttg gagtaattcg tcgacagatg gactctcact ctgtcgccca ggctggagtg
  241  cattggaacg atctcagctc actacaacct ctgcctcct ggttcaagca attctcctgc
  301  ctcagcctcc cgagtagctg ggattatagg cgcacgccac cacgcctggc taattttgt
  361  attcttagta gagatgtgat ttcactgtat tag SEQ ID NO: 8 Human LYRM4 amino acid sequence (isoform 2)
    1  maassraqvl slyramlres krfsaynyrt yavrrirdaf renknvkdpv eiqtlvnkak
   61  rdlgvirrqm dshsvaqagv hwndlsslqp lppwfkqfsc lslpsswdyr rtpprlanfc
  121  ilsrdvisly SEQ ID NO: 9 Human LYRM4 cDNA sequence (transcript variant 3)
    1  atggcagcct ccagtcgcgc acaagtgtta tctctgtacc gggcgatgct gagagagagc
   61  aagcgtttca gcgcctacaa ttacagaaca tatgctgtca ggaggataag agatgccttc
  121  agagaaaata aaaatgtaaa ggatcctgta gaaattcaaa ccctagtgaa taaagccaag
  181  agagaccttg gagtaattcg tcgacaggta gctgagcaag gcacagccgc caggaggaag
  241  tcggggaaca gcagccggag cctggggaag ccctgcacaa gttggccttg a SEQ ID NO: 10 Human LYRM4 amino acid sequence (isoform 3)
    1  maassraqvl slyramlres krfsaynyrt yavrrirdaf renknvkdpv eiqtlvnkak
   61  rdlgvirrqv aeqgtaarrk sgnssrslgk pctswp SEQ ID NO: 11 Human ISCU cDNA sequence (transcript variant 1)
    1  atggttctca ttgacatgag tgtagacctt tctactcagg ttgttgatca ttatgaaaat
   61  cctagaaacg tggggtccct tgacaagaca tctaaaaatg ttggaactgg actggtgggg
  121  gctccagcat gtggtgacgt aatgaaatta cagattcaag tggatgaaaa ggggaagatt
  181  gtggatgcta ggtttaaaac atttggctgt ggttccgcaa ttgcctccag ctcattagcc
  241  actgaatggg tgaaaggaaa gacggtggag gaagcctga ctatcaaaa cacagatatc
  301  gccaaggagc tctgccttcc tcccgtgaaa ctgcactgct ccatgctggc tgaagatgca
  361  atcaaggccg ccctggctga ttacaaattg aaacaagaac caaaaaagg agaggcagag
  421  aagaaatga SEQ ID NO: 12 Human ISCU amino acid seciucncc (isoform 1)
    1  mvlidmsvdl stqvvdhyen prnvgsldkt sknvgtglvg apacgdvmkl qiqvdekgki
   61  vdarfktfgc gsaiasssla tewvkgktve ealtikntdi akelclppvk lhcsmlaeda
  121  ikaaladykl kqepkkgeae kk SEQ ID NO: 13  Human ISCU cDNA sequence (transcript variant 2)
    1  atggcggcgg ctggggcttt ccgtctgagg cgggcggcat cggctctgct gctgcggagc
   61  cccgcctgc ccgcccggga gctgtcggcc ccggcccgac tctatcacaa gaaggttgtt
  121  gatcattatg aaaatcctag aaacgtgggg tcccttgaca agacatctaa aaatgttgga
  181  actggactgg tgggggctcc agcatgtggt gacgtaatga aattacagat tcaagtggat
  241  gaaaagggga gattgtgga tgctaggttt aaaacatttg gctgtggttc cgcaattgcc
  301  tccagctcat tagccactga atgggtgaaa ggaaagacgg tggaggaagc cctgactatc
  361  aaaaacacag atatcgccaa ggagctctgc cttcctcccg tgaaactgca ctgctccatg
  421  ctggctgaag atgcaatcaa ggccgccctg gctgattaca aattgaaaca agaacccaaa
  481  aaaggagagg cagagaagaa atga SEQ ID NO: 14 Human ISCU amino acid sequence (isoform 2)
    1  maaagafrlr raasalllrs prlparelsa parlyhkkvv dhyenprnvg sldktsknvg
   61  tglvgapacg dvmklqiqvd ekgkivdarf ktfgcgsaia ssslatewvk gktveealti
  121  kntdiakelc lppvklhcsm laedaikaal adyklkqepk kgeaekk SEQ ID NO: 15 Human FXN cDNA sequence (transcript variant 1)
    1  atgtggactc tcgggcgccg cgcagtagcc ggcctcctgg cgtcacccag cccagcccag
   61  gcccagaccc tcacccgggt cccgcggccg gcagagttgg ccccactctg cggccgccgt
  121  ggcctgcgca ccgacatcga tgcgacctgc acgccccgcc gcgcaagtcc gaaccaacgt
  181  ggcctcaacc agatttggaa tgtcaaaaag cagagtgtct atttgatgaa tttgaggaaa
  241  tctggaactt tgggccaccc aggctctcta gatgagacca cctatgaaag actagcagag
  201  gaaacgctgg actctttagc agagttttt gaagaccttg cagacaagcc atacacgttt
  361  gaggactatg atgtctcctt gggagtggt gtcttaactg tcaaactggg tggagatcta
  421  ggaacctatg tgatcaacaa gcagacgcca aacaagcaaa tctggctatc ttctccatcc
  481  agtggaccta gcgttatga ctggactggg aaaaactggg tgtactccca cgacggcgtg
  541  tcccctccatg agctgctggc cgcagagctc actaaagcct taaaaaccaa actggacttg
  601  tcttccttgg cctattccgg aaaagatgct tga SEQ ID NO: 16 Human FXN amino acid sequence (isoform 1)
    1  mwtlgrrava gllaspspaq aqtltrvprp aelaplcgrr glrtdidatc tprrassnqr
   61  glnqiwnvkk qsvylmnlrk sgtlghpgsl dettyerlae etldslaeff edladkpytf
  121  edydvsfgsg vltvklggdl gtyvinkqtp nkqiwlssps sgpkrydwtg knwvyshdgv
  181  slhellaael tkalktkldl sslaysgkda SEQ ID NO: 17 Human FXN cDNA sequence (transcript variant 2)
    1  atgtggactc tcgggcgccg cgcagtagcc ggcctcctgg cgtcacccag cccagcccag
   61  gcccagaccc tcacccgggt cccgcggccg gcagagttgg ccccactctg cggccgccgt
  121  ggcctgcgca ccgacatcga tgcgacctgc acgccccgcc gcgcaagttc gaaccaacgt
  181  ggcctcaacc agatttggaa tgtcaaaaag cagagtgtct atttgatgaa tttgaggaaa
```

TABLE 1-continued

```
241  tctggaactt tgggccaccc aggctctcta gatgagacca cctatgaaag actagcagag
301  gaaacgctgg actctttagc agagtttttt gaagaccttg cagacaagcc atacacgttt
361  gaggactatg atgtctcctt tgggagtggt gtcttaactg tcaaactggg tggagatcta
421  ggaacctatg tgatcaacaa gcagacgcca aacaagcaaa tctggctatc ttctccatcc
481  aggtatgtag tggacctaag cgttatgact ggactgggaa aaactgggtg tactcccacg
541  acggcgtgtc cctccatgag ctgctggccg cagagctcac taaagcctta a
```

SEQ ID NO: 18 Human FXN amino acid sequence (isoform 2)
```
  1  mwtlgrrava gllaspspaq aqtltrvprp aelaplcgrr glrtdidatc tprrassnqr
 61  glnqiwnvkk qsvylmnlrk sgtlghpgsl dettyerlae etldslaeff edladkpytf
121  edydvafgsg vltvklggdl gtyvinkqtp nkqiwlssps ryvvdlsvmt glgktgctpt
181  tacpsmscwp qsslkp
```

SEQ ID NO: 19 Human FXN cDNA sequence (transcript variant 3)
```
  1  atgtggactc tcgggcgccg cgcagtagcc ggcctcctgg cgtcacccag cccagcccag
 61  gcccagaccc tcacccgggt cccgcggccg gcagagttgg ccccactctg cggccgccgt
121  ggcctgcgca ccgacatcga tgccacctgc acgccccgcc gcgcaagttc gaaccaacgt
181  ggcctcaacc agatttggaa tgtcaaaaag cagagtgtct atttgatgaa tttgaggaaa
241  tctggaactt tgggccaccc aggctctcta gatgagacca cctatgaaag actagcagag
301  gaaacgctgg actctttagc agagtttttt gaagaccttg cagacaagcc atacacgttt
361  gaggactatg atgtctcctt tgggagtggt gtcttaactg tcaaactggg tggagatcta
421  ggaacctatg tgatcaacaa gcagacgcca aacaagcaaa tctggctatc ttctccatcc
481  aggttaacgt ggctcctgtg gctgttccat ccctga
```

SEQ ID NO: 20 Human FXN amino acid sequence (isoform 3)
```
  1  mwtlgrrava gllaspspaq aqtltrvprp aelaplcgrr glrtdidatc tprrassnqr
 61  glnqiwnvkk qsvylmnlrk sgtlghpgsl dettyerlae etldslaeff edladkpytf
121  edydvsfgsg vltvklggdl gtyvinkqtp nkqiwlssps rltwllwlfh p
```

SEQ ID NO: 21 Human NFU1 cDNA sequence (transcript variant 1)
```
  1  atgttgaaga atccatacac cattaagaaa cagcctctgc atcagtttgt acaaagacca
 61  cttttcccac tacctgcagc ttttatcac ccagtgagat acatgtttat tcaaacacaa
121  gataccccaa atccaaacag cttaaagttt ataccaggaa aaccagttct tgaacacaagg
181  accatggatt ttcccaccc agctgcagca tttcgctccc ctctggctag gcagttattt
241  aggattgaag gagtaaaaag tgtcttcttt ggaccagatt tcatcactgt cacaaaggaa
301  aatgaagaat tagactggaa tttactgaaa ccagatattt atgcaacaat catggacttc
361  tttgcatctg gcttacccct ggttactgag gaaacaccct caggagaagc aggatctgaa
421  gaagatgatg aagttgtggc aatgattaag gaattgttag atactagaat acggccaact
481  gtgcaggaag atggaggtga tgtaatctac aaaggctttg aagatggcat tgtacagctg
541  aaactccagg gttcttgtac cagctgccct agttcaatca ttactctgaa aaatggaatt
601  cagaacatgc tgcagtttta tattccggag gtagaaggcg tagaacaggt tatggatgat
661  gaatcagatg aaaagaagc aaaactcacct taa
```

SEQ ID NO: 22 Human NFU1 amino acid sequence (isoform 1)
```
  1  mlknpytikk qplhqfvqrp lfplpaafyh pvrymfiqtq dtpnpnslkf ipgkpvletr
 61  tmdfptpaaa frsplarqlf riegvksvff gpdfitvtke neeldwnllk pdiyatimdf
121  fasglplvte etpsgeagse eddevvamik elldtrirpt vqedggdviy kgfedgivql
181  klqgsctscp ssiitlkngi qnmlqfyipe vegveqvmdd esdekeansp
```

SEQ ID NO: 23 Human NFU1 cDNA sequence (transcript variant 2)
```
  1  atggcggcga cggccaggcg gggctgggga gctgcggctg ttgccgccgg gctgcgcagg
 61  cggttctgtc atatgttgaa gaatccatac accattaaga acagcctct gcatcagttt
121  gtacaaagac cacttttccc actacctgca gccttttatc acccagtgag atacatgttt
181  attcaaacac aagataccc aaatccaaac agcttaaagt ttataccagg aaaaccagtt
241  cttgagacaa ggaccatgga ttttcccacc ccagctgcag catttcgctc ccctctggct
301  aggcagttat ttaggattga aggagtaaaa agtgtcttct ttggaccaga tttcatcact
361  gtcacaaagg aaaatgaaga attagactgg aatttactga accagatat ttatgcaaca
421  atcatggact ctttgcatc tggcttaccc ctggttactg aggaaacacc ttcaggagaa
481  gcaggatctg aagaagatga tgaagttgtg gcaatgatta aggaattgtt agatactaga
541  atacggccaa ctgtgcagga agatggaggg gatgtaatct acaaaggctt tgaagatggc
601  attgtacagc tgaaactcca gggttcttgt accagctgcc ctagttcaat cattactctg
661  aaaaatggaa ttcagaacat gctgcagttt tatattccgg aggtagaagg cgtagaacag
721  gttatggatg atgaatcaga tgaaaagaa gcaaaactcac cttaa
```

SEQ ID NO: 24 Human NFU1 amino acid sequence (isoform 2)
```
  1  maatarrqwg aaavaaglrr rfchmlknpy tikkqplhqf vqrplfplpa afyhpvryraf
 61  iqtqdtpnpn slkfipgkpv letrtmdfpt paaafrspla rqlfriegvk svffgpdfit
121  vtkeneeldw nllkpdiyat imdffasglp lvteetpsge agseeddevv amikelldtr
181  irptvqedgg dviykgfedg ivqlklqgsc tscpssiitl kngiqnmlqf yipevegveq
241  vmddesdeke ansp
```

SEQ ID NO: 25 Human NFU1 cDNA sequence (transcript variant 3)
```
  1  atggacttct ttgcatctgg cttacccctg gttactgagg aaacaccttc aggagaagca
 61  ggatctgaag aagatgatga agttgtggca atgattaaga attgttaga tactagaata
121  cggccaactg tgcaggaaga tggaggggat gtaatctaca aaggctttga agatggcatt
181  gtacagctga aactccaggg ttcttgtacc agctgcccta gttcaatcat tactctgaaa
241  aatggaattc agaacatgct gcagttttat attccggagg tagaaggcgt agaacaggtt
301  atggatgatg aatcagatga aaagaagca aactcaccctt aa
```

TABLE 1-continued

```
SEQ ID NO: 26 Human NFU1 amino acid sequence (isoform 3)
    1 mdffasglpl vteetpsgea gseeddevva mikelldtri rptvqedggd viykgfedgi
   61 vqlklqgsct scpssiitlk ngiqnmlqfy ipevegveqv mddesdekea nsp SEQ ID NO: 27 Human GLRX5 cDNA sequence
    1 atgagcgggt ccctcggccg agctgcggcg gctctgctcc gctgggggcg cggcgcgggc
   61 ggcggtggcc tttggggtcc gggcgtgcgg geggcgggct cggcgcgggc cggcggcggc
  121 tcggcggagc agttggacgc gctggtgaag aaggacaagg tggtggtctt cctcaagggg
  181 acgccggagc agccccagtg cggcttcagc aacgccgtgg tgcagatcct gcggctgcac
  241 ggcgtccgcg attacgcggc ctacaacgtg ctggacgacc cggagctccg acaaggcatt
  301 aaagactatt ccaactggcc caccatcccg caagtgtacc tcaatggcga gtttgtaggg
  361 ggctgtgaca ttcttctgca gatgcaccag aacggggact tggtggaaga actgaaaaag
  421 ctggggatcc actccgccct tttagatgaa aagaaagacc aagactccaa gtga SEQ ID NO: 28 Human GLRX5 amino acid sequence
    1 msgslgraaa allrwgrgag ggglwgpgvr aagsgagggg saeqldaivk kdkvvvflkg
   61 tpeqpqcgfs navvqilrlh gvrdyaaynv lddpelrqgi kdysnwptip qvylngefvg
  121 gcdillqmhq ngdlveelkk lgihsallde kkdqdsk SEQ ID NO: 29 Human BOLA3 cDNA sequence (transcript variant 1)
    1 atggctgcat ggagcccggc cgcggcagcg cctctcctcc gcgggatccg cgggcttcca
   61 cttcaccatc ggatgtttgc cactcagact gaggggagc tcagagtgac ccaaattctc
  121 aaagaaaagt tccacgagc tacagctata aaagtcactg acatttcagg aggttgtggg
  181 gcgatgtatg aaattaaat tgaatcagaa gaatttaagg agaagaaac tgtccagcag
  241 caccagatgg ttaatcaggc actaaaagaa gaaatcaaag agatgcatgg attgcggata
  301 tttacctctg tccccaaacg ctga SEQ ID NO: 30 Human BOLA3 amino acid sequence (isoform 1)
    1 maawspaaaa pllrgirglp lhhrmfatqt egelrvtqil kekfpratai kvtdisggcg
   61 amyeikiese efkekrtvqq hqmvnqalke eikemhglri ftsvpkr SEQ ID NO: 31  Human BOLA3 cDNA sequence (transcript variant 2)
    1 atggctgcat ggagcccggc cgcggcagcg cctctcctcc gcgggatccg cgggcttcca
   61 cttcaccatc ggatgtttgc cactcagact gaggggagc tcagagtgac ccaaattctc
  121 aaagaaaagt tccacgagc tacagctata aaagtcactg acatttcagg cactaaaaga
  181 agaaatcaaa gagatgcatg gattgcggat atttacctct gtccccaaac gctgaccacg
  241 ccctggctgc atagatgctg ctgcttaaga ccttggatga acttcactga catcattctt
  301 ccctaa SEQ ID NO: 32 Human BOLA3 amino acid sequence (isoform 2)
    1 maawspaaaa pllrgirglp lhhrmfatqt egelrvtqil kekfpratai kvtdisgtkr
   61 rnqrdawiad iylcpqtltt pwlhrccclr pwmnftdiil p SEQ ID NO: 33 Human HSCB cDNA sequence
    1 atgtggcggg ggagagccgg ggctttgctc cgggtgtggg ggttttggcc gacaggggtt
   61 cccagaagga gaccgctaag ctgcgatgct gcgtccgcgg cgggaagcaa ttatcccgc
  121 tgttggaact gcggcgggcc atggggcccc gggcgggagg acaggttctt ctgcccacag
  181 tgccgagcgc tgcaggcacc tgacccccact cgagactact tcagccttat ggactgcaac
  241 cgttccttca gagttgatac agcgaagctc cagcacaggt accagcaact gcagcgtctt
  301 gtccacccag atttcttcag ccagaggtct cagactgaaa aggacttctc agagaagcat
  361 tcgaccctgg tgaatgatgc ctataagacc ctcctggccc cctgagcag aggactgtac
  421 cttctaaagc tccatgaat agagattcct gaaggacag attatgaaat ggacaggcaa
  481 ttcctcatag aaataatgga atcaatgaa aaactcgcag agctgaaag tgaagctgcc
  541 atgaaagaga ttgaatccat tgtcaaagct aaacagaaag aatttactga caatgtgagc
  601 agtgcttttg aacaagatga ctttgaagaa gccaaggaaa ttttgacaaa gatgagatac
  661 ttttcaaata tagaagaaaa gatcaagtta aagaagattc ccctttaa SEQ ID NO: 34 Human HSCB amino acid sequence
    1 mwrgragall rvwgfwptgv prrrplscda asqagsnypr cwncggpwgp gredrffepq
   61 cralqapdpt rdyfslmdcn rsfrvdtakl qhryqqlqrl vhpdffsqrs qtekdfsekh
  121 stlvndaykt llaplsrgly llklhgieip ertdyemdrq flieimeine klaeaeseaa
  181 mkeiesivka kqkeftdnvs safeqddfee akeiltkmry fsnieekikl kkipl SEQ ID NO: 35 Human HSPA9 cDNA sequence
    1 atgacaagtg ccagccgagc tgcagcagcc cgtcgtgg gcgccgcagc ctccggggc
   61 cctacggccg cccgccacca ggatagctgg aatggcctta gtcatgaggc ttttagactt
  121 gtttcaaggc ggattatgc atcagaagca atcaaggcag cagttgttgg tattgatttg
  181 ggtactacca actcctgcgt ggcagttatg gaaggtaaac aagcaaggt gctggagaat
  241 gccgaagtg ccagaaccac ccttcagtt gtggccttta gcagatgg tgagcgactt
  301 gttggaatgc cggccaagcg acaggctgtc accaacccaa acaatacatt ttatgctacc
  361 aagcgtctca ttggccggca tatgatgat cctgaagtac agaaagacat taaaaatgtt
  421 ccctttaaaa ttgtccgtgc ctccaatggt gatgcctggg ttgaggctga tgggaaattg
  481 tattctccga gtcagattgg agcatttgtg ttgatgaaga tgaaagagac tgcagaaaat
  541 tacttgggc acacagcaaa aaatgctgtg atcacagtcc cagcttattt caatgactcg
  601 cagagacagg ccactaaaga tgctggccag atatcgtgac tgaatgtgct tcgggtgatt
  661 aatgagccca cagctgctgc tcttgcctat ggtctagaca aatcagaaga caaagtcatt
  721 gctgtatatg atttaggtgg tggaactttt gatatttcta tcctggaaat tcagaaagga
  781 gtatttgagg tgaaatccac aaatgggat accttcttag gtggggaaga ctttgaccag
  841 gccttgctac ggcacattgt gaaggagttc aagagagaga caggggttga tttgactaaa
  901 gacaacatgg cacttcagag ggtacgggaa gctgctgaaa aggctaaatg tgaactctcc
```

TABLE 1-continued

```
 961   tcatctgtgc agactgacat caatttgccc tatcttacaa tggattcttc tggacccaag
1021   catttgaata tgaagttgac ccgtgctcaa tttgaaggga ttgtcactga tctaatcaga
1081   aggactatcg ctccatgcca aaaagctatg caagatgcag aagtcagcaa gagtgacata
1141   ggagaagtga ttcttgtggg tggcatgact aggatgccca aggttcagca gactgtacag
1201   gatcttttg gcagagcccc aagtaaagct gtcaatcctg atgaggctgt ggccattgga
1261   gctgccattc agggaggtgt gttggccggc gatgtcacgg atgtgctgct ccttgatgtc
1321   actcccctgt ctctgggtat tgaaactcta ggaggtgtct ttaccaaact tattaatagg
1381   aataccacta ttccaaccaa gaagagccag gtattctcta ctgccgctga tggtcaaacg
1441   caagtcgaaa ttaaagtgtg tcagggtgaa agagagatgg ctggagacaa caaactcctt
1501   ggacagttta ctttgattgg aattccacca gcccctcgtg gagttcctca gattgaagtt
1561   acatttgaca ttgatgccaa tgggatagta catgtttctg ctaaagataa aggcacagga
1621   cgtgagcagc agattgtaat ccagtcttct ggtggattaa gcaaagatga tattgaaaat
1681   atggttaaaa atgcagagaa atatgctgaa gagaccggc gaagaaagga acgagttgaa
1741   gcagttaata tggctgaagg aatcattcac gacacagaaa ccaagatgga gaattcaag
1801   gaccaattac ctgctgatga gtgcaacaag ctgaaagaag agatttccaa aatgagggag
1861   ctcctggcta gaaaagacag cgaaacagga gaaaatatta gacaggcagc atcctctctt
1921   cagcaggcat cactgaagct gttcgaaatg gcatacaaaa agatggcatc tgagcgagaa
1981   ggctctggaa gttctggcac tggggaacaa aaggaagatc aaaaggagga aaaacagtaa
```

SEQ ID NO: 36 Human HSPA9 amino acid sequence

```
  1    misasraaaa rlvgaaasrg ptaarhqdsw nglsheafrl vsrrdyasea ikgavvgidl
 61    gttnscvavm egkqakvlen aegartxpsv vaftadgerl vgmpakrqav tnpnntlyat
121    krligrrydd pevqkdiknv pfkivrasng dawveahgkl yspsqigafv lmkmketaen
181    ylghtaknav itvpayfnds qrqatkdagq isglnvlrvi neptaaalay gldksedkvi
241    avydlgggtf disileiqkg vfevkstngd tflggedfdq allrhivkef kretgvdltk
301    dnmalqrvre aaekakcels ssvqtdinlp yltmdssgpk hlnmkltraq fegivtdlir
361    rtiapcqkam qdaevsksdi gevilvggmt rmpkvqqtvq dlfgrapska vnpdeavaig
421    aaiqggvlag dvtdvllldv tplslgietl ggvftklinr nttiptkksq vfstaadgqt
481    qveikvcqge remagdnkll gqftligipp aprgvpqiev tfdidangiv hvsakdkgtg
541    reqqiviqss gglskddien mvknaekyae edrrkkerve avnmaegiih dtetkmeefk
601    dqlpadecnk lkeeiskmre llarkdsetg enirqaassl qqaslklfem aykkmasere
661    gsgssgtgeq kedqkeekq
```

SEQ ID NO: 37 Human ISCA1 cDNA sequence

```
  1    atgtcggctt ccttagtccg ggcaactgtc cgggctgtga gcaagaggaa gctgcagccc
 61    acccgggcag ccctcaccct gacaccttca gcagtaaaca agataaaaca acttcttaaa
121    gataagcctg agcatgtagg tgtaaaagtt ggtgtccgaa ccaggggctg taatggcctt
181    tcttatactc tagaatatac aaagacaaaa ggagattctg atgaagaagt tattcaagat
241    ggagtcgagg tattcatcga aaagaaagca cagctaacac tttaggaac agaaatggac
301    tatgttgaag acaaattatc cagtgagttt gtgttcaata acccaaacat caaagggact
361    tgtggctgtg agaaagctt taatatttga
```

SEQ ID NO: 38 Human ISCA2 amino acid sequence

```
  1    msaslvratv ravskrklqp traaltltps avnkikqllk dkpehvgvkv gvrtrgcngl
 61    sytleytktk gdsdeeviqd gvrvfiekka qltllgtemd yvedklssef vfnnpnikgt
121    cgcgesfni
```

SEQ ID NO: 39 Human ISCA2 cDNA sequence (transcript variant 1)

```
  1    atggctgccg cctgggggtc gtccctaacg gccgcgacgc agagagcggt cactccctgg
 61    ccgaggggca ggctcctcac ggcctccctg gaccccagg cgcgtcggga ggcgtcgtcc
121    tccagccccg aggccggcga agggcagatc cgcctcacag acagttgcgt ccagaggctt
181    ttggaaatca ccgaaggtc agaattcctc aggctgcaag tggaggagg tggatgctcc
241    ggattccaat acaaattttc actggataca gttatcaacc ccgacgacag gtatttgaa
301    cagggtgggg caagagtggt ggttgactct gatagcttgg ccttcgtgaa aggggcccag
361    gtggacttca gccaagaact gatccgaagc tcatttcaag tgttgaacaa tcctcaagca
421    cagcaaggct gctcctgtgg gtcatctttc tctatcaaac tttga
```

SEQ ID NO: 40 Human ISCA2 amino acid sequence (isoform 1)

```
  1    maaawgsslt aatqravtpw prgrlltasl gpqarreass sspeagegqi rltdscvqrl
 61    leitegsefl rlqveggges gfykfsldt vinpddrvfe qggarwvds dslafvkgaq
121    vdfsqelirs sfqvlnnpqa qggcscgssf sikl
```

SEQ ID NO: 41 Human ISCA2 cDNA sequence (transcript variant 2)

```
  1    atggctgccg cctgggggtc gtccctaacg gccgcgacgc agagagcggt cactccctgg
 61    ccgaggggca ggctcctcac ggcctccctg gaccccagg cgcgtcggga ggcgtcgtcc
121    tccagccccg aggccggcga agggcagatc cgcctcacag acagttgcgt ccagggtatt
181    tga
```

SEQ ID NO: 42 Human ISCA2 amino acid sequence (isoform 2)

```
  1    maaawgsslt aatqravtpw prgrlltasl gpqarreass sspeagegqi rltdscvqgi
```

SEQ ID NO: 43 Human IBA57 cDNA sequence

```
  1    atgcgaccg cggcgctgct tcgaggcgcc actccggggc gggcggccc ggtctggcgc
 61    tggcggctgc gcgcggcccc aaggtgccgc ctggcccaca gctcctgcag tcctggtggc
121    gaccaacgg cgggagcggc ctgggcctgc ttccggctgg acgggcgcac cctgctgcgg
181    gtgcgtggcc ccgacgcggc gccttcctg ctaggctgc tgaccaatga actgccgctt
241    ccgagtcctg cggccgcggg ggcccgcct gctgcgcg cgggctacgc ccacttcctg
301    aacgtgcagg gccgacgcg ctatgacgtc atcttgtacg ggctccagga acactcggag
361    gtgtctggct tccttctgga gtgtgacagc tcggtgcagg gcgcgctgca gaagcacctc
421    gcgctataca ggatccggcg gaaggtcacg gtggagccgc accggagct gcgagtgtgg
```

TABLE 1-continued

```
 481   gcggtgttgc ccagttcccc tgaggcctgc ggggctgcat cgctgcagga gagggcaggg
 541   gctgccgcca tcctcatccg cgacccgcga acagcacgca tggggtggcg gctcctcacc
 601   caggatgaag gcccagccct ggtgcccggg gccggctcg gggacttgtg ggattatcac
 661   cagcaccgat acctgcaagg cgttcctgag ggggtccgag acttgcctcc tggggtggcc
 721   ctgcccctgg agtccaacct ggccttcatg aacggcgtga gcttcaccaa aggctgctac
 781   attggccagg agctgacggc ccgcacccac acatggggc tcatccgcaa gcgcctcttc
 841   cctgtccggt tcttggaccc ccttcccacc agtggcatca ccctggtgc cacggtgctg
 901   actgcctcag acagactgt gggcaagttc agggctggcc agggcaacgt ggggctggcc
 961   ctgctgtggt cagagaagat caagggtcct ctgcacatca gagcctctga gggtgcccag
1021   gtggccttag ccgcatctgt gccagactgg tggcctacag tctccaagta g
```

SEQ ID NO: 44 Human IBA57 amino acid sequence
```
   1   mataallrga tpgrggpvwr wrlraaprcr lahsscspgg dptagaawac frldgrtllr
  61   vrgpdaapfl lglltnelpl pspaaagapp aaragyahfl nvqgrtlydv ilyglqehse
 121   vsgfllecds svqgalqkhl alyirrrkvt vephpelrvw avlpsspeac gaaslqerag
 181   aaailirdpr tarmgwrllt qdegpalvpg grlgdlwdyh qhrylqgvpe gvrdlppgva
 241   lplesnlafm ngvsftkgcy igqeltarth hmgvirkxlf pvrfldplpt sgitpgatvl
 301   tasgqtvgkf ragqgnvgla llwsekikgp lhirasegaq valaasvpdw wptvsk
```

SEQ ID NO: 45 Human NUBPL cDNA sequence (transcript variant 1)
```
   1   atggggattt ggcagcgtct gctgcttttt ggtggggtgt cgctccgggc tggtggcggg
  61   gccactgccc cgcttggggg aagccgagcg atggtttgtg ggcgccagtt gtctggcgcc
 121   gggagtgaga ccctaaaaca aagaagaaca caaatcatgt cccgaggact tccaaagcag
 181   aaaccgatag aaggtgttaa acaagttata gttgtggctt ctggaaaggg tggagtcgga
 241   aaatctacta cagcagttga tcttgcactt gcactagcag cgaacgattc gtccaaggcc
 301   attggtttgc tagatgtgga tgtgtatgga ccttcagttc caaagatgat gaatctgaaa
 361   ggaaatccgg aattatcaca gagcaaccta atgaggctc tcttgaatta tggtattgct
 421   tgtatgtcta tgggcttttct ggttgaagaa agtgaaccag tagtttggag aggccttatg
 481   gtaatgtcgg ccattgaaaa attgttgagg caggtagatt ggggtcaact ggactactta
 541   gttgtagaca tgccaccagg aactggagat gtgcagttat cagtctcaca gaatattcct
 601   ataacaggtg ctgtgattgt ctccacgccc caggacatcg cattgatgga tgcacacaag
 661   ggtgctgaga tgtttcgcag agtccacgtg cccgtccttg gccttgtcca aaacatgagt
 721   gttttccagt gtccaaaatg taaacacaaa actcatattt ttggtgctga tggtgcaagg
 781   aaactagcac agacccttgg tcttgaagtt ctaggagaca ttcccttaca cctaaatata
 841   agggaagctt cagatacagg ccagccaatt gtgttttcac agcctgaaag tgatgaggcc
 901   aaagcttact tgaggattgc tgtggaagtg gtaagaagat tgccatcacc ttcagaatga
```

SEQ ID NO: 46 Human NUBPL amino acid sequence (isoform 3)
```
   1   mgiwqrlllf ggvslraggg ataplggsra mvcgrqlsga gsetlkqrrt qimsrglpkq
  61   kpiegvkqvi vvasgkggvg ksttavnlal alaandsska iglldvdvyg psvpkmmnlk
 121   gnpelsqsnl mrpllnygia cmsmgflvee SEQvvwrglm vmsaiekllr qvdwgqldyl
 181   vvdmppgtgd vqlsvsqnip itgavivstp qdialmdahk gaemfrrvhv pvlglvqnms
 241   vfqcpkckhk thifgadgar klaqtlglev lgdiplhlni reasdtgqpi vfsqpesdea
 301   kaylriavev vrrlpspse
```

SEQ ID NO: 47 Human NUBPL cDNA sequence (transcript variant 2)
```
   1   atgtccaagg ccattggttt gctagatgtg gatgtgtatg gaccttcagt tccaaagatg
  61   atgaatctga aaggaaatcc ggaattatca cagagcaacc taatgaggcc tctcttgaat
 121   tatggtattg cttgtatgtc tacgggcttt ctggttgaag aaagtgaacc agtagtttgg
 181   agaggcctta tggtaatgcc ggccattgag aaattgttga ggcaggtaga ttgggtcaa
 241   ctggactact tagttgtaga catgccacca ggaactggag atgtgcagtt atcagtctca
 301   cagaatattc ctataacagg tgctgtgatt gtctccacgc ccaggacat cgcattgatg
 361   gatgcacaca agggtgctga tgtttcgc agagtccacg tgcccgtcct tggccttgtc
 421   caaaacatga gtgttttcca gtgtccaaaa tgtaaacaca aactcatat ttttggtgct
 481   gatggtgcaa ggaaactagc acagaccctt ggtcttgaag ttctaggaga cattccctta
 541   caccttaata agggaagc ttcagataca ggccagccaa ttgtgtttc acagcctgaa
 601   agtgatgagg ccaaagctta cttgaggatt gctgtggaag tggtaagaag attgccatca
 661   ccttcagaat ga
```

SEQ ID NO: 48 Human NUBPL amino acid sequence (isoform 2)
```
   1   mskaiglldv dvygpsvpkm mnlkgnpels qsnlmrplln ygiacmsmgf lveeSEQvvw
  61   rglmvmsaie kllrqvdwgq ldylvvdmpp gtgdvqlsvs qnipitgavi vstpqdialm
 121   dahkgaemfr rvhvpvlglv qnmsvfqcpk ckhkthifga dgarklaqtl glevlgdipl
 181   hlnireasdt gqpivfsqpe sdeakaylri avevvrrlps pse
```

SEQ ID NO: 49 Human NUBPL cDNA sequence (transcript variant 3)
```
   1   atgccaccag gaactggaga tgtgcagtta tcagtctcac agaatattcc tataacaggt
  61   gctgtgattg tctccacgcc caggacatc gcattgatgg atgcacacaa gggtgctgag
 121   atgtttcgca gagtccacgt gcccgtcctt ggccttgtcc aaaacatgag tgttttccag
 181   tgtccaaaat gtaaacacaa aactcatatt tttggtgctg atggtgcaag gaaactagca
 241   cagacccttg gtcttgaagt tctaggagac attcccttac accttaatat aagggaagct
 301   tcagatacag gccagccaat tgtgttttca gcctgaaa gtgatgaggc caaagcttac
 361   ttgaggattg ctgtggaagt ggtaagaaga ttgccatcac cttcagaatg a
```

SEQ ID NO: 50 Human NUBPL amino acid sequence (isoform 3)
```
   1   mppgtgdvql svsqnipitg avivstpgdi almdahkgae mfrrvhvpvl glvqnmsvfq
  61   cpkckhkthi fgadgarkla qtlglevlgd iplhlnirea sdtgqpivfs qpesdeakay
 121   lriavevvrr lpspse
```

TABLE 1-continued

```
SEQ ID NO: 51 Human SLC25A28 cDNA sequence
    1  atggagttgg aggggcgggg tgctggcggt gtggcggggg ggccggcggc agggcccggg
   61  cggagccccg gggagtcggc gctgctggac gggtggctgc agcggggcgt gggccggggg
  121  gccggcggcg ggaggccgg ggcctgcagg ccccggtac gacaagatcc ggactccggc
  181  ccggactacg aggcgctgcc ggctggagcc actgtcacca cgcacatggt ggcaggcgcc
  241  gtggcaggga tcctggagca ctgcgtgatg taccccatcg actgcgtcaa gacccggatg
  301  cagagtctac agcctgaccc agctgcccgc tatcgcaatg tgttggaggc cctctggagg
  361  attataagaa cggagggcct atggaggccc atgaggggc tgaacgtcac agcaacaggc
  421  gcagggcctg cccacgccct ttattttgcc tgctacgaaa agttaaaaaa gacattgagt
  481  gatgtaatcc accctgggg caatagccat attgccaatg gtgcggccgg tgtgtgtggca
  541  acattacttc atgatgcagc catgaacct gcggaagtgg tcaagcagag gatgcagatg
  601  tacaactcac cataccaccg ggtgacagac tgtgtacggg cagtgtggca aaatgaaggg
  661  gccggggcct tttaccgcag ctacaccacc cagctgacca tgaacgttcc tttccaagcc
  721  attcacttca tgacctatga attcctgcag gagcacttta accccagag acggtacaac
  781  ccaagctccc acgtcctctc tggagcttgc gcaggagctg tagctgccgc agccacaacc
  841  ccactggacg tttgcaaaac actgctcaac cccaggagt ccttggcttt gaactcacac
  901  attacaggac atatcacagg catggctagt ggccttcagga cggtatatca agtaggtggg
  961  gtgaccgcct atttccgagg ggtgcaggcc agagtaattt accagatccc ctccacagcc
 1021  atcgcatggt ctgtgtatga gttcttcaaa tacctaatca ctaaaaggca agaagagtgg
 1081  agggctggca agtga SEQ ID NO: 52 Human SLC25A28 amino acid sequence
    1  melegrgagg vaggpaagpg rspgesalld gwlqrgvgrg agggeagacr ppvrqdpdag
   61  pdyealpaga tvtthmvaga vagilehcvm ypidcvktrm qslqpdpaar yrnvlealwr
  121  iirteglwrp mrglnvtatg agpahalyfa cyeklkktls dvihpggnsh iangaageva
  181  tllhdaamnp aevvkqrmqm ynspyhrvtd cvravwqneg agafyrsytt qltmnvpfqa
  241  ihfmtyeflq ehfnpqrryn psshvlsgac agavaaaatt pldvcktlln tqeslalnsh
  301  itghitgmas afrtvyqvgg vtayfrgvqa rviyqipsta iawsvyeffk ylitkrqeew
  361  ragk SEQ ID NO: 53 Human FDXR cDNA sequence (transcript variant 1)
    1  atggcttcgc gctgctggcg ctggtgggc tggtcggcgt ggcctcggac ccggctgcct
   61  cccgccggga gcaccccgag cttctgccac catttctcca cacaggagaa gacccccag
  121  atctgtgtgg tgggcagtgg cccagctggc ttctacacgg cccaacactt gctaaagcac
  181  ccccaggccc acgtggacat ctacgagaaa cagcctgtgc ccttttggcct ggtgcgcttt
  241  ggtgtggcgc ctgatcaccc cgaggtgaag aatgtcatca acacattac ccagacggcc
  301  cattctgcc gctgtgcctt ctggggcaac gtggaggtgg cagggacgt gacggtgccg
  361  gagctgcggg aggcctacca cgctgtggtg ctgagctacg gggcagagga ccatcgggcc
  421  ctggaaattc ctggtgagga gctgccaggt gtgtgctccg cccgggcctt cgtgggctgg
  481  tacaacgggg ttcctgagaa ccaggagctg agccagacc tgagctgtga cacagccgtg
  541  attctggggc aggggaacgt ggctctggac gtggcccgca tcctactgac cccacctgag
  601  cacctggaga gaacggacat cacgaaggca gccctgggtg tactgaggca gagtcgagtg
  661  aagacagtgt ggctagtggg ccggcgtgga cccctgcaag tggccttcac cattaaggag
  721  cttcgggaga tgattcagtt accgggagcc cggcccattt ggatcctgt ggatttcttg
  781  ggtctccagg acaagatcaa ggaggtcccc cgcccgagga gcggctgac ggaactgctg
  841  cttcgaaccg ccacagagaa gccagggccg gcggaagctc cccgccaggc atggcctcc
  901  cgtgcctggg gcctccgctt ttccgaagc cccagcagg tgctgccctc accagatggg
  961  cggcgggcag caggtgtccg cctagcagtc actagactgg agggtgtcga tgaggccacc
 1021  cgtgcagtgc ccacgggaga catggaagac ctcccttgtg ggctggtgct cagcagcatt
 1081  gggtataaga gccgcccttgt cgacccaaga gtgccctttg actccaagct tgggtcatc
 1141  cccaatgtgg agggccgggt tatggatgtg ccaggcctct actgcagcgg ctgggtgaag
 1201  agaggaccta caggtgtcat agccacaacc atgactgaca gcttcctcac cggccagatg
 1261  ctgccgcagg acctgaaggc tgggttgctc ccctctggcc ccaggcctgg ctacgcagcc
 1321  atccaggccc tgctcagcag ccgaggggtc cggccagtct ctttctcaga ctgggagaag
 1381  ctggatgccg aggaggtggc ccgggggcag ggcacgggga agcccaggga gaagctggtg
 1441  gatcctcagg agatgctgcg cctcctgggc cactga SEQ ID NO: 54 Human FDXR amino acid sequence (isoform 1)
    1  masrcwrwwg wsawprtrlp pagstpsfch hfstqektpq icvvgspag fytaqhllkh
   61  pqahvdiyek qpvpfglvrf gvapdhpevk nvintftqta hsgrcafwgn vevgrdvtvp
  121  elreayhavv lsygaedhra leipgeelpg vcsarafvgw ynglpenqel epdlscdtav
  181  ilgqgnvald varilltppe hlertditka algvlrqsrv ktvwlvgrrg plqvaftike
  241  lremiqlpga rpildpvdfl glqdkikevp rprkrlltell lrtatekpgp aeaarqasas
  301  rawglrffrs pqqvlpspdg rraagvrlav trlegvdeat ravptgdmed lpcglvlssi
  361  gyksrpvdps vpldsklgvl pnvegrvmdv pglycsgwvk rgptgviatt mtdsfltgqm
  421  llqdlkagll psgprpgyaa iqallssrgv rpvsfsdwek ldaeevargq gtgkpreklv
  481  dpqemlrllg h SEQ ID NO: 55 Human FDXR cDNA sequence (transcript variant 2)
    1  masrcwrwwg wsawprtrlp pagstpsfch hfstqektpq icvvgspag fytaqhllkh
   61  pqahvdiyek qpvpfglvrf gvapdhpevk nvintftqta hsgrcafwgn vevgrdvtvp
  121  elreayhavv lsygaedhra leipgeelpg vcsarafvgw ynglpenqel epdlscdtav
  181  ilgqgnvald varilltppe hlealllcqr tditkaalgv lrqsrvktvw lvgrrgplqv
  241  aftikelrem iqlpgarpil dpvdflglqd kikevprprk rltellllrta tekpgpaeaa
  301  rqasasrawg lrffrspqqv lpspdgrraa gvrlavtrle gvdeatravp tgdmedlpcg
  361  lvlssigyks rpvdpsvpfd sklgvipnve grvmdvpgly csgwvkrgpt gviattmtds
  421  fltgqmllqd lkagllpsgp rpgyaaiqal lssrgvrpvs fsdwekldae evargqgtgk
  481  preklvdpce mlrllgh
```

TABLE 1-continued

SEQ ID NO: 56 Human FDXR amino acid sequence (isoform 2)
```
   1  masrcwrwwg wsawprtrlp pagstpsfch hfstqektpq icvvgsgpag fytaqhllkh
  61  pqahvdiyek qpvpfglvrf gvapdhpevk nvintftqta hsgrcafwgn vevgrdvtvp
 121  elreayhavv lsygaedhra leipgeelpg vcsarafvgw ynglpenqel epdlscdtav
 181  ilgqgnvald varilltppe hleallllcqr tditkaalgv lrqscvktvw lvgrrgplqv
 241  aftikelrem iqlpgarpil dpvdflglqd kikevprprk rltelllrta tekpgpaeaa
 301  rqasasrawg lrffrspqqv lpspdgrraa gvrlavtrle gvdeatravp tgdmedlpcg
 361  lvlssigyks rpvdpsvpfd sklgvipnve grvmdvpgly csgwvkrgpt gviattmtds
 421  fltgqmllqd lkagllpsgp rpgyaaiqal lssrgvrpvs fsdwekldae evargqgtgk
 481  preklvdpqe mlrllgh
```

SEQ ID NO: 57 Human FDXR cDNA sequence (transcript variant 3)
```
   1  atggcttcgc gctgctggcg ctggtggggc tggtcggcgt ggcctcggac ccggctgcct
  61  cccgccggga gcaccccgag cttctgccac catttctcca cacaggagaa gacccccccag
 121  atctgtgtgg tgggcagtgg cccagctggc Ctctacacgg cccaacacct gctaaagagg
 181  gtggaagcct tgtgttctca gcccagggtc ctgaactctc ctgctctgtc tggggaaggg
 241  gaggacctgg gggcgtccca gcctctctct ctcgacccca ccagctgccc ccctgttccc
 301  cagcagcacc cccaggccca cgtggacatc tacgagaaac agcctgtgcc cttttggcctg
 361  gtgcgccttg gtgtggcgcc tgatcacccc gaggtgaaga atgtcatcaa cacatttacc
 421  cagacggccc attctgccg ctgtgccttc tggggcaacg tggaggtggg cagggacgtg
 481  acggtgccgg agctgcggga ggctaccac gctgtgggtc tgagctacgg ggcagaggac
 541  catcgggccc tggaaattcc tggtgaggag ctgccaggtg tgtgctccgc ccgggccttc
 601  gtgggctggt acaacgggct tcctcagaac caggagctgg agccagacct gagctgtgac
 661  acagccgtga ttctgggca ggggaacgtg gctctggacg tggcccgcat cctactgacc
 721  ccacctgagc acctggagag aacggacatc acgaaggcag ccctgggtgt actgaggcag
 781  agtcgagtga agacagtgtg gctagtgggc cggcgtggac ccctgcaagt ggccttcacc
 841  attaaggagc ttcgggagat gattcagtta ccgggagccc ggcccatttt ggatcctgtg
 901  gatttcttgg gtctccagga caagatcaag gaggtccccc gcccgaggaa gcggctgacg
 961  gaactgctgc ttcgaacggc cacagagaag ccagggccgg cggaagctgc ccgccaggca
1021  tcggcctccc gtgcctgggg cctccgcttt tccgaagcc cccagcaggt gctgccctca
1081  ccagatgggc ggcgggcagc aggtgtccgc ctagcagtca ctagactgga gggtgtcgat
1141  gaggccaccc gtgcagtgcc cacgggagac atggaagacc tcccttgtgg gctggtgctc
1201  agcagcattg gtataaagag ccgccctgtc gacccaagcg tgcccttttga ctccaagctt
1261  ggggtcatcc ccaatgtgaa gggccggtt atggatgtgc caggcctcta ctgcagcggc
1321  tgggtgaaga aggacctac aggtgtcata gccacaacca tgactgacag cttcctcacc
1381  ggccagatgc tgctgcagga cctgaaggct gggttgctcc cctctggccc caggcctggc
1441  tacgcagcca tccaggccct gctcagcagc cgaggggtcc ggccagtctc tttctcagac
1501  tgggagaagc tggatgccga ggaggtggcc cggggccagg gcacggggaa gcccagggag
1561  aagctggtgg atcctcagga gatgctgcgc ctcctgggcc actga
```

SEQ ID NO: 58 Human FDXR amino acid sequence (isoform 3)
```
   1  masrcwrwwg wsawprtrlp pagstpsfch hfstqektpq icvvgsgpag fytaqhllkr
  61  vealcsqprv lnspalsgeg edlgasqpls ldptschpvp qqhpqahvdi yekqpvpfgl
 121  vrfgvapdhp evknvintft qtahsgrcaf wgnvevgrdv tvpelreayh avvlsygaed
 181  hraleipgee lpgvcsaraf vgwynglpen qelepdlscd tavilgqgnv aldvarillt
 241  ppehlertdi tkaalgvlrq arvktvwlvg rrgplqvaft ikelremiql pgarpildpv
 301  dflglqdkik evprprkrlt elllrtatek pgpaeaarqa sasrawglrf frspqgvlps
 361  pdgrraagvr lavtrlegvd eatravptgd medlpcglvl ssigyksrpv dpsvpfdskl
 421  gvipnvegrv mdvpglycsg wvkrgptgvi attmtdsflt gqmllqdlka gllpsgprpg
 481  yaaiqallss rgvrpvsfsd wekidaeeva rgqgtgkpre klvdpqemlr llgh
```

SEQ ID NO: 59 Human FDXR cDNA sequence (transcript variant 4)
```
   1  atggcttcgc gctgctggcg ctggtggggc tggtcggcgt ggcctcggac ccggctgcct
  61  cccgccggga gcaccccgac ctttgggggt tcagatgaag taagagaccc tgcaaatgcc
 121  aaagccttga ggaacaagag aaggaggatg caggtgaggg tgaagcttgg gaagttccag
 181  cttctgttgg atattcagga gaagaccccc cagatctgtg tggtgggcag tggcccagct
 241  ggcttctaca cggcccaaca cctgctaaag cacccccagg cccacgtgga catctacgag
 301  aaacagcctg tgcccttttgg cctggtgcgc tttggtgtgg cgcctgatca ccccgaggtg
 361  aagaatgtca tcaacacatt tacccagacg gcccattctg gccgctgtgc cttctggggc
 421  aacgtggagg tgggcaggga cgtgacggtg ccggagctgc gggaggccta ccacgctgtg
 481  gtgctgagct acggggcaga ggaccatcgg gccctggaaa ttcctggtga ggagctgcca
 541  ggtgtgtgct ccgcccgggc cttcgtgggc tggtacaacg gcttcctga accaggag
 601  ctggagccag acctgagctg tgacacagcc gtgattctgg gacagggaaa cgtggctctg
 661  gacgtggccc gcatcctact gaccccacct gagcacctgg agaacgaca tcacgaag
 721  gcagccctgg gtgtactgag gcagagtcga gtgaagacag tgtggctagt gggccggcgt
 781  ggaccctgc aagtggcctt caccattaag gagcttcggg agatgattca gttaccggga
 841  gcccggccca ttttggatcc tgtggatttc ttgggtctcc aggacaagat caaggaggtc
 901  ccccgcccga ggaagcggct gacggaactg ctgcttcgaa cggccacaga gaagccaggg
 961  ccggcggaag ctgcccgcca ggcatcggcc tcccgtgcct ggggcctccg cttttccgga
1021  agccccagc aggtgctgcc ctcaccagat gggcggcggg cagcaggtgt ccgcctagca
1081  gtcactagac tggagggtgt cgatgaggcc accgtgcag tgcccacgg agacatggaa
1141  gacctcccctt gtgggctggt gctcagcagc attgggtata agagccgccc tgtcgaccca
1201  agcgtgccct ttgactccaa gcttggggtc atccccaatg tggaggccg ggtatggat
1261  gtgccaggcc tctactgcag cggctgggtg aagagaggac tacaggtgt catagccaca
1321  accatgactg acagcttcct caccggccag atgctgctgc aggacctgaa ggctgggttg
1381  ctcccctctg gccccaggcc tggctacgca gccatccagg ccctgctcag cagccgaggg
1441  gtccggccag tctctttctc agactgggag aagctggatg ccgaggaggt ggcccggggc
1501  cagggcacgg ggaagcccag ggagaagctg gtggatcctc aggagatgct gcgcctcctg
1561  ggccactga
```

TABLE 1-continued

SEQ ID NO: 60 Human FDXR amino acid sequence (isoform 4)
```
  1 masrcwrwwg waawprtrlp pagstptfgg sdevrdpana kalrnkrrrm qvrvklgkfq
 61 llldiqektp qicvvgsgpa gfytaqhllk hpqahvdiye kqpvpfglvr fgvapdhpev
121 knvintftqt ahsgccafwg nvevgrdvtv pelreayhav vlsygaedhr aleipgeelp
181 gvcsarafvg wynglpenqe lepdlscdta vilgqgnval dvarilltpp ehlertditk
241 aalgvlrqsr vktvwlvgrr gplqvaftik elremiqlpg arpildpvdf lglqdkikev
301 prprkrltel llrtatekpg paeaarqasa srawglrffr spqqvlpspd grraagvrla
361 vtrlegvdea travptgdme dlpcglvlss igyksrpvdp svpfdaklgv ipnvegrvmd
421 vpglycsgwv krgptgviat tmtdsfltgq mllqdlkagl lpsgprpgya aiqallssrg
481 vrpvsfsdwe kldaeevarg qgtgkprekl vdpqemlrll gh
```

SEQ ID NO: 61 Human FDXR cDNA sequence (transcript variant 5)
```
   1 atggcttcgc gctgctggcg ctggtggggc tggtcggcgt ggcctcggac ccggctgcct
  61 cccgccggga gcaccccgag cttctgccac catttctcca cacaggagaa gacccccag
 121 atctgtgtgg tgggcagtgg cccagctggc ttctacacgg cccaacacct gctaaagcac
 181 ccccaggccc acgtggacat ctacgagaaa cagcctgtgc cctttggcct ggtgcgcttt
 241 ggtgtggcgc ctgatcaccc cgaggtgaag acggcccatt ctggccgctg tgccttctgg
 301 ggcaacgtgg aggtgggcag ggacgtgacg gtgccggayc tgcgggaggc ccaccacgct
 361 gtggtgctga gctacgggc agaggaccat cgggcctgg aaattcctgg tgaggagctg
 421 ccaggtgtgt gctccgcccg ggccttcgtg ggctggtaca acgggcttcc tgagaaccag
 481 gagctggagc cagacctgag ctgtgacaca ccgtgattc tggggcaggg gaacgtggct
 541 ctggacgtgg cccgcatcct actgacccca cctgagcacc tggagagaac ggacatcacg
 601 aaggcagccc tgggtgtact gaggcagagt cgagtgaaga cagtgtggct agtgggccgg
 661 cgtggacccc tgcaagtggc cttcaccatt aaggagcttc gggagatgat tcagttaccg
 721 ggagcccggc ccatttgga tcctgtggat ttcttgggtc tccaggacaa gatcaaggag
 781 gtccccgcc cgaggaagcg gctgacggaa ctgctgcttc gaaccgccac agagaagcca
 841 gggccggcgg aagccgcccg ccaggcatcg gcctcccgtg cctggggcct ccgcttttc
 901 cgaagccccc agcaggtgct gccctcacca gatgggcggc gggcagcagg tgtccgccta
 961 gcagtcacta gactgaggg tgtcgatgag gccaccgtg cagtgcccac gggagacatg
1021 gaagacctcc cttgtgggct ggtgctcagc agcattggt ataagagccg ccctgtcgac
1081 ccaagcgtgc cctttgactc caagcttggg gtcatcccca atgtggaggg ccgggttatg
1141 gatgtgccag gcctctactg cagcggctgg gtgaagagag gacctacagg tgtcatagcc
1201 acaaccatga ctgacagctt cctcaccggc cagatgctgc tgcaggacct gaaggctggg
1261 ttgctcccct ctggccccag gcctggctac gcagccatcc aggccctgct cagcagccga
1321 ggggtccggc cagtctcttt ctcagactgg gagaagctag atgccgagga ggtggccgg
1381 ggccaggca cggggaagcc cagggagaag ctggtggatc ctcaggagat gctgcgcctc
1441 ctgggccact ga
```

SEQ ID NO: 62 Human FDXR amino acid sequence (isoform 5)
```
  1 masrcwrwwg wsawprtrlp pagstpsfch hfstqektpq icvvgsgpag fytaqhllkh
 61 pqahvdiyek qpvpfglvrf gvapdhpevk tahsgrcafw gnvevgrdvt vpelreayha
121 vvlsygaedh raleipgeel pgvcsarafv gwynglpenq elepdlscdt avilgqgnva
181 ldvarilltp pehlertdit kaalgvlrqs rvktvwlvgr rgplqvafti kelremiqlp
241 garpildpvd flglqdkike vprprkrlte lllrtatekp gpaeaarqas asrawglrff
301 rspqqvlpsp dgrraagvrl avtrlegvde atravptgdm edlpcglvls sigyksrpvd
361 psvpfdsklg vipnvegrvm dvpglycsgw vkrqptgvia ttmtdsfltg qmllqdlkag
421 llpsgprpgy aaiqallssr gvrpvsfsdw ekldaeevar gqgtgkprek lvdpqemlrl
481 lgh
```

SEQ ID NO: 63 Human FDXR cDNA sequence (transcript variant 6)
```
   1 atggcttcgc gctgctggcg ctggtggggc tggtcggcgt ggcctcggac ccggctgcct
  61 cccgccggga gcaccccgag cttctgccac catttctcca cacaggagaa gacccccag
 121 atctgtgtgg tgggcagtgg cccagctggc ttctacacgg cccaacacct gctaaagcag
 181 caccccaggc ccacgtggat catctacgag aaacagctgt gccctttgg cctggtgcgc
 241 tttggtgtgg cgcctgatca ccccgaggtg aagagctacg gggcagagga ccatcgggcc
 301 ctggaaattc ctggtgagga gctgccaggt gtgtgctccg cccgggcctt cgtgggctgg
 361 tacaacgggc ttcctgagaa ccaggagctg gagccagacc tgagctgtga cacagccgtg
 421 attctggggc aggggaacgt ggctctggac gtggcccgca tcctactgac cccacctgag
 481 cacctggaga acgagaac cacgaaggca gccctgggtg tactgaggca gagtcgagtg
 541 aagacagtgt ggctagtggg ccggcgtgga ccctgcaag tggccttcac cattaaggag
 601 cttcgggaga tgattcagtt accgggagcc cggcccattt ggatcctgt ggatttcttg
 661 ggtctccagg acaagatcaa ggaggtcccc cgcccgagga agcggctgac ggaactgctg
 721 cttcgaacg ccacagagaa gccagggccg gcggaagcc catcccgtcc
 781 cgtgcctggg gcctccgctt tttccgaagc ccccagcagg tgctgccctc accagatggg
 841 cggcgggcag caggtgtccg cctagcagtc actagactgg agggtgtcga tgaggccacc
 901 cgtgcagtgc ccacggggaga catggaagac ctcccttgtg gctggtgct cagcagcatt
 961 gggtataaga gccgccctgt cgacccaagc gtgcccttga actccaagct tggggtcatc
1021 cccaatgtgg agggccgggt tatggatgtg ccaggccct actgcagcgg ctgggtgaag
1081 agaggaccta caggtgtcat agccacaacc atgactgaca gcttcctcac cggccagatg
1141 ctgctgcagg acctgaaggc tgggttgctc cctctggcc caggcctgg ctacgcagcc
1201 atccaggccc tgctcagcag ccgagggtc cggccagtct ctttctcaga ctgggagaag
1261 ctggatgccg aggaggtggc ccggggccag gcacgggga gcccaggga gaagctggtg
1321 gatcctcagg agatgctgcg cctcctgggc cactga
```

SEQ ID NO: 64 Human FDXR amino acid sequence (isoform 6)
```
  1 masrcwrwwg wsawprtrlp pagstpsfch hfatqektpq icvvgsgpag fytaqhllkq
 61 hpqahvdiye kqpvpfglvr fgvapdhpev ksygaedhra leipgeelpg vcsarafvgw
121 ynglpenqel epdlscdtav ilgqgnvald varilltppe hlertditka algvlrqsrv
181 ktvwlvgrrg plqvaftike lremiqlpga rpildpvdfl glqdkikevp rprkrltell
241 lrtatekpgp aeaarqasas rawglrffrs pqqvlpspdg rraagvrlav trlegvdeat
```

```
301  ravptgdmed lpcglvlssi gyksrpvdps vpfdsklgvi pnvegrvmdv pglycsgwvk
361  rgptgviatt mtdsfltgqm ilqdlkagll psgprpgyaa iqallssrgv rpvsfsdwek
421  ldaeevargq gtgkpreklv dpqemlrllg h SEQ ID NO: 65 Human FDXR cDNA sequence (transcript variant 7)
   1  atggaagata aggacagaga gcaccccag gcccacgtgg acatctacga gaaacagcct
  61  gtgccctttg gcctggtgcg ctttggtgtg gcgcctgatc accccgaggt gaagaatgtc
 121  atcaaacacat ttacccagac ggcccattct ggccgctgtg ccttctgggg caacgtggag
 181  gtgggcaggg acgtgacggt gccggagctg cggggaggcct accacgctgt ggtgctgagc
 241  tacgggccag aggaccatcg ggccctggaa attcctggtg aggagctgcc aggtgtgtgc
 301  tccgcccggg ccttcgtggg ctggtacaac gggcttcctg agaaccagga gctggagcca
 361  gacctgagct gtgacacagc cgtgattctg ggcagggga acgtggctct ggacgtggcc
 421  cgcatcctac tgaccccacc tgagcacctg gagagaacgg acatcacgaa ggcagccctg
 481  ggtgtactga ggcagagtcg agtgaagaca gtgtggctag tgggccggcg tggacccctg
 541  caagtggcct tcaccattaa ggagcttcgg gagatgattc agttaccggg agcccggccc
 601  attttggatc ctgtggattt cttgggtctc caggacaaga tcaaggaggt cccccgcccg
 661  aggaagcggc tgacggaact gctgcttcga acggccacag agaagccagg gccggcggaa
 721  gctgcccgcc aggcatcggc ctcccgtgcc tggggcctcc gcttttccg aagccccag
 781  caggtgctgc cctcaccaga tgggcggcgg gcagcaggtg tccgcctagc agtcactaga
 841  ctggagggtg tcgatgaggc cacccgtgca gtgcccacgg agacatgag agacctccct
 901  tgtgggctgg tgctcagcag cattgggtat gagagccgcc ctgtcgaccc aagcgtgccc
 961  tttgactcca agcttgggt catccccaat gtggagggcc gggttatgga tgtgccaggc
1021  ctctactgca gcggctgggt gaagagagga cctacaggtg tcatagccac aaccatgact
1081  gacagcttcc tcaccggcca gatgctgctg caggacctga aggctgggtt gctcccctct
1141  ggccccaggc ctggctacgc agccatccag gccctgctca gcagccgagg ggtccggcca
1201  gtctctttct cagactggga gaagctggat gccgaggagg tggccggggg ccagggcacg
1261  gggaagccca gggagaagct ggtggatcct caggagatgc tgcgcctcct gggccactga SEQ ID NO: 66 Human FDXR amino acid sequence (isoform 7)
   1  medkdrehpq ahvdiyekqp vpfglvrfgv apdhpevknv intftqtahs grcafwgnve
  61  vgrdvtvpel reayhavvls ygaedhrale ipgeelpgvc sarafvgwyn glpenqelep
 121  dlscdtavil gqgnvaldva riiltppehl ertditkaal gvlrqsrvkt vwlvgrrgpl
 181  qvaftikelr emiqlpgarp ildpvdflgl qdkikevprp rkrltelllr tatekpgpae
 241  aarqasasra wglrffrspq qvlpspdgrr aagvrlavtr legvdeatra vptgdmedlp
 301  cglvlssigy ksrpvdpsvp fdsklgvipn vegrvmdvpg lycsgwvkrg ptgviattmt
 361  dsfltgqmll qdlkagllps gprpgyaaiq allssrgvrp vsfsdwekld aeevargqgt
 421  gkpreklvdp qemlrllgh SEQ ID NO: 67 Human FDX2 cDNA sequence
   1  atggccgcct ccatggcccg gggaggcgtg agtgccaggg ttctactgca ggctgccagg
  61  ggcacctggt ggaacgacc tggggcact tccgggtcgg ggagggggt ggcgctgggg
 121  acaaccagaa agtttcaagc gacaggctcg cgcccggctg gagaggagga cgcgggcggc
 181  ccggagcggc ccggggacgt ggtgaacgtg gtgttcgtag accgctcagg ccagcggatc
 241  ccagtgagtg gcagagtcgg ggacaatgtt cttcacctgg cccagcgcca cggggtggac
 301  ctggaagggg cctgtgaagc ctccctggcc tgctccacct gccatgtgta tgtgagtgaa
 361  gaccaccgg atctcctgcc tcctcccgag gagagggaag acgacatgct agacatggcc
 421  ccctcctcc aggagaactc gcggctgggc tgccagattg tgctgacacc ggagctggaa
 481  ggagcggaat tcacccctgcc caagatcacc aggaacttct acgtggatgg ccatgtcccc
 541  aagccccact ga SEQ ID NO: 68 Human FDX2 amino acid sequence
   1  maasmarggv sarvllqaar gtwwnrpggt sgsgegvalg ttrkfqatgs rpageedagg
  61  perpgdvvnv vfvdrsgqri pvsgrvgdnv lhlaqrhgvd legaceasla cstchvyvse
 121  dhldllpppe ereddmldma pllqensrig cqivltpele gaeftlpkit rnfyvdghvp
 181  kph b) NFS1 Pharmacodynamic Biomarkers SEQ ID NO: 69 Human Aco1 cDNA sequence (transcript variant 1)
   1  atgagcaacc cattcgcaca ccttgctgag ccattggatc ctgtacaacc aggaaagaaa
  61  ttcttcaatt tgaataaatt ggaggattca agatatgggc gcttaccatt ttcgatcaga
 121  gttcttctgg aagcagccat tcggaattgt gatgagtttt tggtgaagaa acaggatatt
 181  gaaaatattc tacattggaa tgtcacgcag cacaagaaca tagaagtgcc atttaagcct
 241  gctcgtgtca tcctgcagga ctttacgggt gtgcccgctg tggttgactt tgctgcaatg
 301  cgtgatgctg tgaaaaagtt aggaggagat ccagagaaaa taaaccctgt ctgccctgct
 361  gatcttgtaa tagatcattc catccaggtt gatttcaaca aagggcaga cagtttacag
 421  aagaatcaag acctggaatt tgaaagaaat agagagcagt tgaattttt aaagtggggt
 481  tcccaggctt ttcacaacat gcggattatt ccccctggct caggaatcat ccaccaggtg
 541  aatttggaat atttggcaag agtggtattt gatcaggatg gatattatta cccagacagc
 601  ctcgtgggca gactcgca cactaccatg attgatggct ggggcattct tggttggggt
 661  gtcggtggta ttgaagcaga agtgtcatg ctgggtcagc caatcagtat ggtgcttcct
 721  caggtgactg gctacaggct gatggggaag ccccacccctc tggtaacatc cactgacatc
 781  gtgctcacca ttaccagca cctccgccag ttggggtag tgggcaaatt tgtcgagttc
 841  ttcggcctg gagtagccca gttgtccatt gctgaccgag ctacgattgc taacatgtgt
 901  ccagagtacg gagcaactgc tgccttttc ccagttgata aagttagtat cacgtacctg
 961  gtgcaaacag tcgtgatga agaaaaatta aagtatatta aaaaatatct tcaggctgta
1021  ggaatgtttc gagatttcaa tgacccttct caagaccag acttcaccca ggttgtggaa
1081  ttagatttga aaacagtagt gccttgctgt agtggaccca aaggcctca ggacaaagtt
1141  gctgtgtccg acatgaaaa ggactttgag agctgccttg gagccaagca aggatttaaa
1201  ggattccaag ttgctcctga acatcataat gaccataaga cctttatcta tgataaacact
```

TABLE 1-continued

```
1261    gaattcaccc ttgctcatgg ttctgtggtc attgctgcca ttactagctg cacaaacacc
1321    agtaatccgt ctgtgatgtt aggggcagga ttgttagcaa agaaagctgt ggatgctggc
1381    ctgaacgtga tgccttacat caaaactagc ctgtctcctg ggagtggcgt ggtcacctac
1441    tacctacaag aaagcggagt catgccttat ctgtctcctg ttgggtttga cgtggtgggc
1501    tatggctgca tgacctgcat tggcaacagt gggcctttac ctgaacctgt ggtagaagcc
1561    atcacacagg gagaccttgt agctgttgga gtactatctg gaaacaggaa ttttgaaggt
1621    cgagttcacc ccaacacccg ggccaactat ttagcctctc cccccttagt aatagcatat
1681    gcaattgctg gaaccatcag aatcgacttt gagaaagagc cattgggagt aaatgcaaag
1741    ggacagcagg tatttctgaa agatatctgg ccgactagg acgagatcca ggcagtggag
1801    cgtcagtatg tcatcccggg gatgtttaag gaagtctatc agaaaataga gactgtgaat
1861    gaaagctgga atgccttagc aaccccatca gataagctgt ttttctggaa ttccaaatct
1921    acgtatatca aatcaccacc attctttgaa aacctgactt tggatcttca gccccctaaa
1981    tctatagtgg atgcctatgt gctgctaaat ttgggagatt cggtaacaac tgaccacatc
2041    tccccagctg gaaatattgc aagaaacagt cctgctctc gctacttaac taacagaggc
2101    ctaactccac gagaattcaa ctcctatggc tcccgccgag gtaatgacgc cgtcatggca
2161    cggggaacat tgccaacat tcgcttgtta aacagatttt gaacaagca ggcaccacag
2221    actatccatc tgccttctgg ggaaatcctt gatgtgtttg atgctgctga gcggtaccag
2281    caggcaggcc ttcccctgat cgttctggct ggcaaagagt acggtgcagg cagctcccga
2341    gactgggcag ctaagggccc tttcctgctg gaatcaaag ccgtcctggc cgagagctac
2401    gagcgcattc accgcagtaa cctggttggg atgggtgtga tcccacttga atatctccct
2461    ggtgagaatg cagatgccct ggggctcaca gggcaagaac gatacactat cattattcca
2521    gaaaacctca aaccacaaat gaaagtccag gtcaagctgg acactggcaa gaccttccag
2581    gctgtcatga ggtttgacac tgatgtggag ctcacttatt tcctcaacgg gggcatcctc
2641    aactacatga tccgcaagat ggccaagtag SEQ ID NO: 70 Human Acol cDNA sequence (transcript variant 2)
   1    atgagcaacc cattcgcaca ccttgctgag ccattggatc ctgtacaacc aggaaagaaa
  61    ttcttcaatt tgaataaatt ggaggattca agatatgggc gcttaccatt ttcgatcaga
 121    gttcttctgg aagcagccat tcggaattgt gatgagtttt ggtgaagaa acagatatt
 181    gaaaatattc tacattggaa tgtcacgcag cacaagaaca tagaagtgcc atttaagcct
 241    gctcgtgtca tcctgcagga ctttacgggt gtgcccgctg tggttgactt tgctgcaatg
 301    cgtgatgctg tgaaaaagtt aggaggagat ccagagaaaa taaaccctgt ctgccctgct
 361    gatcttgtaa tagatcattc catccaggtt gatttcaaca aagggcaga cagtttacag
 421    aagaatcaag acctggaact tgaaagaaat agagagcgat ttgaattttt aaagtgggat
 481    tcccaggctt ttcacaacat gcggattatt ccccctggct caggaatcat ccaccaggtg
 541    aatttggaat atttggcaag agtggtattt gatcaggatg gatattata cccagacagc
 601    ctcgtgggca cagactcgca cactaccatg attgatggct tgggcattct tggttggggt
 661    gtcggtggta ttgaagcaga agctgtcatg ctgggtcaac caatcagtat ggtgcttcct
 721    caggtgattg ctacaggct gatggggaag cccaccctc tggtaacatc cactgacatc
 781    gtgctcacca ttaccaagca cctccgccag gttggggtag tgggcaaatt tgtcgagttc
 841    ttcgggcctg gagtagccca gttgtccatt gctgaccgag ctacgattgc taacatgtgt
 901    ccagagtacg gagcaactgc tgccttttc ccagttgatg aagttagtat cacgtacctg
 961    gtgcaaacag gtcgtgatga agaaaaatta aagtatatta aaaaatatct tcaggctgta
1021    ggaatgtttc gagatttcaa tgacccttct caagaccag acttcaccca ggttgtggaa
1081    ttagatttga aaacagtagt gccttgctgt agtggaccca aaaggcctca ggacaaagtt
1141    gctgtgtccg acatgaaaaa ggactttgag agctgccttg gagccaagca aggatttaaa
1201    ggattccaag ttgctcctga acatcataat gaccataaga cctttatcta tgataacact
1261    gaattcaccc ttgctcatgg ttctgtggtc attgctgcca ttactagctg cacaaacacc
1321    agtaatccgc ctgtgatgtt aggggcagga ttgttagcaa agaaagctgt ggatgctggc
1381    ctgaacgtga tgccttacat caaaactagc ctgtctcctg ggagtggcgt ggtcacctac
1441    tacctacaag aaagcggagt catgccttat ctgtctcagc ttgggtttga cgtggtgggc
1501    tatggctgca tgacctgcat tggcaacagt gggcctttac ctgaacctgt ggtagaagcc
1561    atcacacagg gagaccttgt agctgttgga gtactatctg gaaacaggaa ttttgaaggt
1621    cgagttcacc ccaacacccg ggccaactat ttagcctctc cccccttagt aatagcatat
1681    gcaattgctg gaaccatcag aatcgacttt gagaaagagc cattgggagt aaatgcaaag
1741    ggacagcagg tatttctgaa agatatctgg ccgactagag acgagatcca ggcagtggag
1801    cgtcagtatg tcatcccggg gatgtttaag gaagtctatc agaaaataga gactgtgaat
1861    gaaagctgga atgccttagc aaccccatca gataagctgt ttttctggaa ttccaaatct
1921    acgtatatca aatcaccacc attctttgaa aacctgactt tggatcttca gccccctaaa
1981    tctatagtgg atgcctatgt gctgctaaat ttgggagatt cggtaacaac tgaccacatc
2041    tccccagctg gaaatattgc aagaaacagt cctgctctc gctacttaac taacagaggc
2101    ctaactccac gagaattcaa ctcctatggc tcccgccgag gtaatgacgc cgtcatggca
2161    cggggaacat ctgccaacat tcgcttgtta aacagatttt gaacaagca ggcaccacag
2221    actatccatc tgccttctgg ggaaatcctt gatgtgtttg atgctgctga gcggtaccag
2281    caggcaggcc ttcccctgat cgttctggct ggcaaagagt acggtgcagg cagctcccga
2341    gactgggcag ccaagggccc cttcctgctg gaaccaaag ccgcctggc cgagagctac
2401    gagcgcattc accgcagtaa cctggttggg atgggtgtga tcccacttga atatctccct
2461    ggtgagaatg cagatgccct ggggctcaca gggcaagaac gatacactat cattattcca
2521    gaaaacctca aaccacaaat gaaagtccag gtcaagctgg atactggcaa gaccttccag
2581    gctgtcatga ggtttgacac tgatgtggag ctcacttatt tcctcaacgg gggcatcctc
2641    aactacatga tccgcaagat ggccaagtag SEQ ID NO: 71 Human Acol amino acid sequence
   1    msnpfahlae pldpvqpgkk ffnlnkleds rygrlpfsir vlleaairnc deflvkkqdi
  61    enilhwnvtq hknievpfkp arvilqdftg vpavvdfaam rdavkklggd pekinpvcpa
 121    dlvidhsiqv dfnrradslq knqdlefern rerfeflkwg sqafhnmrii ppsgiihqv
 181    nleylarvvf dqdgyypds lvgtdshttm idglgilgwg vgieaeavm lgqpismvlp
 241    qvigyrlmgk phplvtstdi vltitkhlrq vgvvgkfvef fgpgvaqlsi adratianmc
 301    peygataaff pvdevsityl vqtgrdeekl kyikkylqav gmfrdfndps qdpdftqvve
 361    ldlktvvpcc sgpkrpqdkv avsdmkkdfe sclgakqgfk gfqvapehhn dhktfiydnt
```

TABLE 1-continued

```
 421   eftlahgsvv  iaaitsctnt  snpsvmlgag  llakkavdag  lnvmpyikts  lspgsgvvty
 481   ylqesgvmpy  lsqlgfdvvg  ygemtcigns  gplpepvvea  itqgdlvavg  vlsgnrnfeg
 541   rvhpntrany  laspplviay  aiagtiridf  ekeplgvnak  gqqvflkdiw  ptrdeiqave
 601   rqyvipgmfk  evyqkietvn  eswnalatps  dklffwnsks  tyikspffe   nltldlqppk
 661   sivdayvlln  lgdsvttdhi  spagniarns  paaryltnrg  ltprefnsyg  srrgndavma
 721   rgtfanirll  nrflnkqapq  tihlpsgeil  dvfdaaeryq  qaglplivla  gkeygagssr
 781   dwaakgpfll  gikavlaesy  erihrsnlvg  mgvlpleylp  genadalglt  gqerytiiip
 841   enlkpqmkvq  vkldtgktfq  avmrfdtdve  ltyflnggil  nymirkmak
```

SEQ ID NO: 72 Human Aco2 cDNA sequence
```
    1   atggcgccct  acagcctact  ggtgactcgg  ctgcagaaag  ctctgggtgt  gcggcagtac
   61   catgtggcct  cagtcctgtg  ccaacgggcc  aaggtggcga  tgagccactt  tgagcccaac
  121   gagtacatcc  attatgacct  gctagagaag  aacattaaca  ttgttcgcaa  acgactgaac
  181   cggccgctga  cactctcgga  gaagattgtg  tatggacacc  tggatgaccc  cgccagccag
  241   gaaattgagc  gaggcaagtc  gtacctgcgg  ctgcggccgg  accgtgtggc  catgcaggat
  301   gcgacggccc  agatggccat  gctccagttc  atcagcagcg  ggctgtccaa  ggtggctgtg
  361   ccatccacca  tccactgtga  ccatctgatt  gaagcccagg  ttggggcga   gaaagacctg
  421   cgccgggcca  aggacatcaa  ccaggaagtt  tataatttcc  tggcaactgc  aggtgccaaa
  481   tatggcgtgg  gcttctggaa  gcctggatct  ggaatcattc  accagattat  tctggaaaac
  541   tatgcgtacc  ctggtgttct  tctgattggc  actgactccc  acccccaa    tggtggcggc
  601   cttggggca   tctgcattgg  agttgggggt  ggcgatgctg  tggatgtcat  ggctgggatc
  661   ccctgggagc  tgaagtgccc  caaggtgatt  ggcgtgaagc  tgacgggctc  tctctccggt
  721   tggtcctcac  ccaaagatgt  gatcctgaag  gtggcaggca  tcctcacggt  gaaaggtggc
  781   acaggtgcaa  tcgtggaata  ccacgggcct  ggtgtagact  ccatctcctg  cactggcatg
  841   gcgacaatct  gcaacatggg  tgcagaaatt  ggggccacca  cttccgtgtt  ccctacaac
  901   cacaggatga  agaagtacct  gagcaagacc  ggccgggaag  acattgccaa  tctagctgat
  961   gaattcaagg  atcacttggt  gcctgaccct  ggctgccatt  atgaccaact  aattgaaatt
 1021   aacctcagtg  agctgaagcc  acacatcaat  gggccttca   ccctgacct   ggctcaccct
 1081   gtggcagaag  tgggcaaggt  ggcagagaag  gaaggatggc  ctctggacat  ccgagtgggt
 1141   ctaattggta  gctgcaccaa  ttcaagctat  gaagatatgg  ggcgctcagc  agctgtggcc
 1201   aagcaggcac  tggcccatgg  cctcaagtgc  aagtcccagt  tcaccatcac  tccaggttct
 1261   gagcagatcc  gcgccaccat  tgagcgggac  ggctatgcac  agatcttgag  ggatctgggt
 1321   ggcattgtcc  tggccaatgc  ttgtggcccc  tgcattggcc  agtgggacag  gaaggacatc
 1381   aagaagggg   agaagaacac  aatcgtcacc  tcctacaaca  ggaacttcac  gggccgcaac
 1441   gacgcaaacc  ccgagaccca  tgcctttgtc  acgtcccag   agattgtcac  agccctggcc
 1501   attgcggaa   ccctcaagtt  caacccagag  accgactacc  tgacgggcac  ggatggcaag
 1561   aagttcaggc  tggaggctcc  ggatgcagat  gagcttccca  agggggagtt  tgacccaggg
 1621   caggacaccc  accagcaccc  acccaaggac  agcagcgggc  agcatgtgga  cgtgagcccc
 1681   accagccagc  gcctgcagct  cctggagcct  tttgacaagt  gggatggcaa  ggacctggag
 1741   gacctgcaga  tcctcatcaa  ggtcaagggg  aagtgtacca  ctgaccacat  ctcagctgct
 1801   ggccctggc   tcaagttccg  tgggcacttg  gataacatct  ccaacaacct  gctcattggt
 1861   gccatcaaca  ttgaaaacgg  caaggccaac  tccgtgcgca  atgccgtcac  tcaggagttt
 1921   ggccccgtcc  ctgacactgc  ccgctactac  aagaaacatg  gcatcaggtg  ggtggtgatc
 1981   ggagacgaga  actacgcga   gggctcgagc  cgggagcatg  cagctctgga  gcctcgccac
 2041   cttggggcc   gggccatcat  caccaagagc  tttgccagga  tccacgagac  caacctgaag
 2101   aaacagggcc  tgctgcctct  gaccttcgct  gacccggctg  actacaacaa  gattcaccct
 2161   gtggacaagc  tgaccattca  gggcctgaag  gacttcaccc  ctggcaagcc  cctgaagtgc
 2221   atcatcaagc  accccaacgg  gacccaggag  accatcctcc  tgaaccacac  cttcaacgag
 2281   acgcagattg  agtggttccg  cgctggcagt  gccctcaaca  gaatgaagga  actgcaacag
 2341   tga
```

SEQ ID NO: 73 Human Aco2 amino acid sequence
```
    1   mapysllvtr  lqkalgvrqy  hvasvlcqra  kvamshfepn  eyihydllek  ninivrkrln
   61   rpltlsekiv  yghlddpasq  eiergksylr  lrpdrvamqd  ataqmamlqf  issglskvav
  121   pstihcdhli  eaqvggekdl  rrakdinqev  ynflatagak  ygvgfwkpgs  giihqiilen
  181   yaypgvllig  tdshtpnggg  lggicigvgg  adavdvmagi  pwelkcpkvi  gvkltgslsg
  241   wsspkdvilk  vagiltvkgg  tgaiveyhgp  gvdsisctgm  aticnmgaei  gattsvfpyn
  301   hrmkkylskt  gredianlad  efkdhlvpdp  gchydqliei  nlselkphin  gpftpdlahp
  361   vaevgkvaek  egwpldirvg  ligsctnssy  edmgrsaavk  kqalahglkc  ksqftitpgs
  421   eqiratierd  gyaqilrdlg  givlanacgp  cigqwdrkdi  kkgekntivt  synrnftgrn
  481   danpethafv  tspeivtala  iagtlkfnpe  tdyltgtdgk  kfrleapdad  elpkgefdpg
  541   qdtyqhppkd  ssgqhvdvsp  tsqrlqllep  fdkwdgkdle  dlqilikvkg  kcttdhisaa
  601   gpwlkfrghl  dnisnnllig  ainiengkan  svrnavtqef  gpvpdtaryy  kkhgirwvvi
  661   gdenygegss  rehaaleprh  lggraiitks  farihetnlk  kqgllpltfa  dpadynkihp
  721   vdkltiqglk  dftpgkplkc  iikhpngtqe  tillnhtfne  tqiewfrags  alnrmkelqq
```

SEQ ID NO: 74 Human TFR1 cDNA sequence (transcript variant 1)
```
    1   atgatggatc  aagctagatc  agcattctct  aacttgtttg  gtgagaacc   attgtcatat
   61   acccggttca  gcctggctcg  gcaagtagat  ggcgataaca  gtcatgtgga  gatgaaactt
  121   gctgtagatg  aagaagaaaa  tgctgacaat  aacacaaagg  ccaatgtcac  aaaaccaaaa
  181   aggtgtagtg  gaagtatctg  ctatgggact  attgctgtga  tcgtcttttt  cttgattgga
  241   tttatgattg  gctacttggg  ctattgtaaa  ggggtagaac  caaaaactga  gtgtgagaga
  301   ctggcaggaa  ccgagtctcc  agtgagggag  gagccaggag  aggacttccc  tgcagcacgt
  361   cgcttatatt  gggatgacct  gaagagaaag  ttgtcggaga  actggacag   cacagacttc
  421   accggcacca  tcaagctgct  gaatgaaaat  tcatatgtcc  ctcgtgaggc  tggatctcaa
  481   aaagatgaaa  tcttcgtt   gtatgttgaa  atcaatttc   gtgaatttaa  actcagcaaa
  541   gtctggcgtg  atcaacattt  tgttaagatt  caggtcaaag  acagcgctca  aaactcggtg
  601   atcatagttg  ataagaacgg  tagacttgtt  tacctggtgg  agaatcctgg  gggttatgtg
  661   gcgtatagta  aggctgcaac  agttactggt  aaactggtcc  atgctaattt  tggtactaaa
  721   aaagatttg   aggatttata  cactcctgtg  aatggatcta  tagtgattgt  cagagcaggg
```

TABLE 1-continued

```
 781   aaaatcacct ttgcagaaaa ggttgcaaat gctgaaagct taaatgcaat tggtgtgttg
 841   atatacatgg accagactaa atttcccatt gttaacgcag aactttcatt cttttggacat
 901   gctcatctgg ggacaggtga cccttacaca cctgattcc cttccttcaa tcacactcag
 961   cttccaccat ctcggtcatc aggattgcct aatatacctg tccagacaat ctccagagct
1021   gctgcagaaa agctgtttgg gaatatggaa ggagactgtc cctctgactg gaaaacagac
1081   tctacatgta ggatggtaac ctcagaaagc aagaatgtga agctcactgt gagcaatgtg
1141   ctgaaagaga taaaaattct taacatcttt ggagttatta aaggctttgt agaaccagat
1201   cactatgttg tagttggggc ccagagagat gcatgggcc ctggagctgc aaaatccggt
1261   gtaggcacag ctctcctatt gaaacttgcc cagatgttct cagatatggt cttaaaagat
1321   gggtttcagc ccagcagaag cattatcttt gccagttgga gtgctggaga cttttggatcg
1381   gttggtgcca ctgaatggct agagggatac cttcgtccc tgcatttaaa ggctttcact
1441   tatattaatc tggataaagc ggttcttggt accagcaact tcaaggtttc tgccagccca
1501   ctgttgtata cgcttattga gaaaacaatg caaaatgtga agcatccggt tactgggcaa
1561   tttctatatc aggacagcaa ctgggccagc aaagttgaga aactcacttt agacaatgct
1621   gctttcccctt tccttgcata tctggaatc ccagcagttt cttttctgttt ttgcgaggac
1681   acagattatc cttatttggg taccaccatg acacctata aggaactgat tgagaggatt
1741   cctgagttga acaaagtggc acgagcagct gcagaggtcg ctggtcagtt cgtcgattaaa
1801   ctaacccatg atgttgaatt gaacctggac tatgagaggt acaacagcca actgctttca
1861   tttgtgaggg atctgaacca atacagagca gacataaagg aaatgggcct gagtttacag
1921   tggctgtatt ctgctcgtgg agacttcttc cgtgctactt ccagactaac aacagatttc
1981   gggaatgctg agaaaacaga cagatttgtc atgaagaaac tcaatgatcg tgtcatgaga
2041   gtggagtatc acttcctctc tccctacgta tctccaaaag agtctccttt ccgacatgtc
2101   ttctggggct ccggctctca cacgctgcca gctttactgg agaacttgaa actgcgtaaa
2161   caaaataacg gtgcttttaa tgaaacgctg ttcagaaacc agttggctct agctacttgg
2221   actattcagg gagctgcaaa tgccctctct ggtgacgttt gggacattga caatgagttt
2281   taa SEQ ID NO: 75 Human TFR1 cDNA sequence (transcript variant 2)
   1   atgatggatc aagctctagat cagcattctct aacttgtttg gtggagaacc attgtcatat
  61   acccggttca gcctggctcg gcaagtagat ggcgataaca gtcatgtgga gatgaaactt
 121   gctgtagatg aagaagaaaa tgctgacaat aacacaaagg ccaatgtcac aaaaccaaaa
 181   aggtgtagtg gaagtatctg ctatgggact attgctgtga tcgtcttttt cttgattgga
 241   tttatgattg gctacttggg ctattgtaaa ggggtagaac caaaaactga gtgtgagaga
 301   ctggcaggaa ccgagtctcc agtgagggag gagcagtgga aggacttccc tgcagcacgt
 361   cgcttatatt gggatgacct gaagagaaag ttgtcggaga aactggacag cacagacttc
 421   accggcacca tcaagctgct gaatgaaaat tcatatgtcc ctcgtgaggc tggatctcaa
 481   aaagacgaaa atcttgcgtt gtatgttgaa aatcaatttc gtgaatttaa actcagcaaa
 541   gtctggcgtg atcaacattt tgttaagatt caggtcaaag acagcgctca aaactcggtg
 601   atcatagttg ataagaacgg tagacttgtt tacctggtgg agaatcctgg ggttatgtg
 661   gcgtatagta aggctgcaac agttactggt aaactggtcc atgctaattt tggtactaaa
 721   aaagattttg aggatttata cactcctgtg aatggatcta tagtgattgt cagagcaggg
 781   aaaatcacct ttgcagaaaa ggttgcaaat gctgaaagct taaatgcaat tggtgtgttg
 841   atatacatgg accagactaa atttcccatt gttaacgcag aactttcatt cttttggacat
 901   gctcatctgg ggacaggtga cccttacaca cctgattcc cttccttcaa tcacactcag
 961   tttccaccat ctcggtcatc aggattgcct aatatacctg tccagacaat ctccagagct
1021   gctgcagaaa agctgtttgg gaatatggaa ggagactgtc cctctgactg gaaaacagac
1081   tctacatgta ggatggtaac ctcagaaagc aagaatgtga agctcactgt gagcaatgtg
1141   ctgaaagaga taaaaattct taacatcttt ggagttatta aaggctttgt agaaccagat
1201   cactatgttg tagttggggc ccagagagat gcatgggcc ctggagctgc aaaatccggt
1261   gtaggcacag ctctcctatt gaaacttgcc cagatgttct cagatatggt cttaaaagat
1321   gggtttcagc ccagcagaag cattatcttt gccagttgga gtgctggaga cttttggatcg
1381   gttggtgcca ctgaatggct agagggatac cttcgtccc tgcatttaaa ggctttcact
1441   tatattaatc tggataaagc ggttcttggt accagcaact tcaaggtttc tgccagccca
1501   ctgttgtata cgcttattga gaaaacaatg caaaatgtga agcatccggt tactgggcaa
1561   tttctatatc aggacagcaa ctgggccagc aaagttgaga aactcacttt agacaatgct
1621   gctttcccctt tccttgcata ttctggaatc ccagcagttt cttttctgttt ttgcgaggac
1681   acagattatc cttatttggg taccaccatg acacctata aggaactgat tgagaggatt
1741   cctgagttga acaaagtggc acgagcagct gcagaggtcg ctggtcagtt cgtcgattaaa
1801   ctaacccatg atgttgaatt gaacctggac tatgagaggt acaacagcca actgctttca
1861   tttgtgaggg atctgaacca atacagagca gacataaagg aaatgggcct gagtttacag
1921   tggctgtatt ctgctcgtgg agacttcttc cgtgctacct ccagactaac aacagatttc
1981   gggaatgctg agaaaacaga cagatttgtc atgaagaaac tcaatgatcg tgtcatgaga
2041   gtggagtacc acttcctctc tccctacgta tctccaaaag agtctccttt ccgacatgtc
2101   ttctggggct ccggctctca cacgctgcca gctttactgg agaacttgaa actgcgtaaa
2161   caaaataacg gtgcttttaa tgaaacgctg ttcagaaacc agttggctct agctacttgg
2221   actattcagg gagctgcaaa tgccctctct ggtgacgttt gggacattga caatgagttt
2281   taa SEQ ID NO: 76 Human TFR1 amino acid sequence
   1   mmdqarsafs nlfggcplsy trfslarqvd gdnshvemkl avdeeenadn ntkanvtkpk
  61   rcsgsicygt iavivfflig fmigylgyck gvepktecer lagtespvrc epgedfpaar
 121   rlywddlkrk lsekldstdf tgtikllnen syvpreagsq kdenlalyve nqfrefklsk
 181   vwrdqhfvki qvkdsaqnsv iivdkngrlv ylvenpggyv ayskaatvtg klvhanfgtk
 241   kdfedlytpv ngsivivrag kitfaekvan aeslnaigvl iymdqtkfpi vnaelsffgh
 301   ahlgtgdpyt pgfpsfnhtq fppsrssglp nipvqtisra aaeklfgnme gdcpsdwktd
 361   stcrmvtses knvkltvsnv lkeikilnif gvikgfvepd hyvvvgaqrd awgpgaaksg
 421   vgtalllkla qmfsdmvlkd gfqpsrsiif aswsagdfgs vgatewlegy lsslhlkaft
 481   yinldkavlg tsnfkvsasp llytliektm qnvkhpvtgq flyqdsnwaa kvekltldna
 541   afpflaysgi pavsfefced cdypylgttm dtykelieri pelnkvaraa aevagqfvik
 601   lthdvelnld yerynsqlls fvrdlnqyra dikemglslq wlysargdff ratsrlttdf
```

TABLE 1-continued

```
 661  gnaektdrfv mkklndrvmr veyhflspyv spkespfrhv fwgsgshtlp allenlklrk
 721  qnngafnetl frnqlalatw tiqgaanals gdvwdidnef
```

SEQ ID NO: 77 Human TFR2 cDNA sequence (transcript variant 1)
```
    1  atggagcggc tttggggtct attccagaga gcgcaacaac tgtcccaag atcctctcag
   61  accgtctacc agcgtgtgga aggcccccgg aaagggcacc tggaggagga agaggaagac
  121  ggggaggagg gggcggagac attggcccac ttctgcccca tggagctgag gggccctgag
  181  cccctgggct ctagacccag cagccaaac ctcattccct gggcggcagc aggacggagg
  241  gctgccccct acctggtcct gacggccctg ctgatcttca ctggggcctt cctactgggc
  301  tacgtcgcct tccgagggtc ctgccaggcg tgcggagact ctgtgttggt ggtcagtgag
  361  gatgtcaact atgagcctga cctggatttc accagggca gactctactg gagcgacctc
  421  caggccatgt tcctgcagtt cctgggggag gggcgcctgg aggacaccat caggcaaacc
  481  agccttcggg aacgggtggc aggctcggcc gggatggcgg ctctgactca ggacattcgc
  541  gcggcgctct cccgccagaa gctggaccac gtgtggaccg acacgcacta cgtggggctg
  601  caattcccgg atccggctca cccaacacc ctgcactggg tcgatgaggc cgggaaggtc
  661  ggagagcagc tgccgctgga ggaccctgac gtctactgcc cctacagcgc catcggcaac
  721  gtcacggagg agctggtgta cgcccactac gggcgggccg aagacctgca ggacctgcgg
  781  gccaggggcg tggatccagt gggccgcctg ctgctggtgc gcgtgggggt gatcagcttc
  841  gcccagaagg tgaccaatgc tcaggacttc ggggctcaag gagtgctcat atacccagag
  901  ccagcggact ctccccagga cccacccaag ccaagcctgt ccagccagca ggcagtgtat
  961  ggacatgtgc acctgggaac tggagacccc tacacacctg gcttccctc cttcaatcaa
 1021  acccagttcc ctccagttgc atcatcaggc cttcccagca tccagccca gcccatcagt
 1081  gcagacattg cctcccgcct gctgaggaag ctcaaaggcc ctgtgccccc caagaatggg
 1141  caggggagcc tcctaggctc cccttatcac ctgggcccg ggccacgact gcggctagtg
 1201  gtcaacaatc acaggacctc caccccccatc aacaacatct tcggctgcat cgaacggccgc
 1261  tcagagccag atcactacgt tgtcatcggg gcccagaggg atgcatgggg cccaggagca
 1321  gctaaatccg ctgtggggac ggctatactc ctggagctgg tgcggacctt ttcctccatg
 1381  gtgagcaacg gcttccggcc ccgcagaagt ctcctcttca tcagctggga cggtggtgac
 1441  tttggaagcg tgggctccac ggagtggcta gagggctacc tcagcgtgct gcacctcaaa
 1501  gccgtagtgt actgtgagcct ggacaacgca gtgctggggg atgacaagtt tcatgccaag
 1561  accagccccc ttctgacaag tctcattgag agtgtcctga gcaggtgga ttctcccaac
 1621  cacagtgggc agactctcca tgaacaggtg gtgttcacca atcccagctg ggatgctgag
 1681  gtgatccggc ccctacccat ggacagcagt gcctattcct tcacggcctt tgtgggagtc
 1741  cctgccgtcg agttctcctt tatggaggac gaccaggcct acccattcct gcacacaaag
 1801  gaggacactt atgagaacct gcataaggtg ctgcaaggcc gcctgcccgc cgtggcccag
 1861  gccgtggccc agctcgcagg gcagctcctc atccggctca gccacgatcg cctgctgccc
 1921  ctcgacttcg gccgctacgg ggacgtcgtc ctcaggcaca tcgggaacct caacgagttc
 1981  tctggggacc tcaaggcccg cgggctgacc ctgcagtgga tgtactcgg gcggggggac
 2041  tacatccggg cggcggaaaa gctgcggcag gagatctaca gctcggagga gagagacgag
 2101  cgactgacac gcatgtacaa cgtgcgcata atgcgggtgg agttctactt cctttcccag
 2161  tacgtgtcgc cagccgactc ccgttccgc cacatcttca tgggccgtgg agaccacgcg
 2221  ctggggcgcc tgctggacca cctgcggctg gtgcgctcca acagctccgg gaccccgggg
 2281  gccacctcct ccactggctt ccaggagagc cgtttccggc gtcagctagc cctgctcacc
 2341  tggacgctgc aaggggcagc caatgcgctt agcggggatg tctggaacat tgataacaac
 2401  ttctga
```

SEQ ID NO: 78 Human TFR2 amino acid sequence (isoform 1)
```
    1  merlwglfqr aqqlsprssq tvyqrvegpr kghleeeeed geegaetlah fcpmelrgpe
   61  plgsrprqpn lipwaaagrr aapylvltal liftgafllg yvafrgscqa cgdsvlvvse
  121  dvnyepdldf hqgrlywsdl qamflqflge grledtirqt slrervagsa gmaaltqdir
  181  aalsrqkldh vwtdthyvgl qfpdpahpnt lhwvdeagkv geqlpledpd vycpysaign
  241  vtgelvyahy grpedlqdlr argvdpvgrl llvrvgvisf aqkvtnaqdf gaqgvliype
  301  padfsqdppk pslssqqavy ghvhlgtgdp ytpgfpsfnq tqfppvassg lpsipaqpis
  361  adiasrllrk lkgpvapqew qgsllgspyh lgpgprlrlv vnnhrtstpi nnifgciegr
  421  SEQdhyvvig aqrdawgpga aksavgtail lelvrtfssm vsngfrprrs llfiswdggd
  481  fgsvgstewl egylsvlhlk avvyvsldna vlgddkfhak tsplltslie svlkqvdspn
  541  hsgqtlyeqv vftnpswdae virplpmdss aysftafvgv pavefsfmed dqaypflhtk
  601  edtyenlhkv lqgrlpavaq avaqlagqll irlshdrllp ldfgrygdvv lrhignlnef
  661  sgdlkarglt lqwvysargd yiraaeklrq eiysseerde rltrmynvri mrvefyflsq
  721  yvspadspfr hifmgrgdht lgalldhlrl lrsnssgtpg atsstgfqes rfrrqlallt
  781  wtlqgaanal sgdvwnidnn f
```

SEQ ID NO: 79 Human TFR2 cDNA sequence (transcript variant 2)
```
    1  atggccgctc tgactcagga cattcgcgcg gcgctctccc gccagaagct ggaccacgtg
   61  tggaccgaca cgcactacgt ggggctgcaa ttcccggatc cggctcaccc caacaccctg
  121  cactgggtcg atgaggccgg gaaggtcgga gagcagctgc cgctggagga ccctgacgtc
  181  tactgcccct acagcgccat cggcaacgtc acgggagagc tggtgtacgc ccactacggg
  241  cggcccgaag acctgcagga cctgcgggcc aggggcgtgg atccagtggg ccgcctgctg
  301  ctggtgcgcg tgggggtgat cagcttcgcc cagaaggtga ccaatgctca ggacttcggg
  361  gctcaaggag tgctcatata cccagagcca gcggacttct ccaggaccc acccaagcca
  421  agcctgtcca gccagcaggc agtgtatgga catgtgcacc tgggaactgg agaccccta c
  481  acacctggct tccttcctt caatcaaacc cagttccctc cagttgcatc atcaggcctt
  541  cccagcatcc agcccagcc catcagtgca gacattgctc ccgcctgctg aggaagctca
  601  aaaggccctg tgcccccca gaatggcag gggagcctcc taggctcccc ttatcacctg
  661  ggccccgggc cacgactgcg gctagtggtc aacaatcaca ggacctccac cccccatcaa
  721  aacatcttcg gctgcatcga aggccgctca gagccagatc actacgttgt catcggggcc
  781  cagagggatg catggggccc aggagcagct aaatccgctg tggggacggc tatactcctg
  841  gagctggtgc ggacctttc ctccatggtg agcaacggct tccggcccg cagaagtctc
  901  ctcttcatca gctgggacgg tggtgacttt ggaagcgtgg gctccacgga gtggctagaa
  961  ggctacctca gcgtgctgca cctcaaagcc gtagtgtacg tgagcctgga caacgcagtg
```

TABLE 1-continued

```
1021  ctggggacg   acaagtttca  tgccaagacc  agcccccttc  tgacaagtct  cattgagagt
1081  gtcctgaagc  aggtggattc  tcccaaccac  agtgggcaga  ctctctatga  acaggtggtg
1141  ttcaccaatc  ccagctggga  tgctgaggtg  atccggcccc  tacccatgga  cagcagtgcc
1201  tattccttca  cggcctttgt  gggagtccct  gccgtcgagt  tctcctttat  ggaggacgac
1261  caggcctacc  cattcctgca  cacaaaggag  gacacttatg  agaacctgca  taaggtgctg
1321  caaggccgcc  tgcccgccgt  ggcccaggcc  gtggcccagc  tcgcagggca  gctcctcatc
1381  cggctcagcc  acgatcgcct  gctgcccctc  gacttcggcg  gctacgggga  cgtcgtcctc
1441  aggcacatcg  ggaacctcaa  cgagttctct  ggggacctca  aggcccgcgg  gctgaccctg
1501  cagtgggtgt  actcggcgcg  ggggactac   atccgggcgg  cggaaaagct  gcggcaggag
1561  atctacagct  cggaggagag  agacgagcga  ctgacacgca  tgtacaacgt  gcgcataatg
1621  cgggtggagt  tctacttcct  ttcccagtac  gtgtcgcag   ccgactcccc  gttccgccac
1681  atcttcatgg  gccgtggaga  ccacacgctg  ggcgccctgc  tggaccacct  cgggctgctg
1741  cgctccaaca  gctccgggac  ccccggggcc  acctcctcca  ctggcttcca  ggagagccgt
1801  ttccggcgtc  agctagccct  gctcacctgg  acgctgcaag  gggcagccaa  tgccgcttagc
1861  ggggatgtct  ggaacattga  taacaacttc  tga
```

SEQ ID NO: 80 Human TFR2 amino acid sequence (isoform 2)

```
  1  maaltqdira  alsrqkldhv  vtdthyvglq  fpdpahpntl  hwvdeagkvg  eqlpledpdv
 61  yepysaignv  tgelvyahyg  rpedlqdlra  rgvdpvgrll  lvrvgvisfa  qkvtnaqdfg
121  aqgvliypep  adfsqdppkp  slsaqqavyg  hvhlgtgdpy  tpgfpsfnqt  qfppvassgl
181  psipaqpisa  diasrllrkl  kgpvapqewq  gsllgspyhl  gpgprlrlvv  nnhrtstpin
241  nifgeiegrs  epdhyvviga  qrdawgpaa   ksavgtaill  elvrtfssmv  sngfrprrsl
301  lfiswdggdf  gsvgstewle  gylsvlhlka  vvyvsldnav  lgddkfhakt  splltslies
361  vlkqvdspnh  sgqtlyeqvv  ftnpswdaev  irplpmdssa  ysftafvgvp  avefsfmedd
421  qaypflhtke  dtyenlhkvl  qgrlpavaqa  vaqlagqlli  rlshdrllpl  dfgrygdvvl
481  rhignlnefs  gdlkargltl  qwvysargdy  iraaeklrqe  iyssedrdcr  ltrmynvrim
541  rvefyflsqy  vspadspfrh  ifmgrgdhtl  galldhlrll  rsnssgtpga  tsstgfqesr
601  frrqlalltw  tlqgaanals  gdvwnidnnf
```

SEQ ID NO: 81 Human Hif2a cDNA sequence

```
   1  atgacagctg  acaaggagaa  gaaaaggagt  agctcggaga  ggaggaagga  gaagtcccgg
  61  gatgctgcgc  ggtgccggcg  gagcaaggag  acggaggtgt  tctatgagct  ggcccatgag
 121  ctgcctctgc  cccacagtgt  gagctccat   ctggacaagg  cctccatcat  gcgactggca
 181  atcagcttcc  tgcgaacaca  caagctcctc  tcctcagttt  gctctgaaaa  cgagtccgaa
 241  gccgaagctg  accagcagat  ggacaacttg  tacctgaaag  ccttggaggg  tttcattgcc
 301  gtggtgaccc  aagatggcga  catgatcttt  ctgtcagaaa  acatcagcaa  gttcatggga
 361  cttacacagg  tggagctaac  aggacatagt  atctttgact  tcactcatcc  ctgcgaccat
 421  gaggagattc  gtgagaacct  gagtctcaaa  aatggctctg  gttttggaaa  aaaagcaaa
 481  gacatgtcca  cagagcggga  cttcttcatg  aggatgaagt  gcacggtcac  caacagaggc
 541  cgtactgtca  acctcaagtc  agccacctgg  aaggtcttgc  actgcacggg  ccaggtgaaa
 601  gtctacaaca  actgccctcc  tcacaatagt  ctgtgtggct  acaaggagcc  cctgctgtcc
 661  tgcctcatca  tcatgtgtga  accaatccag  cacccatcc   acatggacat  cccccctgat
 721  agcaagacct  tcctgagccg  ccacagcatg  gacatgaagt  tcacctactg  tgatgacaga
 781  atcacagaac  tgattggtta  ccaccctgag  gagctgcttg  gccgctcagc  ctatgaattc
 841  taccatgcgc  tagactccga  gaacatgacc  aagagtcacc  agaacttgtg  caccaagggt
 901  caggtagtaa  gtggccagta  ccggatgctc  gcaaagcatg  ggggctacgt  gtggctggaa
 961  acccagggga  cggtcatcta  caaccctcgc  aacctgcagc  cccagtgcat  catgtgtgtc
1021  aactacgtcc  tgagtgagat  tgagaagaat  gacgtggtgt  tctccatgga  ccagactgaa
1081  tccctgttca  gcccccacct  gatggccatg  aacagcatct  ttgatagcag  tggcaagggg
1141  gctgtgtctg  agaagagtaa  cttcctattc  accaagctaa  gggggatca   ccggagagctg
1201  gcccagctgg  ctcccacccc  aggagacgcc  atcatctctc  tggatttcgg  gaatcagaac
1261  ttcgaggagt  cctcagccta  tggcaaggcc  atcctgcccc  gagccagcc   atgggccacg
1321  gagttgagga  gccacagcac  ccagagcgag  gctgggagcc  tgcctgcctt  caccgtgccc
1381  caggcagttg  ccccggggca  caccaccccc  agtgctcaca  gcaggagcag  cagctgctcc
1441  acgcccaata  gccctgaaga  ctattacaca  tctttggata  acgacctgga  gattgaagtg
1501  attgagaagc  tcttcgccat  ggacacagag  gccaaggacc  aatgcagtac  ccagacggat
1561  ttcaatgagc  tggacttgga  gacactggca  cctatatcc   ccatggacgg  ggaagacctc
1621  cagctaagcc  ccatctgccc  cgaggagcgg  ctcttggcgg  agaacccaca  gtccacccc
1681  cagcactgct  tcagtgccat  gacaaacatc  ttccagccac  tggccccgca  agccccgcac
1741  agtcccttcc  tcctggacaa  gtttcagcag  cagctggaga  gcaagaagac  agagcccgag
1801  caccggccca  tgcctccat   cttctttgat  gccgaagca   aagcatccct  gccaccgtgc
1861  tgtggccagg  ccagcacccc  tctctcttcc  atgggggca   gatccaatac  ccagtggccc
1921  ccagatccac  cattacattt  tgggcccaca  aagtgggacg  tcgggagtca  ggcacagag
1981  ttcttgggag  cagcgccgt   ggggccccct  gtctcCccac  cccatgtctc  caccttcaag
2041  acaagttctg  caaagggttt  tggggctcga  ggcccagacg  tgctgagtcc  ggccatggta
2101  gccctctcca  caagctgaa   gctgaagcga  cagctggagt  atgaagagca  agccttccag
2161  gacctgagcg  ggggggaccc  acctggtggc  gacacctcac  atttgatgtg  gaaacggatg
2221  aagaacctca  ggggtgggag  ctgcccttg   atgccggaca  agccactgag  cgcaaatgta
2281  cccaatgata  gttcaccca   aaaccccatg  aggggcctgg  gccatcccct  gagacatctg
2341  ccgctgccac  agcctccatc  tgccatcagt  cccggggaga  acagcaagag  caggttcccc
2401  ccacagtgct  acgccaccca  gtaccaggac  tacagctcgt  cgtcagccca  caggtgtca
2461  ggcatggcaa  gccggctgct  cgggccctca  tttgagtcct  acctgctgcc  gaactgacc
2521  agatatgact  gtgaggtgaa  cgtgccccgt  ctgggaagct  ccacgctcct  gcaaggaggg
2581  gacctcctca  gagccctgga  ccaggccacc  tga
```

SEQ ID NO: 82 Human Hif2a amino acid sequence

```
  1  mtadkekkrs  sserrkeksr  daaccrrske  tevfyelahe  lplphsvssh  ldkasimria
 61  isflrthkll  asvesenese  aeadqqmdnl  ylkalegfia  vvtqdgdmif  lseniskfmg
121  ltqveltghs  ifdfthpcdh  eeirenlslk  nsgfgkksk   dmsterdffm  rmkctvtnrg
181  rtvnlksatw  kvlhctgqvk  vynncpphns  lcgykeplls  clilmoepiq  hpshmdipld
```

TABLE 1-continued

```
 241    sktflarhsm dmkftycddr iteligyhpe ellgrsayef yhaldsenmt kshqnlctkg
 301    qvvsgqyrml akhggyvwle tqgtviynpr nlqpqcimcv nyvlseiekn dwfsmdqte
 361    slfkphlmam nsifdssgkg avseksnflf tklkeepeel aqlaptpgda iisldfgnqn
 421    feessaygka ilppsqpwat elrshstqse agslpaftvp qaaapgsttp satsssssscs
 481    tpnspedyyt sldndlkiev ieklfamdte akdqcstqtd fneldletla pyipmdgedf
 541    qlspicpeer llaenpqstp qhcfsamtni fqplapvaph spflldkfqq qleskktepe
 601    hrpmssiffd agskaslppc cgqastplss mggrsntqwp pdpplhfgpt kwavgdqrte
 661    flgaaplgpp vspphvstfk trsakgfgar gpdvlspamv alsnklklkr qleyeeqafq
 721    dlsggdppgg stshlmwkrm knlrggscpl mpdkplsanv pndkftqnpm cglghplrhl
 781    plpqppsais pgensksrfp pqcyatqyqd yslssahkvs gmasrllgps fesyllpelt
 841    rydcevnvpv lgsstllqgg dllraldqat SEQ ID NO: 83 Human PTGS2 cDNA sequence
    1   atgctcgccc gcgccctgct gctgtgcgcg gtcctggcgc tcagccatac agcaaatcct
   61   tgctgttccc acccatgtca aaaccgaggt gtatgtatga gtgtgggatt tgaccagtat
  121   aagtgcgatt gtacccggac aggattctat ggagaaaact gctcaacacc ggaattttg
  181   acaagaataa aattatttct gaaacccact ccaaacacag tgcactacat acttacccac
  241   ttcaagggat tttggaacgt tgtgaataac attccctcc ttcgaaatgc aattatgagt
  301   tatgtgttga catccagatc acatttgatt gacagtccac caacttacaa tgctgactat
  361   ggctacaaaa gctgggaagc cttctctaac ctctcctatt atactagagc ccttcctcct
  421   gtgcctgatg attgcccgac tcccttgggt gtcaaaggta aaaagcagct tcctgattca
  481   aatgagattg tggaaaaatt gcttctaaga agaaagttca tccctgatcc ccagggctca
  541   aacatgatgt ttgcattctt tgcccagcac ttcacgcatc agttttcaa gacagatcat
  601   aagcgagggc cagctttcac caacgggctg ggccatgggg tggacttaaa tcatatttac
  661   ggtgaaactc tggctagaca gcgtaaactg cgcctttca aggatgaaaa aatgaaatat
  721   cagataattg atggagagat gtatcctccc acagtcaaag atactcaggc agagatgatc
  781   taccctcctc aagtccctga gcatctacgg tttgctgtgg ggcaggaggt ctttggtctg
  841   gtgcctggtc tgatgatgta tgccacaatc tggctgcggg aacacaacag agtatgcgat
  901   gtgcttaaac aggagcatcc tgaatggggt gatgagcagt tgttccagac aagcaggcta
  961   atactgatag gagagactat taagattgcg attgaagatt atgtgcaaca cttgagtggc
 1021   tatcacttca aactgaaatt tgacccagaa ctactttca acaaacaatt ccagtaccaa
 1081   aatcgtattg ctgctgaatt taacaccctc tatcactggc atccccttct gcctgacacc
 1141   tttcaaattc atgaccagaa atacaactat caacagttta tctacaacaa ctctatattg
 1201   ctggaacatg gaattaccca gtttgttgaa tcattcacca ggcaaattgc tggcagggtt
 1261   gctggtggta ggaacgttcc acccgcagta cagaaagtat cacaggcttc cattgaccag
 1321   agcaggcaga tgaaatacca gtcttttaat gagtaccgca aacgctttat gctgaagccc
 1381   tatgaatcac ttgaagaact tacaggagaa aaggaaatgt ctgcagagtt ggaagcactc
 1441   tatggtgaca tcgatgctgt ggagctgtat ccCgcccttc tggtagaaaa gcctcggcca
 1501   gatgccatct ttggtgaaac catggcagaa gttggagcac cactctcctt gaaaggactt
 1561   atgggtaatg ttatatgttc tcctgcctac tggaagccaa gcacttttgg tggagaagtg
 1621   ggttttcaaa tcatcaacac tgcctcaatt cagtctctca tctgcaataa cgtgaagggc
 1681   tgtcccttta cttcattcag tgttccagat ccagagctca ttaaaacagt caccatcaat
 1741   gcaagttctt cccgctccgg actagatgat atcaatccca cagtactact aaaagaacgt
 1801   tcgactgaac tgtag SEQ ID NO: 84 Human PTGS2 amino acid sequence
    1   mlaralllca vlalshtanp ccshpcqnrg vcmsvgfdqy kcdctrtgfy gencstpefl
   61   triklflkpt pntvhyilth fkgfwnvvnn ipflrnaims yvltsrshli dspptynady
  121   gyksweafsn lsyytralpp vpddcptplg vkgkkqlpds neivekllr rkfipdpqgs
  181   nmmfaffaqh fthqffktdh krgpaftngl ghgvdlnhiy getlarqrkl rlfkdgkmky
  241   qiidgemypp tvkdtqaemi yppqvpehlr favgqevfgl vpglmmyati wlrehnrvcd
  301   vlkqehpewg deqlfqtsrl iligetikiv iedyvqhlsg yhfklkfdpe llfnkqfqyq
  361   nriaaefntl yhwhpllpdt fqihdqkyny qqfiynnsil lehgitqfve sftrqiagrv
  421   aggrnvppav qkvsqasidq srqmkyqsfn eyrkrfmlkp yesfeeltge kemsaeleal
  481   ygdidavely pallvekprp daifgetmve vgapfslkgl mgnvicspay wkpstfggev
  541   gfqiintasi qslicnnvkg cpftsfsvpd peliktvtin asssrsgldd inptvllker
  601   stel
```

Human Succinate Dehydrogenase
Human Ferritin

Lipid Reactive Oxygen Species

1) Decreased conversion of cysteine to alanine or methylene blue
2) Induction and/or promotion of initochondrial dysfunction:
   a) Decrease in aconitase copy number, amount, and/or activity
   b) Decrease in succinate dehydrogenase copy number, amount, and/or activity
3) Induction and/or promotion of iron regulatory protein dysfunction:
   a) Decrease in ferritin copy number, amount, and/or activity
   b) Increase in transferrin-receptor copy number, amount, and/or activity
   c) Decrease in Hif2alpha copy number, amount, and/or activity
4) Induction and/or promotion of ferroptosis
   a) Increase and/or accumulation of lipid reactive oxygen species (ROS)
   b) Increase in PTGS2 (COX2) copy number, amount, and/or activity Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein, Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 04%. 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.

II. Subjects

In one embodiment, the subject liar whom cancer treatment is administered or who is predicted likelihood of efficacy of an anti-cancer therapy (e.g., iron-sulfur cluster biosynthesis pathway inhibitory therapy) is determined, is a mammal (e.g., mouse, rat, primate, non-human mammal, domestic animal such as dog, cat, cow, horse), and is preferably a human.

In another embodiment of the methods of the invention, the subject has not undergone treatment, such as chemotherapy, radiation therapy, targeted therapy, and/or anti-cancer therapy (e.g., non-sulfur cluster biosynthesis pathway inhibitory therapy). In still another embodiment, the subject has undergone treatment, such as chemotherapy, radiation therapy, targeted therapy, and/or anti-cancer therapy (e.g., iron-sulfur cluster biosynthesis pathway inhibitory therapy).

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the invention can be used to determine the responsiveness to anti-cancer therapy (e.g., iron-sulfur cluster biosynthesis pathway inhibitory therapy) of many different cancers in subjects such as those described above. In one embodiment, the cancers are hematologic cancers, such as leukemia. In another embodiment, the cancers are solid tumors, such as lung cancer, melanoma, and/or renal cell carcinoma. In another embodiment, the cancer is an epithelial cancer such as, but not limited to, brain cancer (e.g., glioblastomas) bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer. OT skin cancer.

III. Sample Collection, Preparation and Separation

In some embodiments, biomarker presence, absence, amount, and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples, such as the normal copy number, amount, or activity of a biomarker in the cell or tissue type of a member of the same species as from which the test sample was obtained or a non-diseased cell or tissue from the subject from which the test samples was obtained. As described herein, a "pre-determined" biomarker amount and/or activity measurement(s) may be a biomarker amount and/or activity measurement(s) used to, by way of example only, evaluate a subject that may be selected for treatment, evaluate a response to an anti-cancer therapy (e.g., iron-sulfur duster biosynthesis pathway inhibitory therapy), and/or evaluate a response to a combination anti-cancer therapy (e.g., iron-sulfur cluster biosynthesis pathway inhibitory therapy plus immunoinhibitory inhibitor therapy). A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other Factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., biomarker expression normalized to the expression of a housekeeping gene, or gene expression at various time points).

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.5 fold, about 1.0 fold, about 1.5 fold, about 2.0 fold, about 2.5 fold, about 10 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermeable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred liar separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotochophoresis (cITP) and capillary electrochromatography (CEC). An embodiment to couple CE techniques to electrosmy ionization involves the use of volatile solutions, for example, aqueous mixtures containing a volatile acid and/or base and an organic such as an alcohol or acetonitrile.

Capillary isotachophomsis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid thromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A nucleic acid molecule of the invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

Moreover, a nucleic acid molecule of the invention can comprise only a portion of a nucleic acid sequence, wherein the full length nucleic acid sequence comprises a marker of the invention or which encodes a polypeptide corresponding to a marker of the invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic, acid sequence. Probes based CM the sequence of a biomarker nucleic acid molecule can be used to detect transcripts or genomic sequences corresponding to one or more markers of the invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus, in addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the invention or to a nucleic acid molecule encoding a protein corresponding to a marker of the invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring, allelic variants of a nucleic acid molecule of the invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from the naturally-occurring proteins which correspond to the markers of the invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains glycine, asparagine, glutamine, serine, threonine, tyrosine, cysteine), non-polar side chains (e.g., alanine, valine leucine, isoleucine, proline, phenylalanine, methionine tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the invention, e.g., complementary to the coding strand of a double-stranded cDNA molecule corresponding to a marker of the invention or complementary to an mRNA sequence corresponding to a marker of the invention. Accordingly, an antisense nucleic acid molecule of the invention can hydrogen bond to (i.e. anneal with) a sense nucleic acid of the invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a polypeptide corresponding to a selected marker of the invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res*, 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the invention can be designed based upon the nucleotide sequence of a cDNA corresponding to the marker. For example, a derivative of a *Tetrahymena* L-19 IVS RNA can be constructed in which the nucleotide sequence of the active site is complementary to the nucleotide sequence to be cleaved (See Cech et al. U.S. Pat. No. 4,987,071; and Cech et al. U.S. Pat. No. 5,116,742). Alternatively, an mRNA encoding a polypeptide of the invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):1807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al. 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analog. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn at al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the invention are produced by recombinant DNA techniques. Alternative to recombinant expression, a polypeptide corresponding to a marker of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, bat which includes fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted. Call be prepared by recombinant techniques and evaluated for one or more of the functional activities of the native form of a polypeptide of the invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the BLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See the National Center for Biotechnology Information (NCBI) website at ncbi.nlm.nih.gov. Another preferred, non-limiting example of a mathematical algorithm utilized for the comparison of sequences is the algorithm of Myers and Miller, (1988) *Comput Appl Biosci*, 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The invention also provides chimeric or fusion proteins corresponding to a biomarker protein. As used herein, a "chimeric protein" or "fusion protein" comprises all or part (preferably a biologically active part) of a polypeptide corresponding to a marker of the invention operably linked to a heterologous polypeptide (i.e., a polypeptide other than the polypeptide corresponding to the marker). Within the fusion protein, the term "operably linked" is intended to indicate that the polypeptide of the invention and the heterologous polypeptide are fused in-frame to each other. The heterologous polypeptide can be fused to the amino-terminus or the carboxyl-terminus of the polypeptide of the invention.

One useful fusion protein is a GST fusion protein in which a polypeptide corresponding to a marker of the invention is fused to the carboxyl terminus of GST sequences. Such fusion proteins can facilitate the purification of a recombinant polypeptide of the invention.

In another embodiment, the fusion protein contains a heterologous signal sequence, immunoglobulin fusion protein, toxin, or other useful protein sequence. Chimeric and fusion proteins of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into Which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with GST domain.

The present invention also pertains to variants of the biomarker polypeptides described herein. Such variants have art altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang, 1983, *Tetrahedron* 39:3, Itakura at al., 1984, *Annu. Rev. Biochem.* 53:323; Itakura et al., 1984, *Science* 198: 1056; Ike et al., 1983 *Nucleic Acid Res.* 11:477).

In addition, libraries of fragments of the coding sequence of a polypeptide corresponding, to a marker of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the at for screening gene products of combinatorial libraries made by point mutations or truncation, and for screening, cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvap, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

The recombinant expression vectors for use in the invention can be designed for expression of a polypeptide corresponding to a marker of the invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using 17 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of die recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:3140), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTre (Amann et al., 1988. *Gene* 69:301-315) and pET 11d (Stitcher et al., p. 60-89, In *Gene Expression Technology: Methods in Enzymology* vol. 185, Academic Press, San Diego, Calif., 1991), Target biomarker nucleic acid expression from the pTrc vector relies on host RNA polymerase transcription from a hybrid up-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the invention can be carried out by standard DNA synthesis techniques.

In another embodiment, the expression vector is a yeast expression vector. Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et. al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell. Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter, U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation. DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number and/or Genomic Nucleic Acid Mutations

Methods of evaluating the copy number and/or genomic nucleic acid status (e.g., mutations) of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. In some embodiments, the increased copy number of at least one biomarker listed in Table 1 is predictive of better outcome of iron-sulfur cluster biosynthesis pathway inhibitory therapy. A copy number of at least 3, 4, 5, 6, 7, 8, 9, or 10 of at least one biomarker listed in Table 1 is predictive of likely responsive to iron-sulfur cluster biosynthesis pathway inhibitory therapy.

Methods of evaluating the copy number of a biomarker locus include, but are not limited to, hybridization-based assays. Hybridization-based assays include, but are not limited to, traditional "direct robe" methods, such as Southern blots, in situ, hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long, so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the gnome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO* 3: 1227-1234; Pinkel (1988) *Proc. Natl. Acad. Sci. USA* 85: 9138-9142; EPO Pub. No, 430,402; *Methods in Molecular Biology*, Vol. 33: *In situ* Hybridization Protocols, Choo, ed., Humana Press, Totowa, N.J., (1994), etc.) In another embodiment, the hybridization protocol of Pinkel, et al. (1998) *Nature Genetics* 20: 207-211, or of Kallioniemi (1992). *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR)). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc, N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Citiatelli, et al. (1990) *Proc Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kitnura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Biomarker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (ECM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakaini et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium, thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) *J. immunol. Methods* 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Chu. Chem. 42: 9-13 (19%) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos. 6,618,6796; 6,379,897; 6,664,377; 6,451,536; 548,257; U.S. 20030157485 and Schena et al. (1995) *Science* 20, 467-470; Gerhold et al. (1999) *Trends in Biochem. Sci,* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

e. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an anti-cancer therapy (e.g., iron-sulfur cluster biosynthesis pathway inhibitory therapy). Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays. Western blotting, hinder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (un-labeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C) sulphur ($^{35}$S), tritium ($^{3}$H), indium ($^{112}$In), and technetium ($^{99m}$Tc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$ M, $10^{-7}$ M, $10^{-8}$ M, $10^{-9}$ M, $10^{-10}$ M, $10^{-11}$ M or $10^{-2}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may hind preferentially to the biomarker protein relative to other proteins, such as related proteins.

Antibodies are commercially available or may be prepared according to methods known m the art.

Antibodies and derivatives thereof that may be used encompass polyclonal or monoclonal antibodies, chimeric, human, humanized, primatized (CDR-grafted), veneered or single-chain antibodies as well as functional fragments, biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al. WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify sequences or agents that affect translation of iron-sulfur cluster biosynthesis-related genes.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. at al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463, it is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glyeosylase from HeLa cells cleaves T at G/T mismatches (Hsu et al. (1994) *Carcinogenesis* 15:1657-

1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc. Natl. Acad. Sci USA* 86:2766; see also Cotton (1993) *Mutat. Res.* 285:125-144 and Hayashi (1992) Genet. Anal. Tech. Appl. 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The efficacy of anti-cancer therapy (e.g., iron-sulfur cluster biosynthesis pathway inhibitory therapy) is predicted according to biomarker presence, absence, amount and/or activity associated with a cancer (e.g., cancer) in a subject according to the methods described herein. In one embodiment, such anti-cancer therapy (e.g., iron-sulfur cluster biosynthesis pathway inhibitory therapy) or combinations of therapies (e.g., anti-PD-1 and anti-immunoinhibitory therapies) can be administered to a desired subject or once a subject is indicated as being a likely responder to anti-cancer therapy (e.g., iron-sulfur cluster biosynthesis pathway inhibitory therapy). In another embodiment, such anti-cancer therapy (e.g., iron-sulfur cluster biosynthesis pathway inhibitory therapy) can be avoided once a subject is indicated as not being a likely responder to the anti-cancer therapy (e.g., iron-sulfur duster biosynthesis pathway inhibitory therapy) and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with or without anti-cancer therapy (e.g., iron-sulfur cluster biosynthesis pathway inhibitory therapy).

The iron-sulfur duster biosynthesis pathway and exemplary agents useful for inhibiting the iron-sulfur cluster biosynthesis pathway, or other biomarkers described herein, have been described above.

The term "targeted therapy" refers to administration of agents that selectively interact with a chosen biomolecule to thereby treat cancer. For example, targeted therepy regarding the inhibition of immune checkpoint inhibitor is useful in combination with the methods of the present invention. The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, g49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). Inhibition of one or more immune checkpoint inhibitors can block or otherwise neutralize inhibitory signaling to thereby upregulate an immune response in order to more efficaciously treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, mitochondrial cofactor therapy is useful. For example, vitamin E s known to block cell death via ferroptosis such that mitochondria cofactor therapy can alleviate or improve any toxicity associated with ISC biosynthesis pathway inhibition. Mitochondrial cofactor therapies are well known in the art and include, for example, coenzyme Q10 (ubiquinone), riboflavin, thiamin, niacin, vitamin K (phylloquinone and menadione), creatine, carnitine, and other antioxidants such as ascorbic acid and lipoic acid (see, for example. Marriage et al. (2003) *J. Am. Diet. Assoc.* 103:1029-1038 and Parikh et al. (2009) *Curr. Treat. Options Neurol.* 11:414-430).

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents alkylating agents, arsenic compounds. DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 200.1; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H. et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman. Chapter 16: Principles of Cancer Management: Radiation Therapy, 6th edition, 2001, DeVita et al., eds. J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, ulucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch). PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects, of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers, Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter— less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-cancer therapy (e.g., iron-sulfur cluster biosynthesis pathway inhibitory therapy) may vary according to the particular iron-sulfur cluster biosynthesis pathway inhibitor agent or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific and such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites M a subject (see below).

Nucleic acids can be delivered in any desired vector. These include viral or non viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci, 88:2726-2730, 1991).

A gene delivery vehicle can optionally comprise Viral sequences such as a viral origin of replication or packaging signal. These viral sequences can be selected from viruses such as astrovirus, coronavirus, orthomyxovirus, papovavirus, paramyxovirus, parvovirus, picornavirus, poxviras, retrovirus, togavirus or adenovirus. In a preferred embodiment, the growth factor gene delivery vehicle is a recombinant retroviral vector. Recombinant retroviruses and various uses thereof have been described in numerous references including, for example, Maim et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO90/07936: WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Rain et al., Cancer Res. 53:83-88, 1993; Takamiya et al., S. Neurosci. Res. 33:493-503, 1992; Baba et al., J. Neurosurg. 79:729-735, 1993 (U.S. Pat. No. 4,777,127, GB 2,200,651, EP 0,345242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T ed. Vectors: A survey of molecular amino vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer, New York: Plenum Press; Coupar et al. (1988) Gene, 68:1-10), and several RNA viruses. Preferred viruses include an alphavinis, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation oligomerization, etc.) in order to further enhance desirable biological activities, such as increased bioavailability and decreased proteolytic degradation.

4. Clinical Efficacy

Clinical efficacy can be measured by any method known in the art. For example, the response to an anti-cancer therapy (e.g., iron-sulfur cluster biosynthesis pathway inhibitory therapy), relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the cud of therapy. The shorthand for this formula is CBR=CR+PR+SD over 6 months. In some embodiments, the CBR for a particular iron-sulfur cluster biosynthesis pathway inhibitor therapeutic regimen is at least 25%; 30%, 40%; 45%, 50%, 55%; 60%, 65%, 70%, 75%, 80%, 85%, or more.

Additional criteria for evaluating the response to anti-cancer therapy (e.g., iron-sulfur cluster biosynthesis pathway inhibitory therapy) are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival: disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular iron-sulfur cluster biosynthesis pathway inhibitor therapeutic regimen can be administered to a population of subjects and the outcome can be correlated to biomarker measurements that were determined prior to administration of any anti-cancer therapy iron-sulfur cluster biosynthesis pathway inhibitory therapy). The outcome measurement may be pathologic response to therapy given in the neoadjuvant setting. Alternatively, outcome measures, such as overall survival and disease-free survival can be monitored over a period of time for subjects following anti-cancer therapy (e.g., iron-sulfur cluster biosynthesis pathway inhibitory therapy) for whom biomarker measurement values are known. In certain embodiments, the same doses of iron-sulfur cluster biosynthesis pathway inhibitor agents are administered to each subject. In related embodiments, the doses administered are standard doses known in the art for iron-sulfur cluster biosynthesis pathway inhibitor agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-cancer therapy (e.g., iron-sulfur cluster biosynthesis pathway inhibitory therapy) can be determined using methods such as those described in the Examples section.

5. Further Uses and Methods of the Present Invention

The compositions described herein can be used in a variety of diagnostic, prognostic, and therapeutic applications regarding biomarkers described herein, such as those listed in Table 1.

a. Screening Methods

One aspect of the present invention relates to screening assays, including non-cell based assays. In one embodiment, the assays provide a method for identifying whether a cancer is likely to respond to anti-cancer therapy (e.g., iron-sulfur cluster biosynthesis pathway inhibitory therapy) and/or whether an agent can inhibit the growth of or kill a cancer cell that is unlikely to respond to anti-cancer therapy (e.g., iron-sulfur cluster biosynthesis pathway inhibitory therapy).

In one embodiment, the invention relates to assays for screening test agents which bind to, or modulate the biological activity of, at least one biomarker listed in Table 1. In one embodiment, a method for identifying, such an agent entails determining the ability of the agent to modulate, e.g. inhibit, the at least one biomarker listed in Table 1.

In one embodiment, an assay is a cell-free or cell-based assay, comprising contacting at least one biomarker listed in Table 1, with a test agent, and determining the ability of the test agent to modulate (e.g. inhibit) the enzymatic activity of the biomarker, such as by measuring direct binding of substrates or by measuring indirect parameters as described below.

In another embodiment, an assay is a cell-free or cell-based assay, comprising contacting at least one biomarker listed in Table 1, with a test agent, and determining the ability of the test agent to modulate the ability of the biomarker to regulate NFS1 or other iron-sulfur cluster biosynthesis pathway member, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and its natural binding partner can be accomplished by determining the ability of the test agent to modulate the activity of a polypeptide or other product that functions downstream or upstream of its position within the iron-sulfur cluster biosynthesis pathway.

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly one aspect of the present invention relates to diagnostic assays for determining the presence, absence, amount, and/or activity level of a biomarker described herein, such as those listed in Table 1, in the context of a biological sample (e.g., blood, serum, cells, or tissue) to thereby determine whether an individual afflicted with a cancer is likely to respond to anti-cancer therapy (e.g., iron-sulfur cluster biosynthesis pathway inhibitory therapy whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers described herein, such as those listed in Table 1.

Another aspect of the present invention pertains to monitoring the influence of agents (e.g., drugs, compounds, and small nucleic acid-based molecules) on the expression or activity of a biomarker listed in Table 1. These and other agents are described in further detail in the following sections.

The skilled artisan will also appreciate that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus From MathSoft (Seattle, Wash.).

In certain embodiments, the computer comprises a database for storage of biomarker data. Such stored profiles can be accessed and used to perform comparisons of interest at a later point in tune. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to anti-cancer therapy (e.g., iron-sulfur cluster biosynthesis pathway inhibitory therapy). In some embodiments, the present invention is useful for classifying a sample (e.g., from a subject) as associated with or at risk for responding to or not responding to anti-cancer therapy (e.g., iron-sulfur cluster biosynthesis pathway inhibitory therapy) using a statistical algorithm and/or empirical data e.g., the amount or activity of a biomarker listed in Table 1).

An exemplary method for detecting the amount or activity of a biomarker listed in Table 1, and thus useful for classifying whether a sample is likely or unlikely to respond to anti-cancer therapy (e.g., iron-sulfur cluster biosynthesis pathway inhibitory therapy) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-cancer therapy (e.g., iron-sulfur cluster biosynthesis pathway inhibitory therapy) responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical 21) classifier systems are used, preferably in tandem. Examples of learning, statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to anti-cancer therapy (e.g., iron-sulfur cluster biosynthesis pathway inhibitory therapy), a biological sample from the subject during remission, or a biological sample from the subject during treatment for developing a cancer progressing despite anti-cancer therapy (e.g., iron-sulfur cluster biosynthesis pathway inhibitory therapy).

d. Prognostic Assays

The diagnostic methods described herein can furthermore be utilized to identify subjects having or at risk of developing a cancer that is likely or unlikely to be responsive to anti-cancer therapy (e.g., iron-sulfur cluster biosynthesis pathway inhibitory therapy). The assays described herein, such as the preceding diagnostic assays of the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

Another aspect of the invention pertains to methods of modulating the expression or activity of one or more biomarkers described herein (e.g., those listed in Table 1 and the Examples or fragments thereof) for therapeutic purposes. The biomarkers of the present invention have been demonstrated to correlate with cancers. Accordingly, the activity and/or expression of the biomarker, as well as the interaction between one or more biomarkers or a fragment thereof and its natural binding partner(s) or a fragment(s) thereof, can be modulated in order to treat cancers.

Modulatory methods of the invention involve contacting a con with one or more biomarkers of the invention, including one or more biomarkers of the invention, including one or more biomarkers listed in Table 1 and the Examples or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the invention, including one or more biomarkers listed in Table 1 and the Examples or a fragment thereof is, e.g., an antisense nucleic acid molecule, RNAi molecule, shRNA, mature miRNA, pre-miRNA, pri-miRNA miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In another embodiment, the agent inhibits one or more biomarker activities. In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Table 1 or 2 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular melanoma, being treated, the extent of the disease and other factors familiar to the physician of skill in the art and can be determined by the physician.

6. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes, (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or so filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", J. Pharm. Sci. 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example. Berge et al, supra).

Wetting agents, emulsifiers and lubricants, such as sodium lauryl sulfite and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a respiration uncoupling agent with liquid carriers, or finely divided solid, carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid, dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents in the ease of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing out or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will well in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

EXAMPLES

Example 1

Materials and Methods for Examples 2-5 a. Cell Lines and Culture Conditions

YD38 was obtained from the Korean Cell Line Bank; IM95 was from the Japanese Collection of Research Bioresources Cell Bank: MKN1 and KE97 were from the Riken Cell Bank; SNUJ-1, WI38 and MDA-M468 were from the American Type Culture Center; MKN74 and YCC1 were provided by the P. Janne Lab; and NHBE were purchased from Lonza (CC-2540). Cells were cultured in DMEM (YCC1), DMEM plus 10 mg/E insulin (IM95), RPMI (MDA-MB469, MKN1, MKN74, SNU1, KE97, and YD38), or EMEM (WI38). All media was supplemented with 10% FBS. NHBE were cultured in BEGM growth medium bullet kit (Lonza CC-3170).

b. RNAi and cDNA Rescue Constructs

NFS1 shRNAs target sequences and corresponding Broad TRC (The RNAi Consortium) numbers and match region are listed in Table 2. Negative controls included a non-targeting shRNA (NT1), and two separate shRNAs specific for luciferase (Luc2 and Luc3). shKIF11, which disrupts mitotic spindle dynamics, served as a positive control for cell death. Pairs of oligos were synthesized (Eurofins MWG Operons) for each target sequence, following the general structure of: ACCG-Oligo A and CGAA-Oligo B, to introduce sticky Bbs1 ends, and where Oligo A is: ACCGG-sense target sequence-GTTAATATTCATAGC(loop; SEQ ID NO: 112)-antisense sequence-TTTT, and Oligo B is: the reverse complement of Oligo A. All shRNAs were cloned into the Cellecta vectors pRSI6-U6-(sh)-UbiC-TagGFP-2A-Puro (for constitutive shRNA expression) and pRSIT12-U6/TO-(sh)-CMV-TetR-TagRFP-Puro (for Dox-inducible shRNA expression) at the Bbs1 sites. Insertion of shRNAs was confirmed by sequencing and by Ssp1 restriction digests.

Overlap PCR was used to generate NFS1-shRNA-resistant cDNA constructs (see Table 4). Wild-type NFS1 cDNA was mutagenized as listed in Table 3 using the primer pairs listed in Table 4, generating silent mutations in NFS1 that cause resistance to knockdown by NFS1-sh1, sh4, or sh6. The sequence-confirmed NFS1-shRNA-resistant mutant PCR products were introduced into the pDONR223 Gateway donor vector, then transferred into a Gateway-adapted pLVS-neo entry vector (by Gateway Cloning, Life Technologies). NFS1-sh5 is an UTR-targeted shRNA and was rescued using wild-type NFS1 cDNA.

TABLE 2

NFS1 and control shRNAs

| shRNA Name | shRNA Target Sequence (Sense) | Broad TRC Library # | Match Region |
|---|---|---|---|
| NFS1-1 | GCTACTGAATCCAACAACATA SEQ ID NO: 86 | TRCN0000148031 | CDS |
| NFS1-2 | GCGCACTCTTCTATCAGGTTT SEQ ID NO: 87 | TRCN0000180881 | CDS |
| NFS1-3 | CCACAAGCGAATCTCAAAGTT SEQ ID NO: 88 | TRCN0000179073 | CDS |
| NFS1-4 | CAGTTCCAGAAAGGTATATTT SEQ ID NO: 89 | TRCN0000229753 | CDS |
| NES1-5 | CTGTGACTCCACCAGTTATTC SEQ ID NO: 90 | TRCN0000229756 | 3' UTR |
| NFS1-6 | AGCGGCTGATACAGAATATAA SEQ ID NO: 91 | TRCN0000218827 | CDS |
| NFS1-7 | GGGACCCTAAGCACCATTATC SEQ ID NO: 92 | TRCN0000229754 | CDS |
| NFS1-8 | TGTGAAGCGTCTTCGAGAAAT SEQ ID NO: 93 | TRCN0000229755 | CDS |
| NT1 | CAACAAGATGAAGAGCACCAA SEQ ID NO: 94 | NA | non-targeting |
| shLU2 | CTTCGAAATGTCCGTTCGGTT SEQ ID NO: 95 | TRCN0000072243 | CDS |
| shLUC3 | CAAATCACAGAATCGTCGTAT SEQ ID NO: 96 | TRCN0000072246 | CDS |
| shKIF11 | GCGTACAAGAACATCTATAAT SEQ ID NO: 97 | TRCN0000116500 | CDS |

TABLE 3

Silent mutations introduced into NFS1 coding sequence

| NFS1 shRNA | Target region in CDS | Mutated Target region | bp mutated |
|---|---|---|---|
| sh1 | GCT ACT GAA TCC AAC AAC ATA SEQ ID NO: 98 | GCA ACG GAG TCG AAT AAT ATC SEQ ID NO: 99 | 7 |
| sh4 | TGC AGT TCC AGA AAG GTA TAT TTC SEQ ID NO: 100 | TGT AGC TCT CGC AAA GTC TAC TTC SEQ ID NO: 101 | 8 |

TABLE 3-continued

Silent mutations introduced into NFS1 coding sequence

| NFS1 shRNA | Target region in CDS | Mutated Target region | bp mutated |
|---|---|---|---|
| sh6 | GAG CGG CTG ATA CAG AAT ATA ATG SEQ ID NO: 102 | GAA CGC CTT ATC CAA AAC ATT ATG SEQ ID NO: 103 | 7 |

Underlined nucleotides are the mutated nucleotides

TABLE 4

Primers used for generating shRNA-resistant NFS1 cDNAs

| Primer Name | Primer ID | 5' TO 3' SEQUENCE |
|---|---|---|
| NMS15 | NFS1_P1 | *GGGGACAACTTTGTACAAAAAAGTTGG*CATGCT GCTCCGAGCCGCTTG SEQ ID NO: 104 |
| NMS16 | NES1_P2 | *GGGGACAACTTTGTACAAGAAAGTTGGG*CTAG TGTTGGGTCCACTTGA SEQ ID NO: 105 |
| NMS11 | NFS1_Sh1_P3 | GATATTATTCGACTCCGTTGCACCACTAGTA AAAATGATCT SEQ ID NO: 106 |
| NMS07 | NFS1_Sh1_P4 | GCAACGGAGTCGAATAATATCGCAATTAAG GGGGTGGCCCG SEQ ID NO: 107 |
| NMS13 | NFS1_SH4_P3 | AAGTAGACTTTGCGAGAGCTACAAATCCGC CCTATTTCTGC SEQ ID NO: 108 |
| NMS09 | NFS1_SH4_P4 | TAGCTCTCGCAAAGTCTACTTCCATACTGAT GCAGCCCAGG SEQ ID NO: 109 |
| NMS14 | NFS1_SH6_P3 | TAATGTTTTGGATAAGGCGTTCTGACAACTT TGAGATTCGC SEQ ID NO: 110 |
| NMS10 | NFS1_SH6_P4 | AACGCCTTATCCAAAACATTATGAAGAGCC TTCCAGATUTG SEQ ID NO: 111 |

Bold nucleotides are the silent mutations introduced in the shRNA-resistant CDS
*Italicized* nucleotides are Gateway adapter sequences

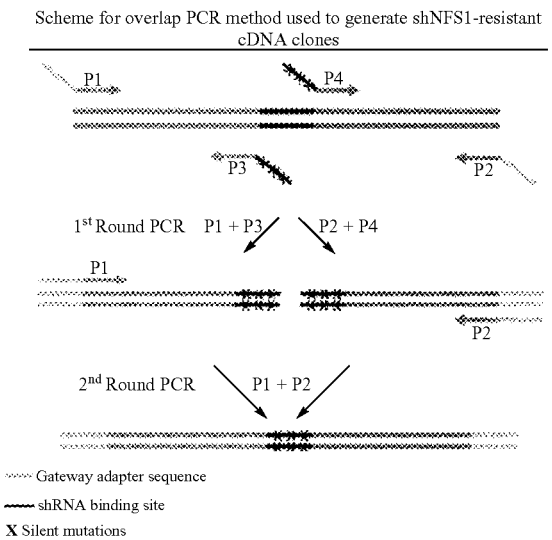

Scheme for overlap PCR method used to generate shNFS1-resistant cDNA clones

- - - - - Gateway adapter sequence
━━━━ shRNA binding site
X Silent mutations c. Virus Production and Infections 293T cells were transfected using Lipofectamine (Life Technologies) and packaging plasmids carrying VSVg and delta 8.2, along with shRNA or (DNA expression vector to generate lentiviral particles. Viral supernatants were collected and cleared by centrifugation. Supernatants containing cDNA virus were concentrated using Lenti-X Concentrator (Clontech), titered by infection in limiting dilution, and used at 8 to 10 uL per 500,000 cells to achieve an MOI of approximately 0.5. Infections using shRNA lentiviruses were carried out using 40 or 50 uL of viral supernatant (using pRS16 or pRSIT12 constructs, respectively) per 100,000 cells, corresponding to an approximate MOI of 3. In generating stable inducible shRNA lines, cells were selected using puromycin (1-3 ug/ml, depending on cell line) for 5-7 days.

d. Proliferation and Enzymatic Assays

Clonogenic assays were performed for longer-term assessment of proliferative phenotypes. Three days following doxycycline (dox)-induction (of stable, inducible shRNA lines using 0.5 ug/mL dox) or infection (for constitutive shRNA expression), cells were trypsinized, counted (Countess Automated Cell Counter. Life Technologies), and re-plated in duplicate or triplicate in 6-well dishes at 750 to 3000 cells per well, depending on cell line. Clonogenic growth was monitored by RFP (pRSIT12 vector) or GFP (pRSI6 vector) expression at 1 week intervals using a laser scanning cytometer to measure colony area and numbers of colonies per well (IsoCyte, ImageXpress Velos). Two to three weeks after plating cells, cells were stained using crystal violet as an additional visualization of colony formation. For shorter-term proliferative assays, cells were also plated onto 96-well plates using the Cell Titer-Glo Luminescent Cell Viability Assay (Promega G7571) to measure cell viability on the day of plating and 6 days post-plating.

Aconitase activity was assessed three to eleven days post-infection or dox induction in one million cells using the Aconitase Activity calorimetric Assay Kit (Biovision K716-100). Succinate dehydrogenase activity was assessed using the Succinate Dehydrogenase Activity Colorimetric Assay Kit (Biovision K660-100).

e. Data Analysis

TCGA (The Cancer Genome Atlas) data were accessed and analyzed via the cBioPortal for Cancer Genomics (through the Computational Biology Center at Memorial Sloan-Kettering Cancer Center (available on the World Wide Web at cbioportal.org/public-portal/). Growth rate normalization was performed when comparing proliferative phenotypes of NFS1 shRNAs and controls across multiple cell lines. Cell Titer-Glo (CTG) measurements were background-corrected, and the specific growth rate, mu, was calculated as $(\ln(aveCTG_{day6}/aveCTG_{day0}))/time$. The data were plotted as $mu/mu_{max}$, where $mu_{max}$ is the average mu of control shRNA-treated wells.

f. RNA Analysis

RNA was purified using the RNeasy Mini Kit (Qiagen), and cDNA synthesized using the SuperScript® VILO Kit (Life Technologies). Quantitative RT-PCR was carried out using Taqman® Assays (Life Technologies, Hs00738907_m1 for NFS1, Hs00153133_m1 for PTGS2, Hs00824723_m1 for Ube, a housekeeping gene control) on a ViiA 7 Real Time PCR System (Life Technologies).

g. Protein Analysis

Cells were lysed in NP-40 lysis buffer (Boston BioProducts) supplemented with 1× Halt Protease/Phosphatase Inhibitor Cocktail (Pierce Biotechnology, Inc.), 1 mM Dithiothreitol, and 1 mM Phenylmethanesulfonylfluoride. Lysates were cleared by centrifugation and quantified using a BCA Protein Assay Kit (Pierce Biotechnology, Inc.). Lysates were resolved by SDS-PAGE (using Mini-Protean TGX gradient gels, Bio-Rad Laboratories), transferred to nitrocellulose (using the iBlot Gel, Transfer Device and Dry Blotting System, Life Technologies) and blocked in 5% nonfat milk (Blotting-Grade Blocker, Bio-Rad). Antibodies for NFS1 (mouse monoclonal antibody B-7, Santa Cruz Biotechnology, Inc.), FTH1 (rabbit monoclonal antibody D1D4 Cell Signaling Technology), and GAPDH (rabbit monoclonal antibody 14C10, Cell Signaling Technology) were diluted 1:1000 in 5% milk in TBS/Tween-20 (Boston BioProducts). Peroxidase-conjugated secondary antibodies (Donkey anti-rabbit IgG or Donkey anti-mouse IgG, Jackson ImmunoResearch Laboratories, Inc.) were used at 1:5000 in 5% blocking solution, and protein bands were detected using Pico SuperSignal West Pico Chemiluminescent substrate (Thermo Scientific, Pierce Biotechnology, Inc.).

Example 2

NFS1 and Other Members of the Iron-Sulfur Cluster Biosynthesis Pathway are Biomarkers of Cancer and Targets for Inhibiting Cancer NFS1 is a pyridoxal-5'-phosphate-dependent cysteine desulfurase that removes inorganic sulfur from cysteine, creating alanine as a byproduct. It is primarily localized to mitochondria and is critical for iron-sulfur cluster biosynthesis and thiomodification of transfer RNAs (tRNAs). The accessory protein ISD11 promotes efficient interaction between NFS1 and its substrate cysteine. NFS1 exists as a heterodimer with ISD11 and binds to ISCU and FXN during iron-sulfur cluster biogenesis. FXN (Frataxin) is an iron-binding protein thought to provide iron for Iron-Sulfur Cluster (ISC) formation. FXN also interacts with NFS1, and may facilitate cysteine binding to NFS1 by exposing its substrate binding sites (Pandey et al. (2013) *J. Biol. Chem.* 288(52)). ISCU serves as a scaffold on which ISC's assemble. A number of proteins (HSCB, HSPA9, GRPEL 1/2, GLRX5, BOLA3, ISCA1/2, IBA57, NUBPL) act as chaperones to transfer ISCs from ISCU to apoproteins requiring ISCs for activity, which include components of the citric acid cycle and oxidative phosphorylation, amongst others. NFU1 may serve as another scaffolding protein for ISC formation (Li et al. (2013) *Biochem.* 52). A schematic diagram further illustrating the iron-sulfur cluster biogenesis pathway is shown in FIG. 1.

Figure 2:
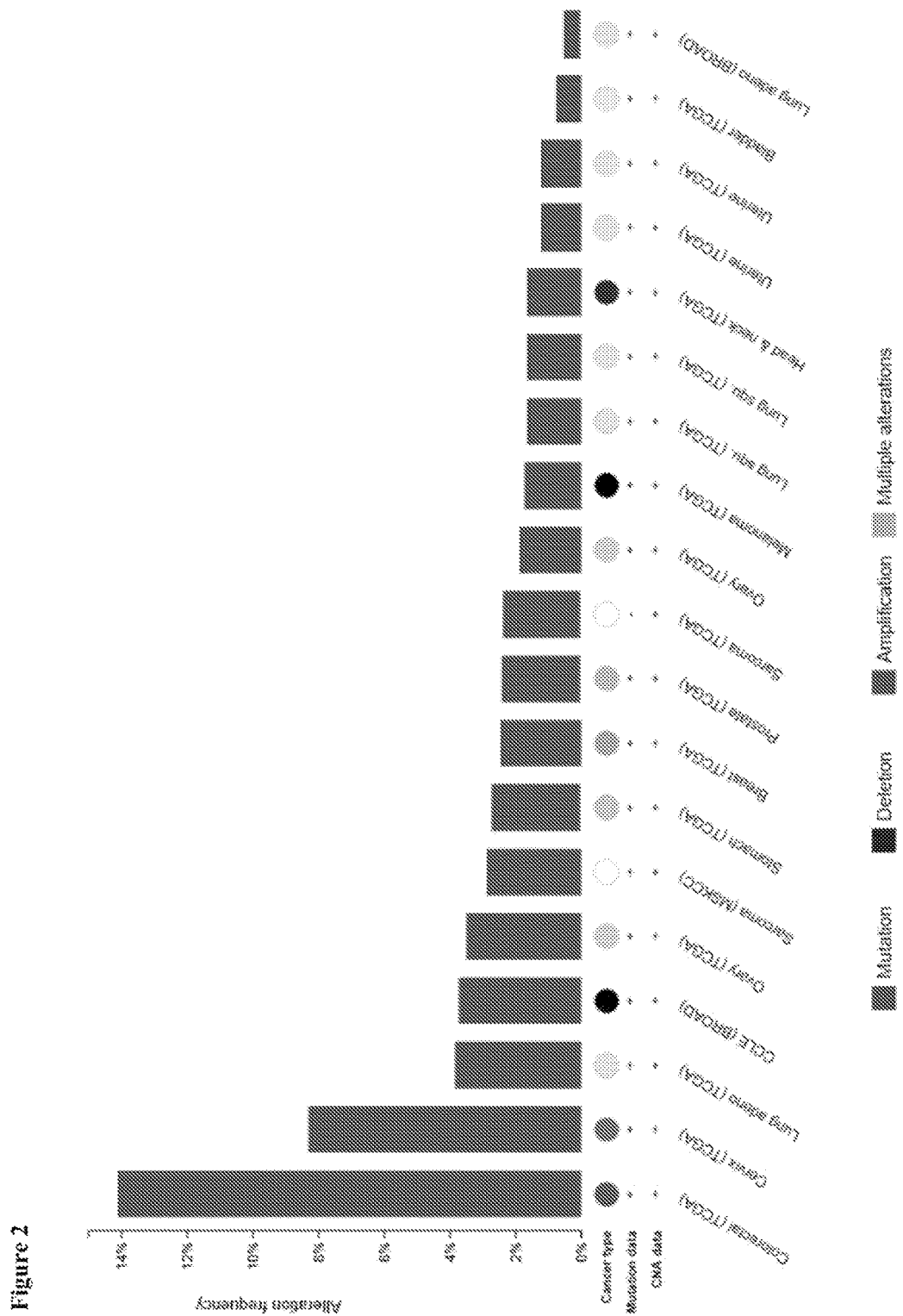
FIG. 2 shows the results of NFS1 amplification assessed across available TCGA (The Cancer Genome Atlas) datasets using the eBioPortal for Cancer Genomics (available on the World Wide Web at cbioportal.org/public-portal/). The inset shows the correlation between copy-number alterations (x-axis, as determined by GISTIC) and mRNA expression (y-axis, by RNASeq) from a representative dataset (colorectal cancer). All histograms shown represent amplifications.

NFS1 is frequently amplified in various human cancers. For example, FIG. 2 shows the results of NFS1 amplification assessed across available TCGA (The Cancer Genome Atlas) datasets using the cBioPortal for Cancer Genomics (available on the World Wide Web at cbioportal.org/public-portal/). Colorectal and cervical cancers exhibit the highest levels of NFS1 amplification. Notably, 15% colorectal cancers of a total of 212 cases showed NFS1 amplification. Approximately 3% stomach cancers of a total of 219 cases also showed NFS1 amplification. Approximately 2-4% of tested breast invasive carcinoma, cervical squamous cancer, king adenocarcinoma, ovarian cystadenoma, prostate carcinoma, sarcoma, and melanoma cases showed NFS1 amplification. NTS1 amplification within a span of 11 genes was also present in recurrent focal amplification in all lung cancers.

Figure 3:
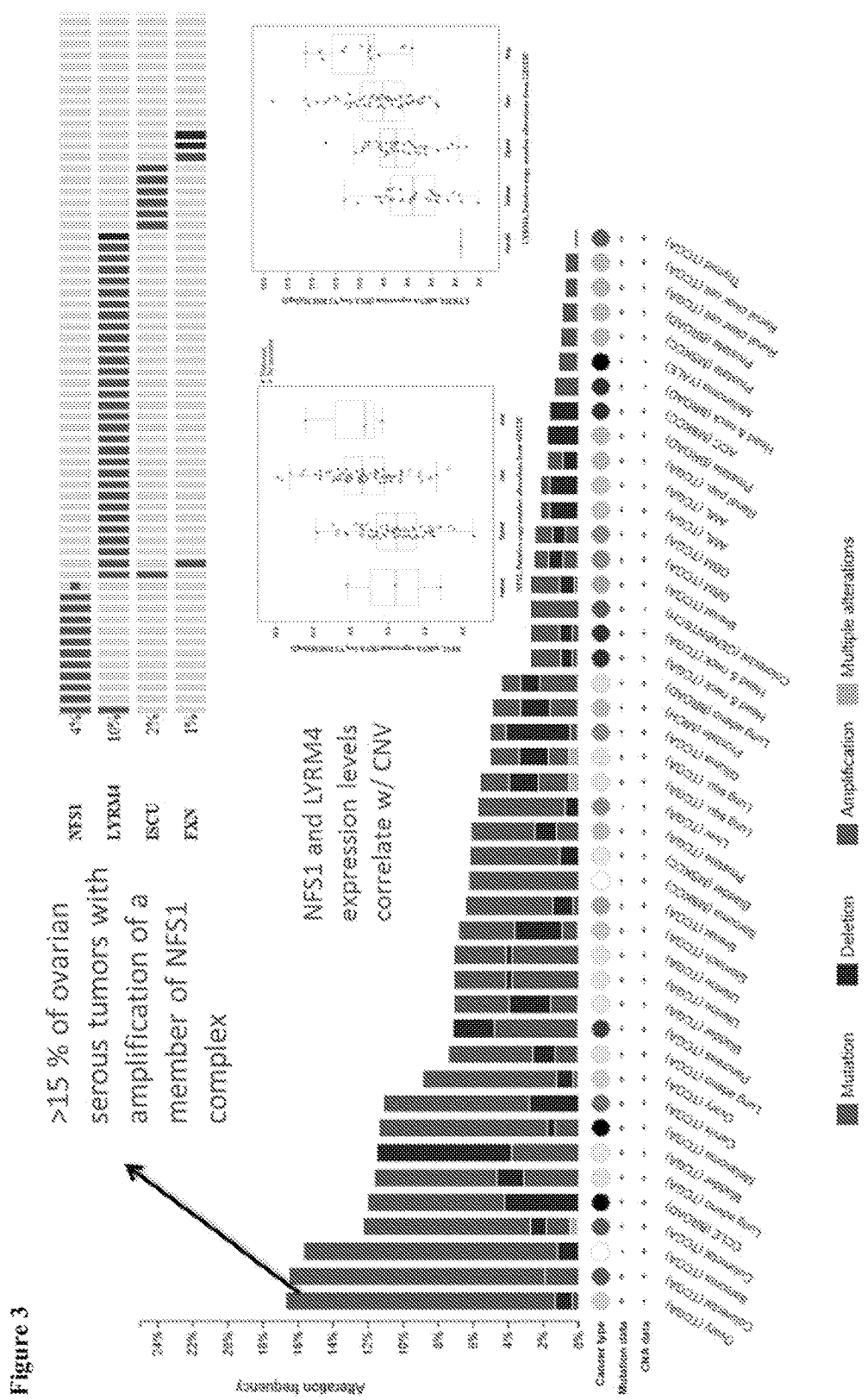
FIG. 3 shows the results of collective alterations of NFS1, LYRM4/ISD11, ISCU, and FXN evaluated across available TCGA datasets using the eBioPortal for Cancer Genomics (available on the World Wide Web at cbioportal.org/public-portal/). Top bar of histogram: amplification; middle bar of histogram; deletion; bottom bar of histogram: mutation; gray: multiple alterations. The upper inset shows the distribution of alterations between NFS1, LYRM4, ISCU, and FXN in ovarian cancers. The lower insets show the correlation between copy-number alterations (x-axis, as determined by GISTIC) and mRNA expression (y-axis, by RNASeq) for NFS1 (left) and LYRM4 (right) from a representative dataset.

In addition to NFS1 amplification, additional iron-sulfur cluster biogenesis pathway members are amplified in tumors. FIG. 3 shows the results of collective alterations of NFS1, LYRM4/ISD11, ISCU, and FXN evaluated across available TCGA datasets using the cBioPortal for Cancer Genomics (available on the World Wide Web at cbioportal.org/public-portal/). These biomarkers were amplified in many different cancers and an even larger percentage of tumors have overexpression of NFS1 and overexpression of other iron-sulfur cluster biogenesis pathway members despite the fact that they lack amplifications. Colorectal cancer, ovarian cancer, and sarcomas exhibit the highest levels of iron-sulfur cluster biogenesis pathway dysregulation.

Figure 4:
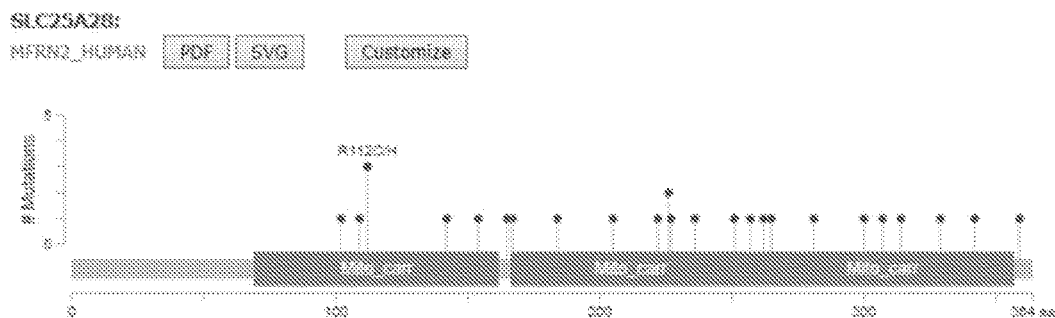
FIG. 4 shows the results of mutation analyses of solute carrier family 25 mitochondrial iron transporter, member 28 (SLC25A28), a mediator of iron uptake, assessed across TCGA samples using datasets from the cBioPortal for Cancer Genomics (available on the World Wide Web at cbioportal.org/public-portal/) and the Memorial Sloan-Kettering Cancer Center (MSKCC). All markers shown represent missense mutations, except for the seventh marker from the left located at the N-terminus of the Mito_carr domain, which represents a frameshift deletion.

Similarly, FIG. 4 shows the results of mutation analyses of solute carrier family 25 mitochondrial iron transporter, member 28 (SLC25A28), a mediator of iron uptake, assessed across TCGA samples using datasets from the cBioPortal for Cancer Genomics (available on the World Wide Web at cbioportal.org/public-portal/) and the Memorial Sloan-Kettering Cancer Center (MSKCC). All markers shown represent missense mutations, except for the seventh marker from the left located at the N-terminus of the Mito_carr domain, which represents a frameshift deletion. SLC25A28 R112C/H is a recurring mutation in colorectal and gastric cancers. SLC25A28 gain-of-function mutations are believed to be particularly dependent on NFS1.

Example 3

Knockdown of NFS1 Inhibits Clonogenic Cell Growth

Figure 5:
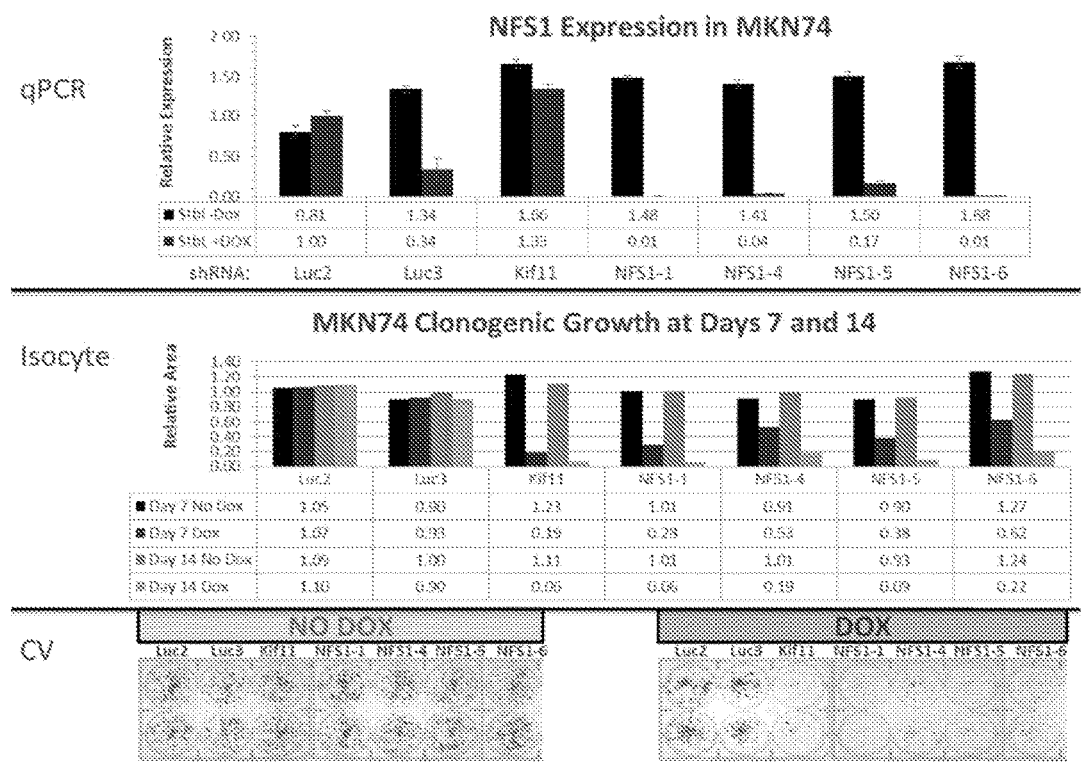
FIG. 5 shows that inducible knockdown of NFS1 using shRNAs causes clonogenic growth inhibition in MKN74 cells.

Knockdown of NFS1 inhibits clonogenic cell growth. For example, inducible knockdown of NFS1 using shRNAs causes potent growth inhibition in cells of the gastric cancer cell line, MKN74. NFS1 is amplified in the MKN74 cell line. Other cell lines that are dependent on NFS1 overexpression are well known in the art and include, for example, the AGS and KE39 cell lines. Such cell lines, including MKN74, can grow as xenografts in NSG mice. MKN74 stable cell lines carrying dox-inducible shRNAs for Kif11 (positive kill control; SEQ ID NO: 97), luciferase (Luc2 or Luc3: negative controls; SEQ ID NOs: 95 and 96, respectively), or NFS1 shRNAs (NFS1-1, -4, -5, -6; SEQ ID NOs: 86, 89, 90, and 91, respectively) were induced to express shRNAs by addition of dox (0.5 ug/mL) to the culture media, or left un-induced (no dox). Three days post-dox-induction, cells were trypsinized, counted, and plated at low density (750 cells per well of a 6-well dish) for assaying clonogenic growth. Additional cells were also collected and assessed by q-RT-PCR for NFS1 knockdown. Clonogenic growth (relative colony area shown in FIG. 5, as well as the number of objects) was monitored by red fluorescent protein (RFP) expression over two weeks scanning the plates on a laser scanning cytometer (IsoCyte, ImageXpress Velos). The average colony area at days 7 or 14 post-plating from 2 replicate wells was normalized to the average of the negative controls (FIG. 5). Clonogenic growth was also visualized by crystal violet (CV) staining at day 14 (FIG. 5; bottom panel).

In order to verify the specificity of the growth inhibition effects to NFS1 knockdown, cDNA rescue experiments were conducted to confirm on-target activity of NFS1 shRNAs. Stable NFS1-shRNA (NFS1-sh5; SEQ ID NO: 90) or shRNA control lines were infected with lentivirus expressing wild-type NFS1 cDNA, and compared to uninfected counterparts. Cells were cultured in the presence or absence of 0.5 µg/mL dox for 3 days, then replated to assay for clonogenic growth. NFS1 knockdown was confirmed by q-RT-PCR, and colony growth was also monitored on a laser scanning cytometer. Cells were fixed and stained with crystal violet at day 14 post-plating. Stable MKN74-shNFS1 cells induced with dox were significantly impaired in colony formation (see, for example, the left boxed images of FIG. 6) relative to the negative controls, while the addition of NFS1 cDNA restores colony formation (see, for example, the right boxed images of FIG. 6). Similar results were obtained from other rescue experiments performed with additional NFS1 shRNAs (sh1, sh4, sh6; SEQ ID NOs: 86, 89, and 91, respectively) with corresponding NFS1 cDNA constructs resistant to knockdown by each shRNA (see Example 1).

Figure 7:
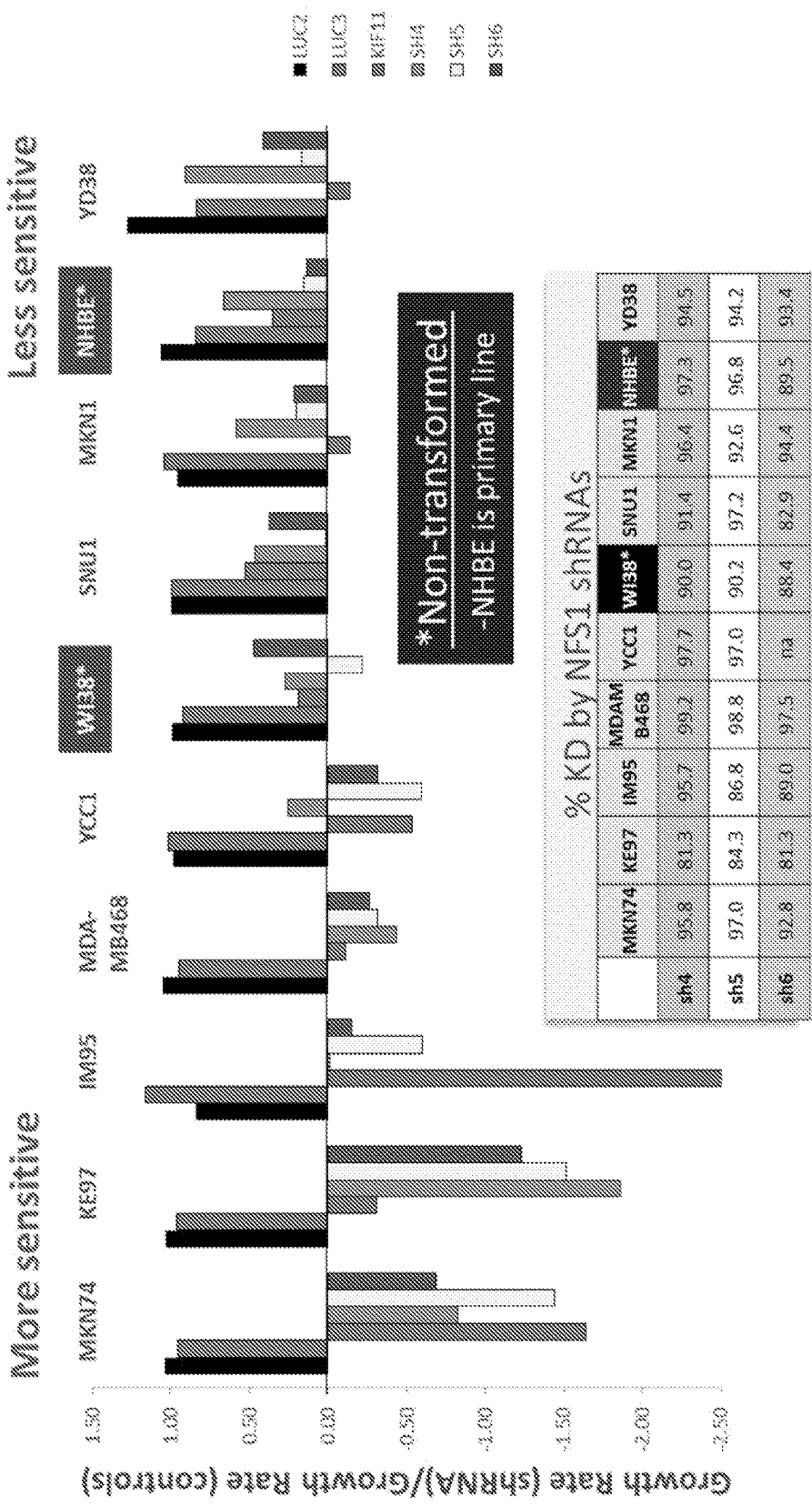
FIG. 7 shows the results of NFS1 knockdown and resulting cell growth effects across a panel of cell lines.

NFS1 knockdown was also determined to cause differential effects on cell growth across a panel of different cell lines. A panel of cell lines were infected with constitutive NFS1 shRNAs (sh4, sh5, sh6; SEQ ID NOs: 89, 90, and 91, respectively), negative control shRNAs (for Luc2, Luc3; SEQ ID NOs: 95 and 96, respectively), and positive kill control shRNA (for Kif11; SEQ ID NO: 97). Three days post-infection, cells were trypsinized, counted, and re-plated in 96-well plates. Cell viability was measured on the day of re-plating and at day 6 post-re-plating by Cell-Titer® Glo, and the data was growth rate normalized (see Example 1). Cells collected on the day of re-plating were assessed for NFS1 KD by q-RT-PCR and FIG. 7 shows that NFS1 knockdown yielded a range of NFS1-dependency with respect to modulation of cell growth.

Figure 8:
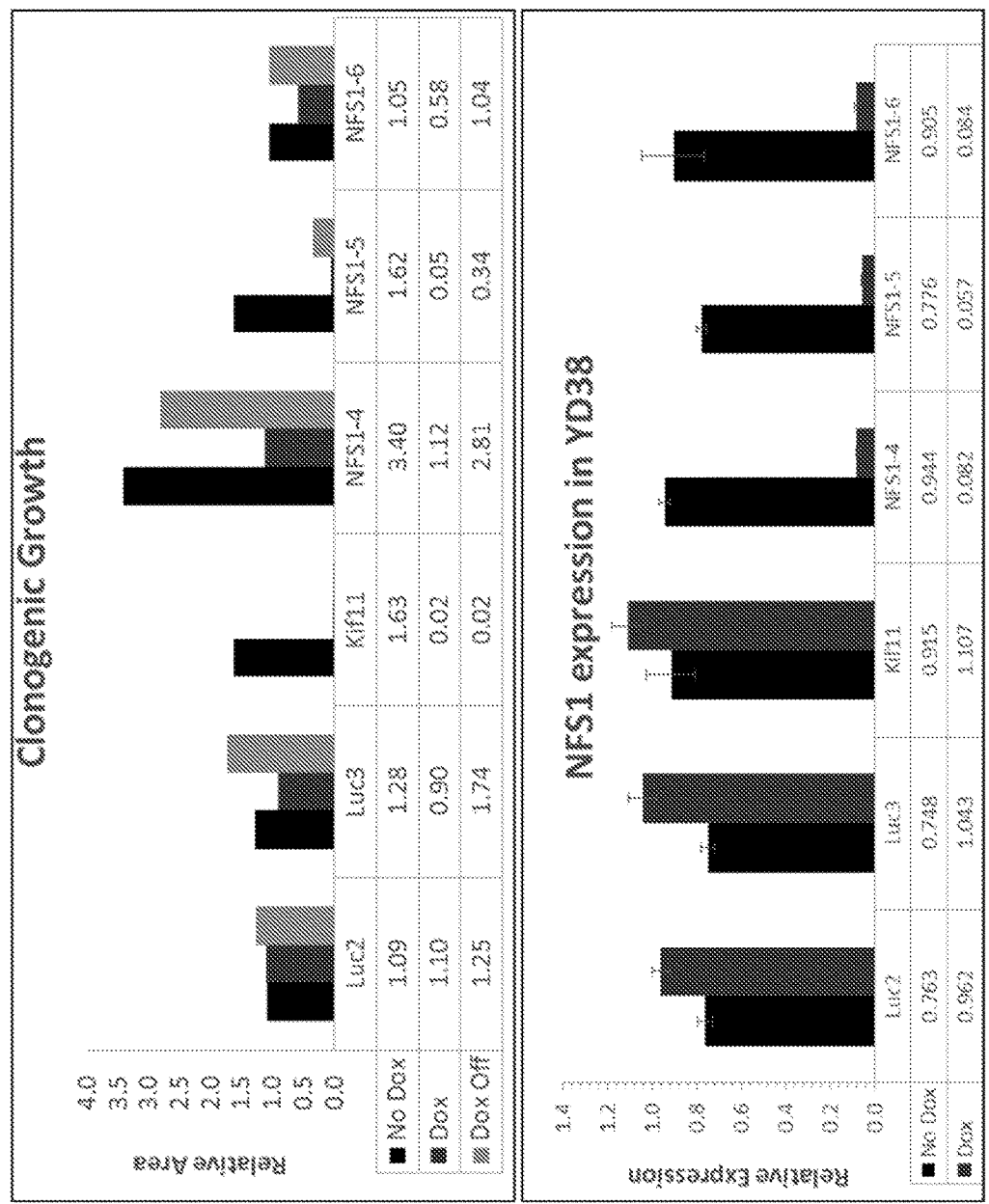
FIG. 8 shows the results of NFS1 shRN A shut-off experiments confirming restoration of clonogenic growth following depression of NFS1 function.

Finally, it was determined that shutting off NFS1 shRNA function restored clonogenic growth. For example, stable YD38 shRNA lines were cultured in the presence or absence of 1 µg/mL Dox for 3 days, then trypsinized and replated to assay for clonogenic growth with 1) continued Dox, 2) continued absence of Dox, or 3) withdrawal of Dox. Knockdown of NFS1 was assessed on the day of replating. At day 11 post-re-plating, colonies were visualized and quantified with a laser scanning cytometer, and colony area was normalized to the average of the negative controls. FIG. 8 shows that withdrawal of Dox allowed increased clonogenic growth for sh4, sh5, and sh6. Thus, growth inhibition induced by NFS1 knockdown in cell lines like YD38 can be reversed by shutting-off shNFS1 expression.

Example 4

Pharmacodynamic Markers Related to NFS1 Act as Biomarkers for NFS1 Activity and Cell Growth Modulation and Cell-Free and Cell-Based Screening Strategies for Identifying Inhibitors of NFS1 and/or Other Biomarkers Listed in Table 1

Figure 9:
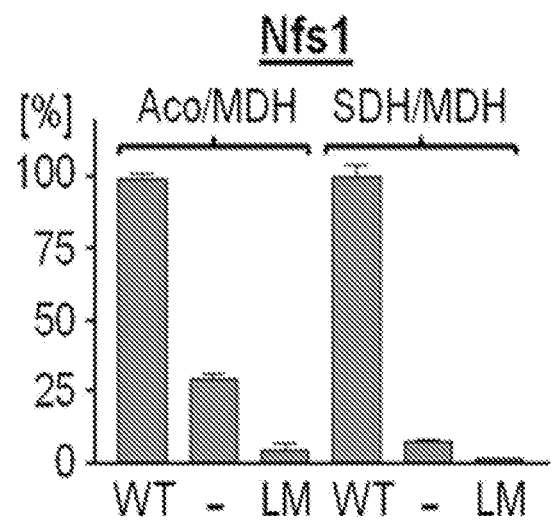
FIG. 9 shows the results of aconitase activity and SDH activity measured in lysates of mitochondria isolated from GAL-NFS1 cells harboring plasmid-borne copies of WT NFS1, nfs1M/AA, or vector without insert, as indicated, and grown for 40 hours in glucose-containing medium. Enzymatic activities were measured and plotted relative to the non-iron-sulfur cluster protein, malate dehydrogenase. The figure is adapted from Majewska al. (2013) *J. Biol. Chem.* 288:29134-29142.
Figure 10:
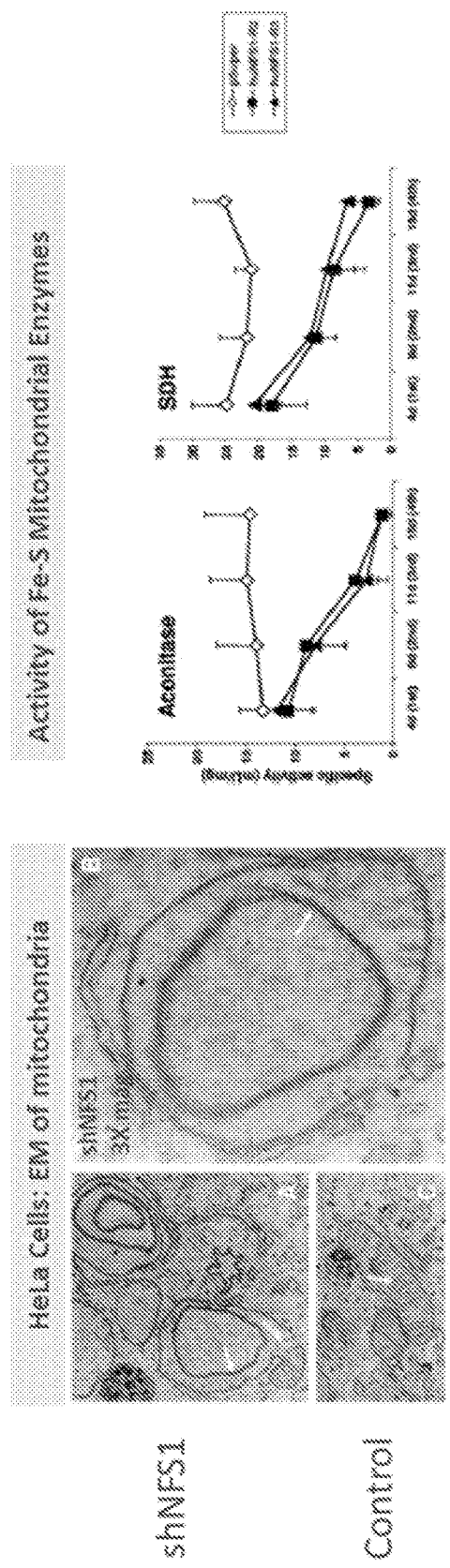
FIG. 10 shows that transient knockdown of NFS1 in Hela cells shows alterations in mitochondrial structure and significantly decreased activity of iron-sulfur-dependent enzymes, including aconitase and SDH. The figure is adapted from Biederbick et al. (2006) *Mol. Cell. Biol.* 26:5675-5687.

Previous studies indicate that iron-sulfur dependent mitochondrial enzymes, such as succinate dehydrogenase (SDH) and aconitase (Aco), act as pharmacodynamic biomarkers for NFS1 function. For example, FIG. 9 shows that SDH and Aco activity are coordinately modulated according to NFS1 activity (Majewska et al. (2013) *J. Biol. Chem.* 28829134-29142) and FIG. 10 further shows that SDH and Aco activity are significantly decreased following NFS1 knockdown.

Figure 11:
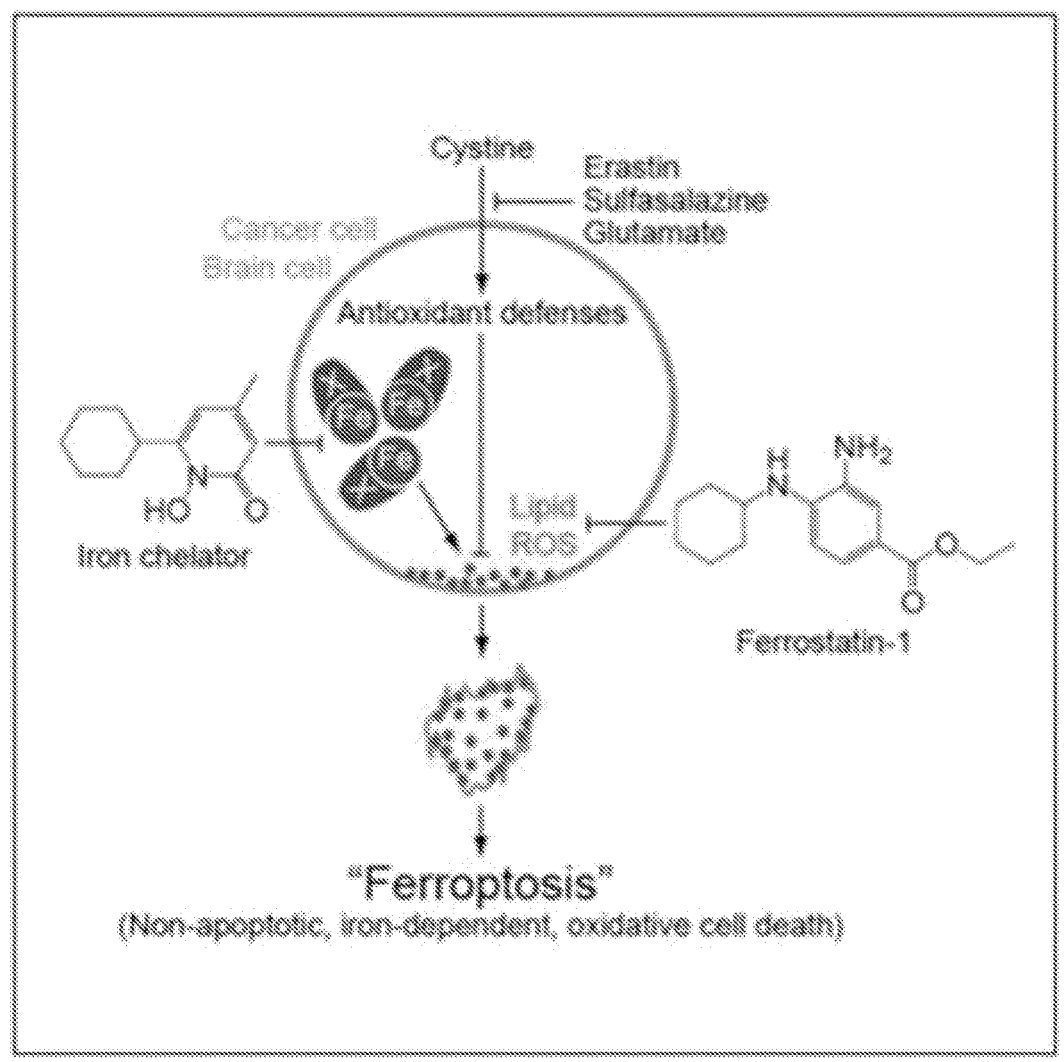
FIG. 11 shows a schematic diagram illustrating an iron-dependent form of non-apoptotic cell death known as ferroptosis. The figure is adapted from Dixon et al. (2012) *Cell* 149:1060-1072.
Figure 12:
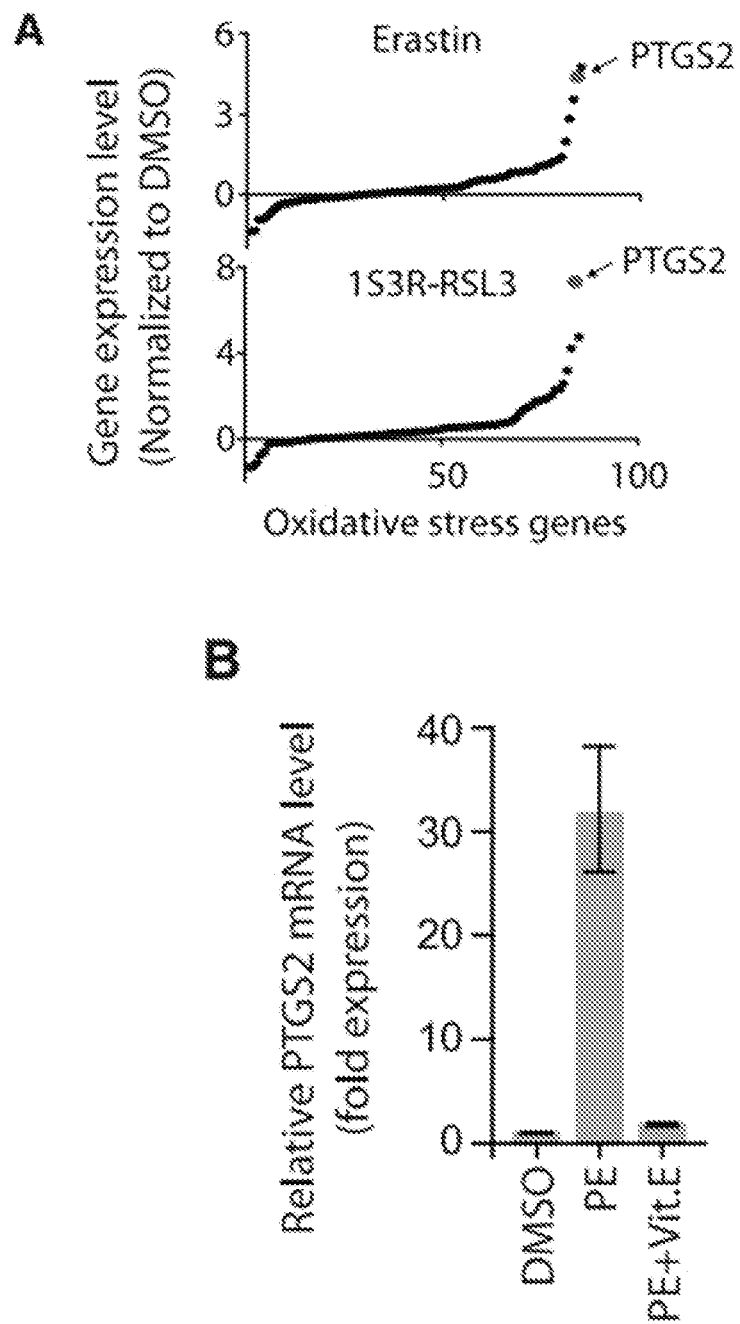
FIG. 12 includes 2 panels, identified as panels A and B, which show data adapted from Yang et al. (2014) *Cell* 156:317-331 indicating that upregulation of PTGS2 expression occurs upon erastin and (1S,3R)-RSL3 treatment (panel A) and further showing that PTGS2 expression is induced by PE (panel B). The oncogenic RAS-selective lethal small molecule crastin triggers ferroptosis, which is dependent upon intracellular iron, but not other metals, and is morphologically, biochemically, and genetically distinct from apoptosis, necrosis, and autophagy. Erastin, like glutamate, inhibits cysteine uptake by cysteine/glutainate antiporter (system xc-), creating a void in the antioxidant defenses of the cell and ultimately leading to iron-dependent, oxidative death.

In addition, it is believed that cell death due to NFS1 knockdown is due, at least in part, to dysregulation of free iron levels through a non-apoptotic, iron-dependent form of cell death known as ferroptosis (FIG. 11). In particular, Erastin, 1S3R-RSL3, & PE induce ferroptosis and PTGS2 (Cox2) is a known biomarker of ferroptosis, as well as biomarker of oxidative stress, which is a hallmark of ferroptosis (FIG. 12 and Yang et al. (2014) *Cell* 156:317-331). The implication of modulation of NFS1 and free iron levels are also believed to involve the change in expression of ferritin and transferrin receptors, whose translation is regulated by iron-response-proteins.

Figure 13:
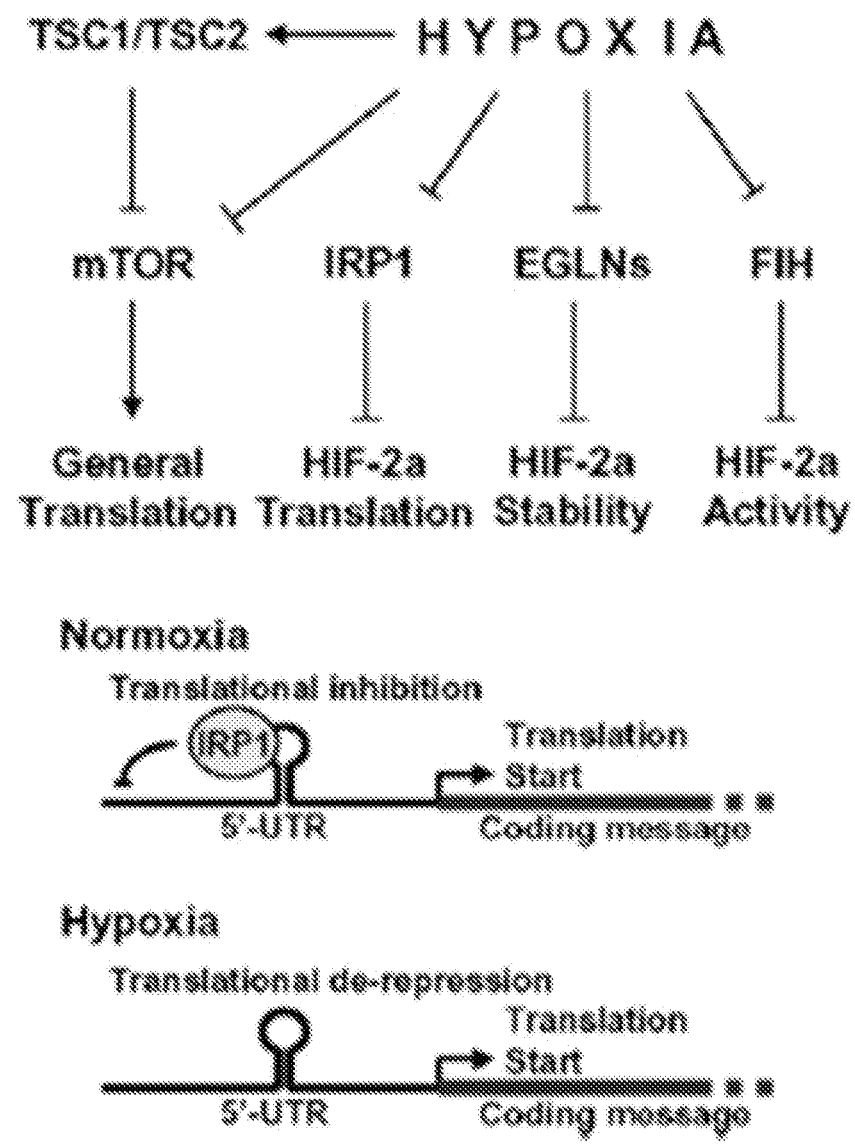
FIG. 13 shows that IRP-1 represses HIF2a translation and activity. The figure is adapted from Zimmer et al. (2008) *Mol. Cell.* 32:838-848.

Moreover, HIF2a is modulated via NFS1 modulation. HIF2a is an "undruggable" transcription factor in oncology and inflammation that is activated by mutations (either directly or indirectly) in a subset of cancers. For example, Thompson et al. (2014) *Blood* 16:366-376 demonstrate that HIF2a regulates neutrophil longevity and modulates inflammation. FIG. 13 shows that iron-regulatory protein 1 (IRP1) inhibits HIF2a translation and activity such that IRP1 activators would downregulate the HIF2a pathway. NFS1 inhibition leads to depletion of Fe—S clusters. It has been determined herein that such depletion leads to activation of Iron Response Element Binding Protein (IRE-BP) since modulation of genes regulated by the Iron Response Element, such as the transferrin receptor and ferritin, was observed in the shRNA knockdown lines described. Thus, it is believed that HIF2a is modulated by this same regulatory mechanism and that NFS1 inhibition leads to decreased HIF2a levels. Zimmer (2008) *Mol. Cell* 32:838-848 demonstrate that compounds that induce IRE-BP activity decrease HIF2a mRNA and protein levels and it is expected that NFS1 inhibition has the same consequences. HIF2a gain-of-function mutations have been described in congenital polycythemia and number of cancers including paragangliomas and these mutations are believed to be driver mutations, Thus, NFS1 inhibition not only affects fundamental iron metabolism in tumors, but also directly shuts down signaling from a mutated driver mutation. Mutations in HIF2a or other mutations that activate HIF levels, such as mutations in succinate dehydrogenase, are thus predictive biomarkers for NFS1 therapy.

Additionally. HIF2a has been demonstrated to be important for myeloid cell function, in particular neutrophils (Thompson et al. (2014) *Blood* 123:366-376), and it is expected that NFS1 will modulate activity of myeloid cells within the hypoxic tumor microenvironment. Tumor-associated myeloid cells have been demonstrated to inhibit the anti-tumor immune response such that inhibition of NFS1 is expected to lead to increased apoptosis of tumor associated myeloid cells which can have therapeutic benefit. These expected anti-tumor mechanisms of NFS1 inhibition (via modulation of HIF2a) could be achieved without chronic long-term NFS1 inhibition.

Figure 14:
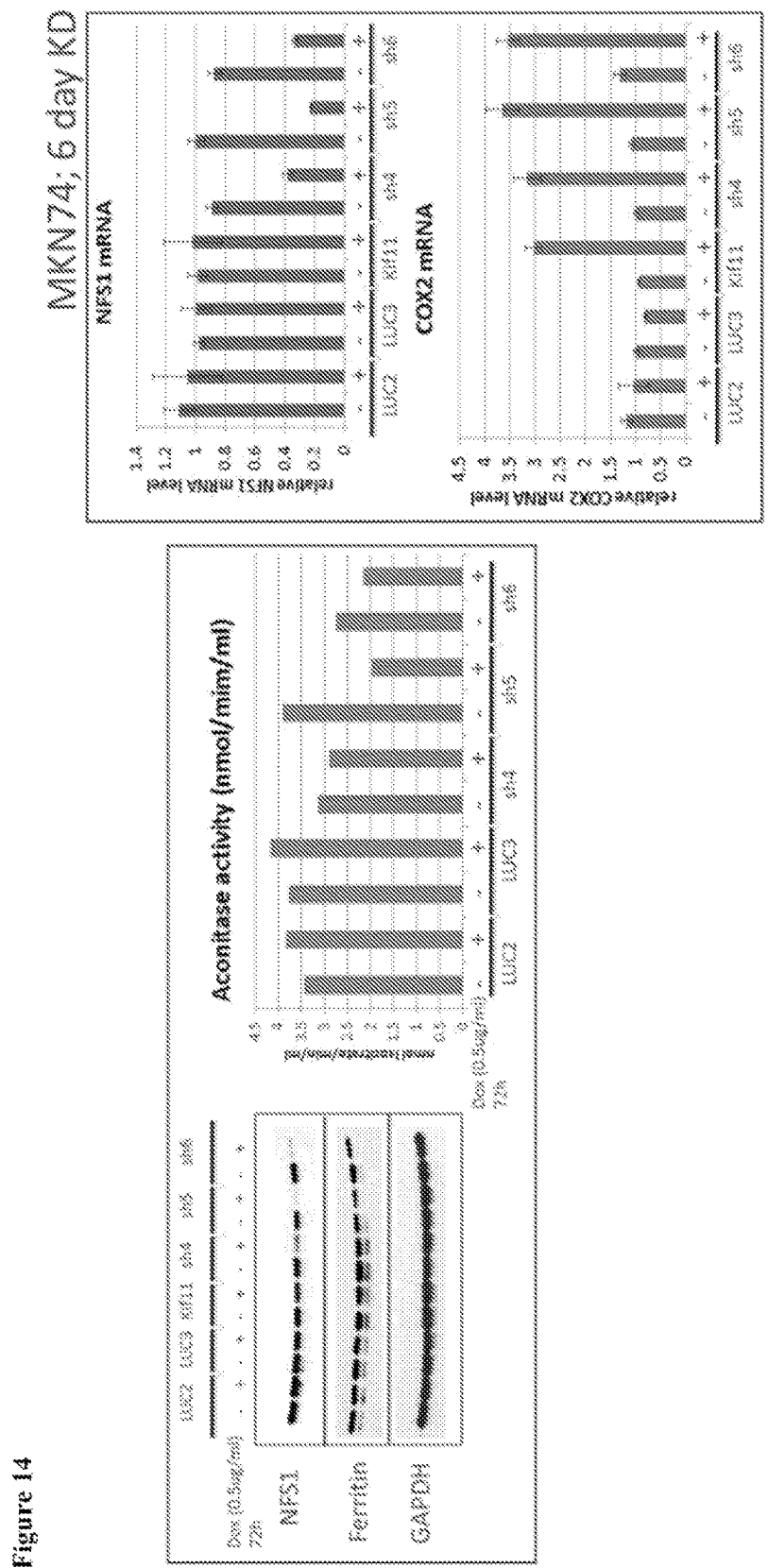
FIG. 14 shows data confirming that candidate biomarkers for iron-sulfur cluster biosynthesis pathway modulation and iron-dependent cell death (ferroptosis) correlate with NFS1 inhibition.

In order to confirm that such pharmacodynamic markers associated with NFS1 can be used as adjuncts or surrogate markers for directly assessing NFS1 modulation, several experiments were performed. FIG. 14 shows the results of MKN74 stable cell lines carrying dox-inducible shRNAs for Kif11 (positive kill control), luciferase (Luc2 or Luc3: negative controls), or NFS1 shRNAs (NFS1-4, -5, -6) that were cultured in the presence or absence of doxycycline ((0.5 ug/mL). Three days post-dox-induction, cells were trypsinized, counted, and some cells assessed by Western blot for NFS1 knockdown and ferritin (FTH1: ferritin heavy chain 1) levels with GAPDH served as a loading control (left panel). Aconitase activity was also assessed at this time point using 1 million cells per condition (middle panel). The stable lines were replated at 3 days post-dox, cultured for 3 days further, and assessed for NFS1 mRNA knockdown (top right panel) or PTGS2 (Cox2) mRNA levels (bottom right panel) by q-RT-PCR. FIG. 14 shows that NFS1 knockdown results in decreased aconitase levels and ferritin levels. In addition, PTCS2 (COX2) mRNA was induced and IRP1 was activated as a result of NFS1 inhibition.

Figure 15:
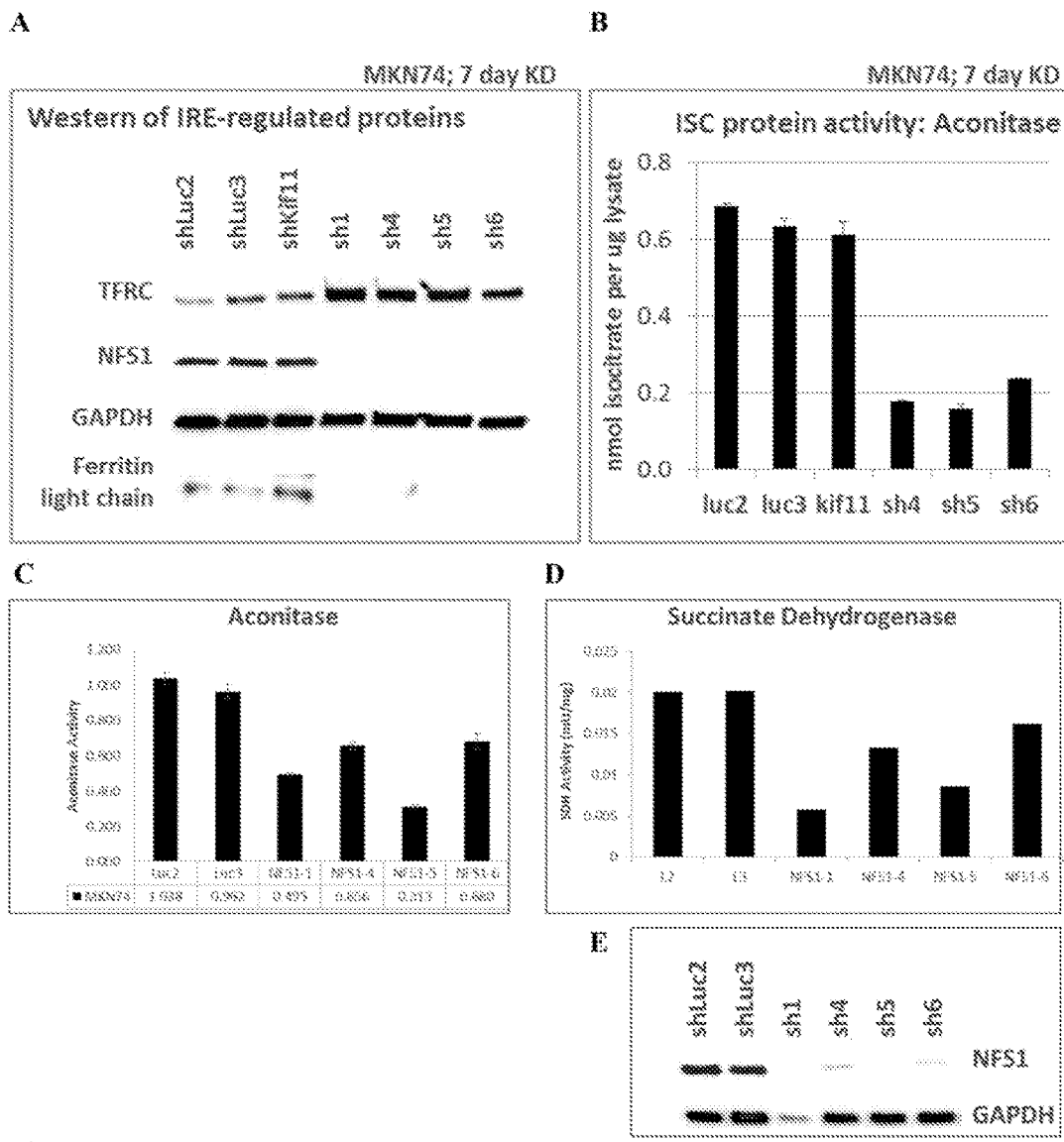
FIG. 15 includes 5 panels, identified as panels A, B, C, D, and E, which demonstrate modulation of biomarkers of ISC biosynthesis pathway modulation and iron-dependent cell-death (ferroptosis) associated with NFS1 knockdown. Panel A shows decreases in ferritin protein levels and increases in TFRC protein levels, Panels B and C shows decreases in aconitase activity. Panel E shows decreases in succinate dehydrogenase activity. Panel F confirms knockdown of NFS1 protein levels in the samples analyzed in panels E and F.

Similarly, after 7 days of NFS1 knockdown, decreases in aconitase activity and ferritin protein levels, along with upregulation of TFRC protein we observed (FIG. 15). Specifically, MKN74 cells stably carrying individual inducible NFS1 shRNAs, negative controls (shLuc2 or shLuc3) or positive kill control (shKif11), were induced with doxycycline for 7 days. These cells were then either lysed in RIPA buffer, quantified, and equally loaded on a SDS-PAGE gel for analysis by Western by staining for TfRC, NFS1, FTL, or GAPDH (loading control); or trypsinized, counted, lysed, and analyzed for aconitase activity. Aconitase activity was normalized to the protein concentration of each lysate. After 11 days of NFS1 knockdown, decreases in aconitase activity were maintained along with decreases in succinate dehydrogenase (SDH) activity as determined by the readout of succinate conversion to fumarate and as normalized against protein concentration of each analyzed lysate. Specifically, stable MKN74 shRNA lines were induced to express NFS1 or negative control shRNAs by doxycycline treatment for 11 days. These cells were then either lysed in RIPA buffer, quantified, and equally loaded on a SDS-PAGE gel for analysis by Western and staining for NFS1 and GAPDH; or trypsinized, counted, lysed and analyzed for succinate dehydrogenase activity and aconitase activity. SDH activity correlated with aconitase activity and NFS1 knockdown and was consistent in replicate experiments.

Figure 16:
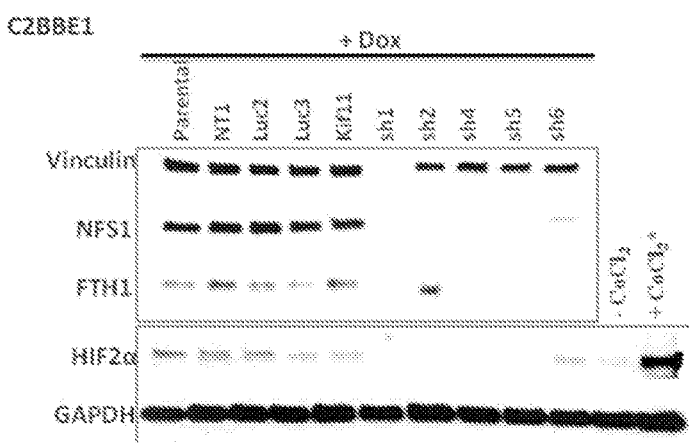
FIG. 16 shows that NFS1 knockdown in the C2BBE1 colorectal cell line correlates with down-regulation of HIF2a protein. The asterisk (*) indicates treatment for 24 hours with cobalt chloride, a hypoxia-mimicking agent.

As described above, HIF2a is an "undruggable" transcription factor that is active in a subset of cancers, regulates neutrophil longevity, and modulates inflammation (Thompson et al. (2014) *Blood* 16:366-376), NFS1 knockdown was determined to be associated with down-regulation of HIF2a protein levels (FIG. 16), which also correlated with the down-regulation of FTH1 protein levels, with the effects on both proteins likely due to the activation of iron-regulatory protein 1 (IRP1). Specifically, stable shRNA lines of the NFS1-amplified colorectal line C2B13E1 were established following infection and puromycin-selection for each respective shRNA constructs (individual inducible. NFS1 shRNAs; sh1, sh2, sh4, sh5, sh6; negative (shLuc2 or shLuc3); or positive kill control (shKif11)). These stable lines were induced with doxycycline for 2 weeks, and split 3 times during the course of culture. These cells were then lysed in the plate with ice cold RIPA buffer, quantified, and equally loaded on a SDS-PAGE gel for analysis by Western analyses. Treatment of parental C2BBE1 cells with the hypoxia mimicking agent, cobalt chloride, showed modulation of HIF2alpha levels relative to untreated parental C2BBE1 cells, as expected, and highlighted the correct molecular weight band to monitor for modulation by NFS1 KD. Western analyses were carried out using antibodies specific for NFS1, FTH1, HIF2alpha, GAPDH and vinculin, with the latter two proteins serving as loading controls.

Thus, candidate biomarkers for iron-sulfur cluster biosynthesis pathway modulation and iron-dependent cell death (ferroptosis) correlate with NFS1 inhibition.

Example 5 cDNA Rescue of NFS1 Confirms On-Target Activity of NFS1 shRNAs

Figure 6:
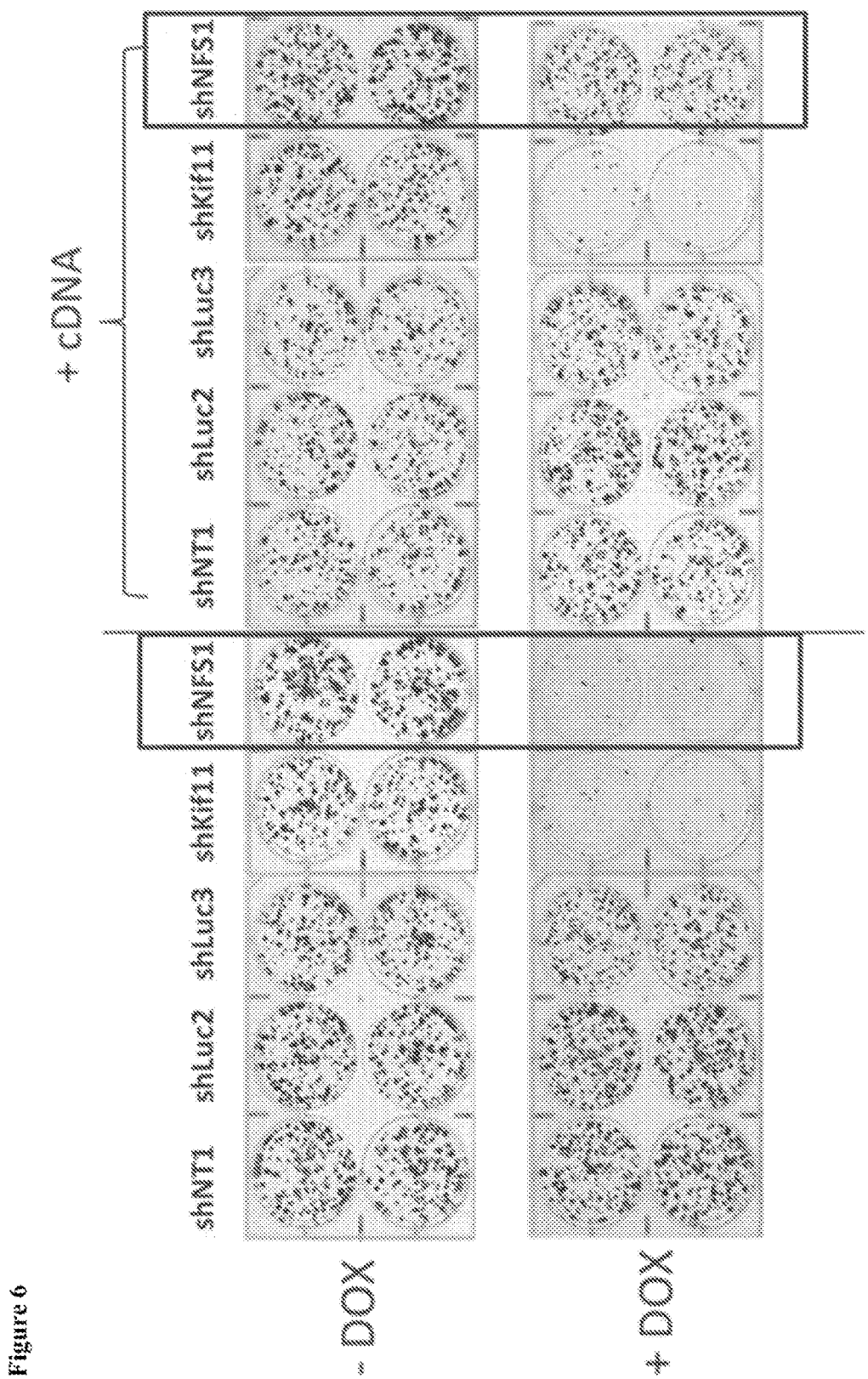
FIG. 6 shows the results of cDNA rescue experiments confirming on-target activity of NFS1 shRNAs.
Figure 17:
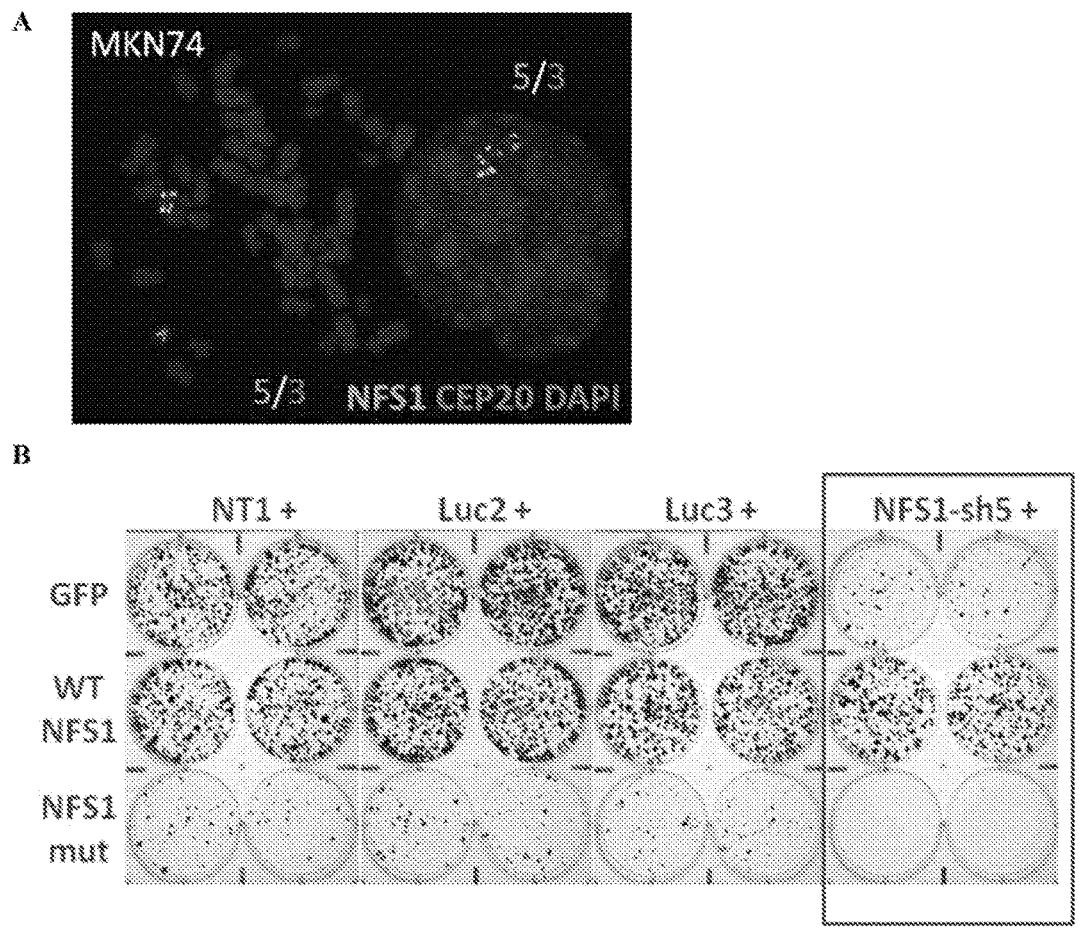
FIG. 17 includes 2 panels, identified as panels A and B, which demonstrate that NFS1 is essential in MKN74, an NFS-1 amplified cell line. Panel A shows that NFS1 is amplified in the MKN74 gastric cell line. Panel B shows the results of cDNA rescue of MKN74 stable inducible NFS1 shRNA lines with either wild type NFS1 or a dominant-negative NFS1 mutant.
Figure 18:
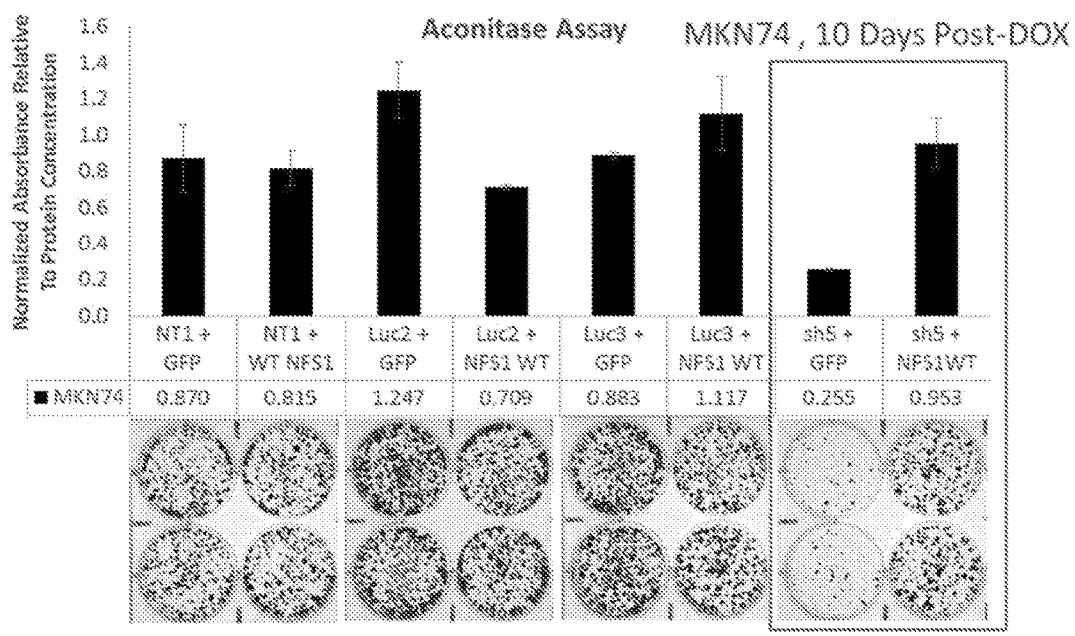
FIG. 18 shows that cDNA rescue with WT NFS1 similar to that described in FIG. 17 restores the NFS1-sh5-dependent effect on aconitase activity.
Figure 19:
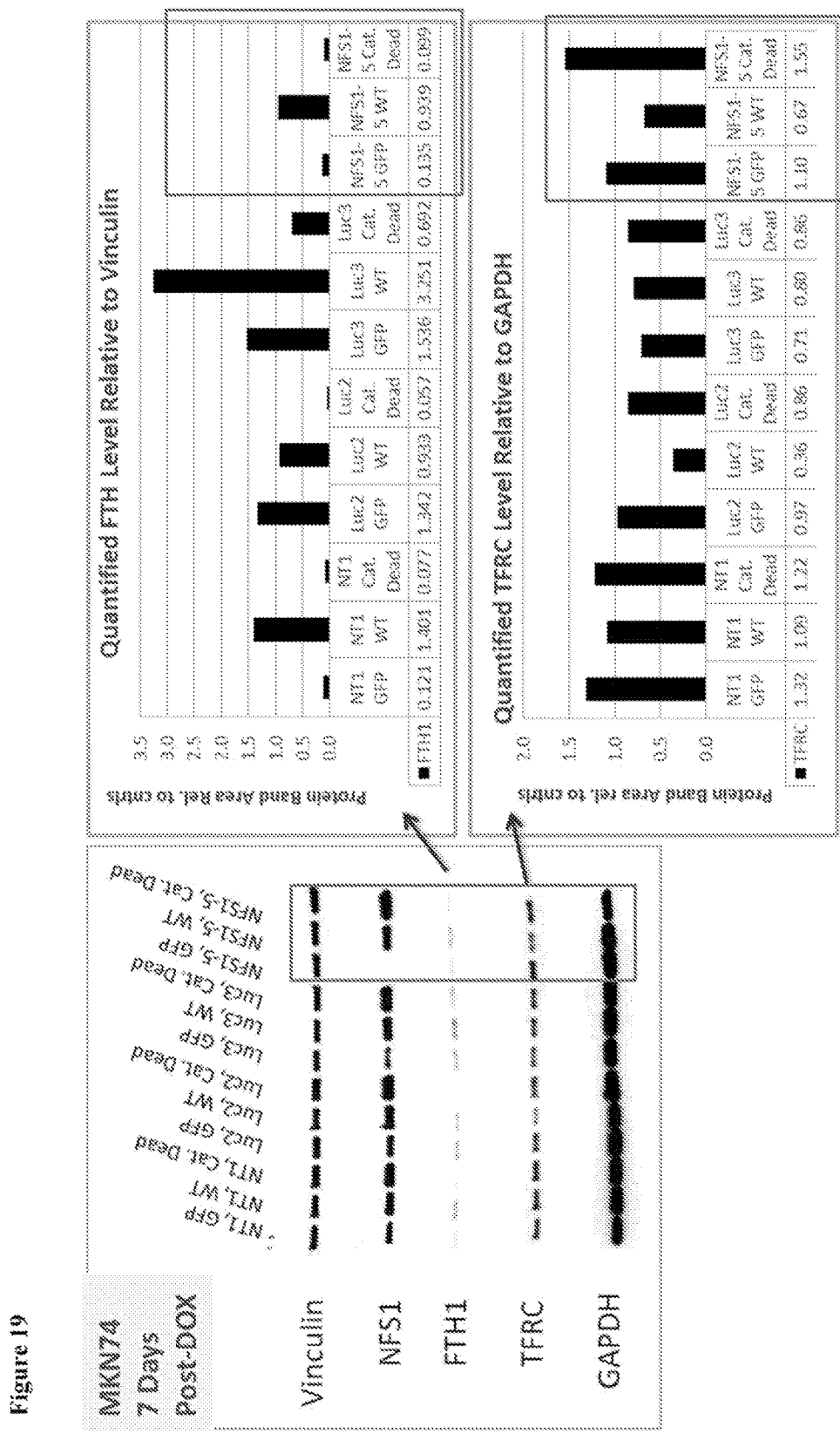
FIG. 19 shows that WT NFS1, but not NFS1$^{C381A}$, rescues the NFS1-sh5-dependent inhibition of FTH1 protein levels and the up-regulation of TfRc protein levels.

As described above, cDNA rescue experiments are useful for confirming the specificity of effects observed with modulating the expression of a gene such as NFS1 by shRNAs (FIG. 6). FIG. 17A confirms that the MKN74 gastric cell line harbors amplifications of NFS1, as determined by fluorescent in situ hybridization (FISH) analyses relative to CEP20, a chromosome 20 centromere marker, and DAPI used to stain genomic DNA. Stable NFS1 shRNA cell lines were allowed to undergo clonogenic growth and were then analyzed thirteen days post-doxycycline activation of the skRNA expression constructs in addition to cDNA rescue. FIG. 17B shows the results of the cells wherein the cells were either rescued with wild-type NFS1 (WT NFS1) or a mutant NFS1 that is catalytically dead due to a C381A mutation (NFS1$^{C381A}$), NFS1$^{C381A}$ acts as a dominant negative mutant with growth inhibitory effects comparable to that of NFS1-sh5, Specifically, the stable MKN74 shRNA lines (for the negative control shRNAs NT1, Luc2, or Luc3, or the NFS1 shRNA) were each infected with lentivirus (generated using, the pLVX-neo vector) at an approximate MOI of 3 to constitutively over-express GFP as a negative control, WT NFS1, or NFS1$^{C381A}$, and selected for one week using neomycin. These selected lines were then treated with doxycycline to induce shRNA expression, and at day 3 post-doxycycline, these cells were trypsinized and replated to assess their clonogenic growth in duplicate in 6-well plates. FIG. 17B shows that impaired clonogenic growth mediated by NFS1-sh5, a UTR-targeted shRNA; KD=87% by q PCR, was restored by WT NFS1, but not by NFS1$^{C381A}$. The combination of NFS1-sh5 and NFS1$^{C381A}$ completely inhibited clonogenic growth. Similarly, FIG. 18 shows that cDNA rescue with WI NFS1 (in the same clonogenic growth experiment described in FIG. 17) restored the NFS1-sh5-dependent effect on aconitase activity. Specifically, cell lysates were prepared from 100 cm plates of the same sets of infected cells described in FIG. 17, and analyzed for aconitase activity ten days after doxycycline treatment. Aconitase activity was normalized to protein concentration of each lysate. Similar experiments with NFS1$^{C381A}$ caused insufficient number of cells for analyses since the mutant NFS1 strongly inhibited cell growth.

WT NFS1, but not NFS1$^{C381A}$, also rescued the NFS1-sh5-dependent inhibition of FTH1 protein levels and the up-regulation of TfRc protein levels (FIG. 1)). Specifically, the same infected cells described in FIG. 17 were used in this experiment. These cells were cultured in 10 cm plates, induced with doxycycline for 7 days to induce shRNA expression, and lysed in cold RIPA buffer. Equal quantities of protein was loaded onto SDS-PAGE gels, and Western analysis done to assess protein levels of NFS1, FTH1 and TfRC, with vinculin and GAPDH staining also done as loading controls. Bands on Westerns were quantified by densitometry, and graphed relative to loading controls. Again, the NFS1$^{C381A}$ effects were similar to those of MFS1-sh5 on biomarker modulation.

Figure 20:
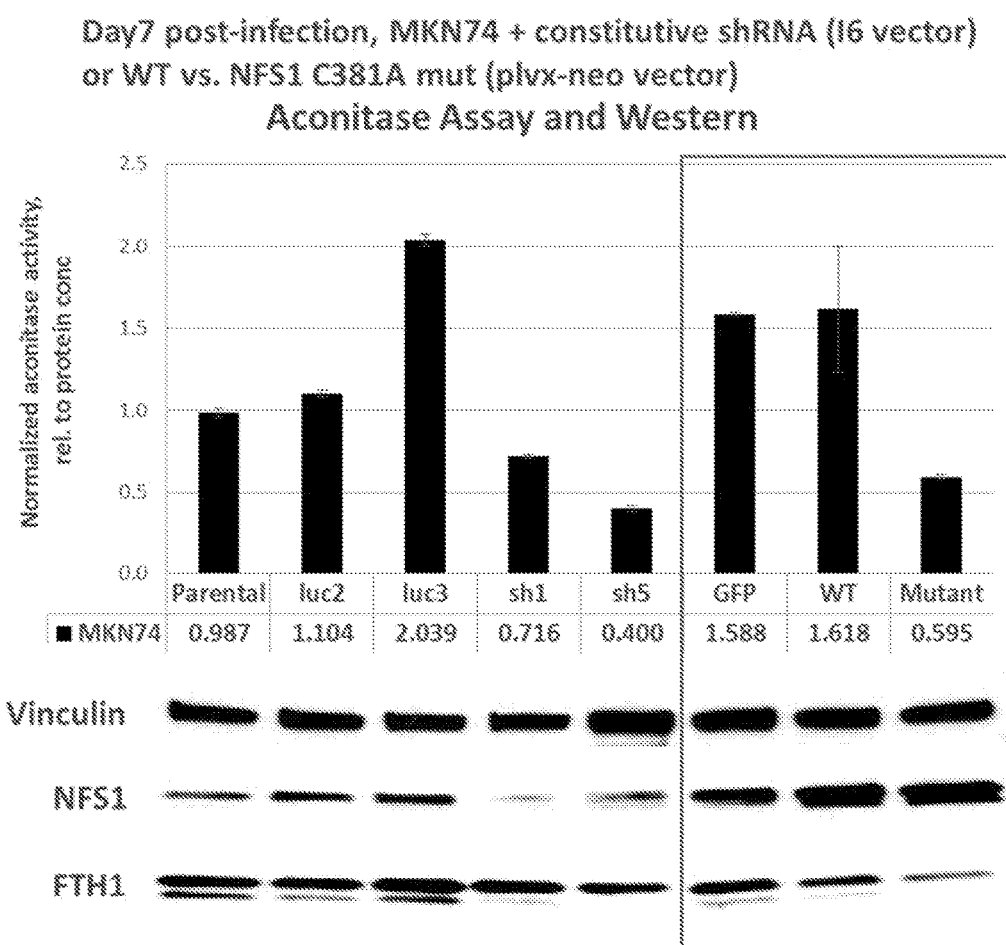
FIG. 20 shows that the NFS1$^{C381A}$ catalytic mutant causes a decrease in aconitase activity and ferritin levels comparable to that with NFS1-sh1 or NFS1-sh5.

It was further determined that the NFS1$^{C381A}$ catalytic mutant causes a decrease in aconitase activity and ferritin levels comparable to that with NFS1-sh1 or NFS1-sh5 (FIG. 20). MKN74 cells were infected at an approximate MOI of 3 at time of cell replating into 10 cm dishes, using lentivirus expressing either constitutive shRNAs (from pRS16 vector: NFS1-sh1, NFS1-sh5, or negative control shRNAs, shluc2 or shluc3), or constitutive cDNAs (from pLVX-neo vector: WT NFS1, C381A catalytic mutant NFS1, or GFP (negative control). Selection of infected cells was carried out using puromycin (for pRS16 vectors) or neomycin (for pLVX-neo vectors), beginning 2 days after infection. Seven days post-infection, cells were either lysed for further analysis of aconitase activity, or lysed with cold RIPA buffer, and lysates were then quantified and loaded in equal protein quantities onto an SDS-PAGE gel. Western analysis was carried out to detect NFS1, FTH1, and vinculin (loading control) levels. Aconitase activity was normalized to protein concentrations.

Example 6

Biochemical Assays Reporting NFS1 Activity

As described above in the specification, iron-sulfur cluster biosynthesis pathway members and pharmacodynamic markers related to same can be used in various screening assay to identify modulators (e.g., inhibitors) of iron-sulfur duster biosynthesis pathway members of interest.

In certain embodiments, biochemical screening for evaluating expression and activity of a biomarker listed in Table 1, such as due to application of inhibitors of a biomarker listed in Table 1 (e.g., NFS1 inhibitors), are presented (see, for example, Li et al. (2004) *Am. J. Physiol. Cell Physiol.* 287:C1547-C1559; Tsai and Barondeau (2010) *Biochem.* 49:9132-9139; Schmucker et al. (2011) *PLoS ONE* 6:e16199), Protein for use in the assays can be purified from any number of natural or recombinant sources (see, for example, Majewska et al. (2013) *J. Biol. Chem.* 288:29134-29142). For example, *E. coli* expressing a bicistronic expression vector encoding both NFS1 and ISD11 can be used to readily purify a complex of NFS1 and ISD11 by, for example, using a tagged protein (see, for example. Marelja et al. (2008) *J. Biol. Chem.* 283:25178-25185). In addition, the expression vector or post-translation modifications can be engineered to remove mitochondrial signal peptides and other domains that are not associated with protein function. The activity of a biomarker of interest, such as the effect of a test agent or compound on a purified protein, can be analyzed using direct or indirect enzymatic assays.

Figure 21:
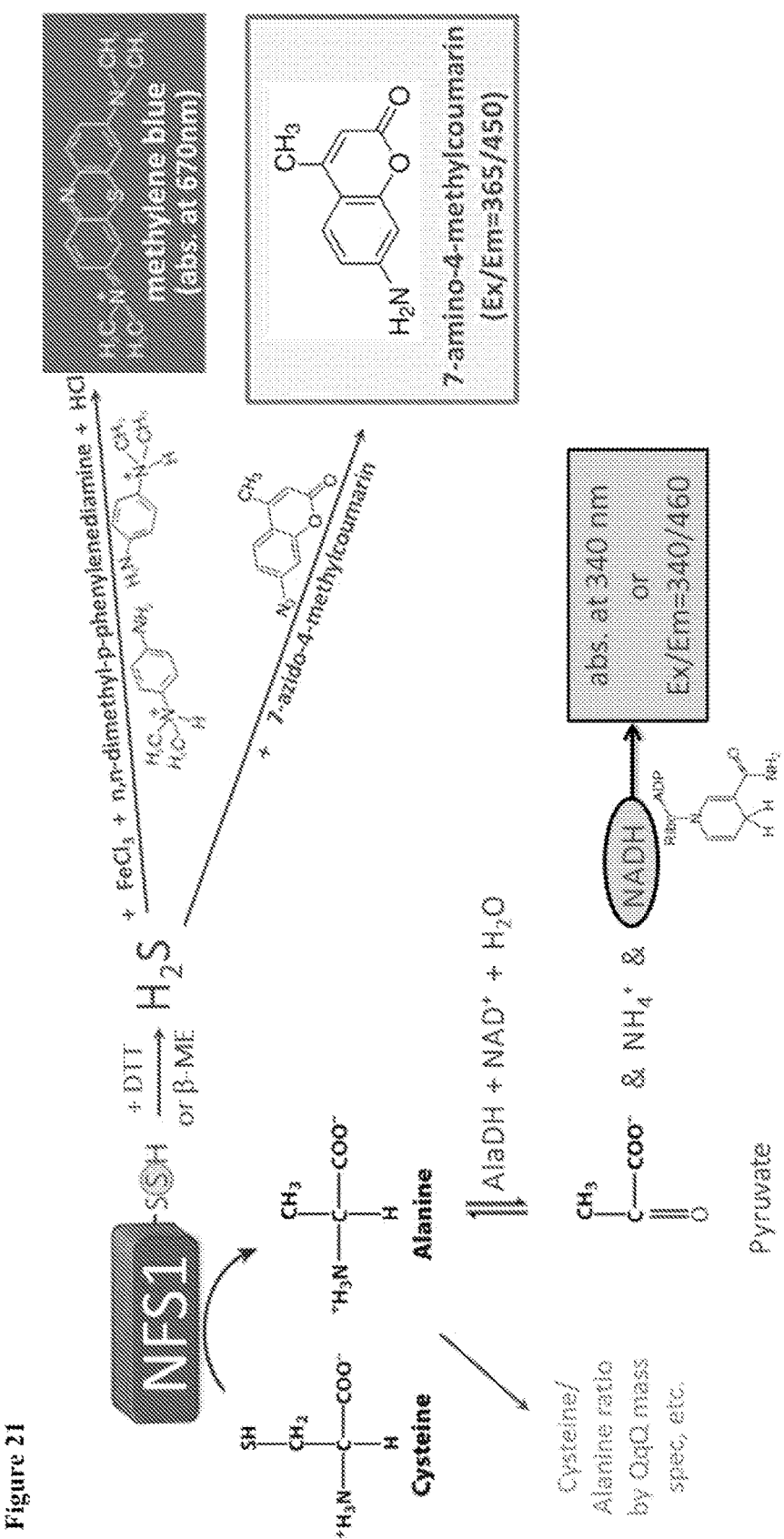
FIG. 21 shows representative sulfide-based (e.g., methylene blue assays or flurogenic sulfide probes, such as AzMC to AMC detection) or alanine-based alanine dehydrogenase activity) detection methods for analyzing NFS1 activity.

In an indirect method, analysis of an enzymatic reaction product can be analyzed as a surrogate for directly measuring enzyme action. For example, sulfide-based (e.g., methylene blue assays or fluorogenic sulfide probes, such as AzMC to AMC detection) or alanine-based (e.g., alanine dehydrogenase activity) detection methods can be used to analyze NFS1 readout (FIG. 21). In one embodiment, a reaction mixture containing a buffer, purified NFS1/ISD11, cysteine, and PLP cofactor can be created in the presence or absence of a test agent or compound and any enzymatic reaction can be stopped with the addition of N,N-dimethyl-p-phenylenediamine and FeCl$_3$ in HCl solution such that monitoring of the production of methylene blue at an absorbance of 670 nm will indicate the extent of inhibition. The methylene blue-cysteine desulfurase assay is a standard colorimetric assay that is well known in the art (see, for example, Pandey et al. (2011). *J. Biol. Chem.* 286:38242-38252). However, the assay has not heretofore been adapted for use in high-throughput format, such as for use in high capacity plates containing 96 wells. FIG. 22A provides a representative methylene blue assay suitable for a high-throughput format. This was accomplished by making a reaction buffer having 100 mM Tris, pH 8.0, 200 mM NaCl, 100 uM pyrodoxial phosphate, 100 uM DTT, and 100 mM of L-Cysteine. This mixture was then added to wells of a clear 96-well plate. After, a range of concentrations of sodium sulfide could be added for use as a standard. To detect the sulfide, 10 µL of N,N-dimethyl-p-phenylenediamine and 10 µL of FeCl$_3$ were added, and after an incubation time of up to one hour, the absorbance of the wells was measured at 670 nm using an EnSpire® plate reader. FIG. 22B demonstrates a representative sulfide detection range, wherein reactions were run with DMPPDA sulfide probe and a standard curve of sodium sulfide concentration as substrate was used to generate methylene blue. Here, the same protocol that was described for FIG. 22A was used. Briefly, wells were set up with the reaction buffer, sodium sulfide was diluted serially to a range of µM and nM concentrations and added to the wells, then methylene blue production was detected after dimethyl-p-phenylenediamine and FeCl$_3$ had been added via a plate reader. The "blanks" for the experiment were wells that received the same reagents, without any sodium sulfide. Z' values were calculated for each sulfide concentration as a measurement of how robust the potential assay would be. Sulfide detection and Z' values at 5 uM and above were especially robust.

Figure 23:
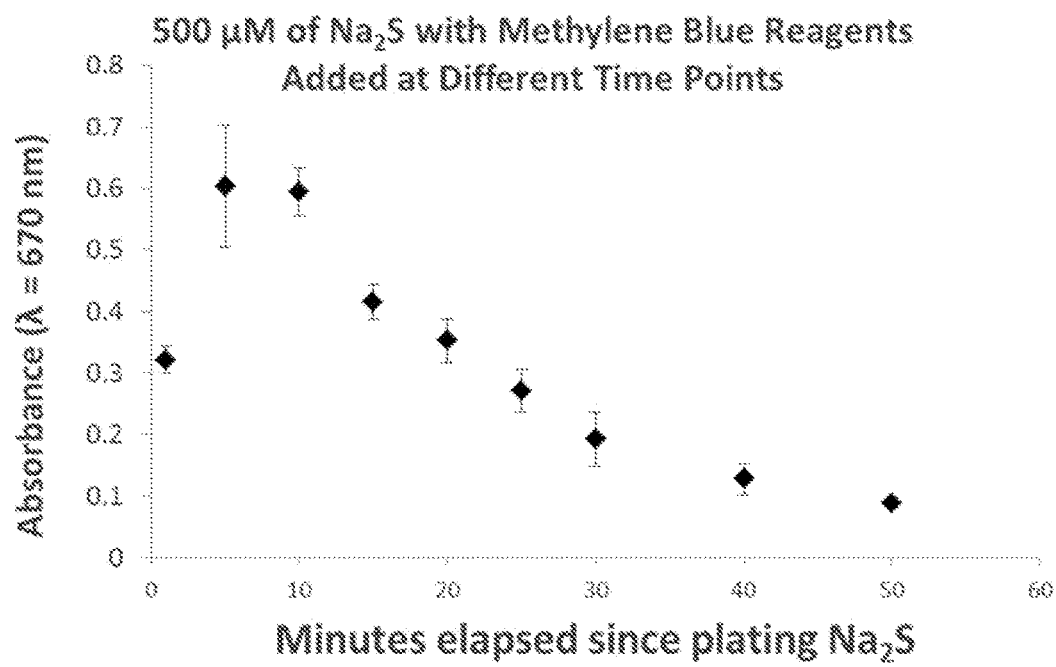
FIG. 23 shows the loss of sulfide from solution in a methylene blue assay over time.

Since hydrogen sulfide does not remain in solution over time, standard curves can become unreliable such that sulfide production is underestimated and sulfide generated by NFS1/IscS can be lost daring the reaction (FIG. 23), In order to avoid sulfide loss, other indirect detection assays can be used. In one embodiment, a fluorogenic probe can be used, such as 7-azido-4-methylcoumarin (AzMC) (Thorson et al. (2013) *Angewandte Chemie. Intl. Ed.* 52:4641-4644). AzMC reacts with and detects sulfide as NFS1 produces it, so sulfide loss is minimized relative to a methylene blue assay in which DMPPDA isn't added until the NFS1 reaction is complete (e.g., for at least 20 minutes). AzMC assays have not heretofore been adapted to measure NFS1 activity. FIG. 24A provides a representative AzMC assay suitable for a high-throughput format. This was accomplished by making a reaction buffer having 100 mM Tris, pH 8.0, 200 mM NaCl, 100 µM pyrodoxial phosphate, 5 nM glutathione. 100 µM of L-cysteine and 0.5 mg/mL of BSA. This mixture was then added to wells of a black, clear-bottom 96-well plate. The AzMC probe was then added to each well to a final concentration of 10 µM. Then, a range of Sodium Sulfide concentrations could be added for use as a standard. The reaction was either incubated in the dark at room temperature for at least an hour prior to measuring the fluorescence, or a time coarse protocol was used via the plate reader to measure the fluorescence over time. Fluorescence was measured at an excitation of 365 nm with an emission of 450 nm. FIG. 24B demonstrates a representative sulfide detection range, wherein reactions were run with AzMC sulfide probe and a standard curve of sodium sulfide concentration as substrate was used to generate the fluorophore, AMC. The same protocol that was described for FIG. 24A was used. Briefly, wells were set up with the reaction buffer, sodium sulfide was diluted serially to a range of μM and nM concentrations and added to the wells, the AzMC probe was added, the reaction was incubated at room temperature for one hour in the dark, after which the fluorescence was measured via a plate reader. The "blanks" for the experiment were wells that received the same reagents, without any sodium sulfide. Z' values were calculated for each sulfide concentration as a measurement of how robust the potential assay would be. Sulfide detection and Z' values at 500 nM and above were especially robust. FIG. 24C demonstrates enzyme kinetics of IscS using the AzMC assay optimized for high-throughput analyses. To study the enzyme kinetics of the IscS protein via the AzMC. Assay, the same reaction buffer described for FIG. 24A was made, without L-cysteine. The reaction mixture was then added to a wells of a black, clear-bottom 96-well plate. Then, the AzMC probe was added, sodium sulfide standards were made as described above, and L-cysteine was added to different wells at different concentrations. The reaction was then carried out at 37° C. with different concentrations of L-cysteine and at several time points in order to find the initial velocities for each substrate concentration. The final IscS concentration used was 250 nM. After calculating the initial velocities, a Michaelis-Menten Graph and a Lineweaver-Burk Plot were made, and the $K_m$ and $V_{max}$ were subsequently determined.

In another embodiment, alanine assays can be used (Colin et al. (2013) *J. Amer. Chem. Soc.* 135:733-740; Tsai and Barondeau (2010) *Biochem.* 49:9132-9139; Anthony et al. (2011) *PLoS ONE* 6:e20374). As with the AzMC assay described herein, alanine assays have not heretofore been adapted to measure NFS1 activity. FIG. 25A provides a representative alanine assay suitable for a high-throughput format. This was accomplished by making an NFS1 reaction buffer having 100 nM Tris, pH 8.0, 200 mM NaCl, 100 μM pyrodoxial phosphate, 100 μM DTT, 100 μM of L-cysteine. This mixture was then added to wells of a clear, UV-transparent 96-well plate. If protein was being tested, it would be added at this point and incubated for the appropriate amount of time. For the alanine dehydrogenase reaction, the pH was increased to 10 by adding a reaction mixture of 100 mM sodium carbonate buffer with the same concentrations of NaCl, pyrodoxial phosphate, and DTT as described. As a co-substrate, 1 mM NAD$^+$ was added. A range of L-alanine concentrations were used as standards, and were added to the same reaction mixture described above. Alanine dehydrogenase was added to a final concentration of 0.03 units/mL to each well, and this reaction was run for 30 minutes at room temperature. The alanine dehydrogenase converts alanine and NAD$^+$ to NADH, which fluoresced and could be measured at an excitation of 340 nm and an emission of 460 nm. The blank for this reaction would be the reaction mixture without L-alanine and FIG. 25B demonstrates a representative NADH detection range, wherein reactions were run with alanine dehydrogenase (AlaDH) and a standard curve of alanine concentration as substrate was used to generate NADH, which fluoresces at 460 nm. The same protocol that was described for FIG. 25A was used. Briefly, wells were set up with the NFS1 reaction buffer, L-alanine was diluted serially to a range of uM and nM concentrations and added to the wells, the AlaDH reaction buffer and subsequently the AlaDH were added, and the reaction was incubated at room temperature for 30 minutes, after which the fluorescence was measured via a plate reader. The "blanks" for the experiment were wells that received the same reagents without any L-alanine. Z' values were calculated for each L-alanine concentration as a measurement of how robust the potential assay would be. Alanine detection and Z' values at 500 nM and above were especially robust. FIG. 25C demonstrates enzyme kinetics of IscS using the alanine assay optimized for high-throughput analyses. To study the enzyme kinetics of the IscS protein via the alanine assay, the same NFS1 reaction buffer described for FIG. 25A was made without L-cysteine. The reaction mixture was then added to a series of PCR tubes. Then, L-alanine was added to the standards tubes, and L-cysteine was added to different tubes at different concentrations. The IscS protein was added to a final concentration of 250 nM. The IscS reaction was then carried out at 37° C. with different concentrations of L-cysteine and at different time points, in order to find the initial velocities for each substrate concentration. The reactions at each time point would be halted via beat inactivation at 95° C., and after all reactions were finished, the AlaDH reaction was run under the conditions described in FIG. 25A. After measuring the fluorescence and calculating the alanine concentration, the initial velocities were found, a Michaelis-Menten Graph and a Lineweaver-Burk Plot were made and the $K_m$ and $V_{max}$ were subsequently determined.

By contrast, a direct enzymatic assay, such as that using the same enzymatic reaction mixture described above, but actively monitoring the production of alanine via a mass-spectrometer (e.g., such as the Agilent RapidFire® platform), can be used to identify the extent of inhibition. Test agents or compounds that reduce the production of alanine, for example, can be identified as NFS1 inhibitors.

In other embodiments, cell-based screening methods to identify modulators of a biomarker listed in Table 1 (e.g., NFS1 inhibitors) are presented (see, for example. Li et al. (2004) *Am. J. Physiol. Cell Physiol*, 287:C1547-C1559). Cells treated with or without a test agent or compound can be monitored for the modulation of Fe—S dependent enzymes such as by assaying decreases in aconitase activity or modulation of other activities listed in Table 1. Cells treated with or without a test agent or compound can also be monitored for the modulation of iron-responsive reporter genes. For example, antibodies can be used to detect levels of endogenous IRE-modulated proteins to provide readout of iron-sulfur cluster depletion which will result from NFS1 inhibition. This assay could be configured as a high content screen (Weerapana et al. (2010) *Nature* 468:790-795). Alternatively, stable cell lines expressing reporter gene (e.g., luciferase, GFP, etc.) with mRNA context that contains iron response elements that will increase mRNA stability and ultimately reporter gene activity can be used. The use of a destabilized reporter gene would likely increase sensitivity. In one embodiment, the mRNA context of transferrin receptor can be used as model, wherein iron response elements in 3' UTR that increase stability of mRNA, under low Fe—S levels.

Figure 26:
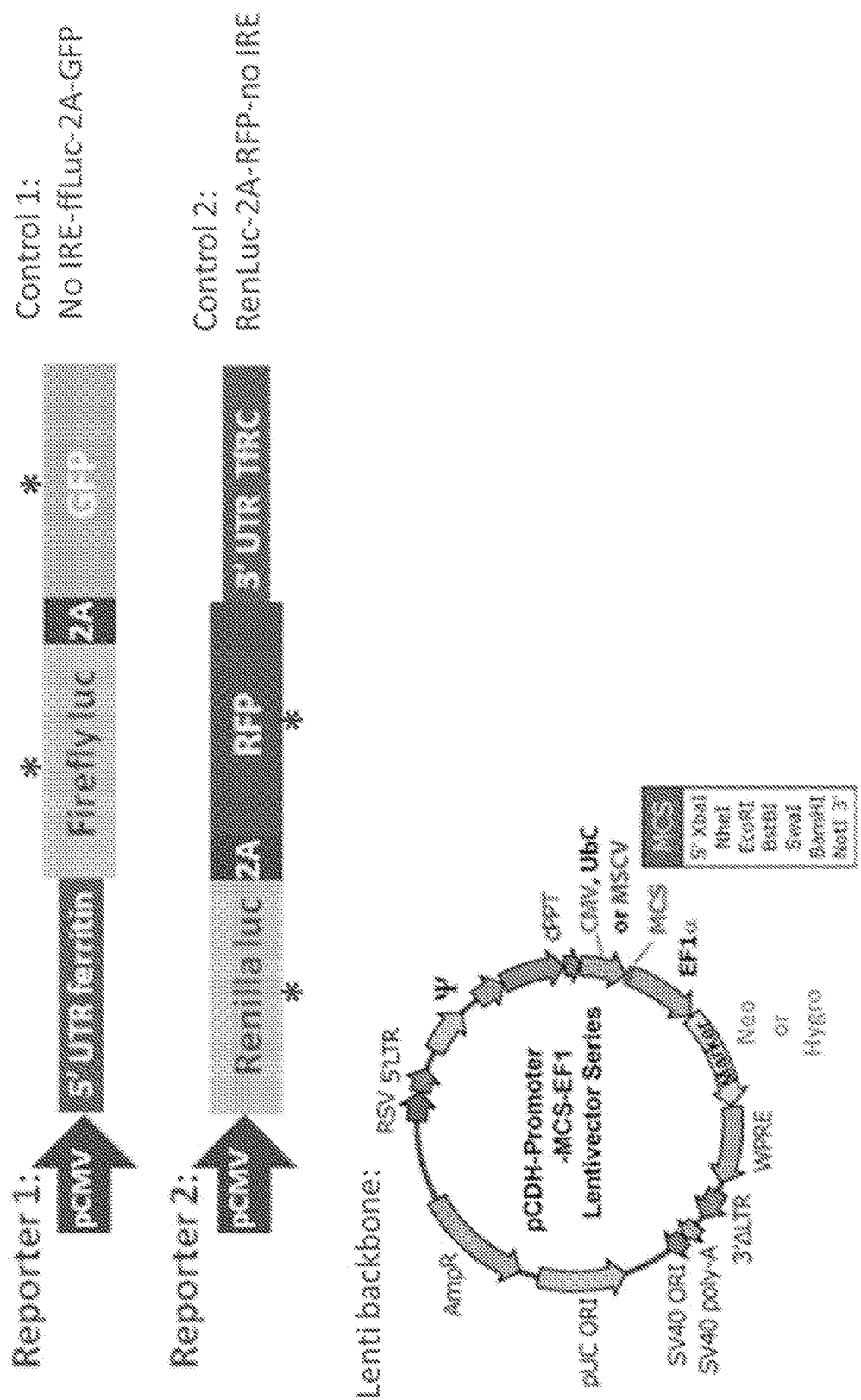
FIG. 26 shows exemplary reporter constructs useful for screening for NFS1 inhibitors and/or inhibitors of the iron-sulfur duster biosynthesis pathway. The asterisks (*) represent the use of luciferase, GFP, and RFP containing destabilizing sequences from mouse ornithine decarboxylase at their C-terminus.

In still another embodiment, the fact that IREs in 3' UTR stabilize mRNA, while IRE in 5' UTR reduces translation, can be exploited by generating a least two reporters, one that will be upregulated and one that will be down regulated upon inhibition, such as NFS1 inhibition (Fe—S cluster depletion), and the ratio of at least two reporters can be monitored. This can be done with either fluorescent proteins or luciferase proteins or a combination of both, FIG. 26 shows an exemplary schematic diagram illustrating possible reporter constructs. For example, the first reporter can have a 5' UTR arrangement similar to ferritin mRNA that will have low protein levels upon NFS1 inhibition (e.g., 5'UTR of ferritin-firefly luficerase-2A-GFP reporter). The second reporter can have a 3' UTR arrangement similar to transferrin receptor mRNA that will have increased protein levels of the report with increases in inhibition (e.g., Renilla luciferase-2A-RFP reporter-3' UTR of transferrin receptor). Drug selection markers, such as puromycin, can also be used. Appropriate control constructs, such as those illustrated in FIG. 26, can also be used. The readout would be the ratio of at least two reporters. For example, NFS1 inhibition will increase the an of Renilla-to-firefly luciferase ratios and/or RFP-to-GFP ratios. Similarly, simplified reporters with just FTL.iron response element (IRE)-luciferase and a corresponding control can be used. The engineered constructs can be expressed via any number of well-known vectors, including viruses, such as lentiviral vectors shown in FIG. 25, plasmids, and the like. Such a strategy, in addition to allowing the use of the luciferase ratio to identify NFS1 inhibitors, could also be adapted for live cell imaging using the ratio of, for example, two fluorescent markers.

Example 7

Microbial Pathogen Growth Inhibited Using Inhibitors of NFS1 Homologs

Inhibitors of NFS1 homologs in microbial pathogens are believed to have therapeutic potential as inhibitors of microbial pathogenic growth since the catalytic cysteine residue is always conserved. Such NFS1 homologs are essential for growth in a variety of bacterial/fungal species including *Helicobacter pylori* via its NFS1 homolog, NifS (Olson et al. (2000) *Biochem.* 30:16213-16219; *Mycobacterium tuberculosis* via its NFS1 homolog, IseSMtb (Rybniker et al. (2014) *Biochem. J. Feb.* 19 e-pub; and yeast via its NFS1 homolog, Nfs1p (Li et al. (1999) *J. Biol. Chem.* 274:33025-22034). Human NFS1 is ~80% similar to the *E. coli* homolog and the conserved deep substrate pocket and conservation of the catalytic cysteine support druggability of NFS1 homologs using agents such as small molecules and covalent inhibitors.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web and/or the National Center for Biotechnology Information (NCBI) on the World Wide Web.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting hyperproliferative growth of a cancer cell or cells, the method comprising contacting the cancer cell or cells with an shRNA or an siRNA targeting NFS1, thereby inhibiting hyperproliferative growth of the cancer cell or cells, wherein the step of contacting occurs ex vivo or in vitro, optionally wherein i) the shRNA or siRNA is administered in a pharmaceutically acceptable formulation;
ii) the NFS1 is human NFS1; and/or
iii) the cancer is selected from the group consisting of paragangliomas, colorectal cancer, cervical cancer, lung adenocarcinoma, ovarian cancer, and myeloid cancer within a hypoxic tumor microenvironment.

* * * * *

SEQUENCE LISTING

```
<160> NUMBER OF SEQ ID NOS: 111

<210> SEQ ID NO 1
<211> LENGTH: 1374
<212> TYPE: DNA
<213> ORGANISM: Homo sapiens

<400> SEQUENCE: 1
atgctgctcc gagccgcttg gaggcgggcg gcagtggcgg tgacagcggc tccagggccg      60
aagcccgcgg cgcccactcg ggggctgcgc ctgcgcgttg gagaccgtgc tcctcagtct     120
gcggttcccg cagatacagc cgctgccccg gaggtggggc cagtgctgcg acctctctat     180
atggatgtgc aagctacaac tcctctggac ccccgggtgc ttgatgccat gctcccttac     240
ctaatcaact actatgggaa cccacactcc cggacacatg cttatggctg ggagagtgag     300
gcagccatgg aacgtgctcg tcagcaagta gcatctctga ttggagctga tcctcgtgag     360
atcattttta ctagtggtgc tactgaatcc aacaacatag caattaaggg ggtggcccga     420
ttctacaggt cacggaaaaa gcacttgatc accacccaga cagaacacaa atgtgtcttg     480
gactcctgcc gttcactgga agctgagggc tttcaggtca cctacctccc agtgcagaag     540
agtgggatca ttgacctaaa ggaactagag gctgctatcc agccagatac tagcctggtg     600
tcagtcatga ctgtgaacaa tgagattgga gtgaagcagc ctattgcaga aatagggcgg     660
atttgcagtt ccagaaaggt atatttccat actgatgcag cccaggctgt tggaaaaatc     720
```

```
ccacttgatg tcaatgacat gaaaattgat ctcatgagca ttagtggtca caaaatctac    780
ggtcccaaag gggttggtgc catctacatc cgtcgccggc cccgtgtgcg tgtggaggcc    840
ctgcagagtg agggggggca ggagcggggt atgcggtctg ggacagtgcc cacaccctta    900 gtggtgggc tggggctgc gtgtgaggtg gcacagcaag agatggagta tgaccacaag     960
cgaatctcaa agttgtcaga gcggctgata cagaatataa tgaagagcct tccagatgtg   1020
gtgatgaatg ggaccctaa gcaccattat cccggctgta tcaacctctc ctttgcatat    1080
gtggaagggg aaagtctgct gatggcactg aaggacgttg ccttatcctc agggagtgcc   1140
tgcacctctg catccctgga gccctcttat gtgcttagag caattggcac tgatgaggat   1200
ttagcgcact cttctatcag gtttggaatt ggccgcttca ctacagagga ggaagtggac   1260
tacacagtgg agaaatgcat tcagcatgtg aagcgtcttc gagaaatgag ccctctctgg   1320
gagatggttc aggatggcat tgacctcaag agcatcaagt ggacccaaca ctag         1374
```

<210> SEQ ID NO 2
<211> LENGTH: 457
<212> TYPE: PRT
<213> ORGANISM: Homo sapiens

<400> SEQUENCE: 2

```
Met Leu Leu Arg Ala Ala Trp Arg Arg Ala Val Ala Val Thr Ala
1               5                   10                  15

Ala Pro Gly Pro Lys Pro Ala Ala Pro Thr Arg Gly Leu Arg Leu Arg
            20                  25                  30

Val Gly Asp Arg Ala Pro Gln Ser Ala Val Pro Ala Asp Thr Ala Ala
        35                  40                  45

Ala Pro Glu Val Gly Pro Val Leu Arg Pro Leu Tyr Met Asp Val Gln
    50                  55                  60

Ala Thr Thr Pro Leu Asp Pro Arg Val Leu Asp Ala Met Leu Pro Tyr
65                  70                  75                  80

Leu Ile Asn Tyr Tyr Gly Asn Pro His Ser Arg Thr His Ala Tyr Gly
                85                  90                  95

Trp Glu Ser Glu Ala Ala Met Glu Arg Ala Arg Gln Gln Val Ala Ser
            100                 105                 110

Leu Ile Gly Ala Asp Pro Arg Glu Ile Ile Phe Thr Ser Gly Ala Thr
        115                 120                 125

Glu Ser Asn Asn Ile Ala Ile Lys Gly Val Ala Arg Phe Tyr Arg Ser
    130                 135                 140

Arg Lys Lys His Leu Ile Thr Thr Gln Thr Glu His Lys Cys Val Leu
145                 150                 155                 160

Asp Ser Cys Arg Ser Leu Glu Ala Glu Gly Phe Gln Val Thr Tyr Leu
                165                 170                 175

Pro Val Gln Lys Ser Gly Ile Ile Asp Leu Lys Glu Leu Glu Ala Ala
            180                 185                 190

Ile Gln Pro Asp Thr Ser Leu Val Ser Val Met Thr Val Asn Asn Glu
        195                 200                 205

Ile Gly Val Lys Gln Pro Ile Ala Glu Ile Gly Arg Ile Cys Ser Ser
    210                 215                 220

Arg Lys Val Tyr Phe His Thr Asp Ala Ala Gln Ala Val Gly Lys Ile
225                 230                 235                 240

Pro Leu Asp Val Asn Asp Met Lys Ile Asp Leu Met Ser Ile Ser Gly
                245                 250                 255

His Lys Ile Tyr Gly Pro Lys Gly Val Gly Ala Ile Tyr Ile Arg Arg
```

```
                    260                 265                 270
Arg Pro Arg Val Arg Val Glu Ala Leu Gln Ser Gly Gly Gly Gln Glu
            275                 280                 285

Arg Gly Met Arg Ser Gly Thr Val Pro Thr Pro Leu Val Val Gly Leu
            290                 295                 300

Gly Ala Ala Cys Glu Val Ala Gln Gln Glu Met Glu Tyr Asp His Lys
305                 310                 315                 320

Arg Ile Ser Lys Leu Ser Glu Arg Leu Ile Gln Asn Ile Met Lys Ser
                325                 330                 335

Leu Pro Asp Val Val Met Asn Gly Asp Pro Lys His His Tyr Pro Gly
            340                 345                 350

Cys Ile Asn Leu Ser Phe Ala Tyr Val Glu Gly Glu Ser Leu Leu Met
            355                 360                 365

Ala Leu Lys Asp Val Ala Leu Ser Ser Gly Ser Ala Cys Thr Ser Ala
            370                 375                 380

Ser Leu Glu Pro Ser Tyr Val Leu Arg Ala Ile Gly Thr Asp Glu Asp
385                 390                 395                 400

Leu Ala His Ser Ser Ile Arg Phe Gly Ile Gly Arg Phe Thr Thr Glu
                405                 410                 415

Glu Glu Val Asp Tyr Thr Val Glu Lys Cys Ile Gln His Val Lys Arg
            420                 425                 430

Leu Arg Glu Met Ser Pro Leu Trp Glu Met Val Gln Asp Gly Ile Asp
            435                 440                 445

Leu Lys Ser Ile Lys Trp Thr Gln His
450                 455

<210> SEQ ID NO 3
<211> LENGTH: 1221
<212> TYPE: DNA
<213> ORGANISM: Homo sapiens

<400> SEQUENCE: 3
atgctgctcc gagccgcttg gaggcgggcg gcagtggcgg tgacagcggc tccagggccg      60
aagcccgcgg cgcccactcg ggggctgcgc ctgcgcgttg agaccgtgc tcctcagtct     120 gcggttcccg cagatacagc cgctgccccg gaggtggggc cagtgctgcg acctctctat     180
atggatgtgc aagctacaac tcctctggac ccccgggtgc ttgatgccat gctcccttac     240
ctaatcaact actatgggaa cccacactcc cggacacatg cttatggctg ggagagtgag     300
gcagccatgg aacgtgctcg tcagcaagta gcatctctga ttggagctga tcctcgtgag     360
atcattttta ctagtggtgc tactgaatcc aacaacatag caattaagga actagaggct     420
gctatccagc cagatactag cctggtgtca gtcatgactg tgaacaatga gattggagtg     480
aagcagccta ttgcagaaat agggcggatt tgcagttcca gaaaggtata tttccatact     540
gatgcagccc aggctgttgg aaaaatccca cttgatgtca atgacatgaa aattgatctc     600
atgagcatta gtggtcacaa atctacggt cccaaagggg ttggtgccat ctacatccgt     660
cgccggcccc gtgtgcgtgt ggaggccctg cagagtggag ggggcaggga gcggggtatg     720
cggtctggga cagtgcccac acccttagtg gtgggctgg ggctgcgtg tgaggtggca     780 cagcaagaga tggagtatga ccacaagcga atctcaaagt tgtcagagcg gctgatacag     840
aatataatga gagccttcc agatgtggtg atgaatgggg accctaagca ccattatccc     900
ggctgtatca acctctcctt tgcatatgtg gaagggaaa gtctgctgat ggcactgaag     960
gacgttgcct atcctcagg gagtgcctgc acctctgcat ccctggagcc ctcttatgtg    1020
```

```
cttagagcaa ttggcactga tgaggattta gcgcactctt ctatcaggtt tggaattggc    1080
cgcttcacta cagaggagga agtggactac acagtggaga aatgcattca gcatgtgaag    1140
cgtcttcgag aaatgagccc tctctgggag atggttcagg atggcattga cctcaagagc    1200
atcaagtgga cccaacacta g                                              1221
```

<210> SEQ ID NO 4
<211> LENGTH: 406
<212> TYPE: PRT
<213> ORGANISM: Homo sapiens

<400> SEQUENCE: 4

```
Met Leu Leu Arg Ala Ala Trp Arg Arg Ala Val Ala Val Thr Ala
1               5                   10                  15

Ala Pro Gly Pro Lys Pro Ala Ala Pro Thr Arg Gly Leu Arg Leu Arg
                20                  25                  30

Val Gly Asp Arg Ala Pro Gln Ser Ala Val Pro Ala Asp Thr Ala Ala
            35                  40                  45

Ala Pro Glu Val Gly Pro Val Leu Arg Pro Leu Tyr Met Asp Val Gln
        50                  55                  60

Ala Thr Thr Pro Leu Asp Pro Arg Val Leu Asp Ala Met Leu Pro Tyr
65                  70                  75                  80

Leu Ile Asn Tyr Tyr Gly Asn Pro His Ser Arg Thr His Ala Tyr Gly
                85                  90                  95

Trp Glu Ser Glu Ala Ala Met Glu Arg Ala Arg Gln Gln Val Ala Ser
            100                 105                 110

Leu Ile Gly Ala Asp Pro Arg Glu Ile Ile Phe Thr Ser Gly Ala Thr
        115                 120                 125

Glu Ser Asn Asn Ile Ala Ile Lys Glu Leu Glu Ala Ala Ile Gln Pro
    130                 135                 140

Asp Thr Ser Leu Val Ser Val Met Thr Val Asn Asn Glu Ile Gly Val
145                 150                 155                 160

Lys Gln Pro Ile Ala Glu Ile Gly Arg Ile Cys Ser Ser Arg Lys Val
                165                 170                 175

Tyr Phe His Thr Asp Ala Ala Gln Ala Val Gly Lys Ile Pro Leu Asp
            180                 185                 190

Val Asn Asp Met Lys Ile Asp Leu Met Ser Ile Ser Gly His Lys Ile
        195                 200                 205

Tyr Gly Pro Lys Gly Val Gly Ala Ile Tyr Ile Arg Arg Arg Pro Arg
    210                 215                 220

Val Arg Val Glu Ala Leu Gln Ser Gly Gly Gly Gln Glu Arg Gly Met
225                 230                 235                 240

Arg Ser Gly Thr Val Pro Thr Pro Leu Val Val Gly Leu Gly Ala Ala
                245                 250                 255

Cys Glu Val Ala Gln Gln Glu Met Glu Tyr Asp His Lys Arg Ile Ser
            260                 265                 270

Lys Leu Ser Glu Arg Leu Ile Gln Asn Ile Met Lys Ser Leu Pro Asp
        275                 280                 285

Val Val Met Asn Gly Asp Pro Lys His His Tyr Pro Gly Cys Ile Asn
    290                 295                 300

Leu Ser Phe Ala Tyr Val Glu Gly Glu Ser Leu Leu Met Ala Leu Lys
305                 310                 315                 320

Asp Val Ala Leu Ser Ser Gly Ser Ala Cys Thr Ser Ala Ser Leu Glu
                325                 330                 335
```

Pro Ser Tyr Val Leu Arg Ala Ile Gly Thr Asp Glu Asp Leu Ala His
                340                 345                 350

Ser Ser Ile Arg Phe Gly Ile Gly Arg Phe Thr Thr Glu Glu Val
            355                 360                 365

Asp Tyr Thr Val Glu Lys Cys Ile Gln His Val Lys Arg Leu Arg Glu
370                 375                 380

Met Ser Pro Leu Trp Glu Met Val Gln Asp Gly Ile Asp Leu Lys Ser
385                 390                 395                 400

Ile Lys Trp Thr Gln His
            405

<210> SEQ ID NO 5
<211> LENGTH: 276
<212> TYPE: DNA
<213> ORGANISM: Homo sapiens

<400> SEQUENCE: 5
atggcagcct ccagtcgcgc acaagtgtta tctctgtacc gggcgatgct gagagagagc      60
aagcgtttca gcgcctacaa ttacagaaca tatgctgtca ggaggataag agatgccttc     120
agagaaaata aaaatgtaaa ggatcctgta gaaattcaaa ccctagtgaa taaagccaag     180
agagaccttg gagtaattcg tcgacaggtc cacattggcc aactgtattc aactgacaag     240
ctgatcattg agaatcgaga catgcccagg acctag                              276

<210> SEQ ID NO 6
<211> LENGTH: 91
<212> TYPE: PRT
<213> ORGANISM: Homo sapiens

<400> SEQUENCE: 6

Met Ala Ala Ser Ser Arg Ala Gln Val Leu Ser Leu Tyr Arg Ala Met
1               5                   10                  15

Leu Arg Glu Ser Lys Arg Phe Ser Ala Tyr Asn Tyr Arg Thr Tyr Ala
            20                  25                  30

Val Arg Arg Ile Arg Asp Ala Phe Arg Glu Asn Lys Asn Val Lys Asp
        35                  40                  45

Pro Val Glu Ile Gln Thr Leu Val Asn Lys Ala Lys Arg Asp Leu Gly
    50                  55                  60

Val Ile Arg Arg Gln Val His Ile Gly Gln Leu Tyr Ser Thr Asp Lys
65                  70                  75                  80

Leu Ile Ile Glu Asn Arg Asp Met Pro Arg Thr
            85                  90

<210> SEQ ID NO 7
<211> LENGTH: 393
<212> TYPE: DNA
<213> ORGANISM: Homo sapiens

<400> SEQUENCE: 7
atggcagcct ccagtcgcgc acaagtgtta tctctgtacc gggcgatgct gagagagagc      60
aagcgtttca gcgcctacaa ttacagaaca tatgctgtca ggaggataag agatgccttc     120
agagaaaata aaaatgtaaa ggatcctgta gaaattcaaa ccctagtgaa taaagccaag     180
agagaccttg gagtaattcg tcgacagatg gactctcact ctgtcgccca ggctggagtg     240
cattggaacg atctcagctc actacaacct ctgcctccct ggttcaagca attctcctgc     300
ctcagcctcc cgagtagctg ggattatagg cgcacgccac cacgcctggc taatttttgt     360
attcttagta gagatgtgat ttcactgtat tag                                    393

<210> SEQ ID NO 8
<211> LENGTH: 130
<212> TYPE: PRT
<213> ORGANISM: Homo sapiens

<400> SEQUENCE: 8

Met Ala Ala Ser Ser Arg Ala Gln Val Leu Ser Leu Tyr Arg Ala Met
1               5                   10                  15

Leu Arg Glu Ser Lys Arg Phe Ser Ala Tyr Asn Tyr Arg Thr Tyr Ala
            20                  25                  30

Val Arg Arg Ile Arg Asp Ala Phe Arg Glu Asn Lys Asn Val Lys Asp
        35                  40                  45

Pro Val Glu Ile Gln Thr Leu Val Asn Lys Ala Lys Arg Asp Leu Gly
    50                  55                  60

Val Ile Arg Arg Gln Met Asp Ser His Ser Val Ala Gln Ala Gly Val
65                  70                  75                  80

His Trp Asn Asp Leu Ser Ser Leu Gln Pro Leu Pro Pro Trp Phe Lys
                85                  90                  95

Gln Phe Ser Cys Leu Ser Leu Pro Ser Ser Trp Asp Tyr Arg Arg Thr
            100                 105                 110

Pro Pro Arg Leu Ala Asn Phe Cys Ile Leu Ser Arg Asp Val Ile Ser
        115                 120                 125

Leu Tyr
    130

<210> SEQ ID NO 9
<211> LENGTH: 291
<212> TYPE: DNA
<213> ORGANISM: Homo sapiens

<400> SEQUENCE: 9
atggcagcct ccagtcgcgc acaagtgtta tctctgtacc gggcgatgct gagagagagc     60
aagcgtttca gcgcctacaa ttacagaaca tatgctgtca ggaggataag agatgccttc    120
agagaaaata aaaatgtaaa ggatcctgta gaaattcaaa ccctagtgaa taagccaag    180 agagaccttg gagtaattcg tcgacaggta gctgagcaag gcacagccgc caggaggaag    240
tcggggaaca gcagccggag cctggggaag ccctgcacaa gttggccttg a             291

<210> SEQ ID NO 10
<211> LENGTH: 96
<212> TYPE: PRT
<213> ORGANISM: Homo sapiens

<400> SEQUENCE: 10

Met Ala Ala Ser Ser Arg Ala Gln Val Leu Ser Leu Tyr Arg Ala Met
1               5                   10                  15

Leu Arg Glu Ser Lys Arg Phe Ser Ala Tyr Asn Tyr Arg Thr Tyr Ala
            20                  25                  30

Val Arg Arg Ile Arg Asp Ala Phe Arg Glu Asn Lys Asn Val Lys Asp
        35                  40                  45

Pro Val Glu Ile Gln Thr Leu Val Asn Lys Ala Lys Arg Asp Leu Gly
    50                  55                  60

Val Ile Arg Arg Gln Val Ala Glu Gln Gly Thr Ala Ala Arg Arg Lys
65                  70                  75                  80

```
Ser Gly Asn Ser Ser Arg Ser Leu Gly Lys Pro Cys Thr Ser Trp Pro
            85                  90                  95
```

<210> SEQ ID NO 11
<211> LENGTH: 429
<212> TYPE: DNA
<213> ORGANISM: Homo sapiens

<400> SEQUENCE: 11

| | |
|---|---|
| atggttctca ttgacatgag tgtagacctt tctactcagg ttgttgatca ttatgaaaat | 60 |
| cctagaaacg tggggtccct tgacaagaca tctaaaaatg ttggaactgg actggtgggg | 120 |
| gctccagcat gtggtgacgt aatgaaatta cagattcaag tggatgaaaa ggggaagatt | 180 |
| gtggatgcta ggtttaaaac atttggctgt ggttccgcaa ttgcctccag ctcattagcc | 240 |
| actgaatggg tgaaaggaaa gacggtggag gaagccttga ctatcaaaaa cacagatatc | 300 |
| gccaaggagc tctgccttcc tcccgtgaaa ctgcactgct ccatgctggc tgaagatgca | 360 |
| atcaaggccg ccctggctga ttacaaattg aaacaagaac caaaaaagg agaggcagag | 420 |
| aagaaatga | 429 |

<210> SEQ ID NO 12
<211> LENGTH: 142
<212> TYPE: PRT
<213> ORGANISM: Homo sapiens

<400> SEQUENCE: 12

```
Met Val Leu Ile Asp Met Ser Val Asp Leu Ser Thr Gln Val Val Asp
1               5                   10                  15

His Tyr Glu Asn Pro Arg Asn Val Gly Ser Leu Asp Lys Thr Ser Lys
            20                  25                  30

Asn Val Gly Thr Gly Leu Val Gly Ala Pro Ala Cys Gly Asp Val Met
        35                  40                  45

Lys Leu Gln Ile Gln Val Asp Glu Lys Gly Lys Ile Val Asp Ala Arg
    50                  55                  60

Phe Lys Thr Phe Gly Cys Gly Ser Ala Ile Ala Ser Ser Ser Leu Ala
65                  70                  75                  80

Thr Glu Trp Val Lys Gly Lys Thr Val Glu Glu Ala Leu Thr Ile Lys
                85                  90                  95

Asn Thr Asp Ile Ala Lys Glu Leu Cys Leu Pro Pro Val Lys Leu His
            100                 105                 110

Cys Ser Met Leu Ala Glu Asp Ala Ile Lys Ala Ala Leu Ala Asp Tyr
        115                 120                 125

Lys Leu Lys Gln Glu Pro Lys Lys Gly Glu Ala Glu Lys Lys
    130                 135                 140
```

<210> SEQ ID NO 13
<211> LENGTH: 504
<212> TYPE: DNA
<213> ORGANISM: Homo sapiens

<400> SEQUENCE: 13

| | |
|---|---|
| atggcggcgg ctggggcttt ccgtctgagg cggcggcat cggctctgct gctgcggagc | 60 |
| ccccgcctgc ccgcccggga gctgtcggcc ccggcccgac tctatcacaa gaaggttgtt | 120 |
| gatcattatg aaaatcctag aaacgtgggg tcccttgaca agacatctaa aaatgttgga | 180 |
| actggactgg tggggctcc agcatgtggt gacgtaatga aattacagat tcaagtggat | 240 |
| gaaaagggga gattgtgga tgctaggttt aaaacatttg gctgtggttc cgcaattgcc | 300 |

```
tccagctcat tagccactga atgggtgaaa ggaaagacgg tggaggaagc cttgactatc    360
aaaaacacag atatcgccaa ggagctctgc cttcctcccg tgaaactgca ctgctccatg    420
ctggctgaag atgcaatcaa ggccgccctg gctgattaca aattgaaaca agaacccaaa    480
aaaggagagg cagagaagaa atga                                          504
```

<210> SEQ ID NO 14
<211> LENGTH: 167
<212> TYPE: PRT
<213> ORGANISM: Homo sapiens

<400> SEQUENCE: 14

```
Met Ala Ala Ala Gly Ala Phe Arg Leu Arg Arg Ala Ala Ser Ala Leu
1               5                   10                  15

Leu Leu Arg Ser Pro Arg Leu Pro Ala Arg Glu Leu Ser Ala Pro Ala
            20                  25                  30

Arg Leu Tyr His Lys Lys Val Val Asp His Tyr Glu Asn Pro Arg Asn
        35                  40                  45

Val Gly Ser Leu Asp Lys Thr Ser Lys Asn Val Gly Thr Gly Leu Val
    50                  55                  60

Gly Ala Pro Ala Cys Gly Asp Val Met Lys Leu Gln Ile Gln Val Asp
65                  70                  75                  80

Glu Lys Gly Lys Ile Val Asp Ala Arg Phe Lys Thr Phe Gly Cys Gly
                85                  90                  95

Ser Ala Ile Ala Ser Ser Ser Leu Ala Thr Glu Trp Val Lys Gly Lys
            100                 105                 110

Thr Val Glu Glu Ala Leu Thr Ile Lys Asn Thr Asp Ile Ala Lys Glu
        115                 120                 125

Leu Cys Leu Pro Pro Val Lys Leu His Cys Ser Met Leu Ala Glu Asp
    130                 135                 140

Ala Ile Lys Ala Ala Leu Ala Asp Tyr Lys Leu Lys Gln Glu Pro Lys
145                 150                 155                 160

Lys Gly Glu Ala Glu Lys Lys
                165
```

<210> SEQ ID NO 15
<211> LENGTH: 633
<212> TYPE: DNA
<213> ORGANISM: Homo sapiens

<400> SEQUENCE: 15

```
atgtggactc tcgggcgccg cgcagtagcc ggcctcctgg cgtcacccag cccagcccag     60
gcccagaccc tcacccgggt cccgcggccg gcagagttgg ccccactctg cggccgccgt    120
ggcctgcgca ccgacatcga tgcgacctgc acgccccgcc gcgcaagttc gaaccaacgt    180
ggcctcaacc agatttggaa tgtcaaaaag cagagtgtct atttgatgaa tttgaggaaa    240
tctggaactt tgggccaccc aggctctcta gatgagacca cctatgaaag actagcagag    300
gaaacgctgg actctttagc agagtttttt gaagaccttg cagacaagcc atacacgttt    360
gaggactatg atgtctcctt tgggagtggt gtcttaactg tcaaactggg tggagatcta    420
ggaacctatg tgatcaacaa gcagacgcca aacaagcaaa tctggctatc ttctccatcc    480
agtggaccta gcgttatga ctggactggg aaaaactggg tgtactccca cgacggcgtg    540
tccctccatg agctgctggc cgcagagctc actaaagcct taaaaaccaa actggacttg    600
tcttccttgg cctattccgg aaaagatgct tga                                 633
```

<210> SEQ ID NO 16
<211> LENGTH: 210
<212> TYPE: PRT
<213> ORGANISM: Homo sapiens

<400> SEQUENCE: 16

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala
    210

<210> SEQ ID NO 17
<211> LENGTH: 591
<212> TYPE: DNA
<213> ORGANISM: Homo sapiens

<400> SEQUENCE: 17
atgtggactc tcgggcgccg cgcagtagcc ggcctcctgg cgtcacccag cccagcccag      60
gcccagaccc tcacccgggt cccgcggccg gcagagttgg ccccactctg cggccgccgt     120
ggcctgcgca ccgacatcga tgcgacctgc acgccccgcc gcgcaagttc gaaccaacgt     180
ggcctcaacc agatttggaa tgtcaaaaag cagagtgtct atttgatgaa tttgaggaaa     240
tctggaactt tgggccaccc aggctctcta gatgagacca cctatgaaag actagcagag     300
gaaacgctgg actctttagc agagttttt gaagaccttg cagacaagcc atacacgttt     360
gaggactatg atgtctcctt tgggagtggt gtcttaactg tcaaactggg tggagatcta     420
ggaacctatg tgatcaacaa gcagacgcca aacaagcaaa tctggctatc ttctccatcc     480
aggtatgtag tggacctaag cgttatgact ggactgggaa aaactggtgt actcccacg      540 acggcgtgtc cctccatgag ctgctggccg cagagctcac taaagcctta a              591

<210> SEQ ID NO 18
<211> LENGTH: 196
<212> TYPE: PRT
<213> ORGANISM: Homo sapiens

<400> SEQUENCE: 18

| | | | | | | | | | | | | | | | |
|---|---|---|---|---|---|---|---|---|---|---|---|---|---|---|---|
| Met | Trp | Thr | Leu | Gly | Arg | Arg | Ala | Val | Ala | Gly | Leu | Leu | Ala | Ser | Pro |
| 1 | | | | 5 | | | | | 10 | | | | | 15 | |
| Ser | Pro | Ala | Gln | Ala | Gln | Thr | Leu | Thr | Arg | Val | Pro | Arg | Pro | Ala | Glu |
| | | | 20 | | | | | 25 | | | | | 30 | | |
| Leu | Ala | Pro | Leu | Cys | Gly | Arg | Arg | Gly | Leu | Arg | Thr | Asp | Ile | Asp | Ala |
| | | | 35 | | | | 40 | | | | | 45 | | | |
| Thr | Cys | Thr | Pro | Arg | Arg | Ala | Ser | Ser | Asn | Gln | Arg | Gly | Leu | Asn | Gln |
| | 50 | | | | | 55 | | | | | 60 | | | | |
| Ile | Trp | Asn | Val | Lys | Lys | Gln | Ser | Val | Tyr | Leu | Met | Asn | Leu | Arg | Lys |
| 65 | | | | | 70 | | | | | 75 | | | | | 80 |
| Ser | Gly | Thr | Leu | Gly | His | Pro | Gly | Ser | Leu | Asp | Glu | Thr | Thr | Tyr | Glu |
| | | | | 85 | | | | | 90 | | | | | 95 | |
| Arg | Leu | Ala | Glu | Glu | Thr | Leu | Asp | Ser | Leu | Ala | Glu | Phe | Phe | Glu | Asp |
| | | | | 100 | | | | | 105 | | | | | 110 | |
| Leu | Ala | Asp | Lys | Pro | Tyr | Thr | Phe | Glu | Asp | Tyr | Asp | Val | Ser | Phe | Gly |
| | | | 115 | | | | | 120 | | | | | 125 | | |
| Ser | Gly | Val | Leu | Thr | Val | Lys | Leu | Gly | Gly | Asp | Leu | Gly | Thr | Tyr | Val |
| | | | 130 | | | | | 135 | | | | | 140 | | |
| Ile | Asn | Lys | Gln | Thr | Pro | Asn | Lys | Gln | Ile | Trp | Leu | Ser | Ser | Pro | Ser |
| 145 | | | | | 150 | | | | | 155 | | | | | 160 |
| Arg | Tyr | Val | Val | Asp | Leu | Ser | Val | Met | Thr | Gly | Leu | Gly | Lys | Thr | Gly |
| | | | | 165 | | | | | 170 | | | | | 175 | |
| Cys | Thr | Pro | Thr | Thr | Ala | Cys | Pro | Ser | Met | Ser | Cys | Trp | Pro | Gln | Ser |
| | | | | 180 | | | | | 185 | | | | | 190 | |
| Ser | Leu | Lys | Pro | | | | | | | | | | | | |
| | | | 195 | | | | | | | | | | | | |

<210> SEQ ID NO 19
<211> LENGTH: 516
<212> TYPE: DNA
<213> ORGANISM: Homo sapiens

<400> SEQUENCE: 19

```
atgtggactc tcgggcgccg cgcagtagcc ggcctcctgg cgtcacccag cccagcccag      60
gcccagaccc tcacccgggt cccgcggccg gcagagttgg ccccactctg cggccgccgt     120
ggcctgcgca ccgacatcga tgcgacctgc acgccccgcc gcgcaagttc gaaccaacgt     180
ggcctcaacc agatttggaa tgtcaaaaag cagagtgtct atttgatgaa tttgaggaaa     240
tctggaactt tgggccaccc aggctctcta gatgagacca cctatgaaag actagcagag     300
gaaacgctgg actctttagc agagtttttt gaagaccttg cagacaagcc atacacgttt     360
gaggactatg atgtctcctt tgggagtggt gtcttaactg tcaaactggg tggagatcta     420
ggaacctatg tgatcaacaa gcagacgcca aacaagcaaa tctggctatc ttctccatcc     480
aggttaacgt ggctcctgtg gctgttccat ccctga                                516
```

<210> SEQ ID NO 20
<211> LENGTH: 171
<212> TYPE: PRT
<213> ORGANISM: Homo sapiens

<400> SEQUENCE: 20

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
                20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
            115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Arg Leu Thr Trp Leu Leu Trp Leu Phe His Pro
                165                 170

<210> SEQ ID NO 21
<211> LENGTH: 693
<212> TYPE: DNA
<213> ORGANISM: Homo sapiens

<400> SEQUENCE: 21
atgttgaaga atccatacac cattaagaaa cagcctctgc atcagtttgt acaaagacca      60
cttttcccac tacctgcagc cttttatcac ccagtgagat acatgtttat tcaaacacaa     120
gataccccaa atccaaacag cttaaagttt ataccaggaa aaccagttct tgagacaagg     180
accatggatt ttcccacccc agctgcagca tttcgctccc ctctggctag gcagttattt     240
aggattgaag agtaaaaag tgtcttcttt ggaccagatt tcatcactgt cacaaaggaa     300
aatgaagaat tagactggaa tttactgaaa ccagatattt atgcaacaat catggacttc     360
tttgcatctg gcttacccct ggttactgag gaaacacctt caggagaagc aggatctgaa     420
gaagatgatg aagttgtggc aatgattaag gaattgttag atactagaat acggccaact     480
gtgcaggaag atggagggga tgtaatctac aaaggctttg aagatggcat tgtacagctg     540
aaactccagg gttcttgtac cagctgccct agttcaatca ttactctgaa aaatggaatt     600
cagaacatgc tgcagtttta tattccggag gtagaaggcg tagaacaggt tatggatgat     660
gaatcagatg aaaaagaagc aaactcacct taa                                  693

<210> SEQ ID NO 22
<211> LENGTH: 230
<212> TYPE: PRT
<213> ORGANISM: Homo sapiens

<400> SEQUENCE: 22

Met Leu Lys Asn Pro Tyr Thr Ile Lys Lys Gln Pro Leu His Gln Phe
1               5                   10                  15

Val Gln Arg Pro Leu Phe Pro Leu Pro Ala Ala Phe Tyr His Pro Val

```
                    20                  25                  30
Arg Tyr Met Phe Ile Gln Thr Gln Asp Thr Pro Asn Pro Asn Ser Leu
                35                  40                  45

Lys Phe Ile Pro Gly Lys Pro Val Leu Glu Thr Arg Thr Met Asp Phe
 50                  55                  60

Pro Thr Pro Ala Ala Ala Phe Arg Ser Pro Leu Ala Arg Gln Leu Phe
 65                  70                  75                  80

Arg Ile Glu Gly Val Lys Ser Val Phe Phe Gly Pro Asp Phe Ile Thr
                 85                  90                  95

Val Thr Lys Glu Asn Glu Glu Leu Asp Trp Asn Leu Leu Lys Pro Asp
                100                 105                 110

Ile Tyr Ala Thr Ile Met Asp Phe Phe Ala Ser Gly Leu Pro Leu Val
                115                 120                 125

Thr Glu Glu Thr Pro Ser Gly Glu Ala Gly Ser Glu Glu Asp Asp Glu
            130                 135                 140

Val Val Ala Met Ile Lys Glu Leu Leu Asp Thr Arg Ile Arg Pro Thr
145                 150                 155                 160

Val Gln Glu Asp Gly Gly Asp Val Ile Tyr Lys Gly Phe Glu Asp Gly
                165                 170                 175

Ile Val Gln Leu Lys Leu Gln Gly Ser Cys Thr Ser Cys Pro Ser Ser
                180                 185                 190

Ile Ile Thr Leu Lys Asn Gly Ile Gln Asn Met Leu Gln Phe Tyr Ile
                195                 200                 205

Pro Glu Val Glu Gly Val Glu Gln Val Met Asp Asp Glu Ser Asp Glu
            210                 215                 220

Lys Glu Ala Asn Ser Pro
225                 230

<210> SEQ ID NO 23
<211> LENGTH: 765
<212> TYPE: DNA
<213> ORGANISM: Homo sapiens

<400> SEQUENCE: 23
atggcggcga cggccaggcg gggctgggga gctgcggctg ttgccgccgg gctgcgcagg      60
cggttctgtc atatgttgaa gaatccatac accattaaga aacagcctct gcatcagttt    120
gtacaaagac cactttttcc actacctgca gcctttatc acccagtgag atacatgttt     180
attcaaacac aagatacccc aaatccaaac agcttaaagt ttataccagg aaaaccagtt    240
cttgagacaa ggaccatgga ttttcccacc ccagctgcag catttcgctc ccctctggct    300
aggcagttat ttaggattga aggagtaaaa agtgtcttct ttggaccaga tttcatcact    360
gtcacaaagg aaaatgaaga attagactgg aatttactga accagatat ttatgcaaca     420 atcatggact tctttgcatc tggcttaccc ctggttactg aggaaacacc ttcaggagaa    480
gcaggatctg aagaagatga tgaagttgtg gcaatgatta ggaattgtt agatactaga     540 atacggccaa ctgtgcagga agatggaggg gatgtaatct acaaaggctt tgaagatggc    600
attgtacagc tgaaactcca gggttcttgt accagctgcc ctagttcaat cattactctg    660
aaaaatggaa ttcagaacat gctgcagttt tatattccgg aggtagaagg cgtagaacag    720
gttatggatg atgaatcaga tgaaaaagaa gcaaactcac cttaa                    765

<210> SEQ ID NO 24
<211> LENGTH: 254
<212> TYPE: PRT
```

<213> ORGANISM: Homo sapiens

<400> SEQUENCE: 24

```
Met Ala Ala Thr Ala Arg Arg Gly Trp Gly Ala Ala Val Ala Ala
1               5                   10                  15
Gly Leu Arg Arg Arg Phe Cys His Met Leu Lys Asn Pro Tyr Thr Ile
            20                  25                  30
Lys Lys Gln Pro Leu His Gln Phe Val Gln Arg Pro Leu Phe Pro Leu
        35                  40                  45
Pro Ala Ala Phe Tyr His Pro Val Arg Tyr Met Phe Ile Gln Thr Gln
    50                  55                  60
Asp Thr Pro Asn Pro Asn Ser Leu Lys Phe Ile Pro Gly Lys Pro Val
65                  70                  75                  80
Leu Glu Thr Arg Thr Met Asp Phe Pro Thr Pro Ala Ala Phe Arg
                85                  90                  95
Ser Pro Leu Ala Arg Gln Leu Phe Arg Ile Glu Gly Val Lys Ser Val
            100                 105                 110
Phe Phe Gly Pro Asp Phe Ile Thr Val Thr Lys Glu Asn Glu Glu Leu
        115                 120                 125
Asp Trp Asn Leu Leu Lys Pro Asp Ile Tyr Ala Thr Ile Met Asp Phe
    130                 135                 140
Phe Ala Ser Gly Leu Pro Leu Val Thr Glu Glu Thr Pro Ser Gly Glu
145                 150                 155                 160
Ala Gly Ser Glu Glu Asp Asp Glu Val Val Ala Met Ile Lys Glu Leu
                165                 170                 175
Leu Asp Thr Arg Ile Arg Pro Thr Val Gln Glu Asp Gly Gly Asp Val
            180                 185                 190
Ile Tyr Lys Gly Phe Glu Asp Gly Ile Val Gln Leu Lys Leu Gln Gly
        195                 200                 205
Ser Cys Thr Ser Cys Pro Ser Ser Ile Ile Thr Leu Lys Asn Gly Ile
    210                 215                 220
Gln Asn Met Leu Gln Phe Tyr Ile Pro Glu Val Glu Gly Val Glu Gln
225                 230                 235                 240
Val Met Asp Asp Glu Ser Asp Glu Lys Glu Ala Asn Ser Pro
                245                 250
```

<210> SEQ ID NO 25
<211> LENGTH: 342
<212> TYPE: DNA
<213> ORGANISM: Homo sapiens

<400> SEQUENCE: 25

| | | | | | |
|---|---|---|---|---|---|
| atggacttct | ttgcatctgg | cttacccctg | gttactgagg | aaacaccttc | aggagaagca | 60 |
| ggatctgaag | aagatgatga | agttgtggca | atgattaagg | aattgttaga | tactagaata | 120 |
| cggccaactg | tgcaggaaga | tggaggggat | gtaatctaca | aaggctttga | agatggcatt | 180 |
| gtacagctga | aactccaggg | ttcttgtacc | agctgcccta | gttcaatcat | tactctgaaa | 240 |
| aatggaattc | agaacatgct | gcagttttat | attccggagg | tagaaggcgt | agaacaggtt | 300 |
| atggatgatg | aatcagatga | aaagaagca | aactcacctt | aa | | 342 |

<210> SEQ ID NO 26
<211> LENGTH: 113
<212> TYPE: PRT
<213> ORGANISM: Homo sapiens

<400> SEQUENCE: 26

```
Met Asp Phe Phe Ala Ser Gly Leu Pro Leu Val Thr Glu Thr Pro
1               5                   10                  15

Ser Gly Glu Ala Gly Ser Glu Asp Asp Glu Val Val Ala Met Ile
                20                  25                  30

Lys Glu Leu Leu Asp Thr Arg Ile Arg Pro Thr Val Gln Glu Asp Gly
            35                  40                  45

Gly Asp Val Ile Tyr Lys Gly Phe Glu Asp Gly Ile Val Gln Leu Lys
        50                  55                  60

Leu Gln Gly Ser Cys Thr Ser Cys Pro Ser Ser Ile Ile Thr Leu Lys
65              70                  75                  80

Asn Gly Ile Gln Asn Met Leu Gln Phe Tyr Ile Pro Glu Val Glu Gly
                85                  90                  95

Val Glu Gln Val Met Asp Asp Glu Ser Asp Glu Lys Glu Ala Asn Ser
            100                 105                 110

Pro
```

<210> SEQ ID NO 27
<211> LENGTH: 474
<212> TYPE: DNA
<213> ORGANISM: Homo sapiens

<400> SEQUENCE: 27

```
atgagcgggt ccctcggccg agctgcggcg gctctgctcc gctgggggcg cggcgcgggc      60
ggcggtggcc tttggggtcc gggcgtgcgg gcggcgggct cgggcgcggg cggcggcggc     120
tcggcggagc agttggacgc gctggtgaag aaggacaagg tggtggtctt cctcaagggg     180
acgccggagc agccccagtg cggcttcagc aacgccgtgg tgcagatcct gcggctgcac     240
ggcgtccgcg attacgcggc ctacaacgtg ctggacgacc cggagctccg acaaggcatt     300
aaagactatt ccaactggcc caccatcccg caagtgtacc tcaatggcga gtttgtaggg     360
ggctgtgaca ttcttctgca gatgcaccag aatgggggact ggtggaaga actgaaaaag     420
ctggggatcc actccgccct tttagatgaa agaaagacc aagactccaa gtga            474
```

<210> SEQ ID NO 28
<211> LENGTH: 157
<212> TYPE: PRT
<213> ORGANISM: Homo sapiens

<400> SEQUENCE: 28

```
Met Ser Gly Ser Leu Gly Arg Ala Ala Ala Leu Leu Arg Trp Gly
1               5                   10                  15

Arg Gly Ala Gly Gly Gly Leu Trp Gly Pro Gly Val Arg Ala Ala
            20                  25                  30

Gly Ser Gly Ala Gly Gly Gly Ser Ala Glu Gln Leu Asp Ala Leu
        35                  40                  45

Val Lys Lys Asp Lys Val Val Val Phe Leu Lys Gly Thr Pro Glu Gln
        50                  55                  60

Pro Gln Cys Gly Phe Ser Asn Ala Val Val Gln Ile Leu Arg Leu His
65              70                  75                  80

Gly Val Arg Asp Tyr Ala Ala Tyr Asn Val Leu Asp Asp Pro Glu Leu
                85                  90                  95

Arg Gln Gly Ile Lys Asp Tyr Ser Asn Trp Pro Thr Ile Pro Gln Val
            100                 105                 110

Tyr Leu Asn Gly Glu Phe Val Gly Gly Cys Asp Ile Leu Leu Gln Met
            115                 120                 125
```

His Gln Asn Gly Asp Leu Val Glu Glu Leu Lys Lys Leu Gly Ile His
        130                 135                 140

Ser Ala Leu Leu Asp Glu Lys Lys Asp Gln Asp Ser Lys
145                 150                 155

<210> SEQ ID NO 29
<211> LENGTH: 324
<212> TYPE: DNA
<213> ORGANISM: Homo sapiens

<400> SEQUENCE: 29
atggctgcat ggagcccggc cgcggcagcg cctctcctcc gcgggatccg cgggcttcca    60
cttcaccatc ggatgtttgc cactcagact gaggggagc tcagagtgac ccaaattctc     120
aaagaaaagt tccacgagc tacagctata aaagtcactg acatttcagg aggttgtggg    180
gcgatgtatg aaattaaaat tgaatcagaa gaatttaagg agaagagaac tgtccagcag    240
caccagatgg ttaatcaggc actaaaagaa gaaatcaaag atgcatgg attgcggata      300 tttacctctg tccccaaacg ctga                                            324

<210> SEQ ID NO 30
<211> LENGTH: 107
<212> TYPE: PRT
<213> ORGANISM: Homo sapiens

<400> SEQUENCE: 30

Met Ala Ala Trp Ser Pro Ala Ala Ala Pro Leu Leu Arg Gly Ile
1               5                   10                  15

Arg Gly Leu Pro Leu His His Arg Met Phe Ala Thr Gln Thr Glu Gly
            20                  25                  30

Glu Leu Arg Val Thr Gln Ile Leu Lys Glu Lys Phe Pro Arg Ala Thr
        35                  40                  45

Ala Ile Lys Val Thr Asp Ile Ser Gly Gly Cys Gly Ala Met Tyr Glu
    50                  55                  60

Ile Lys Ile Glu Ser Glu Glu Phe Lys Glu Lys Arg Thr Val Gln Gln
65                  70                  75                  80

His Gln Met Val Asn Gln Ala Leu Lys Glu Glu Ile Lys Glu Met His
                85                  90                  95

Gly Leu Arg Ile Phe Thr Ser Val Pro Lys Arg
            100                 105

<210> SEQ ID NO 31
<211> LENGTH: 306
<212> TYPE: DNA
<213> ORGANISM: Homo sapiens

<400> SEQUENCE: 31
atggctgcat ggagcccggc cgcggcagcg cctctcctcc gcgggatccg cgggcttcca    60
cttcaccatc ggatgtttgc cactcagact gaggggagc tcagagtgac ccaaattctc     120
aaagaaaagt tccacgagc tacagctata aaagtcactg acatttcagg cactaaaaga    180
agaaatcaaa gagatgcatg gattgcggat atttacctct gtccccaaac gctgaccacg    240
ccctggctgc atagatgctg ctgcttaaga ccttggatga acttcactga catcattctt    300
ccctaa                                                                306

<210> SEQ ID NO 32
<211> LENGTH: 101

-continued

<212> TYPE: PRT
<213> ORGANISM: Homo sapiens

<400> SEQUENCE: 32

```
Met Ala Ala Trp Ser Pro Ala Ala Ala Pro Leu Leu Arg Gly Ile
1               5                   10                  15

Arg Gly Leu Pro Leu His His Arg Met Phe Ala Thr Gln Thr Glu Gly
            20                  25                  30

Glu Leu Arg Val Thr Gln Ile Leu Lys Glu Lys Phe Pro Arg Ala Thr
        35                  40                  45

Ala Ile Lys Val Thr Asp Ile Ser Gly Thr Lys Arg Arg Asn Gln Arg
    50                  55                  60

Asp Ala Trp Ile Ala Asp Ile Tyr Leu Cys Pro Gln Thr Leu Thr Thr
65                  70                  75                  80

Pro Trp Leu His Arg Cys Cys Cys Leu Arg Pro Trp Met Asn Phe Thr
                85                  90                  95

Asp Ile Ile Leu Pro
            100
```

<210> SEQ ID NO 33
<211> LENGTH: 708
<212> TYPE: DNA
<213> ORGANISM: Homo sapiens

<400> SEQUENCE: 33

```
atgtggcggg ggagagccgg ggctttgctc cgggtgtggg ggttttggcc gacaggggtt     60
cccagaagga gaccgctaag ctgcgatgct cgtcgcagg cgggaagcaa ttatccccgc    120
tgttggaact gcggcggccc atggggcccc gggcgggagg acaggttctt ctgcccacag    180
tgccgagcgc tgcaggcacc tgaccccact cgagactact tcagcctttat ggactgcaac    240
cgttccttca gagttgatac agcgaagctc cagcacaggt accagcaact gcagcgtctt    300
gtccacccag atttcttcag ccagaggtct cagactgaaa aggacttctc agagaagcat    360
tcgaccctgg tgaatgatgc ctataagacc ctcctggccc ccctgagcag aggactgtac    420
cttctaaagc tccatggaat agagattcct gaaaggacag attatgaaat ggacaggcaa    480
ttcctcatag aaataatgga atcaatgaa aaactcgcag aagctgaaag tgaagctgcc    540
atgaaagaga ttgaatccat tgtcaaagct aaacagaaag aatttactga caatgtgagc    600
agtgcttttg aacaagatga ctttgaagaa gccaaggaaa ttttgacaaa gatgagatac    660
ttttcaaata tagaagaaaa gatcaagtta agaagattc ccctttaa                 708
```

<210> SEQ ID NO 34
<211> LENGTH: 235
<212> TYPE: PRT
<213> ORGANISM: Homo sapiens

<400> SEQUENCE: 34

```
Met Trp Arg Gly Arg Ala Gly Ala Leu Leu Arg Val Trp Gly Phe Trp
1               5                   10                  15

Pro Thr Gly Val Pro Arg Arg Arg Pro Leu Ser Cys Asp Ala Ala Ser
            20                  25                  30

Gln Ala Gly Ser Asn Tyr Pro Arg Cys Trp Asn Cys Gly Gly Pro Trp
        35                  40                  45

Gly Pro Gly Arg Glu Asp Arg Phe Phe Cys Pro Gln Cys Arg Ala Leu
    50                  55                  60

Gln Ala Pro Asp Pro Thr Arg Asp Tyr Phe Ser Leu Met Asp Cys Asn
```

```
                65                  70                  75                  80
Arg Ser Phe Arg Val Asp Thr Ala Lys Leu Gln His Arg Tyr Gln Gln
                    85                  90                  95

Leu Gln Arg Leu Val His Pro Asp Phe Phe Ser Gln Arg Ser Gln Thr
                    100                 105                 110

Glu Lys Asp Phe Ser Glu Lys His Ser Thr Leu Val Asn Asp Ala Tyr
                    115                 120                 125

Lys Thr Leu Leu Ala Pro Leu Ser Arg Gly Leu Tyr Leu Leu Lys Leu
        130                 135                 140

His Gly Ile Glu Ile Pro Glu Arg Thr Asp Tyr Glu Met Asp Arg Gln
145                 150                 155                 160

Phe Leu Ile Glu Ile Met Glu Ile Asn Glu Lys Leu Ala Glu Ala Glu
                    165                 170                 175

Ser Glu Ala Ala Met Lys Glu Ile Glu Ser Ile Val Lys Ala Lys Gln
                    180                 185                 190

Lys Glu Phe Thr Asp Asn Val Ser Ser Ala Phe Glu Gln Asp Asp Phe
                    195                 200                 205

Glu Glu Ala Lys Glu Ile Leu Thr Lys Met Arg Tyr Phe Ser Asn Ile
        210                 215                 220

Glu Glu Lys Ile Lys Leu Lys Lys Ile Pro Leu
225                 230                 235

<210> SEQ ID NO 35
<211> LENGTH: 2040
<212> TYPE: DNA
<213> ORGANISM: Homo sapiens

<400> SEQUENCE: 35
atgataagtg ccagccgagc tgcagcagcc cgtctcgtgg gcgccgcagc ctcccggggc    60
cctacggccg cccgccacca ggatagctgg aatggcctta gtcatgaggc ttttagactt   120
gtttcaaggc gggattatgc atcagaagca atcaagggag cagttgttgg tattgatttg   180
ggtactacca actcctgcgt ggcagttatg gaaggtaaac aagcaaaggt gctggagaat   240
gccgaaggtg ccagaaccac cccttcagtt gtggccttta cagcagatgg tgagcgactt   300
gttggaatgc cggccaagcg acaggctgtc accaacccaa acaatacatt ttatgctacc   360
aagcgtctca ttggccggcg atatgatgat cctgaagtac agaaagacat taaaaatgtt   420
ccctttaaaa ttgtccgtgc ctccaatggt gatgcctggg ttgaggctca tgggaaattg   480
tattctccga gtcagattgg agcatttgtt ttgatgaaga tgaaagagac tgcagaaaat   540
tacttggggc acacagcaaa aaatgctgtg atcacagtcc cagcttattt caatgactcg   600
cagagacagg ccactaaaga tgctggccag atatctggac tgaatgtgct tcgggtgatt   660
aatgagccca cagctgctgc tcttgcctat ggtctagaca atcagaaga caaagtcatt   720 gctgtatatg atttaggtgg tggaactttt gatatttcta tcctggaaat tcagaaagga   780
gtatttgagg tgaaatccac aaatggggat accttcttag gtggggaaga ctttgaccag   840
gccttgctac ggcacattgt gaaggagttc aagagagaga caggggttga tttgactaaa   900
gacaacatgg cacttcagag ggtacgggaa gctgctgaaa aggctaaatg tgaactctcc   960
tcatctgtgc agactgacat caatttgccc tatcttacaa tggattcttc tggacccaag  1020
catttgaata tgaagttgac ccgtgctcaa tttgaaggga ttgtcactga tctaatcaga  1080
aggactatcg ctccatgcca aaaagctatg caagatgcaa agtcagcaa gagtgacata  1140 ggagaagtga ttcttgtggg tggcatgact aggatgccca aggttcagca gactgtacag  1200
```

```
gatcttttg gcagagcccc aagtaaagct gtcaatcctg atgaggctgt ggccattgga    1260
gctgccattc agggaggtgt gttggccggc gatgtcacgg atgtgctgct ccttgatgtc    1320
actcccctgt ctctgggtat tgaaactcta ggaggtgtct ttaccaaact tattaatagg    1380
aataccacta ttccaaccaa gaagagccag gtattctcta ctgccgctga tggtcaaacg    1440
caagtggaaa ttaaagtgtg tcagggtgaa agagagatgg ctggagacaa caaactcctt    1500
ggacagttta ctttgattgg aattccacca gccctcgtg gagttcctca gattgaagtt    1560
acatttgaca ttgatgccaa tgggatagta catgtttctg ctaaagataa aggcacagga    1620
cgtgagcagc agattgtaat ccagtcttct ggtggattaa gcaaagatga tattgaaaat    1680
atggttaaaa atgcagagaa atatgctgaa gaagaccggc gaaagaagga acgagttgaa    1740
gcagttaata tggctgaagg aatcattcac gacacagaaa ccaagatgga agaattcaag    1800
gaccaattac ctgctgatga gtgcaacaag ctgaaagaag agatttccaa aatgagggag    1860
ctcctggcta gaaaagacag cgaaacagga gaaaatatta gacaggcagc atcctctctt    1920
cagcaggcat cactgaagct gttcgaaatg gcatacaaaa agatggcatc tgagcgagaa    1980
ggctctggaa gttctggcac tggggaacaa aaggaagatc aaaaggagga aaacagtaa     2040
```

<210> SEQ ID NO 36
<211> LENGTH: 679
<212> TYPE: PRT
<213> ORGANISM: Homo sapiens

<400> SEQUENCE: 36

```
Met Ile Ser Ala Ser Arg Ala Ala Ala Arg Leu Val Gly Ala Ala
1               5                  10                  15

Ala Ser Arg Gly Pro Thr Ala Ala Arg His Gln Asp Ser Trp Asn Gly
            20                  25                  30

Leu Ser His Glu Ala Phe Arg Leu Val Ser Arg Arg Asp Tyr Ala Ser
        35                  40                  45

Glu Ala Ile Lys Gly Ala Val Val Gly Ile Asp Leu Gly Thr Thr Asn
    50                  55                  60

Ser Cys Val Ala Val Met Glu Gly Lys Gln Ala Lys Val Leu Glu Asn
65                  70                  75                  80

Ala Glu Gly Ala Arg Thr Thr Pro Ser Val Val Ala Phe Thr Ala Asp
                85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
        115                 120                 125

Asp Asp Pro Glu Val Gln Lys Asp Ile Lys Asn Val Pro Phe Lys Ile
    130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220
```

```
Ala Ala Ala Leu Ala Tyr Gly Leu Asp Lys Ser Glu Asp Lys Val Ile
225                 230                 235                 240

Ala Val Tyr Asp Leu Gly Gly Thr Phe Asp Ile Ser Ile Leu Glu
            245                 250                 255

Ile Gln Lys Gly Val Phe Glu Val Lys Ser Thr Asn Gly Asp Thr Phe
                260                 265                 270

Leu Gly Gly Glu Asp Phe Asp Gln Ala Leu Leu Arg His Ile Val Lys
            275                 280                 285

Glu Phe Lys Arg Glu Thr Gly Val Asp Leu Thr Lys Asp Asn Met Ala
            290                 295                 300

Leu Gln Arg Val Arg Glu Ala Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
            355                 360                 365

Ala Met Gln Asp Ala Glu Val Ser Lys Ser Asp Ile Gly Glu Val Ile
370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
            405                 410                 415

Val Ala Ile Gly Ala Ala Ile Gln Gly Gly Val Leu Ala Gly Asp Val
            420                 425                 430

Thr Asp Val Leu Leu Leu Asp Val Thr Pro Leu Ser Leu Gly Ile Glu
            435                 440                 445

Thr Leu Gly Gly Val Phe Thr Lys Leu Ile Asn Arg Asn Thr Thr Ile
450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
            485                 490                 495

Asn Lys Leu Leu Gly Gln Phe Thr Leu Ile Gly Ile Pro Pro Ala Pro
            500                 505                 510

Arg Gly Val Pro Gln Ile Glu Val Thr Phe Asp Ile Asp Ala Asn Gly
            515                 520                 525

Ile Val His Val Ser Ala Lys Asp Lys Gly Thr Gly Arg Glu Gln Gln
            530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Glu Asp Arg Arg Lys Lys
            565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
            595                 600                 605

Asn Lys Leu Lys Glu Glu Ile Ser Lys Met Arg Glu Leu Leu Ala Arg
            610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
```

```
                      645                 650                 655
Ser Glu Arg Glu Gly Ser Gly Ser Ser Gly Thr Gly Glu Gln Lys Glu
                660                 665                 670

Asp Gln Lys Glu Glu Lys Gln
        675

<210> SEQ ID NO 37
<211> LENGTH: 390
<212> TYPE: DNA
<213> ORGANISM: Homo sapiens

<400> SEQUENCE: 37
atgtcggctt ccttagtccg ggcaactgtc cgggctgtga gcaagaggaa gctgcagccc    60
acccgggcag ccctcaccct gacaccttca gcagtaaaca agataaaaca acttcttaaa   120
gataagcctg agcatgtagg tgtaaaagtt ggtgtccgaa ccaggggctg taatggcctt   180
tcttatactc tagaatatac aaagacaaaa ggagattctg atgaagaagt tattcaagat   240
ggagtcagag tattcatcga aaagaaagca cagctaacac ttttaggaac agaaatggac   300
tatgttgaag acaaattatc cagtgagttt gtgttcaata acccaaacat caagggact   360 tgtggctgtg gagaaagctt taatatttga                                    390

<210> SEQ ID NO 38
<211> LENGTH: 129
<212> TYPE: PRT
<213> ORGANISM: Homo sapiens

<400> SEQUENCE: 38

Met Ser Ala Ser Leu Val Arg Ala Thr Val Arg Ala Val Ser Lys Arg
1               5                   10                  15

Lys Leu Gln Pro Thr Arg Ala Ala Leu Thr Leu Thr Pro Ser Ala Val
            20                  25                  30

Asn Lys Ile Lys Gln Leu Leu Lys Asp Lys Pro Glu His Val Gly Val
        35                  40                  45

Lys Val Gly Val Arg Thr Arg Gly Cys Asn Gly Leu Ser Tyr Thr Leu
    50                  55                  60

Glu Tyr Thr Lys Thr Lys Gly Asp Ser Asp Glu Glu Val Ile Gln Asp
65                  70                  75                  80

Gly Val Arg Val Phe Ile Glu Lys Lys Ala Gln Leu Thr Leu Leu Gly
                85                  90                  95

Thr Glu Met Asp Tyr Val Glu Asp Lys Leu Ser Ser Glu Phe Val Phe
            100                 105                 110

Asn Asn Pro Asn Ile Lys Gly Thr Cys Gly Cys Gly Glu Ser Phe Asn
        115                 120                 125

Ile

<210> SEQ ID NO 39
<211> LENGTH: 465
<212> TYPE: DNA
<213> ORGANISM: Homo sapiens

<400> SEQUENCE: 39
atggctgccg cctgggggtc gtccctaacg gccgcgacgc agagagcggt cactccctgg    60 ccgagggggca ggctcctcac ggcctccctg gaccccagg cgcgtcggga ggcgtcgtcc   120
tccagccccg aggccggcga agggcagatc cgcctcacag acagttgcgt ccagaggctt   180
ttggaaatca ccgaagggtc agaattcctc aggctgcaag tggagggagg tggatgctcc   240
```

-continued

```
ggattccaat acaaattttc actggataca gttatcaacc ccgacgacag ggtatttgaa    300
cagggtgggg caagagtggt ggttgactct gatagcttgg ccttcgtgaa aggggcccag    360
gtggacttca gccaagaact gatccgaagc tcatttcaag tgttgaacaa tcctcaagca    420
cagcaaggct gctcctgtgg gtcatctttc tctatcaaac tttga                   465
```

<210> SEQ ID NO 40
<211> LENGTH: 154
<212> TYPE: PRT
<213> ORGANISM: Homo sapiens

<400> SEQUENCE: 40

```
Met Ala Ala Ala Trp Gly Ser Ser Leu Thr Ala Ala Thr Gln Arg Ala
1               5                   10                  15

Val Thr Pro Trp Pro Arg Gly Arg Leu Leu Thr Ala Ser Leu Gly Pro
            20                  25                  30

Gln Ala Arg Arg Glu Ala Ser Ser Ser Pro Glu Ala Gly Glu Gly
        35                  40                  45

Gln Ile Arg Leu Thr Asp Ser Cys Val Gln Arg Leu Leu Glu Ile Thr
    50                  55                  60

Glu Gly Ser Glu Phe Leu Arg Leu Gln Val Glu Gly Gly Cys Ser
65                  70                  75                  80

Gly Phe Gln Tyr Lys Phe Ser Leu Asp Thr Val Ile Asn Pro Asp Asp
                85                  90                  95

Arg Val Phe Glu Gln Gly Gly Ala Arg Val Val Val Asp Ser Asp Ser
            100                 105                 110

Leu Ala Phe Val Lys Gly Ala Gln Val Asp Phe Ser Gln Glu Leu Ile
        115                 120                 125

Arg Ser Ser Phe Gln Val Leu Asn Asn Pro Gln Ala Gln Gln Gly Cys
    130                 135                 140

Ser Cys Gly Ser Ser Phe Ser Ile Lys Leu
145                 150
```

<210> SEQ ID NO 41
<211> LENGTH: 183
<212> TYPE: DNA
<213> ORGANISM: Homo sapiens

<400> SEQUENCE: 41

```
atggctgccg cctgggggtc gtccctaacg gccgcgacgc agagagcggt cactccctgg    60
ccgaggggca ggctcctcac ggcctccctg gaccccagg cgcgtcggga ggcgtcgtcc    120
tccagccccg aggccggcga agggcagatc cgcctcacag acagttgcgt ccagggtatt    180
tga                                                                 183
```

<210> SEQ ID NO 42
<211> LENGTH: 60
<212> TYPE: PRT
<213> ORGANISM: Homo sapiens

<400> SEQUENCE: 42

```
Met Ala Ala Ala Trp Gly Ser Ser Leu Thr Ala Ala Thr Gln Arg Ala
1               5                   10                  15

Val Thr Pro Trp Pro Arg Gly Arg Leu Leu Thr Ala Ser Leu Gly Pro
            20                  25                  30

Gln Ala Arg Arg Glu Ala Ser Ser Ser Pro Glu Ala Gly Glu Gly
        35                  40                  45
```

```
Gln Ile Arg Leu Thr Asp Ser Cys Val Gln Gly Ile
 50                  55                  60
```

<210> SEQ ID NO 43
<211> LENGTH: 1071
<212> TYPE: DNA
<213> ORGANISM: Homo sapiens

<400> SEQUENCE: 43

```
atggcgaccg cggcgctgct tcgaggcgcc actccggggc gcggcggccc ggtctggcgc      60
tggcggctgc gcgcggcccc aaggtgccgc ctggcccaca gctcctgcag tcctggtggc     120
gacccaacgg ccggagcggc ctgggcctgc ttccggctgg acgggcgcac cctgctgcgc     180
gtgcgtggcc ccgacgcggc gcccttcctg ctagggctgc tgaccaatga actgccgctt     240
ccgagtcctg cggccgcggg ggccccgcct gctgcgcgcg cgggctacgc ccacttcctg     300
aacgtgcagg gccggacgct ctatgacgtc atcttgtacg gcctccagga acactcggag     360
gtgtctggct tccttctgga gtgtgacagc tcggtgcagg gcgcgctgca gaagcacctc     420
gcgctataca ggatccggcg gaaggtcacg gtggagccgc acccggagct gcgagtgtgg     480
gcggtgttgc ccagttcccc tgaggcctgc ggggctgcat cgctgcagga gagggcaggg     540
gctgccgcca tcctcatccg cgacccgcga acagcacgca tggggtggcg gctcctcacc     600
caggatgaag gccagccct ggtgcccggg gccggctcg gggacttgtg ggattatcac     660
cagcaccgat acctgcaagg cgttcctgag ggggtccgag acttgcctcc tggggtggcc     720
ctgcccctgg agtccaacct ggccttcatg aacggcgtga gcttcaccaa aggctgctac     780
attggccagg agctgacggc ccgcacccac acatgggcg tcatccgcaa gcgcctcttc     840
cctgtccggt tcttggaccc ccttcccacc agtggcatca cccctggtgc cacggtgctg     900
actgcctcag acagactgt gggcaagttc agggctggcc agggcaacgt ggggctggcc     960
ctgctgtggt cagagaagat caagggtcct ctgcacatca gagcctctga gggtgcccag    1020
gtggccttag ccgcatctgt gccagactgg tggcctacag tctccaagta g              1071
```

<210> SEQ ID NO 44
<211> LENGTH: 356
<212> TYPE: PRT
<213> ORGANISM: Homo sapiens

<400> SEQUENCE: 44

```
Met Ala Thr Ala Ala Leu Leu Arg Gly Ala Thr Pro Gly Arg Gly Gly
 1               5                  10                  15

Pro Val Trp Arg Trp Arg Leu Arg Ala Ala Pro Arg Cys Arg Leu Ala
                20                  25                  30

His Ser Ser Cys Ser Pro Gly Gly Asp Pro Thr Ala Gly Ala Ala Trp
             35                  40                  45

Ala Cys Phe Arg Leu Asp Gly Arg Thr Leu Leu Arg Val Arg Gly Pro
         50                  55                  60

Asp Ala Ala Pro Phe Leu Leu Gly Leu Leu Thr Asn Glu Leu Pro Leu
 65                  70                  75                  80

Pro Ser Pro Ala Ala Gly Ala Pro Pro Ala Arg Ala Gly Tyr
                85                  90                  95

Ala His Phe Leu Asn Val Gln Gly Arg Thr Leu Tyr Asp Val Ile Leu
                100                 105                 110

Tyr Gly Leu Gln Glu His Ser Glu Val Ser Gly Phe Leu Leu Glu Cys
            115                 120                 125
```

```
Asp Ser Ser Val Gln Gly Ala Leu Gln Lys His Leu Ala Leu Tyr Arg
            130                 135                 140

Ile Arg Arg Lys Val Thr Val Glu Pro His Pro Glu Leu Arg Val Trp
145                 150                 155                 160

Ala Val Leu Pro Ser Ser Pro Glu Ala Cys Gly Ala Ala Ser Leu Gln
                165                 170                 175

Glu Arg Ala Gly Ala Ala Ala Ile Leu Ile Arg Asp Pro Arg Thr Ala
            180                 185                 190

Arg Met Gly Trp Arg Leu Leu Thr Gln Asp Glu Gly Pro Ala Leu Val
            195                 200                 205

Pro Gly Gly Arg Leu Gly Asp Leu Trp Asp Tyr His Gln His Arg Tyr
210                 215                 220

Leu Gln Gly Val Pro Glu Gly Val Arg Asp Leu Pro Pro Gly Val Ala
225                 230                 235                 240

Leu Pro Leu Glu Ser Asn Leu Ala Phe Met Asn Gly Val Ser Phe Thr
                245                 250                 255

Lys Gly Cys Tyr Ile Gly Gln Glu Leu Thr Ala Arg Thr His His Met
            260                 265                 270

Gly Val Ile Arg Lys Arg Leu Phe Pro Val Arg Phe Leu Asp Pro Leu
            275                 280                 285

Pro Thr Ser Gly Ile Thr Pro Gly Ala Thr Val Leu Thr Ala Ser Gly
290                 295                 300

Gln Thr Val Gly Lys Phe Arg Ala Gly Gln Gly Asn Val Gly Leu Ala
305                 310                 315                 320

Leu Leu Trp Ser Glu Lys Ile Lys Gly Pro Leu His Ile Arg Ala Ser
                325                 330                 335

Glu Gly Ala Gln Val Ala Leu Ala Ala Ser Val Pro Asp Trp Trp Pro
            340                 345                 350

Thr Val Ser Lys
            355

<210> SEQ ID NO 45
<211> LENGTH: 960
<212> TYPE: DNA
<213> ORGANISM: Homo sapiens

<400> SEQUENCE: 45
atggggattt ggcagcgtct gctgcttttt ggtggggtgt cgctccgggc tggtggcggg      60
gccactgccc cgcttggggg aagccgagcg atggtttgtg ggcgccagtt gtctggcgcc     120
gggagtgaga ccctaaaaca agaagaacaa caaatcatgt cccgaggact tccaaagcag     180
aaaccgatag aaggtgttaa acaagttata gttgtggctt ctggaaaggg tggagtcgga     240
aaatctacta cagcagtgaa tcttgcactt gcactagcag cgaacgattc gtccaaggcc     300
attggtttgc tagatgtgga tgtgtatgga ccttcagttc aaagatgat gaatctgaaa      360 ggaaatccgg aattatcaca gagcaaccta atgaggcctc tcttgaatta tggtattgct     420
tgtatgtcta tgggcttttct ggttgaagaa agtgaaccag tagtttggag aggccttatg    480
gtaatgtcgg ccattgagaa attgttgagg caggtagatt ggggtcaact ggactactta     540
gttgtagaca tgccaccagg aactggagat gtgcagttat cagtctcaca gaatattcct     600
ataacaggtg ctgtgattgt ctccacgccc caggacatcg cattgatgga tgcacacaag     660
ggtgctgaga tgtttcgcag agtccacgtg cccgtccttg gccttgtcca aaacatgagt     720
gttttccagt gtccaaaatg taaacacaaa actcatattt ttggtgctga tggtgcaagg     780
```

```
aaactagcac agaccttgg tcttgaagtt ctaggagaca ttcccttaca ccttaatata      840
agggaagctt cagatacagg ccagccaatt gtgttttcac agcctgaaag tgatgaggcc      900
aaagcttact tgaggattgc tgtggaagtg gtaagaagat tgccatcacc ttcagaatga      960
```

<210> SEQ ID NO 46
<211> LENGTH: 319
<212> TYPE: PRT
<213> ORGANISM: Homo sapiens

<400> SEQUENCE: 46

```
Met Gly Ile Trp Gln Arg Leu Leu Phe Gly Gly Val Ser Leu Arg
1               5                   10                  15

Ala Gly Gly Ala Thr Ala Pro Leu Gly Gly Ser Arg Ala Met Val
                20                  25                  30

Cys Gly Arg Gln Leu Ser Gly Ala Gly Ser Glu Thr Leu Lys Gln Arg
            35                  40                  45

Arg Thr Gln Ile Met Ser Arg Gly Leu Pro Lys Gln Lys Pro Ile Glu
        50                  55                      60

Gly Val Lys Gln Val Ile Val Ala Ser Lys Gly Gly Val Gly
65              70                  75                  80

Lys Ser Thr Thr Ala Val Asn Leu Ala Leu Ala Leu Ala Ala Asn Asp
                85                  90                  95

Ser Ser Lys Ala Ile Gly Leu Leu Asp Val Asp Val Tyr Gly Pro Ser
                100                 105                 110

Val Pro Lys Met Met Asn Leu Lys Gly Asn Pro Glu Leu Ser Gln Ser
            115                 120                 125

Asn Leu Met Arg Pro Leu Leu Asn Tyr Gly Ile Ala Cys Met Ser Met
130                 135                 140

Gly Phe Leu Val Glu Glu Ser Glu Pro Val Val Trp Arg Gly Leu Met
145                 150                 155                 160

Val Met Ser Ala Ile Glu Lys Leu Leu Arg Gln Val Asp Trp Gly Gln
                165                 170                 175

Leu Asp Tyr Leu Val Val Asp Met Pro Pro Gly Thr Gly Asp Val Gln
            180                 185                 190

Leu Ser Val Ser Gln Asn Ile Pro Ile Thr Gly Ala Val Ile Val Ser
        195                 200                 205

Thr Pro Gln Asp Ile Ala Leu Met Asp Ala His Lys Gly Ala Glu Met
    210                 215                 220

Phe Arg Arg Val His Val Pro Val Leu Gly Leu Val Gln Asn Met Ser
225                 230                 235                 240

Val Phe Gln Cys Pro Lys Cys Lys His Lys Thr His Ile Phe Gly Ala
                245                 250                 255

Asp Gly Ala Arg Lys Leu Ala Gln Thr Leu Gly Leu Glu Val Leu Gly
            260                 265                 270

Asp Ile Pro Leu His Leu Asn Ile Arg Glu Ala Ser Asp Thr Gly Gln
        275                 280                 285

Pro Ile Val Phe Ser Gln Pro Glu Ser Asp Glu Ala Lys Ala Tyr Leu
    290                 295                 300

Arg Ile Ala Val Glu Val Val Arg Arg Leu Pro Ser Pro Ser Glu
305                 310                 315
```

<210> SEQ ID NO 47
<211> LENGTH: 672
<212> TYPE: DNA

<213> ORGANISM: Homo sapiens

<400> SEQUENCE: 47

```
atgtccaagg ccattggttt gctagatgtg gatgtgtatg gaccttcagt tccaaagatg    60
atgaatctga aaggaaatcc ggaattatca cagagcaacc taatgaggcc tctcttgaat   120
tatggtattg cttgtatgtc tatgggcttt ctggttgaag aaagtgaacc agtagtttgg   180
agaggcctta tggtaatgtc ggccattgag aaattgttga ggcaggtaga ttggggtcaa   240
ctggactact tagttgtaga catgccacca ggaactggag atgtgcagtt atcagtctca   300
cagaatattc ctataacagg tgctgtgatt gtctccacgc cccaggacat cgcattgatg   360
gatgcacaca agggtgctga gatgtttcgc agagtccacg tgcccgtcct tggccttgtc   420
caaaacatga gtgttttcca gtgtccaaaa tgtaaacaca aaactcatat ttttggtgct   480
gatggtgcaa ggaaactagc acagacccct ggtcttgaag ttctaggaga cattccctta   540
caccttaata taagggaagc ttcagataca ggccagccaa ttgtgttttc acagcctgaa   600
agtgatgagg ccaaagctta cttgaggatt gctgtggaag tggtaagaag attgccatca   660
ccttcagaat ga                                                       672
```

<210> SEQ ID NO 48
<211> LENGTH: 223
<212> TYPE: PRT
<213> ORGANISM: Homo sapiens

<400> SEQUENCE: 48

```
Met Ser Lys Ala Ile Gly Leu Leu Asp Val Asp Val Tyr Gly Pro Ser
1               5                   10                  15

Val Pro Lys Met Met Asn Leu Lys Gly Asn Pro Glu Leu Ser Gln Ser
            20                  25                  30

Asn Leu Met Arg Pro Leu Leu Asn Tyr Gly Ile Ala Cys Met Ser Met
        35                  40                  45

Gly Phe Leu Val Glu Glu Ser Glu Pro Val Val Trp Arg Gly Leu Met
    50                  55                  60

Val Met Ser Ala Ile Glu Lys Leu Leu Arg Gln Val Asp Trp Gly Gln
65                  70                  75                  80

Leu Asp Tyr Leu Val Val Asp Met Pro Pro Gly Thr Gly Asp Val Gln
                85                  90                  95

Leu Ser Val Ser Gln Asn Ile Pro Ile Thr Gly Ala Val Ile Val Ser
            100                 105                 110

Thr Pro Gln Asp Ile Ala Leu Met Asp Ala His Lys Gly Ala Glu Met
        115                 120                 125

Phe Arg Arg Val His Val Pro Val Leu Gly Leu Val Gln Asn Met Ser
    130                 135                 140

Val Phe Gln Cys Pro Lys Cys Lys His Lys Thr His Ile Phe Gly Ala
145                 150                 155                 160

Asp Gly Ala Arg Lys Leu Ala Gln Thr Leu Gly Leu Glu Val Leu Gly
                165                 170                 175

Asp Ile Pro Leu His Leu Asn Ile Arg Glu Ala Ser Asp Thr Gly Gln
            180                 185                 190

Pro Ile Val Phe Ser Gln Pro Glu Ser Asp Glu Ala Lys Ala Tyr Leu
        195                 200                 205

Arg Ile Ala Val Glu Val Val Arg Arg Leu Pro Ser Pro Ser Glu
    210                 215                 220
```

-continued

```
<210> SEQ ID NO 49
<211> LENGTH: 411
<212> TYPE: DNA
<213> ORGANISM: Homo sapiens

<400> SEQUENCE: 49
atgccaccag gaactggaga tgtgcagtta tcagtctcac agaatattcc tataacaggt      60
gctgtgattg tctccacgcc ccaggacatc gcattgatgg atgcacacaa gggtgctgag     120
atgtttcgca gagtccacgt gcccgtcctt ggccttgtcc aaaacatgag tgttttccag     180
tgtccaaaat gtaaacacaa aactcatatt tttggtgctg atggtgcaag gaaactagca     240
cagacccttg gtcttgaagt tctaggagac attcccttac accttaatat aagggaagct     300
tcagatacag gccagccaat tgtgttttca cagcctgaaa gtgatgaggc caaagcttac     360
ttgaggattg ctgtggaagt ggtaagaaga ttgccatcac cttcagaatg a              411

<210> SEQ ID NO 50
<211> LENGTH: 136
<212> TYPE: PRT
<213> ORGANISM: Homo sapiens

<400> SEQUENCE: 50

Met Pro Pro Gly Thr Gly Asp Val Gln Leu Ser Val Ser Gln Asn Ile
1               5                   10                  15

Pro Ile Thr Gly Ala Val Ile Val Ser Thr Pro Gln Asp Ile Ala Leu
            20                  25                  30

Met Asp Ala His Lys Gly Ala Glu Met Phe Arg Arg Val His Val Pro
        35                  40                  45

Val Leu Gly Leu Val Gln Asn Met Ser Val Phe Gln Cys Pro Lys Cys
    50                  55                  60

Lys His Lys Thr His Ile Phe Gly Ala Asp Gly Ala Arg Lys Leu Ala
65                  70                  75                  80

Gln Thr Leu Gly Leu Glu Val Leu Gly Asp Ile Pro Leu His Leu Asn
                85                  90                  95

Ile Arg Glu Ala Ser Asp Thr Gly Gln Pro Ile Val Phe Ser Gln Pro
            100                 105                 110

Glu Ser Asp Glu Ala Lys Ala Tyr Leu Arg Ile Ala Val Glu Val Val
        115                 120                 125

Arg Arg Leu Pro Ser Pro Ser Glu
    130                 135

<210> SEQ ID NO 51
<211> LENGTH: 1095
<212> TYPE: DNA
<213> ORGANISM: Homo sapiens

<400> SEQUENCE: 51
atggagttgg aggggcgggg tgctggcggt gtggcggggg ggccggcggc agggcccggg      60
cggagccccg gggagtcggc gctgctggac gggtggctgc agcggggcgt gggccggggg     120
gccggcggcg gggaggccgg ggcctgcagg ccccggtac gacaagatcc ggactccggc      180
ccggactacg aggcgctgcc ggctggagcc actgtcacca cgcacatggt ggcaggcgcc     240
gtggcaggga tcctggagca ctgcgtgatg tacccc atcg actgcgtcaa gacccggatg     300
cagagtctac agcctgaccc agctgcccgc tatcgcaatg tgttggaggc cctctggagg     360
attataagaa cggagggcct atggaggccc atgaggggc tgaacgtcac agcaacaggc     420
gcagggcctg cccacgccct ttattttgcc tgctacgaaa agttaaaaaa gacattgagt     480
```

```
gatgtaatcc accctggggg caatagccat attgccaatg gtgcggccgg gtgtgtggca      540
acattacttc atgatgcagc catgaaccct gcggaagtgg tcaagcagag gatgcagatg      600
tacaactcac cataccaccg ggtgacagac tgtgtacggg cagtgtggca aaatgaaggg      660
gccggggcct tttaccgcag ctacaccacc cagctgacca tgaacgttcc tttccaagcc      720
attcacttca tgacctatga attcctgcag gagcacttta accccagag acggtacaac       780 ccaagctccc acgtcctctc tggagcttgc gcaggagctg tagctgccgc agccacaacc      840
ccactggacg tttgcaaaac actgctcaac acccaggagt ccttggcttt gaactcacac      900
attacaggac atatcacagg catggctagt gccttcagga cggtatatca agtaggtggg      960
gtgaccgcct atttccgagg ggtgcaggcc agagtaattt accagatccc ctccacagcc     1020
atcgcatggt ctgtgtatga gttcttcaaa tacctaatca ctaaaaggca agaagagtgg     1080
agggctggca agtga                                                      1095
```

<210> SEQ ID NO 52
<211> LENGTH: 364
<212> TYPE: PRT
<213> ORGANISM: Homo sapiens

<400> SEQUENCE: 52

```
Met Glu Leu Glu Gly Arg Gly Ala Gly Val Ala Gly Gly Pro Ala
1               5                   10                  15

Ala Gly Pro Gly Arg Ser Pro Gly Glu Ser Ala Leu Leu Asp Gly Trp
                20                  25                  30

Leu Gln Arg Gly Val Gly Arg Gly Ala Gly Gly Gly Ala Gly Ala
                35                  40                  45

Cys Arg Pro Pro Val Arg Gln Asp Pro Asp Ser Gly Pro Asp Tyr Glu
50                  55                  60

Ala Leu Pro Ala Gly Ala Thr Val Thr Thr His Met Val Ala Gly Ala
65                  70                  75                  80

Val Ala Gly Ile Leu Glu His Cys Val Met Tyr Pro Ile Asp Cys Val
                85                  90                  95

Lys Thr Arg Met Gln Ser Leu Gln Pro Asp Pro Ala Ala Arg Tyr Arg
                100                 105                 110

Asn Val Leu Glu Ala Leu Trp Arg Ile Ile Arg Thr Glu Gly Leu Trp
                115                 120                 125

Arg Pro Met Arg Gly Leu Asn Val Thr Ala Thr Gly Ala Gly Pro Ala
                130                 135                 140

His Ala Leu Tyr Phe Ala Cys Tyr Glu Lys Leu Lys Lys Thr Leu Ser
145                 150                 155                 160

Asp Val Ile His Pro Gly Gly Asn Ser His Ile Ala Asn Gly Ala Ala
                165                 170                 175

Gly Cys Val Ala Thr Leu Leu His Asp Ala Ala Met Asn Pro Ala Glu
                180                 185                 190

Val Val Lys Gln Arg Met Gln Met Tyr Asn Ser Pro Tyr His Arg Val
                195                 200                 205

Thr Asp Cys Val Arg Ala Val Trp Gln Asn Glu Gly Ala Gly Ala Phe
                210                 215                 220

Tyr Arg Ser Tyr Thr Thr Gln Leu Thr Met Asn Val Pro Phe Gln Ala
225                 230                 235                 240

Ile His Phe Met Thr Tyr Glu Phe Leu Gln Glu His Phe Asn Pro Gln
                245                 250                 255
```

```
Arg Arg Tyr Asn Pro Ser Ser His Val Leu Ser Gly Ala Cys Ala Gly
            260                 265                 270

Ala Val Ala Ala Ala Thr Thr Pro Leu Asp Val Cys Lys Thr Leu
        275                 280                 285

Leu Asn Thr Gln Glu Ser Leu Ala Leu Asn Ser His Ile Thr Gly His
        290                 295                 300

Ile Thr Gly Met Ala Ser Ala Phe Arg Thr Val Tyr Gln Val Gly Gly
305                 310                 315                 320

Val Thr Ala Tyr Phe Arg Gly Val Gln Ala Arg Val Ile Tyr Gln Ile
                325                 330                 335

Pro Ser Thr Ala Ile Ala Trp Ser Val Tyr Glu Phe Phe Lys Tyr Leu
            340                 345                 350

Ile Thr Lys Arg Gln Glu Glu Trp Arg Ala Gly Lys
            355                 360

<210> SEQ ID NO 53
<211> LENGTH: 1476
<212> TYPE: DNA
<213> ORGANISM: Homo sapiens

<400> SEQUENCE: 53
atggcttcgc gctgctggcg ctggtggggc tggtcggcgt ggcctcggac ccggctgcct      60
cccgccggga gcaccccgag cttctgccac catttctcca caggagaaga cccccccag     120 atctgtgtgg tgggcagtgg cccagctggc ttctacacgg cccaacacct gctaaagcac    180
ccccaggccc acgtggacat ctacgagaaa cagcctgtgc cctttggcct ggtgcgcttt    240
ggtgtggcgc tgatcacccc cgaggtgaag aatgtcatca acacatttac ccagacggcc    300
cattctggcc gctgtgcctt ctggggcaac gtggaggtgg cagggacgt gacggtgccg     360 gagctgcggg aggcctacca cgctgtggtg ctgagctacg ggcagagga ccatcgggcc     420 ctggaaattc ctggtgagga gctgccaggt gtgtgctccg cccgggcctt cgtgggctgg    480
tacaacgggc ttcctgagaa ccaggagctg agccagacc tgagctgtga cacagccgtg     540
attctggggc aggggaacgt ggctctggac gtggcccgca tcctactgac cccacctgag    600
cacctggaga gaacggacat cacgaaggca gccctgggtg tactgaggca gagtcgagtg    660
aagacagtgt ggctagtggg ccggcgtgga ccctgcaag tggccttcac cattaaggag     720
cttcgggaga tgattcagtt accgggagcc cggcccattt tggatcctgt ggatttcttg    780
ggtctccagg acaagatcaa ggaggtcccc cgcccgagga gcggctgac ggaactgctg     840 cttcgaacgg ccacagagaa gccagggccg gcggaagctg cccgccaggc atcggcctcc    900
cgtgcctggg gcctccgctt tttccgaagc ccccagcagg tgctgccctc accagatggg    960
cggcgggcag caggtgtccg cctagcagtc actagactgg agggtgtcga tgaggccacc   1020
cgtgcagtgc ccacgggaga catggaagac ctcccttgtg ggctggtgct cagcagcatt   1080
gggtataaga gccgccctgt cgacccaagc gtgccctttg actccaagct gggggtcatc   1140
cccaatgtgg agggccgggt tatggatgtg ccaggcctct actgcagcgg ctgggtgaag   1200
agaggaccta caggtgtcat agccacaacc atgactgaca gcttcctcac cggccagatg   1260
ctgctgcagg acctgaaggc tgggttgctc ccctctggcc ccaggcctgg ctacgcagcc   1320
atccaggccc tgctcagcag ccgaggggtc cggccagtct ctttctcaga ctgggagaag   1380
ctggatgccg aggaggtggc ccggggccag gcacgggga agcccaggga gaagctggtg   1440
gatcctcagg agatgctgcg cctcctgggc cactga                             1476
```

<210> SEQ ID NO 54
<211> LENGTH: 491
<212> TYPE: PRT
<213> ORGANISM: Homo sapiens

<400> SEQUENCE: 54

```
Met Ala Ser Arg Cys Trp Arg Trp Trp Gly Trp Ser Ala Trp Pro Arg
1               5                   10                  15

Thr Arg Leu Pro Pro Ala Gly Ser Thr Pro Ser Phe Cys His His Phe
            20                  25                  30

Ser Thr Gln Glu Lys Thr Pro Gln Ile Cys Val Val Gly Ser Gly Pro
        35                  40                  45

Ala Gly Phe Tyr Thr Ala Gln His Leu Leu Lys His Pro Gln Ala His
    50                  55                  60

Val Asp Ile Tyr Glu Lys Gln Pro Val Pro Phe Gly Leu Val Arg Phe
65                  70                  75                  80

Gly Val Ala Pro Asp His Pro Glu Val Lys Asn Val Ile Asn Thr Phe
                85                  90                  95

Thr Gln Thr Ala His Ser Gly Arg Cys Ala Phe Trp Gly Asn Val Glu
            100                 105                 110

Val Gly Arg Asp Val Thr Val Pro Glu Leu Arg Glu Ala Tyr His Ala
        115                 120                 125

Val Val Leu Ser Tyr Gly Ala Glu Asp His Arg Ala Leu Glu Ile Pro
    130                 135                 140

Gly Glu Glu Leu Pro Gly Val Cys Ser Ala Arg Ala Phe Val Gly Trp
145                 150                 155                 160

Tyr Asn Gly Leu Pro Glu Asn Gln Glu Leu Glu Pro Asp Leu Ser Cys
                165                 170                 175

Asp Thr Ala Val Ile Leu Gly Gln Gly Asn Val Ala Leu Asp Val Ala
            180                 185                 190

Arg Ile Leu Leu Thr Pro Pro Glu His Leu Glu Arg Thr Asp Ile Thr
        195                 200                 205

Lys Ala Ala Leu Gly Val Leu Arg Gln Ser Arg Val Lys Thr Val Trp
    210                 215                 220

Leu Val Gly Arg Arg Gly Pro Leu Gln Val Ala Phe Thr Ile Lys Glu
225                 230                 235                 240

Leu Arg Glu Met Ile Gln Leu Pro Gly Ala Arg Pro Ile Leu Asp Pro
                245                 250                 255

Val Asp Phe Leu Gly Leu Gln Asp Lys Ile Lys Glu Val Pro Arg Pro
            260                 265                 270

Arg Lys Arg Leu Thr Glu Leu Leu Arg Thr Ala Thr Glu Lys Pro
        275                 280                 285

Gly Pro Ala Glu Ala Ala Arg Gln Ala Ser Ala Ser Arg Ala Trp Gly
    290                 295                 300

Leu Arg Phe Phe Arg Ser Pro Gln Gln Val Leu Pro Ser Pro Asp Gly
305                 310                 315                 320

Arg Arg Ala Ala Gly Val Arg Leu Ala Val Thr Arg Leu Glu Gly Val
                325                 330                 335

Asp Glu Ala Thr Arg Ala Val Pro Thr Gly Asp Met Glu Asp Leu Pro
            340                 345                 350

Cys Gly Leu Val Leu Ser Ser Ile Gly Tyr Lys Ser Arg Pro Val Asp
        355                 360                 365

Pro Ser Val Pro Phe Asp Ser Lys Leu Gly Val Ile Pro Asn Val Glu
    370                 375                 380
```

```
Gly Arg Val Met Asp Val Pro Gly Leu Tyr Cys Ser Gly Trp Val Lys
385                 390                 395                 400

Arg Gly Pro Thr Gly Val Ile Ala Thr Thr Met Thr Asp Ser Phe Leu
                405                 410                 415

Thr Gly Gln Met Leu Leu Gln Asp Leu Lys Ala Gly Leu Leu Pro Ser
            420                 425                 430

Gly Pro Arg Pro Gly Tyr Ala Ala Ile Gln Ala Leu Leu Ser Ser Arg
        435                 440                 445

Gly Val Arg Pro Val Ser Phe Ser Asp Trp Glu Lys Leu Asp Ala Glu
    450                 455                 460

Glu Val Ala Arg Gly Gln Gly Thr Gly Lys Pro Arg Glu Lys Leu Val
465                 470                 475                 480

Asp Pro Gln Glu Met Leu Arg Leu Leu Gly His
                485                 490
```

<210> SEQ ID NO 55
<211> LENGTH: 497
<212> TYPE: PRT
<213> ORGANISM: Homo sapiens

<400> SEQUENCE: 55

```
Met Ala Ser Arg Cys Trp Arg Trp Trp Gly Trp Ser Ala Trp Pro Arg
1               5                   10                  15

Thr Arg Leu Pro Pro Ala Gly Ser Thr Pro Ser Phe Cys His His Phe
                20                  25                  30

Ser Thr Gln Glu Lys Thr Pro Gln Ile Cys Val Val Gly Ser Gly Pro
            35                  40                  45

Ala Gly Phe Tyr Thr Ala Gln His Leu Leu Lys His Pro Gln Ala His
    50                  55                  60

Val Asp Ile Tyr Glu Lys Gln Pro Val Pro Phe Gly Leu Val Arg Phe
65                  70                  75                  80

Gly Val Ala Pro Asp His Pro Glu Val Lys Asn Val Ile Asn Thr Phe
                85                  90                  95

Thr Gln Thr Ala His Ser Gly Arg Cys Ala Phe Trp Gly Asn Val Glu
            100                 105                 110

Val Gly Arg Asp Val Thr Val Pro Glu Leu Arg Glu Ala Tyr His Ala
        115                 120                 125

Val Val Leu Ser Tyr Gly Ala Glu Asp His Arg Ala Leu Glu Ile Pro
    130                 135                 140

Gly Glu Glu Leu Pro Gly Val Cys Ser Ala Arg Ala Phe Val Gly Trp
145                 150                 155                 160

Tyr Asn Gly Leu Pro Glu Asn Gln Glu Leu Glu Pro Asp Leu Ser Cys
                165                 170                 175

Asp Thr Ala Val Ile Leu Gly Gln Gly Asn Val Ala Leu Asp Val Ala
            180                 185                 190

Arg Ile Leu Leu Thr Pro Pro Glu His Leu Glu Ala Leu Leu Leu Cys
        195                 200                 205

Gln Arg Thr Asp Ile Thr Lys Ala Ala Leu Gly Val Leu Arg Gln Ser
    210                 215                 220

Arg Val Lys Thr Val Trp Leu Val Gly Arg Arg Gly Pro Leu Gln Val
225                 230                 235                 240

Ala Phe Thr Ile Lys Glu Leu Arg Glu Met Ile Gln Leu Pro Gly Ala
                245                 250                 255

Arg Pro Ile Leu Asp Pro Val Asp Phe Leu Gly Leu Gln Asp Lys Ile
```

```
                260                 265                 270
Lys Glu Val Pro Arg Pro Arg Lys Arg Leu Thr Glu Leu Leu Leu Arg
                275                 280                 285

Thr Ala Thr Glu Lys Pro Gly Pro Ala Glu Ala Ala Arg Gln Ala Ser
        290                 295                 300

Ala Ser Arg Ala Trp Gly Leu Arg Phe Phe Arg Ser Pro Gln Gln Val
305                 310                 315                 320

Leu Pro Ser Pro Asp Gly Arg Arg Ala Ala Gly Val Arg Leu Ala Val
                325                 330                 335

Thr Arg Leu Glu Gly Val Asp Glu Ala Thr Arg Ala Val Pro Thr Gly
                340                 345                 350

Asp Met Glu Asp Leu Pro Cys Gly Leu Val Leu Ser Ser Ile Gly Tyr
                355                 360                 365

Lys Ser Arg Pro Val Asp Pro Ser Val Pro Phe Asp Ser Lys Leu Gly
                370                 375                 380

Val Ile Pro Asn Val Glu Gly Arg Val Met Asp Val Pro Gly Leu Tyr
385                 390                 395                 400

Cys Ser Gly Trp Val Lys Arg Gly Pro Thr Gly Val Ile Ala Thr Thr
                405                 410                 415

Met Thr Asp Ser Phe Leu Thr Gly Gln Met Leu Leu Gln Asp Leu Lys
                420                 425                 430

Ala Gly Leu Leu Pro Ser Gly Pro Arg Pro Gly Tyr Ala Ala Ile Gln
                435                 440                 445

Ala Leu Leu Ser Arg Gly Val Arg Pro Val Ser Phe Ser Asp Trp
450                 455                 460

Glu Lys Leu Asp Ala Glu Glu Val Ala Arg Gly Gln Gly Thr Gly Lys
465                 470                 475                 480

Pro Arg Glu Lys Leu Val Asp Pro Gln Glu Met Leu Arg Leu Leu Gly
                485                 490                 495

His

<210> SEQ ID NO 56
<211> LENGTH: 497
<212> TYPE: PRT
<213> ORGANISM: Homo sapiens

<400> SEQUENCE: 56

Met Ala Ser Arg Cys Trp Arg Trp Trp Gly Trp Ser Ala Trp Pro Arg
1               5                   10                  15

Thr Arg Leu Pro Pro Ala Gly Ser Thr Pro Ser Phe Cys His His Phe
                20                  25                  30

Ser Thr Gln Glu Lys Thr Pro Gln Ile Cys Val Val Gly Ser Gly Pro
            35                  40                  45

Ala Gly Phe Tyr Thr Ala Gln His Leu Leu Lys His Pro Gln Ala His
        50                  55                  60

Val Asp Ile Tyr Glu Lys Gln Pro Val Pro Phe Gly Leu Val Arg Phe
65              70                  75                  80

Gly Val Ala Pro Asp His Pro Glu Val Lys Asn Val Ile Asn Thr Phe
                85                  90                  95

Thr Gln Thr Ala His Ser Gly Arg Cys Ala Phe Trp Gly Asn Val Glu
                100                 105                 110

Val Gly Arg Asp Val Thr Val Pro Glu Leu Arg Glu Ala Tyr His Ala
            115                 120                 125

Val Val Leu Ser Tyr Gly Ala Glu Asp His Arg Ala Leu Glu Ile Pro
```

```
            130                 135                 140
Gly Glu Glu Leu Pro Gly Val Cys Ser Ala Arg Ala Phe Val Gly Trp
145                 150                 155                 160

Tyr Asn Gly Leu Pro Glu Asn Gln Glu Leu Glu Pro Asp Leu Ser Cys
                165                 170                 175

Asp Thr Ala Val Ile Leu Gly Gln Gly Asn Val Ala Leu Asp Val Ala
            180                 185                 190

Arg Ile Leu Leu Thr Pro Pro Glu His Leu Glu Ala Leu Leu Cys
            195                 200                 205

Gln Arg Thr Asp Ile Thr Lys Ala Ala Leu Gly Val Leu Arg Gln Ser
    210                 215                 220

Arg Val Lys Thr Val Trp Leu Val Gly Arg Arg Gly Pro Leu Gln Val
225                 230                 235                 240

Ala Phe Thr Ile Lys Glu Leu Arg Glu Met Ile Gln Leu Pro Gly Ala
                245                 250                 255

Arg Pro Ile Leu Asp Pro Val Asp Phe Leu Gly Leu Gln Asp Lys Ile
                260                 265                 270

Lys Glu Val Pro Arg Pro Arg Lys Arg Leu Thr Glu Leu Leu Leu Arg
            275                 280                 285

Thr Ala Thr Glu Lys Pro Gly Pro Ala Glu Ala Ala Arg Gln Ala Ser
            290                 295                 300

Ala Ser Arg Ala Trp Gly Leu Arg Phe Arg Ser Pro Gln Gln Val
305                 310                 315                 320

Leu Pro Ser Pro Asp Gly Arg Arg Ala Ala Gly Val Arg Leu Ala Val
                325                 330                 335

Thr Arg Leu Glu Gly Val Asp Glu Ala Thr Arg Ala Val Pro Thr Gly
            340                 345                 350

Asp Met Glu Asp Leu Pro Cys Gly Leu Val Leu Ser Ser Ile Gly Tyr
            355                 360                 365

Lys Ser Arg Pro Val Asp Pro Ser Val Pro Phe Asp Ser Lys Leu Gly
    370                 375                 380

Val Ile Pro Asn Val Glu Gly Arg Val Met Asp Val Pro Gly Leu Tyr
385                 390                 395                 400

Cys Ser Gly Trp Val Lys Arg Gly Pro Thr Gly Val Ile Ala Thr Thr
                405                 410                 415

Met Thr Asp Ser Phe Leu Thr Gly Gln Met Leu Leu Gln Asp Leu Lys
            420                 425                 430

Ala Gly Leu Leu Pro Ser Gly Pro Arg Pro Gly Tyr Ala Ala Ile Gln
            435                 440                 445

Ala Leu Leu Ser Ser Arg Gly Val Arg Pro Val Ser Phe Ser Asp Trp
450                 455                 460

Glu Lys Leu Asp Ala Glu Val Ala Arg Gly Gln Gly Thr Gly Lys
465                 470                 475                 480

Pro Arg Glu Lys Leu Val Asp Pro Gln Glu Met Leu Arg Leu Leu Gly
            485                 490                 495

His

<210> SEQ ID NO 57
<211> LENGTH: 1605
<212> TYPE: DNA
<213> ORGANISM: Homo sapiens

<400> SEQUENCE: 57
atggcttcgc gctgctggcg ctggtggggc tggtcggcgt ggcctcggac ccggctgcct    60
```

```
cccgccggga gcaccccgag cttctgccac catttctcca cacaggagaa gaccccccag    120
atctgtgtgg tgggcagtgg cccagctggc ttctacacgg cccaacacct gctaaagagg    180
gtggaagcct tgtgttctca gcccagggtc ctgaactctc ctgctctgtc tggggaaggg    240
gaggacctgg gggcgtccca gcctctctct ctcgacccca ccagctgcca ccctgttccc    300
cagcagcacc cccaggccca cgtggacatc tacgagaaac agcctgtgcc ctttggcctg    360
gtgcgctttg tgtggcgcc tgatcacccc gaggtgaaga atgtcatcaa cacatttacc     420
cagacggccc attctggccg ctgtgccttc tggggcaacg tggaggtggg cagggacgtg    480
acggtgccgg agctgcggga ggcctaccac gctgtggtgc tgagctacgg ggcagaggac    540
catcgggccc tggaaattcc tggtgaggag ctgccaggtg tgtgctccgc ccgggccttc    600
gtgggctggt acaacgggct tcctgagaac caggagctgg agccagacct gagctgtgac    660
acagccgtga ttctggggca ggggaacgtg gctctggacg tggcccgcat cctactgacc    720
ccacctgagc acctggagag aacggacatc acgaaggcag ccctgggtgt actgaggcag    780
agtcgagtga agacagtgtg gctagtgggc cggcgtggac ccctgcaagt ggccttcacc    840
attaaggagc ttcgggagat gattcagtta ccggagcccc ggcccatttt ggatcctgtg    900
gatttcttgg gtctccagga caagatcaag gaggtccccc gcccgaggaa gcggctgacg    960
gaactgctgc ttcgaacggc cacagagaag ccagggccgg cggaagctgc ccgccaggca   1020
tcggcctccc gtgcctgggg cctccgcttt ttccgaagcc cccagcaggt gctgccctca   1080
ccagatgggc ggcgggcagc aggtgtccgc ctagcagtca ctagactgga gggtgtcgat   1140
gaggccaccc gtgcagtgcc cacgggagac atggaagacc tcccttgtgg gctggtgctc   1200
agcagcattg ggtataagag ccgccctgtc gacccaagcg tgcccttrga ctccaagctt   1260
ggggtcatcc ccaatgtgga gggccgggtt atggatgtgc caggcctcta ctgcagcggc   1320
tgggtgaaga gaggacctac aggtgtcata gccacaacca tgactgacag cttcctcacc   1380
ggccagatgc tgctgcagga cctgaaggct gggttgctcc cctctggccc caggcctggc   1440
tacgcagcca tccaggccct gctcagcagc cgagggtcc ggccagtctc tttctcagac   1500
tgggagaagc tggatgccga ggaggtggcc cggggccagg gcacgggaa gcccagggag   1560 aagctggtgg atcctcagga gatgctgcgc ctcctgggcc actga                  1605
```

<210> SEQ ID NO 58
<211> LENGTH: 534
<212> TYPE: PRT
<213> ORGANISM: Homo sapiens

<400> SEQUENCE: 58

```
Met Ala Ser Arg Cys Trp Arg Trp Trp Gly Trp Ser Ala Trp Pro Arg
1               5                   10                  15

Thr Arg Leu Pro Pro Ala Gly Ser Thr Pro Ser Phe Cys His His Phe
            20                  25                  30

Ser Thr Gln Glu Lys Thr Pro Gln Ile Cys Val Val Gly Ser Gly Pro
        35                  40                  45

Ala Gly Phe Tyr Thr Ala Gln His Leu Leu Lys Arg Val Glu Ala Leu
    50                  55                  60

Cys Ser Gln Pro Arg Val Leu Asn Ser Pro Ala Leu Ser Gly Glu Gly
65                  70                  75                  80

Glu Asp Leu Gly Ala Ser Gln Pro Leu Ser Leu Asp Pro Thr Ser Cys
                85                  90                  95
```

-continued

```
His Pro Val Pro Gln Gln His Pro Gln Ala His Val Asp Ile Tyr Glu
            100                 105                 110

Lys Gln Pro Val Pro Phe Gly Leu Val Arg Phe Gly Val Ala Pro Asp
        115                 120                 125

His Pro Glu Val Lys Asn Val Ile Asn Thr Phe Thr Gln Thr Ala His
    130                 135                 140

Ser Gly Arg Cys Ala Phe Trp Gly Asn Val Glu Val Gly Arg Asp Val
145                 150                 155                 160

Thr Val Pro Glu Leu Arg Glu Ala Tyr His Ala Val Val Leu Ser Tyr
                165                 170                 175

Gly Ala Glu Asp His Arg Ala Leu Glu Ile Pro Gly Glu Glu Leu Pro
            180                 185                 190

Gly Val Cys Ser Ala Arg Ala Phe Val Gly Trp Tyr Asn Gly Leu Pro
        195                 200                 205

Glu Asn Gln Glu Leu Glu Pro Asp Leu Ser Cys Asp Thr Ala Val Ile
    210                 215                 220

Leu Gly Gln Gly Asn Val Ala Leu Asp Val Ala Arg Ile Leu Leu Thr
225                 230                 235                 240

Pro Pro Glu His Leu Glu Arg Thr Asp Ile Thr Lys Ala Ala Leu Gly
                245                 250                 255

Val Leu Arg Gln Ser Arg Val Lys Thr Val Trp Leu Val Gly Arg Arg
            260                 265                 270

Gly Pro Leu Gln Val Ala Phe Thr Ile Lys Glu Leu Arg Glu Met Ile
        275                 280                 285

Gln Leu Pro Gly Ala Arg Pro Ile Leu Asp Pro Val Asp Phe Leu Gly
    290                 295                 300

Leu Gln Asp Lys Ile Lys Glu Val Pro Arg Pro Arg Lys Arg Leu Thr
305                 310                 315                 320

Glu Leu Leu Leu Arg Thr Ala Thr Glu Lys Pro Gly Pro Ala Glu Ala
                325                 330                 335

Ala Arg Gln Ala Ser Ala Ser Arg Ala Trp Gly Leu Arg Phe Phe Arg
            340                 345                 350

Ser Pro Gln Gln Val Leu Pro Ser Pro Asp Gly Arg Arg Ala Ala Gly
        355                 360                 365

Val Arg Leu Ala Val Thr Arg Leu Glu Gly Val Asp Glu Ala Thr Arg
    370                 375                 380

Ala Val Pro Thr Gly Asp Met Glu Asp Leu Pro Cys Gly Leu Val Leu
385                 390                 395                 400

Ser Ser Ile Gly Tyr Lys Ser Arg Pro Val Asp Pro Ser Val Pro Phe
                405                 410                 415

Asp Ser Lys Leu Gly Val Ile Pro Asn Val Glu Gly Arg Val Met Asp
            420                 425                 430

Val Pro Gly Leu Tyr Cys Ser Gly Trp Val Lys Arg Gly Pro Thr Gly
        435                 440                 445

Val Ile Ala Thr Thr Met Thr Asp Ser Phe Leu Thr Gly Gln Met Leu
    450                 455                 460

Leu Gln Asp Leu Lys Ala Gly Leu Leu Pro Ser Gly Pro Arg Pro Gly
465                 470                 475                 480

Tyr Ala Ala Ile Gln Ala Leu Leu Ser Ser Arg Gly Val Arg Pro Val
                485                 490                 495

Ser Phe Ser Asp Trp Glu Lys Leu Asp Ala Glu Glu Val Ala Arg Gly
            500                 505                 510

Gln Gly Thr Gly Lys Pro Arg Glu Lys Leu Val Asp Pro Gln Glu Met
```

Leu Arg Leu Leu Gly His
        530

<210> SEQ ID NO 59
<211> LENGTH: 1569
<212> TYPE: DNA
<213> ORGANISM: Homo sapiens

<400> SEQUENCE: 59

| | | |
|---|---|---|
| atggcttcgc gctgctggcg ctggtggggc tggtcggcgt ggcctcggac ccggctgcct | 60 |
| cccgccggga gcaccccgac ctttgggggt tcagatgaag taagagaccc tgcaaatgcc | 120 |
| aaagccttga ggaacaagag aaggaggatg caggtgaggg tgaagcttgg aagttccag | 180 |
| cttctgttgg atattcagga gaagaccccc cagatctgtg tggtgggcag tggcccagct | 240 |
| ggcttctaca cggcccaaca cctgctaaag caccccagg cccacgtgga catctacgag | 300 |
| aaacagcctg tgccctttgg cctggtgcgc tttggtgtgg cgcctgatca ccccgaggtg | 360 |
| aagaatgtca tcaacacatt tacccagacg gcccattctg gccgctgtgc cttctggggc | 420 |
| aacgtggagg tgggcaggga cgtgacggtg ccggagctgc gggaggccta ccacgctgtg | 480 |
| gtgctgagct acggggcaga ggaccatcgg gccctggaaa ttcctggtga ggagctgcca | 540 |
| ggtgtgtgct ccgcccgggc cttcgtgggc tggtacaacg gcttcctga gaaccaggag | 600 |
| ctggagccag acctgagctg tgacacagcc gtgattctgg gcaggggaa cgtggctctg | 660 |
| gacgtggccc gcatcctact gacccccacct gagcacctgg agagaacgga catcacgaag | 720 |
| gcagccctgg gtgtactgag gcagagtcga gtgaagacag tgtggctagt gggccggcgt | 780 |
| ggaccccctgc aagtggcctt caccattaag gagcttcggg agatgattca gttaccggga | 840 |
| gcccggccca ttttggatcc tgtggatttc ttgggtctcc aggacaagat caaggaggtc | 900 |
| ccccgcccga ggaagcggct gacggaactg ctgcttcgaa cggccacaga aagccaggg | 960 |
| ccggcggaag ctgcccgcca ggcatcggcc tcccgtgcct ggggcctccg cttttttccga | 1020 |
| agccccccagc aggtgctgcc ctcaccagat gggcggcggg cagcaggtgt ccgcctagca | 1080 |
| gtcactagac tggagggtgt cgatgaggcc acccgtgcag tgcccacggg agacatggaa | 1140 |
| gacctcccctt gtgggctggt gctcagcagc attgggtata agagccgccc tgtcgaccca | 1200 |
| agcgtgccct ttgactccaa gcttgggtc atccccaatg tggagggccg ggttatggat | 1260 |
| gtgccaggcc tctactgcag cggctgggtg aagagaggac ctacaggtgt catagccaca | 1320 |
| accatgactg acagcttcct caccggccag atgctgctgc aggacctgaa ggctgggttg | 1380 |
| ctcccctctg gccccaggcc tggctacgca gccatccagg ccctgctcag cagccgaggg | 1440 |
| gtccggccca tctctttctc agactgggag aagctggatg ccgaggaggt ggcccggggc | 1500 |
| cagggcacgg ggaagcccag ggagaagctg gtggatcctc aggagatgct cgcctcctg | 1560 |
| ggccactga | 1569 |

<210> SEQ ID NO 60
<211> LENGTH: 522
<212> TYPE: PRT
<213> ORGANISM: Homo sapiens

<400> SEQUENCE: 60

Met Ala Ser Arg Cys Trp Arg Trp Trp Gly Trp Ser Ala Trp Pro Arg
1               5                   10                  15

Thr Arg Leu Pro Pro Ala Gly Ser Thr Pro Thr Phe Gly Gly Ser Asp

```
            20              25              30
Glu Val Arg Asp Pro Ala Asn Ala Lys Ala Leu Arg Asn Lys Arg Arg
         35              40              45
Arg Met Gln Val Arg Val Lys Leu Gly Lys Phe Gln Leu Leu Leu Asp
         50              55              60
Ile Gln Glu Lys Thr Pro Gln Ile Cys Val Val Gly Ser Gly Pro Ala
 65              70              75              80
Gly Phe Tyr Thr Ala Gln His Leu Leu Lys His Pro Gln Ala His Val
                 85              90              95
Asp Ile Tyr Glu Lys Gln Pro Val Pro Phe Gly Leu Val Arg Phe Gly
                100             105             110
Val Ala Pro Asp His Pro Glu Val Lys Asn Val Ile Asn Thr Phe Thr
                115             120             125
Gln Thr Ala His Ser Gly Arg Cys Ala Phe Trp Gly Asn Val Glu Val
                130             135             140
Gly Arg Asp Val Thr Val Pro Glu Leu Arg Glu Ala Tyr His Ala Val
145             150             155             160
Val Leu Ser Tyr Gly Ala Glu Asp His Arg Ala Leu Glu Ile Pro Gly
                165             170             175
Glu Glu Leu Pro Gly Val Cys Ser Ala Arg Ala Phe Val Gly Trp Tyr
                180             185             190
Asn Gly Leu Pro Glu Asn Gln Glu Leu Glu Pro Asp Leu Ser Cys Asp
                195             200             205
Thr Ala Val Ile Leu Gly Gln Gly Asn Val Ala Leu Asp Val Ala Arg
210             215             220
Ile Leu Leu Thr Pro Pro Glu His Leu Glu Arg Thr Asp Ile Thr Lys
225             230             235             240
Ala Ala Leu Gly Val Leu Arg Gln Ser Arg Val Lys Thr Val Trp Leu
                245             250             255
Val Gly Arg Arg Gly Pro Leu Gln Val Ala Phe Thr Ile Lys Glu Leu
                260             265             270
Arg Glu Met Ile Gln Leu Pro Gly Ala Arg Pro Ile Leu Asp Pro Val
                275             280             285
Asp Phe Leu Gly Leu Gln Asp Lys Ile Lys Glu Val Pro Arg Pro Arg
                290             295             300
Lys Arg Leu Thr Glu Leu Leu Leu Arg Thr Ala Thr Glu Lys Pro Gly
305             310             315             320
Pro Ala Glu Ala Ala Arg Gln Ala Ser Ala Ser Arg Ala Trp Gly Leu
                325             330             335
Arg Phe Phe Arg Ser Pro Gln Gln Val Leu Pro Ser Pro Asp Gly Arg
                340             345             350
Arg Ala Ala Gly Val Arg Leu Ala Val Thr Arg Leu Glu Gly Val Asp
                355             360             365
Glu Ala Thr Arg Ala Val Pro Thr Gly Asp Met Glu Asp Leu Pro Cys
                370             375             380
Gly Leu Val Leu Ser Ser Ile Gly Tyr Lys Ser Arg Pro Val Asp Pro
385             390             395             400
Ser Val Pro Phe Asp Ser Lys Leu Gly Val Ile Pro Asn Val Glu Gly
                405             410             415
Arg Val Met Asp Val Pro Gly Leu Tyr Cys Ser Gly Trp Val Lys Arg
                420             425             430
Gly Pro Thr Gly Val Ile Ala Thr Thr Met Thr Asp Ser Phe Leu Thr
                435             440             445
```

Gly Gln Met Leu Leu Gln Asp Leu Lys Ala Gly Leu Leu Pro Ser Gly
            450                 455                 460

Pro Arg Pro Gly Tyr Ala Ala Ile Gln Ala Leu Leu Ser Ser Arg Gly
465                 470                 475                 480

Val Arg Pro Val Ser Phe Ser Asp Trp Glu Lys Leu Asp Ala Glu Glu
                485                 490                 495

Val Ala Arg Gly Gln Gly Thr Gly Lys Pro Arg Glu Lys Leu Val Asp
            500                 505                 510

Pro Gln Glu Met Leu Arg Leu Leu Gly His
            515                 520

<210> SEQ ID NO 61
<211> LENGTH: 1452
<212> TYPE: DNA
<213> ORGANISM: Homo sapiens

<400> SEQUENCE: 61

| | | | | | |
|---|---|---|---|---|---|
| atggcttcgc | gctgctggcg | ctggtggggc | tggtcggcgt | ggcctcggac | ccggctgcct | 60 |
| cccgccggga | gcaccccgag | cttctgccac | catttctcca | cacaggagaa | gaccccccag | 120 |
| atctgtgtgg | tgggcagtgg | cccagctggc | ttctacacgg | cccaacacct | gctaaagcac | 180 |
| ccccaggccc | acgtggacat | ctacgagaaa | cagcctgtgc | cctttggcct | ggtgcgcttt | 240 |
| ggtgtgcgc | tgatcaccc | cgaggtgaag | acggccatt | ctggccgctg | tgccttctgg | 300 |
| ggcaacgtgg | aggtgggcag | ggacgtgacg | gtgccggagc | tgcgggaggc | ctaccacgct | 360 |
| gtggtgctga | gctacgggc | agaggaccat | cgggccctgg | aaattcctgg | tgaggagctg | 420 |
| ccaggtgtgt | gctccgcccg | ggccttcgtg | ggctggtaca | acgggcttcc | tgagaaccag | 480 |
| gagctggagc | cagacctgag | ctgtgacaca | gccgtgattc | tggggcaggg | gaacgtggct | 540 |
| ctggacgtgg | cccgcatcct | actgaccca | cctgagcacc | tggagagaac | ggacatcacg | 600 |
| aaggcagccc | tgggtgtact | gaggcagagt | cgagtgaaga | cagtgtggct | agtgggccgg | 660 |
| cgtggacccc | tgcaagtggc | cttcaccatt | aaggagcttc | gggagatgat | tcagttaccg | 720 |
| ggagcccggc | ccattttgga | tcctgtggat | ttcttgggtc | tccaggacaa | gatcaaggag | 780 |
| gtcccccgcc | cgaggaagcg | gctgacggaa | ctgctgcttc | gaacggccac | agagaagcca | 840 |
| gggccggcg | aagctgcccg | ccaggcatcg | gcctcccgtg | cctggggcct | cgctttttc | 900 |
| cgaagcccc | agcaggtgct | gccctcacca | gatgggcggc | gggcagcagg | tgtccgccta | 960 |
| gcagtcacta | gactggaggg | tgtcgatgag | gccacccgtg | cagtgcccac | gggagacatg | 1020 |
| gaagacctcc | cttgtgggct | ggtgctcagc | agcattgggt | ataagagccg | ccctgtcgac | 1080 |
| ccaagcgtgc | cctttgactc | caagcttggg | gtcatcccca | atgtggaggg | ccgggttatg | 1140 |
| gatgtgccag | gcctctactg | cagcggctgg | gtgaagagag | acctacagg | tgtcatagcc | 1200 |
| acaaccatga | ctgacagctt | cctcaccggc | cagatgctgc | tgcaggacct | gaaggctggg | 1260 |
| ttgctcccct | ctggccccag | gcctggctac | gcagccatcc | aggccctgct | cagcagccga | 1320 |
| ggggtccggc | cagtctcttt | ctcagactgg | gagaagctgg | atgccgagga | ggtggcccgg | 1380 |
| ggccagggca | cggggaagcc | caggagaag | ctggtggatc | ctcaggagat | gctgcgcctc | 1440 |
| ctgggccact | ga | | | | | 1452 |

<210> SEQ ID NO 62
<211> LENGTH: 483
<212> TYPE: PRT
<213> ORGANISM: Homo sapiens

<400> SEQUENCE: 62

Met Ala Ser Arg Cys Trp Arg Trp Trp Gly Trp Ser Ala Trp Pro Arg
1               5                   10                  15

Thr Arg Leu Pro Pro Ala Gly Ser Thr Pro Ser Phe Cys His His Phe
            20                  25                  30

Ser Thr Gln Glu Lys Thr Pro Gln Ile Cys Val Val Gly Ser Gly Pro
        35                  40                  45

Ala Gly Phe Tyr Thr Ala Gln His Leu Leu Lys His Pro Gln Ala His
    50                  55                  60

Val Asp Ile Tyr Glu Lys Gln Pro Val Pro Phe Gly Leu Val Arg Phe
65                  70                  75                  80

Gly Val Ala Pro Asp His Pro Glu Val Lys Thr Ala His Ser Gly Arg
                85                  90                  95

Cys Ala Phe Trp Gly Asn Val Glu Val Gly Arg Asp Val Thr Val Pro
            100                 105                 110

Glu Leu Arg Glu Ala Tyr His Ala Val Val Leu Ser Tyr Gly Ala Glu
        115                 120                 125

Asp His Arg Ala Leu Glu Ile Pro Gly Glu Leu Pro Gly Val Cys
130                 135                 140

Ser Ala Arg Ala Phe Val Gly Trp Tyr Asn Gly Leu Pro Glu Asn Gln
145                 150                 155                 160

Glu Leu Glu Pro Asp Leu Ser Cys Asp Thr Ala Val Ile Leu Gly Gln
                165                 170                 175

Gly Asn Val Ala Leu Asp Val Ala Arg Ile Leu Leu Thr Pro Pro Glu
            180                 185                 190

His Leu Glu Arg Thr Asp Ile Thr Lys Ala Ala Leu Gly Val Leu Arg
        195                 200                 205

Gln Ser Arg Val Lys Thr Val Trp Leu Val Gly Arg Arg Gly Pro Leu
    210                 215                 220

Gln Val Ala Phe Thr Ile Lys Glu Leu Arg Glu Met Ile Gln Leu Pro
225                 230                 235                 240

Gly Ala Arg Pro Ile Leu Asp Pro Val Asp Phe Leu Gly Leu Gln Asp
                245                 250                 255

Lys Ile Lys Glu Val Pro Arg Pro Arg Lys Arg Leu Thr Glu Leu Leu
            260                 265                 270

Leu Arg Thr Ala Thr Glu Lys Pro Gly Pro Ala Glu Ala Ala Arg Gln
        275                 280                 285

Ala Ser Ala Ser Arg Ala Trp Gly Leu Arg Phe Phe Arg Ser Pro Gln
    290                 295                 300

Gln Val Leu Pro Ser Pro Asp Gly Arg Arg Ala Ala Gly Val Arg Leu
305                 310                 315                 320

Ala Val Thr Arg Leu Glu Gly Val Asp Glu Ala Thr Arg Ala Val Pro
                325                 330                 335

Thr Gly Asp Met Glu Asp Leu Pro Cys Gly Leu Val Leu Ser Ser Ile
            340                 345                 350

Gly Tyr Lys Ser Arg Pro Val Asp Pro Ser Val Pro Phe Asp Ser Lys
        355                 360                 365

Leu Gly Val Ile Pro Asn Val Glu Gly Arg Val Met Asp Val Pro Gly
    370                 375                 380

Leu Tyr Cys Ser Gly Trp Val Lys Arg Gly Pro Thr Gly Val Ile Ala
385                 390                 395                 400

Thr Thr Met Thr Asp Ser Phe Leu Thr Gly Gln Met Leu Leu Gln Asp

Leu Lys Ala Gly Leu Leu Pro Ser Gly Pro Arg Pro Gly Tyr Ala Ala
         420                 425                 430

Ile Gln Ala Leu Leu Ser Ser Arg Gly Val Arg Pro Val Ser Phe Ser
             435                 440                 445

Asp Trp Glu Lys Leu Asp Ala Glu Val Ala Arg Gly Gln Gly Thr
         450                 455                 460

Gly Lys Pro Arg Glu Lys Leu Val Asp Pro Gln Glu Met Leu Arg Leu
465                 470                 475                 480

Leu Gly His

<210> SEQ ID NO 63
<211> LENGTH: 1356
<212> TYPE: DNA
<213> ORGANISM: Homo sapiens

<400> SEQUENCE: 63

```
atggcttcgc gctgctggcg ctggtggggc tggtcggcgt ggcctcggac ccggctgcct     60
cccgccggga gcaccccgag cttctgccac catttctcca cacaggagaa gacccccag    120
atctgtgtgg tgggcagtgg cccagctggc ttctacacgg cccaacacct gctaaagcag    180
caccccagg cccacgtgga catctacgag aaacagcctg tgccctttgg cctggtgcgc    240
tttggtgtgc gcctgatca ccccgaggtg aagagctacg ggcagagga ccatcgggcc    300
ctggaaattc tggtgagga gctgccaggt gtgtgctccg cccgggcctt cgtgggctgg    360
tacaacgggc ttcctgagaa ccaggagctg agcccagacc tgagctgtga cacagccgtg    420
attctggggc aggggaacgt ggctctggac gtggcccgca tcctactgac cccacctgag    480
cacctggaga gaacggacat cacgaaggca gccctgggtg tactgaggca gagtcgagtg    540
aagacagtgt ggctagtggg ccggcgtgga ccctgcaag tggccttcac cattaaggag    600
cttcgggaga tgattcagtt accgggagcc cggcccattt tggatcctgt ggatttcttg    660
ggtctccagg acaagatcaa ggaggtcccc cgcccgagga agcggctgac ggaactgctg    720
cttcgaacgg ccacagagaa gccagggccg gcggaagctg cccgccaggc atcggcctcc    780
cgtgcctggg gcctccgctt tttccgaagc ccccagcagg tgctgccctc accagatggg    840
cggcgggcag caggtgtccg cctagcagtc actagactgg agggtgtcga tgaggccacc    900
cgtgcagtgc ccacgggaga catggaagac ctcccttgtg ggctggtgct cagcagcatt    960
gggtataaga gccgccctgt cgacccaagc gtgcccttg actccaagct ggggtcatc   1020
cccaatgtgg agggccgggt tatggatgtg ccaggcctct actgcagcgg ctgggtgaag   1080
agaggaccta caggtgtcat agccacaacc atgactgaca gcttcctcac cggccagatg   1140
ctgctgcagg acctgaaggc tgggttgctc ccctctggcc ccaggcctgg ctacgcagcc   1200
atccaggccc tgctcagcag ccgaggggtc cggccagtct ctttctcaga ctgggagaag   1260
ctggatgccg aggaggtggc ccggggccag ggcacgggga gcccaggga gaagctggtg   1320
gatcctcagg agatgctgcg cctcctgggc cactga                             1356
```

<210> SEQ ID NO 64
<211> LENGTH: 451
<212> TYPE: PRT
<213> ORGANISM: Homo sapiens

<400> SEQUENCE: 64

Met Ala Ser Arg Cys Trp Arg Trp Trp Gly Trp Ser Ala Trp Pro Arg

-continued

```
  1               5                  10                 15
Thr Arg Leu Pro Ala Gly Ser Thr Pro Ser Phe Cys His His Phe
                 20                  25                 30

Ser Thr Gln Glu Lys Thr Pro Gln Ile Cys Val Val Gly Ser Gly Pro
                 35                  40                 45

Ala Gly Phe Tyr Thr Ala Gln His Leu Leu Lys Gln His Pro Gln Ala
                 50                  55                 60

His Val Asp Ile Tyr Glu Lys Gln Pro Val Pro Phe Gly Leu Val Arg
 65                  70                  75                 80

Phe Gly Val Ala Pro Asp His Pro Glu Val Lys Ser Tyr Gly Ala Glu
                 85                  90                 95

Asp His Arg Ala Leu Glu Ile Pro Gly Glu Leu Pro Gly Val Cys
                100                 105                110

Ser Ala Arg Ala Phe Val Gly Trp Tyr Asn Gly Leu Pro Glu Asn Gln
                115                 120                 125

Glu Leu Glu Pro Asp Leu Ser Cys Asp Thr Ala Val Ile Leu Gly Gln
                130                 135                 140

Gly Asn Val Ala Leu Asp Val Ala Arg Ile Leu Leu Thr Pro Pro Glu
145                 150                 155                 160

His Leu Glu Arg Thr Asp Ile Thr Lys Ala Ala Leu Gly Val Leu Arg
                165                 170                 175

Gln Ser Arg Val Lys Thr Val Trp Leu Val Gly Arg Arg Gly Pro Leu
                180                 185                 190

Gln Val Ala Phe Thr Ile Lys Glu Leu Arg Glu Met Ile Gln Leu Pro
                195                 200                 205

Gly Ala Arg Pro Ile Leu Asp Pro Val Asp Phe Leu Gly Leu Gln Asp
                210                 215                 220

Lys Ile Lys Glu Val Pro Arg Pro Arg Lys Arg Leu Thr Glu Leu Leu
225                 230                 235                 240

Leu Arg Thr Ala Thr Glu Lys Pro Gly Pro Ala Glu Ala Ala Arg Gln
                245                 250                 255

Ala Ser Ala Ser Arg Ala Trp Gly Leu Arg Phe Phe Arg Ser Pro Gln
                260                 265                 270

Gln Val Leu Pro Ser Pro Asp Gly Arg Arg Ala Ala Gly Val Arg Leu
                275                 280                 285

Ala Val Thr Arg Leu Glu Gly Val Asp Glu Ala Thr Arg Ala Val Pro
                290                 295                 300

Thr Gly Asp Met Glu Asp Leu Pro Cys Gly Leu Val Leu Ser Ser Ile
305                 310                 315                 320

Gly Tyr Lys Ser Arg Pro Val Asp Pro Ser Val Pro Phe Asp Ser Lys
                325                 330                 335

Leu Gly Val Ile Pro Asn Val Glu Gly Arg Val Met Asp Val Pro Gly
                340                 345                 350

Leu Tyr Cys Ser Gly Trp Val Lys Arg Gly Pro Thr Gly Val Ile Ala
                355                 360                 365

Thr Thr Met Thr Asp Ser Phe Leu Thr Gly Gln Met Leu Leu Gln Asp
                370                 375                 380

Leu Lys Ala Gly Leu Leu Pro Ser Gly Pro Arg Pro Gly Tyr Ala Ala
385                 390                 395                 400

Ile Gln Ala Leu Leu Ser Ser Arg Gly Val Arg Pro Val Ser Phe Ser
                405                 410                 415

Asp Trp Glu Lys Leu Asp Ala Glu Glu Val Ala Arg Gly Gln Gly Thr
                420                 425                 430
```

Gly Lys Pro Arg Glu Lys Leu Val Asp Pro Gln Glu Met Leu Arg Leu
         435                 440                 445

Leu Gly His
    450

<210> SEQ ID NO 65
<211> LENGTH: 1320
<212> TYPE: DNA
<213> ORGANISM: Homo sapiens

<400> SEQUENCE: 65

| | | | | | |
|---|---|---|---|---|---|
| atggaagata | aggacagaga | gcaccccag | gcccacgtgg | acatctacga | gaaacagcct | 60 |
| gtgccctttg | gcctggtgcg | ctttggtgtg | gcgcctgatc | accccgaggt | gaagaatgtc | 120 |
| atcaacacat | ttacccagac | ggcccattct | ggccgctgtg | ccttctgggg | caacgtggag | 180 |
| gtgggcaggg | acgtgacggt | gccggagctg | cgggaggcct | accacgctgt | ggtgctgagc | 240 |
| tacgggcag | aggaccatcg | ggccctggaa | attctggtg | aggagctgcc | aggtgtgtgc | 300 |
| tccgcccggg | ccttcgtggg | ctggtacaac | gggcttcctg | agaaccagga | gctggagcca | 360 |
| gacctgagct | gtgacacagc | cgtgattctg | ggcaggggga | acgtggctct | ggacgtggcc | 420 |
| cgcatcctac | tgaccccacc | tgagcacctg | agagaacgg | acatcacgaa | ggcagccctg | 480 |
| ggtgtactga | gcagagtcg | agtgaagaca | gtgtggctag | tgggccggcg | tggacccctg | 540 |
| caagtggcct | tcaccattaa | ggagcttcgg | gagatgattc | agttaccggg | agcccggccc | 600 |
| attttggatc | ctgtggattt | cttgggtctc | caggacaaga | tcaaggaggt | cccccgcccg | 660 |
| aggaagcggc | tgacggaact | gctgcttcga | acggccacag | agaagccagg | gccggcggaa | 720 |
| gctgccgcc | aggcatcggc | ctcccgtgcc | tggggcctcc | gctttttccg | aagccccag | 780 |
| caggtgctgc | cctcaccaga | tgggcggcgg | gcagcaggtg | tccgcctagc | agtcactaga | 840 |
| ctggagggtg | tcgatgaggc | caccgtgca | gtgcccacgg | gagacatgga | agacctccct | 900 |
| tgtgggctgg | tgctcagcag | cattgggtat | aagagccgcc | ctgtcgaccc | aagcgtgccc | 960 |
| tttgactcca | gcttggggt | catccccaat | gtggagggcc | gggttatgga | tgtgccaggc | 1020 |
| ctctactgca | gcggctgggt | gaagagagga | cctacaggtg | tcatagccac | aaccatgact | 1080 |
| gacagcttcc | tcaccggcca | gatgctgctg | caggacctga | aggctgggtt | gctcccctct | 1140 |
| ggccccaggc | ctggctacgc | agccatccag | gccctgctca | gcagccgagg | ggtccggcca | 1200 |
| gtctctttct | cagactggga | gaagctggat | gccgaggagg | tggcccgggg | ccagggcacg | 1260 |
| gggaagccca | gggagaagct | ggtggatcct | caggagatgc | tgcgcctcct | gggccactga | 1320 |

<210> SEQ ID NO 66
<211> LENGTH: 439
<212> TYPE: PRT
<213> ORGANISM: Homo sapiens

<400> SEQUENCE: 66

Met Glu Asp Lys Asp Arg Glu His Pro Gln Ala His Val Asp Ile Tyr
1               5                   10                  15

Glu Lys Gln Pro Val Pro Phe Gly Leu Val Arg Phe Gly Val Ala Pro
            20                  25                  30

Asp His Pro Glu Val Lys Asn Val Ile Asn Thr Phe Thr Gln Thr Ala
        35                  40                  45

His Ser Gly Arg Cys Ala Phe Trp Gly Asn Val Glu Val Gly Arg Asp
    50                  55                  60

Val Thr Val Pro Glu Leu Arg Glu Ala Tyr His Ala Val Val Leu Ser
65                  70                  75                  80

Tyr Gly Ala Glu Asp His Arg Ala Leu Glu Ile Pro Gly Glu Glu Leu
            85                  90                  95

Pro Gly Val Cys Ser Ala Arg Ala Phe Val Gly Trp Tyr Asn Gly Leu
            100                 105                 110

Pro Glu Asn Gln Glu Leu Glu Pro Asp Leu Ser Cys Asp Thr Ala Val
            115                 120                 125

Ile Leu Gly Gln Gly Asn Val Ala Leu Asp Val Ala Arg Ile Leu Leu
            130                 135                 140

Thr Pro Pro Glu His Leu Glu Arg Thr Asp Ile Thr Lys Ala Ala Leu
145                 150                 155                 160

Gly Val Leu Arg Gln Ser Arg Val Lys Thr Val Trp Leu Val Gly Arg
                165                 170                 175

Arg Gly Pro Leu Gln Val Ala Phe Thr Ile Lys Glu Leu Arg Glu Met
            180                 185                 190

Ile Gln Leu Pro Gly Ala Arg Pro Ile Leu Asp Pro Val Asp Phe Leu
            195                 200                 205

Gly Leu Gln Asp Lys Ile Lys Glu Val Pro Arg Pro Arg Lys Arg Leu
210                 215                 220

Thr Glu Leu Leu Leu Arg Thr Ala Thr Glu Lys Pro Gly Pro Ala Glu
225                 230                 235                 240

Ala Ala Arg Gln Ala Ser Ala Ser Arg Ala Trp Gly Leu Arg Phe Phe
                245                 250                 255

Arg Ser Pro Gln Gln Val Leu Pro Ser Pro Asp Gly Arg Ala Ala
            260                 265                 270

Gly Val Arg Leu Ala Val Thr Arg Leu Glu Gly Val Asp Glu Ala Thr
            275                 280                 285

Arg Ala Val Pro Thr Gly Asp Met Glu Asp Leu Pro Cys Gly Leu Val
            290                 295                 300

Leu Ser Ser Ile Gly Tyr Lys Ser Arg Pro Val Asp Pro Ser Val Pro
305                 310                 315                 320

Phe Asp Ser Lys Leu Gly Val Ile Pro Asn Val Glu Gly Arg Val Met
            325                 330                 335

Asp Val Pro Gly Leu Tyr Cys Ser Gly Trp Val Lys Arg Gly Pro Thr
            340                 345                 350

Gly Val Ile Ala Thr Thr Met Thr Asp Ser Phe Leu Thr Gly Gln Met
            355                 360                 365

Leu Leu Gln Asp Leu Lys Ala Gly Leu Leu Pro Ser Gly Pro Arg Pro
370                 375                 380

Gly Tyr Ala Ala Ile Gln Ala Leu Leu Ser Ser Arg Gly Val Arg Pro
385                 390                 395                 400

Val Ser Phe Ser Asp Trp Glu Lys Leu Asp Ala Glu Val Ala Arg
            405                 410                 415

Gly Gln Gly Thr Gly Lys Pro Arg Glu Lys Leu Val Asp Pro Gln Glu
            420                 425                 430

Met Leu Arg Leu Leu Gly His
            435

<210> SEQ ID NO 67
<211> LENGTH: 552
<212> TYPE: DNA
<213> ORGANISM: Homo sapiens

<400> SEQUENCE: 67

```
atggccgcct ccatggcccg gggaggcgtg agtgccaggg ttctactgca ggctgccagg    60
ggcacctggt ggaacagacc tgggggcact tccgggtcgg gggaggggt ggcgctgggg   120
acaaccagaa agtttcaagc gacaggctcg cgcccggctg gagaggagga cgcgggcggc   180
ccggagcggc ccggggacgt ggtgaacgtg gtgttcgtag accgctcagg ccagcggatc   240
ccagtgagtg gcagagtcgg ggacaatgtt cttcacctgg cccagcgcca cggggtggac   300
ctggaagggg cctgtgaagc ctccctggcc tgctccacct gccatgtgta tgtgagtgaa   360
gaccacctgg atctcctgcc tcctcccgag gagagggaag acgacatgct agacatggcc   420
cccctcctcc aggagaactc gcggctgggc tgccagattg tgctgacacc ggagctggaa   480
ggagcggaat tcaccctgcc caagatcacc aggaacttct acgtggatgg ccatgtcccc   540
aagccccact ga                                                       552

<210> SEQ ID NO 68
<211> LENGTH: 183
<212> TYPE: PRT
<213> ORGANISM: Homo sapiens

<400> SEQUENCE: 68

Met Ala Ala Ser Met Ala Arg Gly Gly Val Ser Ala Arg Val Leu Leu
1               5                   10                  15
Gln Ala Ala Arg Gly Thr Trp Trp Asn Arg Pro Gly Gly Thr Ser Gly
            20                  25                  30
Ser Gly Glu Gly Val Ala Leu Gly Thr Thr Arg Lys Phe Gln Ala Thr
        35                  40                  45
Gly Ser Arg Pro Ala Gly Glu Glu Asp Ala Gly Pro Glu Arg Pro
    50                  55                  60
Gly Asp Val Val Asn Val Val Phe Val Asp Arg Ser Gly Gln Arg Ile
65                  70                  75                  80
Pro Val Ser Gly Arg Val Gly Asp Asn Val Leu His Leu Ala Gln Arg
                85                  90                  95
His Gly Val Asp Leu Glu Gly Ala Cys Glu Ala Ser Leu Ala Cys Ser
            100                 105                 110
Thr Cys His Val Tyr Val Ser Glu Asp His Leu Asp Leu Leu Pro Pro
        115                 120                 125
Pro Glu Glu Arg Glu Asp Asp Met Leu Asp Met Ala Pro Leu Leu Gln
    130                 135                 140
Glu Asn Ser Arg Leu Gly Cys Gln Ile Val Leu Thr Pro Glu Leu Glu
145                 150                 155                 160
Gly Ala Glu Phe Thr Leu Pro Lys Ile Thr Arg Asn Phe Tyr Val Asp
                165                 170                 175
Gly His Val Pro Lys Pro His
            180

<210> SEQ ID NO 69
<211> LENGTH: 2670
<212> TYPE: DNA
<213> ORGANISM: Homo sapiens

<400> SEQUENCE: 69
atgagcaacc cattcgcaca ccttgctgag ccattggatc ctgtacaacc aggaaagaaa    60
ttcttcaatt tgaataaatt ggaggattca agatatgggc gcttaccatt ttcgatcaga   120
gttcttctgg aagcagccat tcggaattgt gatgagtttt tggtgaagaa acaggatatt   180
```

```
gaaaatattc tacattggaa tgtcacgcag cacaagaaca tagaagtgcc atttaagcct    240
gctcgtgtca tcctgcagga ctttacgggt gtgcccgctg tggttgactt tgctgcaatg    300
cgtgatgctg tgaaaaagtt aggaggagat ccagagaaaa taaaccctgt ctgccctgct    360
gatcttgtaa tagatcattc catccaggtt gatttcaaca aagggcaga cagtttacag    420 aagaatcaag acctggaatt tgaaagaaat agagagcgat ttgaattttt aaagtggggt    480
tcccaggctt ttcacaacat gcggattatt cccctggct caggaatcat ccaccaggtg    540
aatttggaat atttggcaag agtggtattt gatcaggatg atattatta cccagacagc    600 ctcgtgggca cagactcgca cactaccatg attgatggct gggcattct tggttggggt    660 gtcggtggta ttgaagcaga agctgtcatg ctgggtcagc caatcagtat ggtgcttcct    720
caggtgattg gctacaggct gatggggaag ccccaccctc tggtaacatc cactgacatc    780
gtgctcacca ttaccaagca cctccgccag gttggggtag tgggcaaatt tgtcgagttc    840
ttcgggcctg gagtagccca gttgtccatt gctgaccgag ctacgattgc taacatgtgt    900
ccagagtacg gagcaactgc tgccttttc ccagttgatg aagttagtat cacgtacctg    960
gtgcaaacag gtcgtgatga agaaaaatta aagtatatta aaaatatct tcaggctgta    1020 ggaatgtttc gagatttcaa tgacccttct caagacccag acttcacca ggttgtggaa    1080 ttagatttga aaacagtagt gccttgctgt agtggaccca aaaggcctca ggacaaagtt    1140
gctgtgtccg acatgaaaaa ggactttgag agctgccttg gagccaagca aggatttaaa    1200
ggattccaag ttgctcctga acatcataat gaccataaga cctttatcta tgataacact    1260
gaattcaccc ttgctcatgg ttctgtggtc attgctgcca ttactagctg cacaaacacc    1320
agtaatccgt ctgtgatgtt aggggcagga ttgttagcaa agaaagctgt ggatgctggc    1380
ctgaacgtga tgccttacat caaaactagc ctgtctcctg gagtggcgt ggtcacctac    1440 tacctacaag aaagcggagt catgccttat ctgtctcagc ttgggtttga cgtggtgggc    1500 tatgctgca tgacctgcat tggcaacagt gggcctttac ctgaacctgt ggtagaagcc    1560
atcacacagg gagaccttgt agctgttgga gtactatctg gaaacaggaa ttttgaaggt    1620
cgagttcacc ccaacacccg ggccaactat ttagcctctc cccccttagt aatagcatat    1680
gcaattgctg gaaccatcag aatcgacttt gagaaagagc cattgggagt aaatgcaaag    1740
ggacagcagg tatttctgaa agatatctgg ccgactagag acgagatcca ggcagtggag    1800
cgtcagtatg tcatcccggg gatgtttaag gaagtctatc agaaaataga gactgtgaat    1860
gaaagctgga tgccttagc aaccccatca gataagctgt tttttctggaa ttccaaatct    1920 acgtatatca aatcaccacc attctttgaa aacctgactt tggatcttca gcccctaaa    1980 tctatagtgg atgcctatgt gctgctaaat ttgggagatt cggtaacaac tgaccacatc    2040
tccccagctg gaaatattgc aagaaacagt cctgctgctc gctacttaac taacagaggc    2100
ctaactccac gagaattcaa ctcctatggc tcccgccgag gtaatgacgc cgtcatggca    2160
cggggaacat ttgccaacat tcgcttgtta aacagatttt tgaacaagca ggcaccacag    2220
actatccatc tgccttctgg ggaaatcctt gatgtgttg atgctgctga gcggtaccag    2280
caggcaggcc ttcccctgat cgttctggct ggcaaagagt acggtgcagg cagctcccga    2340
gactgggcag ctaagggccc tttcctgctg ggaatcaaag ccgtcctggc cgagagctac    2400
gagcgcattc accgcagtaa cctggttggg atgggtgtga tcccacttga atatctccct    2460
ggtgagaatg cagatgccct ggggctcaca gggcaagaac gatacactat cattattcca    2520
gaaaacctca accacaaaat gaaagtccag gtcaagctgg atactggcaa gaccttccag    2580
```

| | |
|---|---|
| gctgtcatga ggtttgacac tgatgtggag ctcacttatt tcctcaacgg gggcatcctc | 2640 |
| aactacatga tccgcaagat ggccaagtag | 2670 |

<210> SEQ ID NO 70
<211> LENGTH: 2670
<212> TYPE: DNA
<213> ORGANISM: Homo sapiens

<400> SEQUENCE: 70

| | |
|---|---|
| atgagcaacc cattcgcaca ccttgctgag ccattggatc ctgtacaacc aggaaagaaa | 60 |
| ttcttcaatt tgaataaatt ggaggattca agatatgggc gcttaccatt ttcgatcaga | 120 |
| gttcttctgg aagcagccat tcggaattgt gatgagtttt tggtgaagaa acaggatatt | 180 |
| gaaaatattc tacattggaa tgtcacgcag cacaagaaca tagaagtgcc atttaagcct | 240 |
| gctcgtgtca tcctgcagga ctttacgggt gtgcccgctg tggttgactt tgctgcaatg | 300 |
| cgtgatgctg tgaaaaagtt aggaggagat ccagagaaaa taaaccctgt ctgccctgct | 360 |
| gatcttgtaa tagatcattc catccaggtt gatttcaaca aagggcaga cagtttacag | 420 |
| aagaatcaag acctggaatt tgaaagaaat agagagcgat ttgaattttt aaagtggggt | 480 |
| tcccaggctt ttcacaacat gcggattatt cccctggct caggaatcat ccaccaggtg | 540 |
| aatttggaat atttggcaag agtggtattt gatcaggatg atattatta cccagacagc | 600 |
| ctcgtgggca cagactcgca cactaccatg attgatggct tgggcattct tggttggggt | 660 |
| gtcggtggta ttgaagcaga agctgtcatg ctgggtcagc caatcagtat ggtgcttcct | 720 |
| caggtgattg gctacaggct gatggggaag ccccacctc tggtaacatc cactgacatc | 780 |
| gtgctcacca ttaccaagca cctccgccag gttggggtag tgggcaaatt tgtcgagttc | 840 |
| ttcgggcctg gagtagccca gttgtccatt gctgaccgag ctacgattgc taacatgtgt | 900 |
| ccagagtacg gagcaactgc tgcctttttc ccagttgatg aagttagtat cacgtacctg | 960 |
| gtgcaaacag tcgtgatga agaaaaatta agtatatta aaaatatct tcaggctgta | 1020 |
| ggaatgtttc gagatttcaa tgacccttct caagacccag acttcaccca ggttgtggaa | 1080 |
| ttagatttga aaacagtagt gccttgctgt agtggaccca aaaggcctca ggacaaagtt | 1140 |
| gctgtgtccg acatgaaaaa ggactttgag agctgccttg gagccaagca aggatttaaa | 1200 |
| ggattccaag ttgctcctga acatcataat gaccataaga cctttatcta tgataacact | 1260 |
| gaattcaccc ttgctcatgg ttctgtggtc attgctgcca ttactagctg cacaaacacc | 1320 |
| agtaatccgt ctgtgatgtt aggggcagga ttgttagcaa agaaagctgt ggatgctggc | 1380 |
| ctgaacgtga tgccttacat caaaactagc ctgtctcctg ggagtggcgt ggtcacctac | 1440 |
| tacctacaag aaagcggagt catgccttat ctgtctcagc ttgggtttga cgtggtgggc | 1500 |
| tatggctgca tgacctgcat tggcaacagt gggcctttac ctgaacctgt ggtagaagcc | 1560 |
| atcacacagg agaccttgt agctgttgga gtactatctg aaacaggaa ttttgaaggt | 1620 |
| cgagttcacc ccaacacccg ggccaactat ttagcctctc cccccttagt aatagcatat | 1680 |
| gcaattgctg aaccatcag aatcgacttt gagaaagagc cattgggagt aaatgcaaag | 1740 |
| ggacagcagg tatttctgaa agatatctgg ccgactagac gagatcca ggcagtggag | 1800 |
| cgtcagtatg tcatcccggg gatgtttaag gaagtctatc agaaaataga gactgtgaat | 1860 |
| gaaagctgga atgccttagc aaccccatca gataagctgt ttttctggaa ttccaaatct | 1920 |
| acgtatatca aatcaccacc attctttgaa aacctgactt tggatcttca gcccctaaa | 1980 |

-continued

```
tctatagtgg atgcctatgt gctgctaaat ttgggagatt cggtaacaac tgaccacatc    2040
tccccagctg gaaatattgc aagaaacagt cctgctgctc gctacttaac taacagaggc    2100
ctaactccac gagaattcaa ctcctatggc tcccgccgag gtaatgacgc cgtcatggca    2160
cggggaacat tgccaacat tcgcttgtta aacagatttt tgaacaagca ggcaccacag     2220
actatccatc tgccttctgg ggaaatcctt gatgtgtttg atgctgctga gcggtaccag    2280
caggcaggcc ttcccctgat cgttctggct ggcaaagagt acggtgcagg cagctcccga    2340
gactgggcag ctaagggccc tttcctgctg gaatcaaag ccgtcctggc cgagagctac     2400
gagcgcattc accgcagtaa cctggttggg atgggtgtga tcccacttga atatctccct    2460
ggtgagaatg cagatgccct ggggctcaca gggcaagaac gatacactat cattattcca    2520
gaaaacctca acccacaaat gaaagtccag gtcaagctgg atactggcaa gaccttccag    2580
gctgtcatga ggtttgacac tgatgtggag ctcacttatt tcctcaacgg gggcatcctc    2640
aactacatga tccgcaagat ggccaagtag                                     2670
```

<210> SEQ ID NO 71
<211> LENGTH: 889
<212> TYPE: PRT
<213> ORGANISM: Homo sapiens

<400> SEQUENCE: 71

```
Met Ser Asn Pro Phe Ala His Leu Ala Glu Pro Leu Asp Pro Val Gln
  1               5                  10                  15

Pro Gly Lys Lys Phe Asn Leu Asn Lys Leu Glu Asp Ser Arg Tyr
                 20                  25                  30

Gly Arg Leu Pro Phe Ser Ile Arg Val Leu Leu Glu Ala Ala Ile Arg
             35                  40                  45

Asn Cys Asp Glu Phe Leu Val Lys Lys Gln Asp Ile Glu Asn Ile Leu
         50                  55                  60

His Trp Asn Val Thr Gln His Lys Asn Ile Glu Val Pro Phe Lys Pro
 65                  70                  75                  80

Ala Arg Val Ile Leu Gln Asp Phe Thr Gly Val Pro Ala Val Val Asp
                 85                  90                  95

Phe Ala Ala Met Arg Asp Ala Val Lys Lys Leu Gly Gly Asp Pro Glu
                100                 105                 110

Lys Ile Asn Pro Val Cys Pro Ala Asp Leu Val Ile Asp His Ser Ile
            115                 120                 125

Gln Val Asp Phe Asn Arg Arg Ala Asp Ser Leu Gln Lys Asn Gln Asp
        130                 135                 140

Leu Glu Phe Glu Arg Asn Arg Glu Arg Phe Glu Phe Leu Lys Trp Gly
145                 150                 155                 160

Ser Gln Ala Phe His Asn Met Arg Ile Ile Pro Pro Gly Ser Gly Ile
                165                 170                 175

Ile His Gln Val Asn Leu Glu Tyr Leu Ala Arg Val Val Phe Asp Gln
            180                 185                 190

Asp Gly Tyr Tyr Tyr Pro Asp Ser Leu Val Gly Thr Asp Ser His Thr
        195                 200                 205

Thr Met Ile Asp Gly Leu Gly Ile Leu Gly Trp Gly Val Gly Gly Ile
    210                 215                 220

Glu Ala Glu Ala Val Met Leu Gly Gln Pro Ile Ser Met Val Leu Pro
225                 230                 235                 240

Gln Val Ile Gly Tyr Arg Leu Met Gly Lys Pro His Pro Leu Val Thr
                245                 250                 255
```

```
Ser Thr Asp Ile Val Leu Thr Ile Thr Lys His Leu Arg Gln Val Gly
            260                 265                 270

Val Val Gly Lys Phe Val Glu Phe Gly Pro Gly Val Ala Gln Leu
        275                 280                 285

Ser Ile Ala Asp Arg Ala Thr Ile Ala Asn Met Cys Pro Glu Tyr Gly
            290                 295                 300

Ala Thr Ala Ala Phe Phe Pro Val Asp Glu Val Ser Ile Thr Tyr Leu
305                 310                 315                 320

Val Gln Thr Gly Arg Asp Glu Lys Leu Lys Tyr Ile Lys Lys Tyr
            325                 330                 335

Leu Gln Ala Val Gly Met Phe Arg Asp Phe Asn Asp Pro Ser Gln Asp
            340                 345                 350

Pro Asp Phe Thr Gln Val Val Glu Leu Asp Leu Lys Thr Val Val Pro
            355                 360                 365

Cys Cys Ser Gly Pro Lys Arg Pro Gln Asp Lys Val Ala Val Ser Asp
            370                 375                 380

Met Lys Lys Asp Phe Glu Ser Cys Leu Gly Ala Lys Gln Gly Phe Lys
385                 390                 395                 400

Gly Phe Gln Val Ala Pro Glu His His Asn Asp His Lys Thr Phe Ile
            405                 410                 415

Tyr Asp Asn Thr Glu Phe Thr Leu Ala His Gly Ser Val Val Ile Ala
            420                 425                 430

Ala Ile Thr Ser Cys Thr Asn Thr Ser Asn Pro Ser Val Met Leu Gly
            435                 440                 445

Ala Gly Leu Leu Ala Lys Lys Ala Val Asp Ala Gly Leu Asn Val Met
450                 455                 460

Pro Tyr Ile Lys Thr Ser Leu Ser Pro Gly Ser Gly Val Val Thr Tyr
465                 470                 475                 480

Tyr Leu Gln Glu Ser Gly Val Met Pro Tyr Leu Ser Gln Leu Gly Phe
            485                 490                 495

Asp Val Val Gly Tyr Gly Cys Met Thr Cys Ile Gly Asn Ser Gly Pro
            500                 505                 510

Leu Pro Glu Pro Val Val Glu Ala Ile Thr Gln Gly Asp Leu Val Ala
            515                 520                 525

Val Gly Val Leu Ser Gly Asn Arg Asn Phe Glu Gly Arg Val His Pro
            530                 535                 540

Asn Thr Arg Ala Asn Tyr Leu Ala Ser Pro Pro Leu Val Ile Ala Tyr
545                 550                 555                 560

Ala Ile Ala Gly Thr Ile Arg Ile Asp Phe Glu Lys Glu Pro Leu Gly
                565                 570                 575

Val Asn Ala Lys Gly Gln Gln Val Phe Leu Lys Asp Ile Trp Pro Thr
            580                 585                 590

Arg Asp Glu Ile Gln Ala Val Glu Arg Gln Tyr Val Ile Pro Gly Met
            595                 600                 605

Phe Lys Glu Val Tyr Gln Lys Ile Glu Thr Val Asn Glu Ser Trp Asn
            610                 615                 620

Ala Leu Ala Thr Pro Ser Asp Lys Leu Phe Phe Trp Asn Ser Lys Ser
625                 630                 635                 640

Thr Tyr Ile Lys Ser Pro Pro Phe Phe Glu Asn Leu Thr Leu Asp Leu
                645                 650                 655

Gln Pro Pro Lys Ser Ile Val Asp Ala Tyr Val Leu Leu Asn Leu Gly
            660                 665                 670
```

Asp Ser Val Thr Thr Asp His Ile Ser Pro Ala Gly Asn Ile Ala Arg
            675                 680                 685

Asn Ser Pro Ala Ala Arg Tyr Leu Thr Asn Arg Gly Leu Thr Pro Arg
        690                 695                 700

Glu Phe Asn Ser Tyr Gly Ser Arg Arg Gly Asn Asp Ala Val Met Ala
705                 710                 715                 720

Arg Gly Thr Phe Ala Asn Ile Arg Leu Leu Asn Arg Phe Leu Asn Lys
                725                 730                 735

Gln Ala Pro Gln Thr Ile His Leu Pro Ser Gly Glu Ile Leu Asp Val
            740                 745                 750

Phe Asp Ala Ala Glu Arg Tyr Gln Gln Ala Gly Leu Pro Leu Ile Val
        755                 760                 765

Leu Ala Gly Lys Glu Tyr Gly Ala Gly Ser Ser Arg Asp Trp Ala Ala
770                 775                 780

Lys Gly Pro Phe Leu Leu Gly Ile Lys Ala Val Leu Ala Glu Ser Tyr
785                 790                 795                 800

Glu Arg Ile His Arg Ser Asn Leu Val Gly Met Gly Val Ile Pro Leu
                805                 810                 815

Glu Tyr Leu Pro Gly Glu Asn Ala Asp Ala Leu Gly Leu Thr Gly Gln
            820                 825                 830

Glu Arg Tyr Thr Ile Ile Pro Glu Asn Leu Lys Pro Gln Met Lys
        835                 840                 845

Val Gln Val Lys Leu Asp Thr Gly Lys Thr Phe Gln Ala Val Met Arg
            850                 855                 860

Phe Asp Thr Asp Val Glu Leu Thr Tyr Phe Leu Asn Gly Gly Ile Leu
865                 870                 875                 880

Asn Tyr Met Ile Arg Lys Met Ala Lys
                885

<210> SEQ ID NO 72
<211> LENGTH: 2343
<212> TYPE: DNA
<213> ORGANISM: Homo sapiens

<400> SEQUENCE: 72

```
atggcgccct acagcctact ggtgactcgg ctgcagaaag ctctgggtgt gcggcagtac      60
catgtggcct cagtcctgtg ccaacgggcc aaggtggcga tgagccactt tgagcccaac     120
gagtacatcc attatgacct gctagagaag aacattaaca ttgttcgcaa acgactgaac     180
cggccgctga cactctcgga aagattgtg tatggacacc tggatgaccc cgccagccag     240
gaaattgagc gaggcaagtc gtacctgcgg ctgcggccgg accgtgtggc catgcaggat     300
gcgacggccc agatggccat gctccagttc atcagcagcg ggctgtccaa ggtggctgtg     360
ccatccacca tccactgtga ccatctgatt gaagcccagg ttgggggcga gaaagacctg     420
cgccgggcca aggacatcaa ccaggaagtt tataatttcc tggcaactgc aggtgccaaa     480 tatgcgtgg gcttctggaa gcctggatct ggaatcattc accagattat tctgaaaac      540 tatgcgtacc ctggtgttct tctgattggc actgactccc acccccaa tggtggcggc      600 cttgggggca tctgcattgg agttggggt gccgatgctg tggatgtcat ggctgggatc     660
ccctgggagc tgaagtgccc caaggtgatt ggcgtgaagc tgacgggctc tctctccggt     720
tggtcctcac ccaaagatgt gatcctgaag gtgcaggca tcctcacggt gaaaggtggc     780
acaggtgcaa tcgtgaata ccacgggcct ggtgtagact ccatctcctg cactggcatg     840
gcgacaatct gcaacatggg tgcagaaatt ggggccacca cttccgtgtt cccttacaac     900
```

```
cacaggatga agaagtacct gagcaagacc ggccgggaag acattgccaa tctagctgat      960
gaattcaagg atcacttggt gcctgaccct ggctgccatt atgaccaact aattgaaatt     1020
aacctcagtg agctgaagcc acacatcaat gggcccttca cccctgacct ggctcaccct     1080
gtggcagaag tgggcaaggt ggcagagaag gaaggatggc ctctggacat ccgagtgggt     1140
ctaattggta gctgcaccaa ttcaagctat gaagatatgg ggcgctcagc agctgtggcc     1200
aagcaggcac tggcccatgg cctcaagtgc aagtcccagt tcaccatcac tccaggttcc     1260
gagcagatcc gcgccaccat tgagcgggac ggctatgcac agatcttgag ggatctgggt     1320
ggcattgtcc tggccaatgc ttgtggcccc tgcattggcc agtgggacag gaaggacatc     1380 aagaagggg agaagaacac aatcgtcacc tcctacaaca ggaacttcac gggccgcaac     1440
gacgcaaacc ccgagaccca tgcctttgtc acgtcccag agattgtcac agccctggcc     1500
attgcgggaa ccctcaagtt caacccagag accgactacc tgacgggcac ggatggcaag     1560
aagttcaggc tggaggctcc ggatgcagat gagcttccca aggggagtt tgacccaggg     1620 caggacacct accagcaccc acccaaggac agcagcgggc agcatgtgga cgtgagcccc     1680
accagccagc gcctgcagct cctggagcct tttgacaagt gggatggcaa ggacctggag     1740
gacctgcaga tcctcatcaa ggtcaaaggg aagtgtacca ctgaccacat ctcagctgct     1800
ggcccctggc tcaagttccg tgggcacttg ataacatct ccaacaacct gctcattggt     1860
gccatcaaca ttgaaaacgg caaggccaac tccgtgcgca atgccgtcac tcaggagttt     1920
ggccccgtcc ctgacactgc ccgctactac aagaaacatg gcatcaggtg ggtggtgatc     1980
ggagacgaga actacggcga gggctcgagc cgggagcatg cagctctgga gcctcgccac     2040
cttgggggcc gggccatcat caccaagagc tttgccagga tccacgagac caacctgaag     2100
aaacagggcc tgctgcctct gaccttcgct gacccggctg actacaacaa gattcaccct     2160
gtggacaagc tgaccattca gggcctgaag gacttcaccc ctggcaagcc cctgaagtgc     2220
atcatcaagc accccaacgg gacccaggag accatcctcc tgaaccacac cttcaacgag     2280
acgcagattg agtggttccg cgctggcagt gccctcaaca gaatgaagga actgcaacag     2340
tga                                                                   2343
```

<210> SEQ ID NO 73
<211> LENGTH: 780
<212> TYPE: PRT
<213> ORGANISM: Homo sapiens

<400> SEQUENCE: 73

```
Met Ala Pro Tyr Ser Leu Leu Val Thr Arg Leu Gln Lys Ala Leu Gly
1               5                   10                  15

Val Arg Gln Tyr His Val Ala Ser Val Leu Cys Gln Arg Ala Lys Val
            20                  25                  30

Ala Met Ser His Phe Glu Pro Asn Glu Tyr Ile His Tyr Asp Leu Leu
        35                  40                  45

Glu Lys Asn Ile Asn Ile Val Arg Lys Arg Leu Asn Arg Pro Leu Thr
    50                  55                  60

Leu Ser Glu Lys Ile Val Tyr Gly His Leu Asp Asp Pro Ala Ser Gln
65                  70                  75                  80

Glu Ile Glu Arg Gly Lys Ser Tyr Leu Arg Leu Arg Pro Asp Arg Val
                85                  90                  95

Ala Met Gln Asp Ala Thr Ala Gln Met Ala Met Leu Gln Phe Ile Ser
            100                 105                 110
```

```
Ser Gly Leu Ser Lys Val Ala Val Pro Ser Thr Ile His Cys Asp His
        115                 120                 125

Leu Ile Glu Ala Gln Val Gly Glu Lys Asp Leu Arg Arg Ala Lys
    130                 135                 140

Asp Ile Asn Gln Glu Val Tyr Asn Phe Leu Ala Thr Ala Gly Ala Lys
145                 150                 155                 160

Tyr Gly Val Gly Phe Trp Lys Pro Gly Ser Gly Ile Ile His Gln Ile
                165                 170                 175

Ile Leu Glu Asn Tyr Ala Tyr Pro Gly Val Leu Leu Ile Gly Thr Asp
                180                 185                 190

Ser His Thr Pro Asn Gly Gly Leu Gly Ile Cys Ile Gly Val
        195                 200                 205

Gly Gly Ala Asp Ala Val Asp Val Met Ala Gly Ile Pro Trp Glu Leu
    210                 215                 220

Lys Cys Pro Lys Val Ile Gly Val Lys Leu Thr Gly Ser Leu Ser Gly
225                 230                 235                 240

Trp Ser Ser Pro Lys Asp Val Ile Leu Lys Val Ala Gly Ile Leu Thr
                245                 250                 255

Val Lys Gly Gly Thr Gly Ala Ile Val Glu Tyr His Gly Pro Gly Val
        260                 265                 270

Asp Ser Ile Ser Cys Thr Gly Met Ala Thr Ile Cys Asn Met Gly Ala
        275                 280                 285

Glu Ile Gly Ala Thr Thr Ser Val Phe Pro Tyr Asn His Arg Met Lys
    290                 295                 300

Lys Tyr Leu Ser Lys Thr Gly Arg Glu Asp Ile Ala Asn Leu Ala Asp
305                 310                 315                 320

Glu Phe Lys Asp His Leu Val Pro Asp Pro Gly Cys His Tyr Asp Gln
                325                 330                 335

Leu Ile Glu Ile Asn Leu Ser Glu Leu Lys Pro His Ile Asn Gly Pro
                340                 345                 350

Phe Thr Pro Asp Leu Ala His Pro Val Ala Glu Val Gly Lys Val Ala
        355                 360                 365

Glu Lys Glu Gly Trp Pro Leu Asp Ile Arg Val Gly Leu Ile Gly Ser
    370                 375                 380

Cys Thr Asn Ser Ser Tyr Glu Asp Met Gly Arg Ser Ala Ala Val Ala
385                 390                 395                 400

Lys Gln Ala Leu Ala His Gly Leu Lys Cys Lys Ser Gln Phe Thr Ile
                405                 410                 415

Thr Pro Gly Ser Glu Gln Ile Arg Ala Thr Ile Glu Arg Asp Gly Tyr
                420                 425                 430

Ala Gln Ile Leu Arg Asp Leu Gly Gly Ile Val Leu Ala Asn Ala Cys
        435                 440                 445

Gly Pro Cys Ile Gly Gln Trp Asp Arg Lys Asp Ile Lys Lys Gly Glu
    450                 455                 460

Lys Asn Thr Ile Val Thr Ser Tyr Asn Arg Asn Phe Thr Gly Arg Asn
465                 470                 475                 480

Asp Ala Asn Pro Glu Thr His Ala Phe Val Thr Ser Pro Glu Ile Val
                485                 490                 495

Thr Ala Leu Ala Ile Ala Gly Thr Leu Lys Phe Asn Pro Glu Thr Asp
        500                 505                 510

Tyr Leu Thr Gly Thr Asp Gly Lys Lys Phe Arg Leu Glu Ala Pro Asp
        515                 520                 525
```

Ala Asp Glu Leu Pro Lys Gly Glu Phe Asp Pro Gly Gln Asp Thr Tyr
          530                 535                 540

Gln His Pro Pro Lys Asp Ser Ser Gly Gln His Val Asp Val Ser Pro
545                 550                 555                 560

Thr Ser Gln Arg Leu Gln Leu Leu Glu Pro Phe Asp Lys Trp Asp Gly
              565                 570                 575

Lys Asp Leu Glu Asp Leu Gln Ile Leu Ile Lys Val Lys Gly Lys Cys
              580                 585                 590

Thr Thr Asp His Ile Ser Ala Ala Gly Pro Trp Leu Lys Phe Arg Gly
              595                 600                 605

His Leu Asp Asn Ile Ser Asn Asn Leu Leu Ile Gly Ala Ile Asn Ile
    610                 615                 620

Glu Asn Gly Lys Ala Asn Ser Val Arg Asn Ala Val Thr Gln Glu Phe
625                 630                 635                 640

Gly Pro Val Pro Asp Thr Ala Arg Tyr Tyr Lys Lys His Gly Ile Arg
              645                 650                 655

Trp Val Val Ile Gly Asp Glu Asn Tyr Gly Gly Ser Ser Arg Glu
              660                 665                 670

His Ala Ala Leu Glu Pro Arg His Leu Gly Gly Arg Ala Ile Ile Thr
    675                 680                 685

Lys Ser Phe Ala Arg Ile His Glu Thr Asn Leu Lys Lys Gln Gly Leu
    690                 695                 700

Leu Pro Leu Thr Phe Ala Asp Pro Ala Asp Tyr Asn Lys Ile His Pro
705                 710                 715                 720

Val Asp Lys Leu Thr Ile Gln Gly Leu Lys Asp Phe Thr Pro Gly Lys
              725                 730                 735

Pro Leu Lys Cys Ile Ile Lys His Pro Asn Gly Thr Gln Glu Thr Ile
              740                 745                 750

Leu Leu Asn His Thr Phe Asn Glu Thr Gln Ile Glu Trp Phe Arg Ala
    755                 760                 765

Gly Ser Ala Leu Asn Arg Met Lys Glu Leu Gln Gln
770                 775                 780

<210> SEQ ID NO 74
<211> LENGTH: 2283
<212> TYPE: DNA
<213> ORGANISM: Homo sapiens

<400> SEQUENCE: 74

| | |
|---|---|
| atgatggatc aagctagatc agcattctct aacttgtttg gtggagaacc attgtcatat | 60 |
| acccggttca gcctggctcg gcaagtagat ggcgataaca gtcatgtgga gatgaaactt | 120 |
| gctgtagatg aagaagaaaa tgctgacaat aacacaaagg ccaatgtcac aaaaccaaaa | 180 |
| aggtgtagtg aagtatctg ctatgggact attgctgtga tcgtcttttt cttgattgga | 240 |
| tttatgattg ctacttggg ctattgtaaa ggggtagaac caaaaactga gtgtgagaga | 300 |
| ctggcaggaa ccgagtctcc agtgagggag gagccaggag aggacttccc tgcagcacgt | 360 |
| cgcttatatt gggatgacct gaagagaaag ttgtcggaga aactggacag cacagacttc | 420 |
| accggcacca tcaagctgct gaatgaaaat tcatatgtcc ctcgtgaggc tggatctcaa | 480 |
| aaagatgaaa atcttgcgtt gtatgttgaa atcaatttc gtgaatttaa actcagcaaa | 540 |
| gtctggcgtg atcaacattt tgttaagatt caggtcaaag acagcgctca aaactcggtg | 600 |
| atcatagttg ataagaacgg tagacttgtt tacctggtgg agaatcctgg gggttatgtg | 660 |
| gcgtatagta aggctgcaac agttactggt aaactggtcc atgctaattt tggtactaaa | 720 |

```
aaagattttg aggatttata cactcctgtg aatggatcta tagtgattgt cagagcaggg      780
aaaatcacct ttgcagaaaa ggttgcaaat gctgaaagct taaatgcaat tggtgtgttg      840
atatacatgg accagactaa atttcccatt gttaacgcag aactttcatt ctttggacat      900
gctcatctgg ggacaggtga cccttacaca cctggattcc cttccttcaa tcacactcag      960
tttccaccat ctcggtcatc aggattgcct aatatacctg tccagacaat ctccagagct     1020
gctgcagaaa agctgtttgg gaatatggaa ggagactgtc cctctgactg gaaaacagac     1080
tctacatgta ggatggtaac ctcagaaagc aagaatgtga agctcactgt gagcaatgtg     1140
ctgaaagaga taaaaattct taacatcttt ggagttatta aaggctttgt agaaccagat     1200
cactatgttg tagttggggc ccagagagat gcatgggccc tggagctgc aaaatccggt      1260 gtaggcacag ctctcctatt gaaacttgcc cagatgttct cagatatggt cttaaaagat     1320
gggtttcagc ccagcagaag cattatcttt gccagttgga gtgctggaga ctttggatcg     1380
gttggtgcca ctgaatggct agagggatac ctttcgtccc tgcatttaaa ggctttcact     1440
tatattaatc tggataaagc ggttcttggt accagcaact tcaaggtttc tgccagccca     1500
ctgttgtata cgcttattga gaaaacaatg caaaatgtga agcatccggt tactgggcaa     1560
tttctatatc aggacagcaa ctgggccagc aaagttgaga aactcacttt agacaatgct     1620
gctttccctt tccttgcata ttctggaatc ccagcagttt cttttctgttt tgcgaggac      1680 acagattatc cttatttggg taccaccatg gacacctata aggaactgat tgagaggatt     1740
cctgagttga acaaagtggc acgagcagct gcagaggtcg ctggtcagtt cgtgattaaa     1800
ctaacccatg atgttgaatt gaacctggac tatgagaggt acaacagcca actgctttca     1860
tttgtgaggg atctgaacca atacagagca gacataaagg aaatgggcct gagtttacag     1920
tggctgtatt ctgctcgtgg agacttcttc cgtgctactt ccagactaac aacagatttc     1980
gggaatgctg agaaaacaga cagatttgtc atgaagaaac tcaatgatcg tgtcatgaga     2040
gtggagtatc acttcctctc tccctacgta tctccaaaag agtctccttt ccgacatgtc     2100
ttctggggct ccggctctca cacgctgcca gctttactgg agaacttgaa actgcgtaaa     2160
caaaataacg gtgcttttaa tgaaacgctg ttcagaaacc agttggctct agctacttgg     2220
actattcagg gagctgcaaa tgccctctct ggtgacgttt gggacattga caatgagttt     2280
taa                                                                   2283

<210> SEQ ID NO 75
<211> LENGTH: 2283
<212> TYPE: DNA
<213> ORGANISM: Homo sapiens

<400> SEQUENCE: 75
atgatggatc aagctagatc agcattctct aacttgtttg gtggagaacc attgtcatat       60
acccggttca gcctggctcg gcaagtagat ggcgataaca gtcatgtgga gatgaaactt      120
gctgtagatg aagaagaaaa tgctgacaat aacacaaagg ccaatgtcac aaaaccaaaa      180
aggtgtagtg gaagtatctg ctatgggact attgctgtga tcgtcttttt cttgattgga      240
tttatgattg gctacttggg ctattgtaaa ggggtagaac caaaaactga gtgtgagaga      300
ctggcaggaa ccgagtctcc agtgagggag gagccaggag aggacttccc tgcagcacgt      360
cgcttatatt gggatgacct gaagagaaag ttgtcggaga aactggacag cacagacttc      420
accggcacca tcaagctgct gaatgaaaat tcatatgtcc ctcgtgaggc tggatctcaa      480
```

```
aaagatgaaa atcttgcgtt gtatgttgaa atcaatttc gtgaatttaa actcagcaaa    540
gtctggcgtg atcaacattt tgttaagatt caggtcaaag acagcgctca aaactcggtg    600
atcatagttg ataagaacgg tagacttgtt tacctggtgg agaatcctgg gggttatgtg    660
gcgtatagta aggctgcaac agttactggt aaactggtcc atgctaattt tggtactaaa    720
aaagattttg aggatttata cactcctgtg aatggatcta tagtgattgt cagagcaggg    780
aaaatcacct ttgcagaaaa ggttgcaaat gctgaaagct aaatgcaat tggtgtgttg     840
atatacatgg accagactaa atttcccatt gttaacgcag aactttcatt ctttggacat    900
gctcatctgg ggacaggtga cccttacaca cctggattcc cttccttcaa tcacactcag    960
tttccaccat ctcggtcatc aggattgcct aatatacctg tccagacaat ctccagagct    1020
gctgcagaaa agctgtttgg gaatatggaa ggagactgtc cctctgactg gaaaacagac    1080
tctacatgta ggatggtaac ctcagaaagc aagaatgtga agctcactgt gagcaatgtg    1140
ctgaaagaga taaaaattct taacatcttt ggagttatta aaggctttgt agaaccagat    1200
cactatgttg tagttggggc ccagagagat gcatggggcc tggagctgc aaaatccggt     1260
gtaggcacag ctctcctatt gaaacttgcc cagatgttct cagatatggt cttaaaagat    1320
gggtttcagc ccagcagaag cattatcttt gccagttgga gtgctggaga ctttggatcg    1380
gttggtgcca ctgaatggct agagggatac ctttcgtccc tgcatttaaa ggctttcact    1440
tatattaatc tggataaagc ggttcttggt accagcaact tcaaggtttc tgccagccca    1500
ctgttgtata cgcttattga gaaacaatg caaaatgtga agcatccggt tactgggcaa     1560
tttctatatc aggacagcaa ctgggccagc aaagttgaga aactcacttt agacaatgct    1620
gctttcccct tccttgcata ttctggaatc ccagcagttt cttctctgtt tgcgaggac    1680
acagattatc cttatttggg taccaccatg gacacctata ggaactgat tgagaggatt    1740
cctgagttga caaagtggc acgagcagct gcagaggtcg ctggtcagtt cgtgattaaa     1800
ctaacccatg atgttgaatt gaacctggac tatgagaggt acaacagcca actgcttca    1860
tttgtgaggg atctgaacca atacagagca gacataaagg aaatgggcct gagtttacag    1920
tggctgtatt ctgctcgtgg agacttcttc cgtgctactt ccagactaac aacagatttc    1980
gggaatgctg agaaaacaga cagatttgtc atgaagaaac tcaatgatcg tgtcatgaga    2040
gtggagtatc acttcctctc tccctacgta tctccaaaag agtctccttt ccgacatgtc    2100
ttctggggct ccggctctca cacgctgcca gctttactgg agaacttgaa actgcgtaaa    2160
caaaataacg gtgcttttaa tgaaacgctg ttcagaaacc agttggctct agctacttgg    2220
actattcagg gagctgcaaa tgccctctct ggtgacgttt gggacattga caatgagttt    2280
taa                                                                  2283
```

<210> SEQ ID NO 76
<211> LENGTH: 760
<212> TYPE: PRT
<213> ORGANISM: Homo sapiens

<400> SEQUENCE: 76

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45
```

```
Asp Asn Asn Thr Lys Ala Asn Val Thr Lys Pro Lys Arg Cys Ser Gly
 50                  55                  60

Ser Ile Cys Tyr Gly Thr Ile Ala Val Ile Val Phe Phe Leu Ile Gly
 65                  70                  75                  80

Phe Met Ile Gly Tyr Leu Gly Tyr Cys Lys Gly Val Glu Pro Lys Thr
                     85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
            115                 120                 125

Arg Lys Leu Ser Glu Lys Leu Asp Ser Thr Asp Phe Thr Gly Thr Ile
130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                    165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
            195                 200                 205

Leu Val Tyr Leu Val Glu Asn Pro Gly Gly Tyr Val Ala Tyr Ser Lys
210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                    245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
            275                 280                 285

Pro Ile Val Asn Ala Glu Leu Ser Phe Phe Gly His Ala His Leu Gly
290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                    325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                    405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
450                 455                 460

Glu Trp Leu Glu Gly Tyr Leu Ser Ser Leu His Leu Lys Ala Phe Thr
```

```
                    465                 470                 475                 480
    Tyr Ile Asn Leu Asp Lys Ala Val Leu Gly Thr Ser Asn Phe Lys Val
                        485                 490                 495

Ser Ala Ser Pro Leu Leu Tyr Thr Leu Ile Glu Lys Thr Met Gln Asn
                    500                 505                 510

Val Lys His Pro Val Thr Gly Gln Phe Leu Tyr Gln Asp Ser Asn Trp
                    515                 520                 525

Ala Ser Lys Val Glu Lys Leu Thr Leu Asp Asn Ala Ala Phe Pro Phe
                530                 535                 540

Leu Ala Tyr Ser Gly Ile Pro Ala Val Ser Phe Cys Phe Cys Glu Asp
    545                 550                 555                 560

Thr Asp Tyr Pro Tyr Leu Gly Thr Thr Met Asp Thr Tyr Lys Glu Leu
                        565                 570                 575

Ile Glu Arg Ile Pro Glu Leu Asn Lys Val Ala Arg Ala Ala Ala Glu
                    580                 585                 590

Val Ala Gly Gln Phe Val Ile Lys Leu Thr His Asp Val Glu Leu Asn
                595                 600                 605

Leu Asp Tyr Glu Arg Tyr Asn Ser Gln Leu Leu Ser Phe Val Arg Asp
                610                 615                 620

Leu Asn Gln Tyr Arg Ala Asp Ile Lys Glu Met Gly Leu Ser Leu Gln
    625                 630                 635                 640

Trp Leu Tyr Ser Ala Arg Gly Asp Phe Phe Arg Ala Thr Ser Arg Leu
                        645                 650                 655

Thr Thr Asp Phe Gly Asn Ala Glu Lys Thr Asp Arg Phe Val Met Lys
                    660                 665                 670

Lys Leu Asn Asp Arg Val Met Arg Val Glu Tyr His Phe Leu Ser Pro
                675                 680                 685

Tyr Val Ser Pro Lys Glu Ser Pro Phe Arg His Val Phe Trp Gly Ser
                690                 695                 700

Gly Ser His Thr Leu Pro Ala Leu Leu Glu Asn Leu Lys Leu Arg Lys
    705                 710                 715                 720

Gln Asn Asn Gly Ala Phe Asn Glu Thr Leu Phe Arg Asn Gln Leu Ala
                        725                 730                 735

Leu Ala Thr Trp Thr Ile Gln Gly Ala Ala Asn Ala Leu Ser Gly Asp
                    740                 745                 750

Val Trp Asp Ile Asp Asn Glu Phe
                755                 760

<210> SEQ ID NO 77
<211> LENGTH: 2406
<212> TYPE: DNA
<213> ORGANISM: Homo sapiens

<400> SEQUENCE: 77
atggagcggc tttggggtct attccagaga gcgcaacaac tgtccccaag atcctctcag     60
accgtctacc agcgtgtgga aggccccccgg aaagggcacc tggaggagga agaggaagac    120
ggggaggagg gggcggagac attggcccac ttctgcccca tggagctgag ggggccctgag   180 cccctgggct ctagacccag gcagccaaac ctcattccct gggcggcagc aggacggagg    240 gctgcccccct acctggtcct gacggccctg ctgatcttca ctggggcctt cctactgggc    300
tacgtcgcct ccgagggtc ctgccaggcg tgcggagact ctgtgttggt ggtcagtgag      360
gatgtcaact atgagcctga cctggatttc caccagggca gactctactg agcgacctc      420 caggccatgt tcctgcagtt cctggggag gggcgcctgg aggacaccat caggcaaacc     480
```

```
agccttcggg aacgggtggc aggctcggcc gggatggccg ctctgactca ggacattcgc    540
gcggcgctct cccgccagaa gctggaccac gtgtggaccg acacgcacta cgtgggcctg    600
caattcccgg atccggctca ccccaacacc ctgcactggg tcgatgaggc cgggaaggtc    660
ggagagcagc tgccgctgga ggaccctgac gtctactgcc cctacagcgc catcggcaac    720
gtcacgggag agctggtgta cgcccactac gggcggcccg aagacctgca ggacctgcgg    780
gccaggggcg tggatccagt gggccgcctg ctgctggtgc gcgtgggggt gatcagcttc    840
gcccagaagg tgaccaatgc tcaggacttc ggggctcaag gagtgctcat atacccagag    900
ccagcggact ctcccagga cccacccaag ccaagcctgt ccagccagca ggcagtgtat    960
ggacatgtgc acctgggaac tggagacccc tacacacctg gcttcccttc cttcaatcaa   1020
acccagttcc ctccagttgc atcatcaggc cttcccagca tcccagccca gcccatcagt   1080
gcagacattg cctcccgcct gctgaggaag ctcaaaggcc tgtggcccc caagaatgg   1140 caggggagcc tcctaggctc ccctttatcac ctgggcccg gccacgact gcggctagtg   1200 gtcaacaatc acaggacctc accccccatc aacaacatct cggctgcat cgaaggccgc   1260 tcagagccag atcactacgt tgtcatcggg gcccagaggg atgcatgggg cccaggagca   1320
gctaaatccg ctgtggggac ggctatactc ctggagctgg tgcggacctt ttcctccatg   1380
gtgagcaacg gcttccggcc ccgcagaagt ctcctcttca tcagctggga cggtggtgac   1440 tttgaagcg tgggctccac ggagtggcta gagggctacc tcagcgtgct gcacctcaaa   1500
gccgtagtgt acgtgagcct ggacaacgca gtgctggggg atgacaagtt tcatgccaag   1560
accagccccc ttctgacaag tctcattgag agtgtcctga gcaggtgga ttctcccaac   1620 cacagtgggc agactctcta tgaacaggtg gtgttcacca atcccagctg ggatgctgag   1680
gtgatccggc cctacccat ggacagcagt gcctattcct tcacggcctt tgtgggagtc   1740
cctgccgtcg agttctcctt tatggaggac gaccaggcct acccattcct gcacacaaag   1800
gaggacactt atgagaacct gcataaggtg ctgcaaggcc gcctgcccgc cgtggcccag   1860
gccgtggccc agctcgcagg gcagctcctc atccggctca gccacgatcg cctgctgccc   1920
ctcgacttcg gccgctacgg ggacgtcgtc tcaggcaca tcgggaacct caacgagttc   1980
tctggggacc tcaaggcccg cgggctgacc ctgcagtggg tgtactcggc gcgggggac   2040 tacatccggg cggcggaaaa gctgcggcag gagatctaca gctcggagga gagagacgag   2100
cgactgacac gcatgtacaa cgtgcgcata atgcgggtgg agttctactt cctttcccag   2160
tacgtgtcgc cagccgactc cccgttccgc cacatcttca tgggccgtgg agaccacacg   2220
ctgggcgccc tgctggacca cctgcggctg ctgcgctcca acagctccgg gacccccggg   2280
gccacctcct ccactggctt ccaggagagc cgtttccggc gtcagctagc cctgctcacc   2340
tggacgctgc aaggggcagc caatgcgctt agcggggatg tctggaacat tgataacaac   2400
ttctga                                                             2406
```

<210> SEQ ID NO 78
<211> LENGTH: 801
<212> TYPE: PRT
<213> ORGANISM: Homo sapiens

<400> SEQUENCE: 78

```
Met Glu Arg Leu Trp Gly Leu Phe Gln Arg Ala Gln Gln Leu Ser Pro
1               5                   10                  15

Arg Ser Ser Gln Thr Val Tyr Gln Arg Val Glu Gly Pro Arg Lys Gly
```

```
                    20                  25                  30
His Leu Glu Glu Glu Glu Asp Gly Glu Glu Gly Ala Glu Thr Leu
            35                  40                  45
Ala His Phe Cys Pro Met Glu Leu Arg Gly Pro Glu Pro Leu Gly Ser
        50                  55                  60
Arg Pro Arg Gln Pro Asn Leu Ile Pro Trp Ala Ala Gly Arg Arg
 65                  70                  75                  80
Ala Ala Pro Tyr Leu Val Leu Thr Ala Leu Leu Ile Phe Thr Gly Ala
                85                  90                  95
Phe Leu Leu Gly Tyr Val Ala Phe Arg Gly Ser Cys Gln Ala Cys Gly
            100                 105                 110
Asp Ser Val Leu Val Val Ser Glu Asp Val Asn Tyr Glu Pro Asp Leu
        115                 120                 125
Asp Phe His Gln Gly Arg Leu Tyr Trp Ser Asp Leu Gln Ala Met Phe
        130                 135                 140
Leu Gln Phe Leu Gly Glu Gly Arg Leu Glu Asp Thr Ile Arg Gln Thr
145                 150                 155                 160
Ser Leu Arg Glu Arg Val Ala Gly Ser Ala Gly Met Ala Ala Leu Thr
                165                 170                 175
Gln Asp Ile Arg Ala Ala Leu Ser Arg Gln Lys Leu Asp His Val Trp
            180                 185                 190
Thr Asp Thr His Tyr Val Gly Leu Gln Phe Pro Asp Pro Ala His Pro
        195                 200                 205
Asn Thr Leu His Trp Val Asp Glu Ala Gly Lys Val Gly Glu Gln Leu
        210                 215                 220
Pro Leu Glu Asp Pro Asp Val Tyr Cys Pro Tyr Ser Ala Ile Gly Asn
225                 230                 235                 240
Val Thr Gly Glu Leu Val Tyr Ala His Tyr Gly Arg Pro Glu Asp Leu
                245                 250                 255
Gln Asp Leu Arg Ala Arg Gly Val Asp Pro Val Gly Arg Leu Leu Leu
            260                 265                 270
Val Arg Val Gly Val Ile Ser Phe Ala Gln Lys Val Thr Asn Ala Gln
        275                 280                 285
Asp Phe Gly Ala Gln Gly Val Leu Ile Tyr Pro Glu Pro Ala Asp Phe
        290                 295                 300
Ser Gln Asp Pro Pro Lys Pro Ser Leu Ser Ser Gln Gln Ala Val Tyr
305                 310                 315                 320
Gly His Val His Leu Gly Thr Gly Asp Pro Tyr Thr Pro Gly Phe Pro
                325                 330                 335
Ser Phe Asn Gln Thr Gln Phe Pro Pro Val Ala Ser Ser Gly Leu Pro
            340                 345                 350
Ser Ile Pro Ala Gln Pro Ile Ser Ala Asp Ile Ala Ser Arg Leu Leu
        355                 360                 365
Arg Lys Leu Lys Gly Pro Val Ala Pro Gln Glu Trp Gln Gly Ser Leu
        370                 375                 380
Leu Gly Ser Pro Tyr His Leu Gly Pro Gly Pro Arg Leu Arg Leu Val
385                 390                 395                 400
Val Asn Asn His Arg Thr Ser Thr Pro Ile Asn Asn Ile Phe Gly Cys
                405                 410                 415
Ile Glu Gly Arg Ser Glu Pro Asp His Tyr Val Val Ile Gly Ala Gln
            420                 425                 430
Arg Asp Ala Trp Gly Pro Gly Ala Ala Lys Ser Ala Val Gly Thr Ala
        435                 440                 445
```

```
Ile Leu Leu Glu Leu Val Arg Thr Phe Ser Ser Met Val Ser Asn Gly
450                 455                 460
Phe Arg Pro Arg Arg Ser Leu Leu Phe Ile Ser Trp Asp Gly Gly Asp
465                 470                 475                 480
Phe Gly Ser Val Gly Ser Thr Glu Trp Leu Glu Gly Tyr Leu Ser Val
                485                 490                 495
Leu His Leu Lys Ala Val Val Tyr Val Ser Leu Asp Asn Ala Val Leu
            500                 505                 510
Gly Asp Asp Lys Phe His Ala Lys Thr Ser Pro Leu Leu Thr Ser Leu
        515                 520                 525
Ile Glu Ser Val Leu Lys Gln Val Asp Ser Pro Asn His Ser Gly Gln
530                 535                 540
Thr Leu Tyr Glu Gln Val Val Phe Thr Asn Pro Ser Trp Asp Ala Glu
545                 550                 555                 560
Val Ile Arg Pro Leu Pro Met Asp Ser Ser Ala Tyr Ser Phe Thr Ala
                565                 570                 575
Phe Val Gly Val Pro Ala Val Glu Phe Ser Phe Met Glu Asp Asp Gln
            580                 585                 590
Ala Tyr Pro Phe Leu His Thr Lys Glu Asp Thr Tyr Glu Asn Leu His
        595                 600                 605
Lys Val Leu Gln Gly Arg Leu Pro Ala Val Ala Gln Ala Val Ala Gln
610                 615                 620
Leu Ala Gly Gln Leu Leu Ile Arg Leu Ser His Asp Arg Leu Leu Pro
625                 630                 635                 640
Leu Asp Phe Gly Arg Tyr Gly Asp Val Val Leu Arg His Ile Gly Asn
                645                 650                 655
Leu Asn Glu Phe Ser Gly Asp Leu Lys Ala Arg Gly Leu Thr Leu Gln
            660                 665                 670
Trp Val Tyr Ser Ala Arg Gly Asp Tyr Ile Arg Ala Ala Glu Lys Leu
        675                 680                 685
Arg Gln Glu Ile Tyr Ser Ser Glu Glu Arg Asp Glu Arg Leu Thr Arg
690                 695                 700
Met Tyr Asn Val Arg Ile Met Arg Val Glu Phe Tyr Phe Leu Ser Gln
705                 710                 715                 720
Tyr Val Ser Pro Ala Asp Ser Pro Phe Arg His Ile Phe Met Gly Arg
                725                 730                 735
Gly Asp His Thr Leu Gly Ala Leu Leu Asp His Leu Arg Leu Leu Arg
            740                 745                 750
Ser Asn Ser Ser Gly Thr Pro Gly Ala Thr Ser Ser Thr Gly Phe Gln
        755                 760                 765
Glu Ser Arg Phe Arg Arg Gln Leu Ala Leu Leu Thr Trp Thr Leu Gln
770                 775                 780
Gly Ala Ala Asn Ala Leu Ser Gly Asp Val Trp Asn Ile Asp Asn Asn
785                 790                 795                 800
Phe

<210> SEQ ID NO 79
<211> LENGTH: 1893
<212> TYPE: DNA
<213> ORGANISM: Homo sapiens

<400> SEQUENCE: 79
atggccgctc tgactcagga cattcgcgcg gcgctctccc gccagaagct ggaccacgtg      60
```

```
tggaccgaca cgcactacgt ggggctgcaa ttcccggatc cggctcaccc caacaccctg       120
cactgggtcg atgaggccgg gaaggtcgga gagcagctgc cgctggagga ccctgacgtc       180
tactgcccct acagcgccat cggcaacgtc acgggagagc tggtgtacgc ccactacggg       240
cggcccgaag acctgcagga cctgcgggcc aggggcgtgg atccagtggg ccgcctgctg       300
ctggtgcgcg tgggggtgat cagcttcgcc cagaaggtga ccaatgctca ggacttcggg       360
gctcaaggag tgctcatata cccagagcca gcggacttct cccaggaccc acccaagcca       420
agcctgtcca gccagcaggc agtgtatgga catgtgcacc tgggaactgg agacccctac       480
acacctggct tcccttcctt caatcaaacc cagttccctc cagttgcatc atcaggcctt       540
cccagcatcc cagcccagcc catcagtgca gacattgcct cccgcctgct gaggaagctc       600
aaaggccctg tgccccccca gaatggcagg ggagcctcc  taggctcccc ttatcacctg       660
ggccccgggc cacgactgcg gctagtggtc aacaatcaca ggacctccac ccccatcaac       720
aacatcttcg gctgcatcga aggccgctca gagccagatc actacgttgt catcggggcc       780
cagagggatg catgggcccc aggagcagct aaatccgctg tggggacggc tatactcctg       840
gagctggtgc ggaccttttc ctccatggtg agcaacggct ccggccccg cagaagtctc       900 ctcttcatca gctgggacgg tggtgacttt ggaagcgtgg gctccacgga gtggctagaa       960
ggctacctca gcgtgctgca cctcaaagcc gtagtgtacg tgagcctgga caacgcagtg      1020 ctggggggatg acaagtttca tgccaagacc agccccttc  tgacaagtct cattgagagt      1080
gtcctgaagc aggtggattc tcccaaccac agtgggcaga ctctctatga caggtggtg       1140 ttcaccaatc ccagctggga tgctgaggtg atccggcccc tacccatgga cagcagtgcc      1200
tattccttca cggcctttgt gggagtcccct gccgtcgagt tctcctttat ggaggacgac    1260
caggcctacc cattcctgca cacaaaggag gacacttatg agaacctgca taaggtgctg    1320
caaggccgcc tgcccgccgt ggcccaggcc gtggcccagc tcgcagggca gctcctcatc    1380
cggctcagcc acgatcgcct gctgcccctc gacttcggcc gctacgggga cgtcgtcctc    1440
aggcacatcg ggaacctcaa cgagttctct ggggacctca aggcccgcgg gctgaccctg    1500
cagtgggtgt actcggcgcg gggggactac atccggggcgg cggaaaagct gcggcaggag    1560
atctacagct cggaggagag agacgagcga ctgacacgca tgtacaacgt gcgcataatg    1620
cgggtggagt tctacttcct ttcccagtac gtgtcgccag ccgactcccc gttccgccac    1680
atcttcatgg gccgtggaga ccacacgctg ggcgccctgc tggaccacct gcggctgctg    1740
cgctccaaca gctccgggac ccccgggggcc acctcctcca ctggcttcca ggagagccgt    1800
ttccggcgtc agctagccct gctcacctgg acgctgcaag gggcagccaa tgcgcttagc    1860
ggggatgtct ggaacattga taacaacttc tga                                   1893
```

<210> SEQ ID NO 80
<211> LENGTH: 630
<212> TYPE: PRT
<213> ORGANISM: Homo sapiens

<400> SEQUENCE: 80

Met Ala Ala Leu Thr Gln Asp Ile Arg Ala Ala Leu Ser Arg Gln Lys
1               5                   10                  15

Leu Asp His Val Trp Thr Asp Thr His Tyr Val Gly Leu Gln Phe Pro
            20                  25                  30

Asp Pro Ala His Pro Asn Thr Leu His Trp Val Asp Glu Ala Gly Lys
        35                  40                  45

```
Val Gly Glu Gln Leu Pro Leu Glu Asp Pro Asp Val Tyr Cys Pro Tyr
     50                  55                  60

Ser Ala Ile Gly Asn Val Thr Gly Glu Leu Val Tyr Ala His Tyr Gly
 65                  70                  75                  80

Arg Pro Glu Asp Leu Gln Asp Leu Arg Ala Arg Gly Val Asp Pro Val
                 85                  90                  95

Gly Arg Leu Leu Leu Val Arg Val Gly Val Ile Ser Phe Ala Gln Lys
                100                 105                 110

Val Thr Asn Ala Gln Asp Phe Gly Ala Gln Gly Val Leu Ile Tyr Pro
            115                 120                 125

Glu Pro Ala Asp Phe Ser Gln Asp Pro Pro Lys Pro Ser Leu Ser Ser
        130                 135                 140

Gln Gln Ala Val Tyr Gly His Val His Leu Gly Thr Gly Asp Pro Tyr
145                 150                 155                 160

Thr Pro Gly Phe Pro Ser Phe Asn Gln Thr Gln Phe Pro Pro Val Ala
                165                 170                 175

Ser Ser Gly Leu Pro Ser Ile Pro Ala Gln Pro Ile Ser Ala Asp Ile
                180                 185                 190

Ala Ser Arg Leu Leu Arg Lys Leu Lys Gly Pro Val Ala Pro Gln Glu
        195                 200                 205

Trp Gln Gly Ser Leu Leu Gly Ser Pro Tyr His Leu Gly Pro Gly Pro
210                 215                 220

Arg Leu Arg Leu Val Val Asn Asn His Arg Thr Ser Thr Pro Ile Asn
225                 230                 235                 240

Asn Ile Phe Gly Cys Ile Glu Gly Arg Ser Glu Pro Asp His Tyr Val
                245                 250                 255

Val Ile Gly Ala Gln Arg Asp Ala Trp Gly Pro Gly Ala Ala Lys Ser
            260                 265                 270

Ala Val Gly Thr Ala Ile Leu Leu Glu Leu Val Arg Thr Phe Ser Ser
        275                 280                 285

Met Val Ser Asn Gly Phe Arg Pro Arg Arg Ser Leu Leu Phe Ile Ser
290                 295                 300

Trp Asp Gly Gly Asp Phe Gly Ser Val Gly Ser Thr Glu Trp Leu Glu
305                 310                 315                 320

Gly Tyr Leu Ser Val Leu His Leu Lys Ala Val Val Tyr Val Ser Leu
                325                 330                 335

Asp Asn Ala Val Leu Gly Asp Asp Lys Phe His Ala Lys Thr Ser Pro
            340                 345                 350

Leu Leu Thr Ser Leu Ile Glu Ser Val Leu Lys Gln Val Asp Ser Pro
        355                 360                 365

Asn His Ser Gly Gln Thr Leu Tyr Glu Gln Val Val Phe Thr Asn Pro
370                 375                 380

Ser Trp Asp Ala Glu Val Ile Arg Pro Leu Pro Met Asp Ser Ser Ala
385                 390                 395                 400

Tyr Ser Phe Thr Ala Phe Val Gly Val Pro Ala Val Glu Phe Ser Phe
                405                 410                 415

Met Glu Asp Asp Gln Ala Tyr Pro Phe Leu His Thr Lys Glu Asp Thr
            420                 425                 430

Tyr Glu Asn Leu His Lys Val Leu Gln Gly Arg Leu Pro Ala Val Ala
        435                 440                 445

Gln Ala Val Ala Gln Leu Ala Gly Gln Leu Leu Ile Arg Leu Ser His
450                 455                 460

Asp Arg Leu Leu Pro Leu Asp Phe Gly Arg Tyr Gly Asp Val Val Leu
```

```
                465                 470                 475                 480
Arg His Ile Gly Asn Leu Asn Glu Phe Ser Gly Asp Leu Lys Ala Arg
                    485                 490                 495
Gly Leu Thr Leu Gln Trp Val Tyr Ser Ala Arg Gly Asp Tyr Ile Arg
                500                 505                 510
Ala Ala Glu Lys Leu Arg Gln Glu Ile Tyr Ser Ser Glu Glu Arg Asp
            515                 520                 525
Glu Arg Leu Thr Arg Met Tyr Asn Val Arg Ile Met Arg Val Glu Phe
        530                 535                 540
Tyr Phe Leu Ser Gln Tyr Val Ser Pro Ala Asp Ser Pro Phe Arg His
545                 550                 555                 560
Ile Phe Met Gly Arg Gly Asp His Thr Leu Gly Ala Leu Leu Asp His
                    565                 570                 575
Leu Arg Leu Leu Arg Ser Asn Ser Ser Gly Thr Pro Gly Ala Thr Ser
                580                 585                 590
Ser Thr Gly Phe Gln Glu Ser Arg Phe Arg Arg Gln Leu Ala Leu Leu
            595                 600                 605
Thr Trp Thr Leu Gln Gly Ala Ala Asn Ala Leu Ser Gly Asp Val Trp
        610                 615                 620
Asn Ile Asp Asn Asn Phe
625                 630
```

<210> SEQ ID NO 81
<211> LENGTH: 2613
<212> TYPE: DNA
<213> ORGANISM: Homo sapiens

<400> SEQUENCE: 81

| | | | | | |
|---|---|---|---|---|---|
| atgacagctg | acaaggagaa | gaaaaggagt | agctcggaga | ggaggaagga | gaagtcccgg | 60 |
| gatgctgcgc | ggtgccggcg | gagcaaggag | acggaggtgt | tctatgagct | ggcccatgag | 120 |
| ctgcctctgc | cccacagtgt | gagctcccat | ctggacaagg | cctccatcat | gcgactggca | 180 |
| atcagcttcc | tgcgaacaca | caagctcctc | tcctcagttt | gctctgaaaa | cgagtccgaa | 240 |
| gccgaagctg | accagcagat | ggacaacttg | tacctgaaag | ccttggaggg | tttcattgcc | 300 |
| gtggtgaccc | aagatggcga | catgatcttt | ctgtcagaaa | acatcagcaa | gttcatggga | 360 |
| cttacacagg | tggagctaac | aggacatagt | atctttgact | tcactcatcc | ctgcgaccat | 420 |
| gaggagattc | gtgagaacct | gagtctcaaa | aatggctctg | gttttgggaa | aaaaagcaaa | 480 |
| gacatgtcca | cagagcggga | cttcttcatg | aggatgaagt | gcacggtcac | caacagaggc | 540 |
| cgtactgtca | acctcaagtc | agccacctgg | aaggtcttgc | actgcacggg | ccaggtgaaa | 600 |
| gtctacaaca | actgccctcc | tcacaatagt | ctgtgtggct | acaaggagcc | cctgctgtcc | 660 |
| tgcctcatca | tcatgtgtga | accaatccag | cacccatccc | acatggacat | cccctggat | 720 |
| agcaagacct | tcctgagccg | ccacagcatg | gacatgaagt | tcacctactg | tgatgacaga | 780 |
| atcacagaac | tgattggtta | ccaccctgag | gagctgcttg | ccgctcagc | ctatgaattc | 840 |
| taccatgcgc | tagactccga | gaacatgacc | aagagtcacc | agaacttgtg | caccaagggt | 900 |
| caggtagtaa | gtggccagta | ccggatgctc | gcaaagcatg | ggggctacgt | gtggctggag | 960 |
| acccagggga | cggtcatcta | caaccctcgc | aacctgcagc | ccagtgcat | catgtgtgtc | 1020 |
| aactacgtcc | tgagtgagat | tgagaagaat | gacgtggtgt | tctccatgga | ccagactgaa | 1080 |
| tccctgttca | gccccacct | gatggccatg | aacagcatct | ttgatagcag | tgcaagggga | 1140 |
| gctgtgtctg | agaagagtaa | cttcctattc | accaagctaa | aggaggagcc | cgaggagctg | 1200 |

```
gcccagctgg ctcccacccc aggagacgcc atcatctctc tggatttcgg gaatcagaac    1260
ttcgaggagt cctcagccta tggcaaggcc atcctgcccc cgagccagcc atgggccacg    1320
gagttgagga ccacagcac ccagagcgag gctgggagcc tgcctgcctt caccgtgccc    1380
caggcagctg ccccgggcag caccaccccc agtgccacca gcagcagcag cagctgctcc    1440
acgcccaata gccctgaaga ctattacaca tctttggata cgacctgaa gattgaagtg    1500
attgagaagc tcttcgccat ggacacagag gccaaggacc aatgcagtac ccagacggat    1560
ttcaatgagc tggacttgga cactggca ccctatatcc ccatggacgg ggaagacttc      1620
cagctaagcc ccatctgccc cgaggagcgg ctccttggcgg agaacccaca gtccaccccc    1680
cagcactgct tcagtgccat gacaaacatc ttccagccac tggcccctgt agccccgcac    1740
agtcccttcc tcctggacaa gtttcagcag cagctggaga gcaagaagac agagcccgag    1800
caccggccca tgtcctccat cttctttgat gccggaagca aagcatccct gccaccgtgc    1860
tgtggccagg ccagcacccc tctctcttcc atgggggca gatccaatac ccagtggccc      1920
ccagatccac cattacattt tgggcccaca aagtgggccg tcgggatca gcgcacagag      1980
ttcttgggag cagcgccgtt ggggcccct gtctctccac cccatgtctc caccttcaag      2040
acaaggtctg caaagggttt tggggctcga ggcccagacg tgctgagtcc ggccatggta    2100
gccctctcca acaagctgaa gctgaagcga cagctggagt atgaagagca agccttccag    2160
gacctgagcg ggggggaccc acctggtggc agcacctcac atttgatgtg gaaacggatg    2220
aagaacctca ggggtgggag ctgcccttg atgccggaca agccactgag cgcaaatgta    2280
cccaatgata agttcaccca aaaccccatg aggggcctgg gccatcccct gagacatctg    2340
ccgctgccac agcctccatc tgccatcagt cccggggaga acagcaagag caggttcccc    2400
ccacagtgct acgccaccca gtaccaggac tacagcctgt cgtcagccca aaggtgtca    2460
ggcatggcaa gccggctgct cgggccctca tttgagtcct acctgctgcc cgaactgacc    2520
agatatgact gtgaggtgaa cgtgcccgtg ctgggaagct ccacgctcct gcaaggaggg    2580
gacctcctca gagccctgga ccaggccacc tga                                  2613
```

<210> SEQ ID NO 82
<211> LENGTH: 870
<212> TYPE: PRT
<213> ORGANISM: Homo sapiens

<400> SEQUENCE: 82

```
Met Thr Ala Asp Lys Glu Lys Lys Arg Ser Ser Glu Arg Arg Lys
1               5                   10                  15

Glu Lys Ser Arg Asp Ala Ala Arg Cys Arg Arg Ser Lys Glu Thr Glu
            20                  25                  30

Val Phe Tyr Glu Leu Ala His Glu Leu Pro Leu Pro His Ser Val Ser
        35                  40                  45

Ser His Leu Asp Lys Ala Ser Ile Met Arg Leu Ala Ile Ser Phe Leu
    50                  55                  60

Arg Thr His Lys Leu Leu Ser Ser Val Cys Ser Glu Asn Glu Ser Glu
65                  70                  75                  80

Ala Glu Ala Asp Gln Gln Met Asp Asn Leu Tyr Leu Lys Ala Leu Glu
                85                  90                  95

Gly Phe Ile Ala Val Val Thr Gln Asp Gly Asp Met Ile Phe Leu Ser
            100                 105                 110

Glu Asn Ile Ser Lys Phe Met Gly Leu Thr Gln Val Glu Leu Thr Gly
```

```
            115                 120                 125
His Ser Ile Phe Asp Phe Thr His Pro Cys Asp His Glu Glu Ile Arg
            130                 135                 140
Glu Asn Leu Ser Leu Lys Asn Gly Ser Gly Phe Gly Lys Lys Ser Lys
145                 150                 155                 160
Asp Met Ser Thr Glu Arg Asp Phe Phe Met Arg Met Lys Cys Thr Val
                    165                 170                 175
Thr Asn Arg Gly Arg Thr Val Asn Leu Lys Ser Ala Thr Trp Lys Val
                180                 185                 190
Leu His Cys Thr Gly Gln Val Lys Val Tyr Asn Asn Cys Pro Pro His
                195                 200                 205
Asn Ser Leu Cys Gly Tyr Lys Glu Pro Leu Leu Ser Cys Leu Ile Ile
            210                 215                 220
Met Cys Glu Pro Ile Gln His Pro Ser His Met Asp Ile Pro Leu Asp
225                 230                 235                 240
Ser Lys Thr Phe Leu Ser Arg His Ser Met Asp Met Lys Phe Thr Tyr
                    245                 250                 255
Cys Asp Asp Arg Ile Thr Glu Leu Ile Gly Tyr His Pro Glu Glu Leu
                260                 265                 270
Leu Gly Arg Ser Ala Tyr Glu Phe Tyr His Ala Leu Asp Ser Glu Asn
            275                 280                 285
Met Thr Lys Ser His Gln Asn Leu Cys Thr Lys Gly Gln Val Val Ser
290                 295                 300
Gly Gln Tyr Arg Met Leu Ala Lys His Gly Gly Tyr Val Trp Leu Glu
305                 310                 315                 320
Thr Gln Gly Thr Val Ile Tyr Asn Pro Arg Asn Leu Gln Pro Gln Cys
                    325                 330                 335
Ile Met Cys Val Asn Tyr Val Leu Ser Glu Ile Glu Lys Asn Asp Val
                340                 345                 350
Val Phe Ser Met Asp Gln Thr Glu Ser Leu Phe Lys Pro His Leu Met
            355                 360                 365
Ala Met Asn Ser Ile Phe Asp Ser Ser Gly Lys Gly Ala Val Ser Glu
            370                 375                 380
Lys Ser Asn Phe Leu Phe Thr Lys Leu Lys Glu Glu Pro Glu Glu Leu
385                 390                 395                 400
Ala Gln Leu Ala Pro Thr Pro Gly Asp Ala Ile Ile Ser Leu Asp Phe
                    405                 410                 415
Gly Asn Gln Asn Phe Glu Glu Ser Ser Ala Tyr Gly Lys Ala Ile Leu
                420                 425                 430
Pro Pro Ser Gln Pro Trp Ala Thr Glu Leu Arg Ser His Ser Thr Gln
            435                 440                 445
Ser Glu Ala Gly Ser Leu Pro Ala Phe Thr Val Pro Gln Ala Ala Ala
            450                 455                 460
Pro Gly Ser Thr Thr Pro Ser Ala Thr Ser Ser Ser Ser Cys Ser
465                 470                 475                 480
Thr Pro Asn Ser Pro Glu Asp Tyr Tyr Thr Ser Leu Asp Asn Asp Leu
                    485                 490                 495
Lys Ile Glu Val Ile Glu Lys Leu Phe Ala Met Asp Thr Glu Ala Lys
                500                 505                 510
Asp Gln Cys Ser Thr Gln Thr Asp Phe Asn Glu Leu Asp Leu Glu Thr
            515                 520                 525
Leu Ala Pro Tyr Ile Pro Met Asp Gly Glu Asp Phe Gln Leu Ser Pro
            530                 535                 540
```

Ile Cys Pro Glu Glu Arg Leu Leu Ala Glu Asn Pro Gln Ser Thr Pro
545                 550                 555                 560

Gln His Cys Phe Ser Ala Met Thr Asn Ile Phe Gln Pro Leu Ala Pro
            565                 570                 575

Val Ala Pro His Ser Pro Phe Leu Leu Asp Lys Phe Gln Gln Gln Leu
        580                 585                 590

Glu Ser Lys Lys Thr Glu Pro Glu His Arg Pro Met Ser Ser Ile Phe
        595                 600                 605

Phe Asp Ala Gly Ser Lys Ala Ser Leu Pro Pro Cys Cys Gly Gln Ala
    610                 615                 620

Ser Thr Pro Leu Ser Ser Met Gly Gly Arg Ser Asn Thr Gln Trp Pro
625                 630                 635                 640

Pro Asp Pro Pro Leu His Phe Gly Pro Thr Lys Trp Ala Val Gly Asp
                645                 650                 655

Gln Arg Thr Glu Phe Leu Gly Ala Ala Pro Leu Gly Pro Pro Val Ser
            660                 665                 670

Pro Pro His Val Ser Thr Phe Lys Thr Arg Ser Ala Lys Gly Phe Gly
        675                 680                 685

Ala Arg Gly Pro Asp Val Leu Ser Pro Ala Met Val Ala Leu Ser Asn
    690                 695                 700

Lys Leu Lys Leu Lys Arg Gln Leu Glu Tyr Glu Gln Ala Phe Gln
705                 710                 715                 720

Asp Leu Ser Gly Gly Asp Pro Pro Gly Gly Ser Thr Ser His Leu Met
            725                 730                 735

Trp Lys Arg Met Lys Asn Leu Arg Gly Gly Ser Cys Pro Leu Met Pro
            740                 745                 750

Asp Lys Pro Leu Ser Ala Asn Val Pro Asn Asp Lys Phe Thr Gln Asn
        755                 760                 765

Pro Met Arg Gly Leu Gly His Pro Leu Arg His Leu Pro Leu Pro Gln
770                 775                 780

Pro Pro Ser Ala Ile Ser Pro Gly Glu Asn Ser Lys Ser Arg Phe Pro
785                 790                 795                 800

Pro Gln Cys Tyr Ala Thr Gln Tyr Gln Asp Tyr Ser Leu Ser Ser Ala
                805                 810                 815

His Lys Val Ser Gly Met Ala Ser Arg Leu Leu Gly Pro Ser Phe Glu
            820                 825                 830

Ser Tyr Leu Leu Pro Glu Leu Thr Arg Tyr Asp Cys Glu Val Asn Val
        835                 840                 845

Pro Val Leu Gly Ser Ser Thr Leu Leu Gln Gly Gly Asp Leu Leu Arg
850                 855                 860

Ala Leu Asp Gln Ala Thr
865                 870

<210> SEQ ID NO 83
<211> LENGTH: 1815
<212> TYPE: DNA
<213> ORGANISM: Homo sapiens

<400> SEQUENCE: 83
atgctcgccc gcgccctgct gctgtgcgcg gtcctggcgc tcagccatac agcaaatcct    60
tgctgttccc acccatgtca aaaccgaggt gtatgtatga gtgtgggatt tgaccagtat   120
aagtgcgatt gtaccggac aggattctat ggagaaaact gctcaacacc ggaattttg    180 acaagaataa aattatttct gaaacccact ccaaacacag tgcactacat acttacccac   240

```
ttcaagggat tttggaacgt tgtgaataac attcccttcc ttcgaaatgc aattatgagt    300
tatgtgttga catccagatc acatttgatt gacagtccac caacttacaa tgctgactat    360
ggctacaaaa gctgggaagc cttctctaac ctctcctatt atactagagc ccttcctcct    420
gtgcctgatg attgcccgac tcccttgggt gtcaaaggta aaagcagct tcctgattca    480 aatgagattg tggaaaaatt gcttctaaga agaaagttca tccctgatcc ccagggctca    540
aacatgatgt ttgcattctt tgcccagcac ttcacgcatc agttttcaa gacagatcat    600 aagcgagggc cagctttcac caacgggctg ggccatgggg tggacttaaa tcatatttac    660
ggtgaaactc tggctagaca gcgtaaactg cgccttttca aggatggaaa atgaaatat    720 cagataattg atggagagat gtatcctccc acagtcaaag atactcaggc agagatgatc    780
taccctcctc aagtccctga gcatctacgg tttgctgtgg ggcaggaggt ctttggtctg    840
gtgcctggtc tgatgatgta tgccacaatc tggctgcggg aacacaacag agtatgcgat    900
gtgcttaaac aggagcatcc tgaatggggt gatgagcagt tgttccagac aagcaggcta    960
atactgatag agagactat aagattgtg attgaagatt atgtgcaaca cttgagtggc   1020
tatcacttca aactgaaatt tgacccagaa ctacttttca acaaacaatt ccagtaccaa   1080
aatcgtattg ctgctgaatt taacaccctc tatcactggc atcccttct gcctgacacc   1140 tttcaaattc atgaccagaa atacaactat caacagttta tctacaacaa ctctatattg   1200
ctggaacatg gaattaccca gtttgttgaa tcattcacca ggcaaattgc tggcagggtt   1260
gctggtggta ggaatgttcc acccgcagta cagaaagtat cacaggcttc cattgaccag   1320
agcaggcaga tgaaatacca gtcttttaat gagtaccgca aacgctttat gctgaagccc   1380
tatgaatcat ttgaagaact tacaggagaa aaggaaatgt ctgcagagtt ggaagcactc   1440
tatggtgaca tcgatgctgt ggagctgtat cctgcccttc tggtagaaaa gcctcggcca   1500
gatgccatct ttggtgaaac catggtagaa gttggagcac cattctcctt gaaaggactt   1560
atgggtaatg ttatatgttc tcctgcctac tggaagccaa gcacttttgg tggagaagtg   1620
ggttttcaaa tcatcaacac tgcctcaatt cagtctctca tctgcaataa cgtgaagggc   1680
tgtcccttta cttcattcag tgttccagat ccagagctca ttaaaacagt caccatcaat   1740
gcaagttctt cccgctccgg actagatgat atcaatccca cagtactact aaaagaacgt   1800
tcgactgaac tgtag                                                   1815
```

<210> SEQ ID NO 84
<211> LENGTH: 604
<212> TYPE: PRT
<213> ORGANISM: Homo sapiens
<400> SEQUENCE: 84

```
Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
```

-continued

```
                85                  90                  95
Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
            115                 120                 125

Ser Asn Leu Ser Tyr Tyr Thr Arg Ala Leu Pro Pro Val Pro Asp Asp
            130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Arg Arg Lys Phe Ile Pro Asp
            165                 170                 175

Pro Gln Gly Ser Asn Met Met Phe Ala Phe Ala Gln His Phe Thr
            180                 185                 190

His Gln Phe Phe Lys Thr Asp His Lys Arg Gly Pro Ala Phe Thr Asn
            195                 200                 205

Gly Leu Gly His Gly Val Asp Leu Asn His Ile Tyr Gly Glu Thr Leu
            210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
            245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
            275                 280                 285

Thr Ile Trp Leu Arg Glu His Asn Arg Val Cys Asp Val Leu Lys Gln
            290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
            325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
            355                 360                 365

Thr Leu Tyr His Trp His Pro Leu Leu Pro Asp Thr Phe Gln Ile His
            370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
            405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
            435                 440                 445

Phe Asn Glu Tyr Arg Lys Arg Phe Met Leu Lys Pro Tyr Glu Ser Phe
            450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
            485                 490                 495

Lys Pro Arg Pro Asp Ala Ile Phe Gly Glu Thr Met Val Glu Val Gly
            500                 505                 510
```

```
Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Arg Ser Gly Leu Asp Asp Ile Asn
        580                 585                 590

Pro Thr Val Leu Leu Lys Glu Arg Ser Thr Glu Leu
        595                 600

<210> SEQ ID NO 85
<211> LENGTH: 21
<212> TYPE: DNA
<213> ORGANISM: Artificial Sequence
<220> FEATURE:
<223> OTHER INFORMATION: /note="Description of Artificial Sequence:
      Oligo A sequence"

<400> SEQUENCE: 85
tttgcctctt ctccacagac a                                            21

<210> SEQ ID NO 86
<211> LENGTH: 21
<212> TYPE: DNA
<213> ORGANISM: Artificial Sequence
<220> FEATURE:
<223> OTHER INFORMATION: /note="Description of Artificial Sequence:
      sh-NFS1-1 shRNA target sequence"

<400> SEQUENCE: 86
gctactgaat ccaacaacat a                                            21

<210> SEQ ID NO 87
<211> LENGTH: 21
<212> TYPE: DNA
<213> ORGANISM: Artificial Sequence
<220> FEATURE:
<223> OTHER INFORMATION: /note="Description of Artificial Sequence:
      sh-NFS1-2 shRNA target sequence"

<400> SEQUENCE: 87
gcgcactctt ctatcaggtt t                                            21

<210> SEQ ID NO 88
<211> LENGTH: 21
<212> TYPE: DNA
<213> ORGANISM: Artificial Sequence
<220> FEATURE:
<223> OTHER INFORMATION: /note="Description of Artificial Sequence:
      sh-NFS1-3 shRNA target sequence"

<400> SEQUENCE: 88
ccacaagcga atctcaaagt t                                            21

<210> SEQ ID NO 89
<211> LENGTH: 21
<212> TYPE: DNA
<213> ORGANISM: Artificial Sequence
<220> FEATURE:
<223> OTHER INFORMATION: /note="Description of Artificial Sequence:
      sh-NFS1-4 shRNA target sequence"
```

<400> SEQUENCE: 89
cagttccaga aaggtatatt t                                        21

<210> SEQ ID NO 90
<211> LENGTH: 21
<212> TYPE: DNA
<213> ORGANISM: Artificial Sequence
<220> FEATURE:
<223> OTHER INFORMATION: /note="Description of Artificial Sequence:
      sh-NFS1-5 shRNA target sequence"

<400> SEQUENCE: 90
ctgtgactcc accagttatt c                                        21

<210> SEQ ID NO 91
<211> LENGTH: 21
<212> TYPE: DNA
<213> ORGANISM: Artificial Sequence
<220> FEATURE:
<223> OTHER INFORMATION: /note="Description of Artificial Sequence:
      sh-NFS1-6 shRNA target sequence"

<400> SEQUENCE: 91
agcggctgat acagaatata a                                        21

<210> SEQ ID NO 92
<211> LENGTH: 21
<212> TYPE: DNA
<213> ORGANISM: Artificial Sequence
<220> FEATURE:
<223> OTHER INFORMATION: /note="Description of Artificial Sequence:
      sh-NFS1-7 shRNA target sequence"

<400> SEQUENCE: 92
gggaccctaa gcaccattat c                                        21

<210> SEQ ID NO 93
<211> LENGTH: 21
<212> TYPE: DNA
<213> ORGANISM: Artificial Sequence
<220> FEATURE:
<223> OTHER INFORMATION: /note="Description of Artificial Sequence:
      sh-NFS1-8 shRNA target sequence"

<400> SEQUENCE: 93
tgtgaagcgt cttcgagaaa t                                        21

<210> SEQ ID NO 94
<211> LENGTH: 21
<212> TYPE: DNA
<213> ORGANISM: Artificial Sequence
<220> FEATURE:
<223> OTHER INFORMATION: /note="Description of Artificial Sequence:
      sh-NT1 shRNA target sequence"

<400> SEQUENCE: 94
caacaagatg aagagcacca a                                        21

<210> SEQ ID NO 95
<211> LENGTH: 21
<212> TYPE: DNA
<213> ORGANISM: Artificial Sequence
<220> FEATURE:
<223> OTHER INFORMATION: /note="Description of Artificial Sequence:
      sh-LU2 shRNA targetsequence"

<400> SEQUENCE: 95
cttcgaaatg tccgttcggt t                                              21

<210> SEQ ID NO 96
<211> LENGTH: 21
<212> TYPE: DNA
<213> ORGANISM: Artificial Sequence
<220> FEATURE:
<223> OTHER INFORMATION: /note="Description of Artificial Sequence:
      sh-LUC3 shRNA target sequence"

<400> SEQUENCE: 96
caaatcacag aatcgtcgta t                                              21

<210> SEQ ID NO 97
<211> LENGTH: 21
<212> TYPE: DNA
<213> ORGANISM: Artificial Sequence
<220> FEATURE:
<223> OTHER INFORMATION: /note="Description of Artificial Sequence:
      sh-KIF11 shRNA target sequence"

<400> SEQUENCE: 97
gcgtacaaga acatctataa t                                              21

<210> SEQ ID NO 98
<211> LENGTH: 21
<212> TYPE: DNA
<213> ORGANISM: Artificial Sequence
<220> FEATURE:
<223> OTHER INFORMATION: /note="Description of Artificial
      Sequence: sh-NFS1_sh1 target sequence"

<400> SEQUENCE: 98
gctactgaat ccaacaacat a                                              21

<210> SEQ ID NO 99
<211> LENGTH: 21
<212> TYPE: DNA
<213> ORGANISM: Artificial Sequence
<220> FEATURE:
<223> OTHER INFORMATION: /note="Description of Artificial
      Sequence: sh-NFS1_sh1 mutated target sequence"

<400> SEQUENCE: 99
gcaacggagt cgaataatat c                                              21

<210> SEQ ID NO 100
<211> LENGTH: 24
<212> TYPE: DNA
<213> ORGANISM: Artificial Sequence
<220> FEATURE:
<223> OTHER INFORMATION: /note="Description of Artificial
      Sequence: sh-NFS1_sh4 target sequence"

<400> SEQUENCE: 100
tgcagttcca gaaaggtata tttc                                           24

<210> SEQ ID NO 101
<211> LENGTH: 24
<212> TYPE: DNA
<213> ORGANISM: Artificial Sequence
<220> FEATURE:
<223> OTHER INFORMATION: /note="Description of Artificial
      Sequence: sh-NFS1_sh4 mutated target sequence"

<400> SEQUENCE: 101
tgtagctctc gcaaagtcta cttc                                              24

<210> SEQ ID NO 102
<211> LENGTH: 24
<212> TYPE: DNA
<213> ORGANISM: Artificial Sequence
<220> FEATURE:
<223> OTHER INFORMATION: /note="Description of Artificial
      Sequence: sh-NFS1_sh6 target sequence"

<400> SEQUENCE: 102
gagcggctga tacagaatat aatg                                              24

<210> SEQ ID NO 103
<211> LENGTH: 24
<212> TYPE: DNA
<213> ORGANISM: Artificial Sequence
<220> FEATURE:
<223> OTHER INFORMATION: /note="Description of Artificial
      Sequence: sh-NFS1_sh6 mutated target sequence"

<400> SEQUENCE: 103
gaacgcctta tccaaaacat tatg                                              24

<210> SEQ ID NO 104
<211> LENGTH: 48
<212> TYPE: DNA
<213> ORGANISM: Artificial Sequence
<220> FEATURE:
<223> OTHER INFORMATION: /note="Description of Artificial
      Sequence: NFS1_P1 synthetic primer"

<400> SEQUENCE: 104
ggggacaact ttgtacaaaa aagttggcat gctgctccga gccgcttg                    48

<210> SEQ ID NO 105
<211> LENGTH: 48
<212> TYPE: DNA
<213> ORGANISM: Artificial Sequence
<220> FEATURE:
<223> OTHER INFORMATION: /note="Description of Artificial
      Sequence: NFS1_P2 synthetic primer"

<400> SEQUENCE: 105
ggggacaact ttgtacaaga aagttgggct agtgttgggt ccacttga                    48

<210> SEQ ID NO 106
<211> LENGTH: 41
<212> TYPE: DNA
<213> ORGANISM: Artificial Sequence
<220> FEATURE:
<223> OTHER INFORMATION: /note="Description of Artificial
      Sequence: NFS1_SH1_P3 synthetic primer"

<400> SEQUENCE: 106
gatattattc gactccgttg caccactagt aaaaatgatc t                           41

<210> SEQ ID NO 107
<211> LENGTH: 41
<212> TYPE: DNA
<213> ORGANISM: Artificial Sequence
<220> FEATURE:
<223> OTHER INFORMATION: /note="Description of Artificial
      Sequence: NFS1_SH1_P4 synthetic primer"

<400> SEQUENCE: 107

```
gcaacggagt cgaataatat cgcaattaag ggggtggccc g                    41

<210> SEQ ID NO 108
<211> LENGTH: 41
<212> TYPE: DNA
<213> ORGANISM: Artificial Sequence
<220> FEATURE:
<223> OTHER INFORMATION: /note="Description of Artificial
      Sequence: NFS1_SH4_P3 synthetic primer"

<400> SEQUENCE: 108
aagtagactt tgcgagagct acaaatccgc cctatttctg c                    41

<210> SEQ ID NO 109
<211> LENGTH: 41
<212> TYPE: DNA
<213> ORGANISM: Artificial Sequence
<220> FEATURE:
<223> OTHER INFORMATION: /note="Description of Artificial
      Sequence: NFS1_SH4_P4 synthetic primer"

<400> SEQUENCE: 109
tagctctcgc aaagtctact tccatactga tgcagcccag g                    41

<210> SEQ ID NO 110
<211> LENGTH: 41
<212> TYPE: DNA
<213> ORGANISM: Artificial Sequence
<220> FEATURE:
<223> OTHER INFORMATION: /note="Description of Artificial
      Sequence: NFS1_SH6_P3 synthetic primer"

<400> SEQUENCE: 110
taatgttttg gataaggcgt tctgacaact ttgagattcg c                    41

<210> SEQ ID NO 111
<211> LENGTH: 41
<212> TYPE: DNA
<213> ORGANISM: Artificial Sequence
<220> FEATURE:
<223> OTHER INFORMATION: /note="Description of Artificial
      Sequence: NFS1_SH6_P4 synthetic primer"

<400> SEQUENCE: 111
aacgccttat ccaaaacatt atgaagagcc ttccagatgt g                    41
```